ically) United States Patent
Zhao et al.

(10) Patent No.: US 7,067,450 B2
(45) Date of Patent: Jun. 27, 2006

(54) SOLUBLE LATE TRANSITION METAL CATALYSTS FOR OLEFIN OLIGOMERIZATIONS III

(75) Inventors: Baiyi Zhao, Kingwood, TX (US); Enock Berluche, Phillipsburg, NJ (US); Smita Kacker, Houston, TX (US); Jo Ann Marie Canich, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 332 days.

(21) Appl. No.: 10/448,837

(22) Filed: May 30, 2003

(65) Prior Publication Data

US 2004/0044150 A1 Mar. 4, 2004

Related U.S. Application Data

(60) Provisional application No. 60/384,289, filed on May 30, 2002, and provisional application No. 60/396,370, filed on Jul. 17, 2002.

(51) Int. Cl.
*B01J 31/00* (2006.01)
*B01J 37/00* (2006.01)
*C08F 4/02* (2006.01)
*C08F 4/60* (2006.01)

(52) U.S. Cl. .................. 502/102; 502/104; 502/123; 502/150; 502/167; 525/240; 526/90

(58) Field of Classification Search ............ 502/102, 502/104, 123, 150, 167; 525/240; 526/90
See application file for complete search history.

(56) References Cited

U.S. PATENT DOCUMENTS

| 5,571,881 | A | * | 11/1996 | Goodall et al. ............. 526/171 |
| 5,677,405 | A | * | 10/1997 | Goodall et al. ............. 526/281 |
| 5,741,869 | A | * | 4/1998 | Goodall et al. ............. 526/171 |
| 5,866,663 | A | | 2/1999 | Brookhart et al. |
| 5,880,323 | A | | 3/1999 | Brookhart, III et al. |
| 6,303,724 | B1 | * | 10/2001 | Goodall et al. ............. 526/266 |
| 6,790,579 | B1 | * | 9/2004 | Goodall et al. ............. 430/170 |

FOREIGN PATENT DOCUMENTS

| EP | 0924223 | 12/1998 |
| JP | 63039389 | 2/1988 |
| WO | 00/10945 | 3/2000 |

OTHER PUBLICATIONS

Yang, et al. "Dimethyl and Cationic 1,4–Diazabutadiene Complexes of Platinum (II)", Organometallics 1998 (17) 5102–5113.*
Yang, et al. "Unsymmetrical 1,4–Diazabutadiene Complexes of Platinum (II)", Organometallics 1997, (16) 5234–5243.*
Drent and Budzelaar "Palladium Catalyzed Alternating Copolymerization of Alkenes and Carbon Monoxide", Chem. Rev. (1996 663–681.*
B. Elvers, et al., Ed. *Ullmann's Encyclopedia of Industrial Chemistry*, Hydrocarbons, vol. A 13, VCH Verlagsgesellschaft mbH, Weinheim, 1989, pp. 243–247 and 275–276.
B. Cornils, et al., Ed., "Applied Homogeneous Catalysis with Organometallic Compounds", *A Comprehensive Handbook*, vol. 1, VCH Verlagsgesellschaft mbH, Weinheim, 1996, pp. 245–258.
C. Killian, et al., "Preparation of Linear α–Olefins Using Cationic Nickel(II) α–Diimine", *Organometallics*, 1997, 16, pp. 2005–2007.
S. Svejda, et al., "Ethylene Oligomerization and Propylene Dimerization Using Cationic (α–Diimine)nickel(II) Catalysts", *Organometallics*, 1999, 18, pp. 65–74.
Abakumov et al., "Bis(I, 4–di–tert–butyl–1, 4–diazabutadiene)copper(I)[(3,6–di–tert–butyl–o–benzosemiquinono)(3, 6–di–tert –butyl–catecholato)cuprate(II)]. The molecular structure and intramolecular electron transfer", *Russian Chemical Bulletin*, International Edition, vol. 50, No. 11, Nov. 2001, pp. 2193–2199/–*.
Kannan, et al., "Dinuclear diimine palladium (II) and platinum (ii) hydroxo and amido complexes : synthesis and X–ray crystal structures", *Polyhedron* 19 (2000) pp. 155–163.
McCord, et al, "$^{13}$C and 2D NMR Analysis of Propylene Polymers Made with α–Diimine Late Metal Catalysts", *Macromolecules*, 2001, 34, pp. 362–371.
Pappalardo, et al., "Some Evidence of a Dual Stereodifferentation Mechanism in the Polymerization of Propene by α–Diimine Nickel Catalysts", *Macromolecules*, 2000, 33, pp. 9483–9487.
Yang, et al. "Unsymmetrical 1,4–Diazabutadiene Complexes of Platinum (II)", *Organometallics*, 1997, 16, pp. 5234–5243.
Yang, et al. "Dimethyl and Cationic 1,4–Diazabutadiene Complexes of Platinum (II)", *Organometallics*, 1998, 17, pp. 5102–5113.
Benedix, et al. "Electronic Structure and Spectroscopic Properties of Copper Catecholate Complexes with Interligand Charge Transfer Behavior", *Inorganica Chimica Acta*, 1993, 204, pp. 189–193.
Wenzel, et al., "New Indigoid Compounds by Reduction of Bis–Imidoylchlorides of Oxalic Acid—A Further Evidence for Dimeric Isocyanides?", *Monatshefte fur Chemie*, 130, 1999, pp. 1373–1382.

(Continued)

Primary Examiner—J. A. Lorengo
Assistant Examiner—Jennine Brown

(57) ABSTRACT

A series of soluble α-diimine late transition metal catalysts has been invented comprising a substituted or unsubstituted catecholate ligand. The catalysts demonstrate high activity and selectivity for linear α-olefins. As such, these catalysts conveniently oligomerize ethylene. Typical activators as known to those of ordinary skill in the art are used to activate these transition metal catalysts. These catalysts can be used in a supported or unsupported form.

27 Claims, No Drawings

OTHER PUBLICATIONS

Wood, et al., "Synthesis of Polystyrene by Dispersion Polymerization in 1,1,1,2–Tetrafluoroethane (R134a) Using Inexpensive Hydrocarbon Macromonomer Stabilizers", *Macromolecules*, 2003, 36 pp. 7534–7542.

Boussie, et al., "Parallel Solid–Phase Synthesis, Screening, and Encloding Strategies for Olefin–Polymerization Catalysts", *Tetrahedron*, 55, 1999, pp. 11699–11710.

ACS Registry Number 117869–99–5.

* cited by examiner

SOLUBLE LATE TRANSITION METAL CATALYSTS FOR OLEFIN OLIGOMERIZATIONS III

This application claims priority to U.S. Provisional Patent Application No. 60/384,289, filed May 30, 2002 and U.S. Provisional Patent Application No. 60/396,370, filed Jul. 17, 2002. This application also claims priority from U.S. Ser. No. 10/449,273, filed May 30, 2003.

FIELD OF INVENTION

This document relates to late transition metal catalysts for olefin oligomerizations and to methods for making and using these catalysts.

BACKGROUND

Alpha-olefins, especially those containing 6 to 20 carbon atoms, are important items of commerce. They are used as intermediates in the manufacture of detergents, as monomers (especially in linear low-density polyethylene), and as intermediates for many other types of products. As a consequence, improved methods of making these compounds are desired.

Most commercially produced α-olefins are made by the oligomerization of ethylene, catalyzed by various types of compounds, see for instance B. Elvers, et al., Ed. Ullmann's Encyclopedia of Industrial Chemistry, Vol. A13, VCH Verlagsgesellschaft mbH, Weinheim, 1989, p. 243–247 and 275–276, and B. Cornils, et al., Ed., Applied Homogeneous Catalysis with Organometallic Compounds, A Comprehensive Handbook, Vol. 1, VCH Verlagsgesellschaft mbH, Weinheim, 1996, p. 245–458. The major types of commercially used catalysts are alkylaluminum compounds, certain nickel-phosphine complexes, and a titanium halide with a Lewis acid such as $AlCl_3$. In all of these processes, significant amounts of branched and/or internal olefins and/or diolefins are produced. Since in most instances these are undesirable and often difficult to separate, these byproducts are avoided commercially.

Recently, a series of cationic (α-diimine) nickel (II) catalysts for ethylene oligomerization and propylene dimerization were reported. (Organometallics 1999, 18, 65–74; Organometallics 1997, 16, 2005–2007; WO 00/10945; U.S. Pat. No. 5,880,323). These catalysts are highly active. But the corresponding pre-catalysts have low organic-solvent solubility. Therefore, their characterization and application is highly restricted. Catalyst solubility is desired for continuous solution reactors and for supporting the catalysts for use in a slurry phase reactor or fixed-bed reactor. Additionally, a soluble pre-catalyst is easier to completely activate to its catalytic form, and often provides a catalyst with significantly higher catalyst activity. In view of the difficulty and practical limitations in using insoluble or poorly soluble catalysts, soluble, α-olefin-producing catalyst systems need to be developed.

SUMMARY

Invention catalyst systems comprise nickel or palladium components (pre-catalyst or catalyst precursor) and an activator (cocatalyst)) that can produce α-olefins in a solution- or a slurry-phase oligomerization procedure. The soluble oligomerization catalyst precursors of this invention are represented by the general formula I.

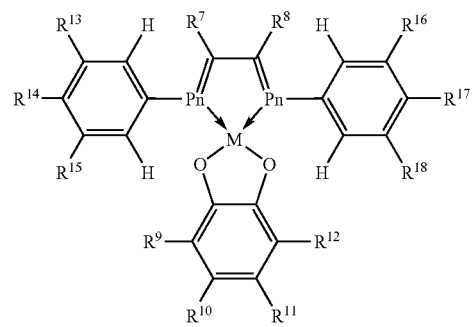

where
M is nickel or palladium;
Pn is a Group 15 atom, preferably nitrogen;
H is hydrogen;
$R^7$ and $R^8$ are independently
  hydrogen or
  $C_1$–$C_{30}$ hydrocarbyl radicals that may be joined to form an aromatic or non-aromatic cyclic ring structure;
$R^{13}$, $R^{14}$, $R^{15}$, $R^{16}$, $R^{17}$, and $R^{18}$ are independently
  hydrogen or
  $C_1$–$C_{30}$ hydrocarbyl radicals
Optionally, one or more aromatic or non-aromatic structures may be formed by independently joining two or more adjacent
  non-hydrogen $R^{13}$, $R^{14}$ or $R^{15}$; or
  non-hydrogen $R^{16}$, $R^{17}$ or $R^{18}$,
$R^9$, $R^{10}$, $R^{11}$ and $R^{12}$ are independently
  hydrogen,
  halogen, hydroxyl, alkoxy, or
  $C_1$–$C_{30}$ hydrocarbyl radicals
provided that at least one $R^{9-12}$ radical is not hydrogen; and two or more $R^{9-12}$ may form a saturated or unsaturated ring structure.

Some invention embodiments relate to compositions comprising:
a metal selected from nickel or palladium;
an ancillary ligand system connected to the metal where the ancillary ligand system comprises
1,4-diazabutadiene; and
substituents connected to the 2 and 3 positions of the diazabutadiene;
phenyl rings connected to the 1 and 4 positions of the diazabutadiene;
  (i) a catecholate ligand.

In another embodiment, this invention relates to a composition comprising:
  (I) a metal selected from nickel or palladium connected to a ligand comprising 1,4-diazabutadiene:
    (a) having a phenyl ring connected to the 1 position of the diazabutadiene, and
    (b) having a phenyl ring connected to the 4 position of the diazabutadiene, and
    (c) where the 2 and 6 positions of both phenyl rings are connected to hydrogen radicals, and
    (d) where the 2 and 3 positions of the diazabutadiene are, each independently, connected to hydrogen or a hydrocarbyl group; and
  (II) a catecholate ligand connected to the metal.

In another embodiment, this invention relates to a composition comprising a catecholate ligand, palladium or nickel, and an ancillary ligand with the following structure:

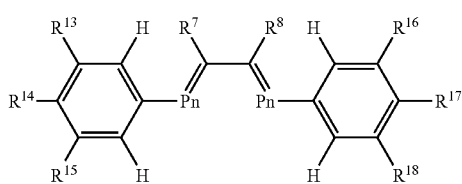

where

Pn is a Group-15 element;

H is hydrogen;

$R^7$ and $R^8$ are independently hydrogen or $C_1$–$C_{30}$ hydrocarbyl radicals, or both are $C_1$–$C_{30}$ hydrocarbyl radicals that form a ring structure comprising one or more aromatic or non-aromatic rings;

$R^{13}$–$R^{18}$ are, independently, hydrogen or $C_1$–$C_{30}$ hydrocarbyl radicals.

The compositions can be activated with cocatalyst activators, as are known in the art. Accordingly, invention embodiments also include such activated compositions. These activated compositions react with ethylene to form ethylene oligomers.

Methods of producing these compositions are, outlined in this document. Because of this, invention embodiments include methods of producing these compositions, as well.

DEFINITIONS

The term "hydrocarbyl radical" is sometimes used interchangeably with "hydrocarbyl" throughout this document. For purposes of this disclosure, "hydrocarbyl radical" encompasses $C_1$–$C_{50}$ radicals. These radicals can be linear, branched, or cyclic, and when cyclic, aromatic or non-aromatic. Thus, the term "hydrocarbyl radical", in addition to unsubstituted hydrocarbyl radicals, encompasses substituted hydrocarbyl radicals, halocarbyl radicals, and substituted halocarbyl radicals, as these terms are defined below.

Substituted hydrocarbyl radicals are radicals in which at least one hydrogen atom has been substituted with at least one functional group such as $NR''_2$, $OR''$, $PR''_2$, $SR''$, $BR''_2$, $SiR''_3$, $GeR''_3$ and the like or where at least one non-hydrocarbon atom or group has been inserted within the hydrocarbyl radical, such as O, S, $NR''$, $PR''$, $BR''$, $SiR''_2$, $GeR''_2$, and the like, where $R''$ is independently a hydrocarbyl or halocarbyl radical.

Halocarbyl radicals are radicals in which one or more hydrocarbyl hydrogen atoms have been substituted with at least one halogen or halogen-containing group (e.g. F, Cl, Br, I).

Substituted halocarbyl radicals are radicals in which at least one hydrocarbyl hydrogen or halogen atom has been substituted with at least one functional group such as $NR''_2$, $OR''$, $PR''_2$, $SR''$, $BR''_2$, $SiR''_3$, $GeR''_3$ and the like or where at least one non-carbon atom or group has been inserted within the halocarbyl radical such as O, S, $NR''$, $PR''$, $BR''$, $SiR''_2$, $GeR''_2$, and the like where $R''$ is independently a hydrocarbyl or halocarbyl radical provided that at least one halogen atom remains on the original halocarbyl radical.

The hydrocarbyl radical can be independently selected from methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, or triacontynyl isomers. The radical may then be subjected to the types of substitutions described above.

The nickel or palladium component can also be described as comprising at least one ancillary ligand that stabilizes the oxidation state of the transition metal. Ancillary ligands serve to enforce the geometry around the metal center. In this disclosure, ancillary ligands comprise 1,4-diazabutadiene to which substituents are connected at the 2 and 3 positions and phenyl rings are connected to the 1 and 4 positions of the diazabutadiene. For purposes of this disclosure, all recited "diazabutadiene" is intended to indicate 1,4-diazabuta-1,3-diene.

The substituents at the 2 and 3 positions are independently hydrogen or a hydrocarbyl radical. In some embodiments, a substituent is independently hydrogen or a $C_1$–$C_{30}$ hydrocarbyl radical. In these or other embodiments, two of these substituents link to form a ring structure comprising one or more, aromatic or non-aromatic rings.

For purposes of this disclosure, "catecholate" or "catecholate ligand" encompasses a ligand comprising a phenyl ring. Two oxygen atoms connect to the phenyl ring at the ring's 1 and 2 positions. The ligand connects to the metal center of the catalyst precursor through both of these oxygen atoms. This leaves four hydrogen atoms connected to the phenyl ring at its 3, 4, 5 and 6 positions. Zero, one, two, three, or four of these hydrogen atoms can be substituted with a $C_1$–$C_{30}$ hydrocarbyl radical. Also, adjacent catecholate hydrocarbyl radicals can join to transform the catecholate into a substituted or unsubstituted, fused-multi-ring system.

For purposes of this disclosure oligomers include about 2–75 mer units.

In some structures throughout this specification, the ligand-metal connection is drawn with an arrow indicating that the electrons for the bond originally came from the ligand. At other times, a solid line showing the bond's covalent nature represents the liquid-metal connection. One of ordinary skill in the art recognizes that these depictions are interchangeable.

DETAILED DESCRIPTION

Due to the presence of a catecholate ligand, the catalyst becomes more soluble in most organic solvents such as hexane, toluene, methylene chloride, and the like.

Examples of specific invention catalyst precursors take the following formula where some components are listed in Table 1. When alkyl, alkenyl and alkynyl radicals are disclosed in this application, the term includes all isomers and all substitution types, as described above, unless otherwise stated. For example, butyl includes n-butyl, isobutyl, and tert-butyl; pentyl includes n-pentyl, 1-methylbutyl, 2-methylbutyl, 3-methylbutyl, 1-ethylpropyl, and neopentyl; butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl. To illustrate members of the transition metal component, select any combination of the species listed in Table 1. For example, choosing the components in the first row, yields [1,4-bis(phenyl)-1,4-diaza-1,3-butadiene]nickel catecholate. Any combination of components may be selected. The column labeled $R^{19}R^{20}$ shows some examples of substituents that can serve as $R^{19}$ and $R^{20}$. Of course, selecting a particular substituent for $R^{19}$ is independent of the selection for $R^{20}$. In other words, the invention allows $R^{19}=R^{20}$, but does not demand it. The same goes for $R^7$, $R^8$, $R^9$, $R^{10}$, $R^{11}$, and $R^{12}$, as well.

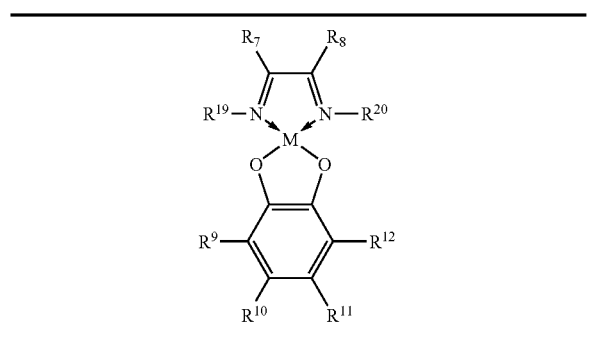

| $R^{19}$ $R^{20}$ | $R^7$ $R^8$ | $R^9$ $R^{10}$ $R^{11}$ $R^{12}$ | M |
|---|---|---|---|
| Phenyl | Hydrogen | hydrogen | nickel |
| 3-methylphenyl | Methyl | dimethoxy | palladium |
| 4-methylphenyl | Ethyl | methyl | |
| 3,4-dimethylphenyl | Propyl | ethyl | |
| 3,4,5-trimethylphenyl | Butyl | propyl | |
| 3-ethylphenyl | Pentyl | butyl | |
| 4-ethylphenyl | Hexyl | pentyl | |
| 3,4-diethylphenyl | Heptyl | hexyl | |
| 3,4,5-triethylphenyl | Octyl | heptyl | |
| 3-propylphenyl | Nonyl | octyl | |
| 4-propylphenyl | Decyl | nonyl | |
| 3,4-dipropylphenyl | Undecyl | decyl | |
| 3,4,5-tripropylphenyl | Dodecyl | undecyl | |
| 3-butylphenyl | Tridecyl | dodecyl | |
| 4-butylylphenyl | Tetradecyl | tridecyl | |
| 3,4-dibutylphenyl | Octacosyl | tetradecyl | |
| 3,4,5-tributylphenyl | Nonacosyl | octacosyl | |
| 3-pentylphenyl | Triacontyl | nonacosyl | |
| 4-pentylphenyl | Cyclohexyl | triacontyl | |
| 3,4-dipentylphenyl | Cyclopentyl | cyclohexyl | |
| 3,4,5-tripentylphenyl | Cycloheptyl | cyclopentyl | |
| 3-hexylphenyl | Cyclooctyl | cycloheptyl | |
| 4-hexylphenyl | Cyclodecyl | cyclooctyl | |
| 3,4-dihexylphenyl | Cyclododecyl | cyclodecyl | |
| 3,4,5-trihexylphenyl | Naphthyl | cyclododecyl | |
| 3-heptylphenyl | Phenyl | naphthyl | |
| 4-heptylphenyl | Tolyl | phenyl | |
| 3,4-diheptylphenyl | Benzyl | tolyl | |
| 3,4,5-triheptylphenyl | Phenethyl | benzyl | |
| 3-octylphenyl | $R^7$ joined to $R^8$ | phenethyl | |
| 4-octylphenyl | 1,8-naphthalene | chloro | |
| 3,4-dioctylphenyl | 2,2'-biphenyl | bromo | |
| 3,4,5-trioctylphenyl | | fluoro | |
| 3-nonylphenyl | | | |
| 4-nonylphenyl | | | |
| 3,4-dinonylphenyl | | | |
| 3,4,5-trinonylphenyl | | | |
| 3-decylphenyl | | | |
| 4-decylphenyl | | | |
| 3,4-didecylphenyl | | | |
| 3,4,5-tridecylphenyl | | | |
| 3-undecylphenyl | | | |
| 4-undecylphenyl | | | |
| 3,4-diundecylphenyl | | | |
| 3,4,5-triundecylphenyl | | | |
| 3-dodecylphenyl | | | |
| 4-dodecylphenyl | | | |
| 3,4-didodecylphenyl | | | |
| 3,4,5-tridodecylphenyl | | | |

The following structure illustrates an invention embodiment where $R^7$ is joined to $R^8$:

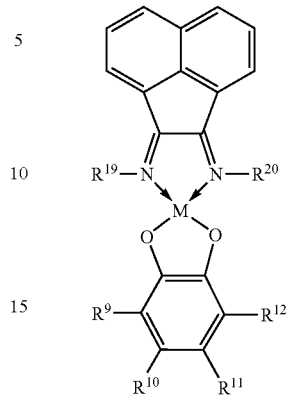

Of course, the naphthalenic ring structure can be hydrocarbyl-substituted, as well.

$R^{19}$ and $R^{20}$ can further independently be defined as the following substituent:

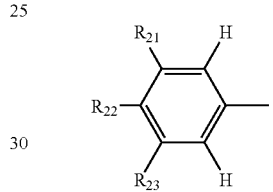

where $R^{21}$, $R^{22}$, and $R^{23}$ are independently hydrogen or hydrocarbyl radicals. $R^{21}$, $R^{22}$ and $R^{23}$ can be selected from radicals comprising: methyl, ethyl, ethenyl, ethynyl and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, or triacontynyl. In some embodiments $R^{21}$ and $R^{22}$ or $R^{22}$ and $R^{23}$ join together to form a ring structure.

The catecholate ligand can take the following formula:

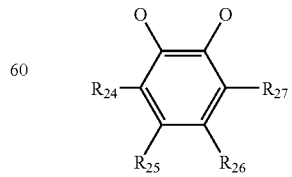

where $R^{24}$, $R^{25}$, $R^{26}$ and $R^{27}$ are independently, hydrogen, methyl, ethyl, ethenyl, ethynyl and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl, phenyl, benzyl, fluoro, chloro, bromo, iodo, methoxy, ethoxy, propoxy, butoxy, and phenoxy. Some embodiments select at least one or two $R^{24}$, $R^{25}$, $R^{26}$ or $R^{27}$ to be a hydrocarbyl substituent such as butyl. Adjacent $R^{24}$–$R^{27}$ can connect to form substituted or unsubstituted ring structures, as well.

Below are examples in which the catecholate has been transformed into a fused ring system.

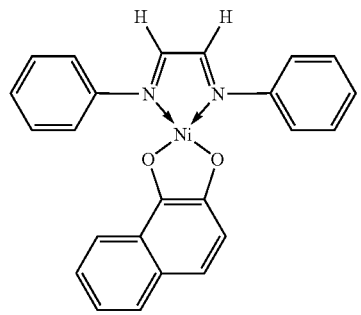

[1,4-diphenyl-diazobuta-1,3-diene][naphthalene-1,2-bis(olate)]nickel;

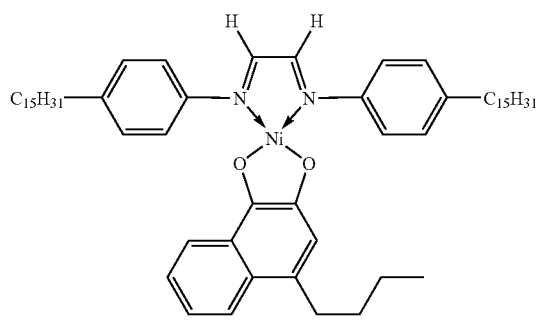

[1,4-bis(4-pentadecylphenyl)-diazobuta-1,3-diene][4-butyl-naphthalene-1,2-bis(olate)]nickel

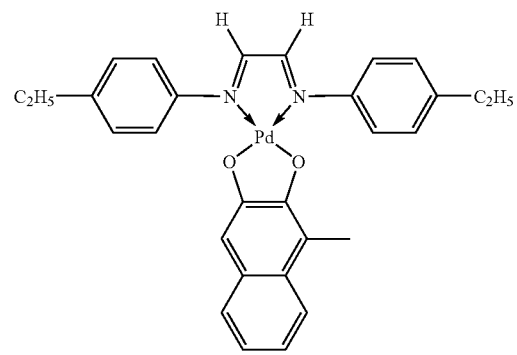

[1,4-bis(4-ethylphenyl)-diazobuta-1,3-diene][1-butyl-naphthalene-2,3-bis(olate)]nickel These complexes can be synthesized by methods well known in the literature. First, the ancillary ligand should be prepared. One way of making these ancillary ligands is by the acid-catalyzed addition of an aniline (for phenyl-substituted diazo ligands) to a substituted or unsubstituted 2,3-butanedione.

Next comes preparation of the metal complex. Its preparation method uses a metal carbonyl complex, a bidentate or tridentate chelating ligand, and a 1,2-benzoquinone complex to form the desired complex. The metal carbonyl, the ancillary ligand, and a benzoquinone are mixed in a 1:1:1 molar ratio. The benzoquinone serves as an oxidizing agent. After its reduction, the molecule becomes the catecholate ligand that coordinates to the now-ancillary-ligand-coordinated transition metal. The synthesis of similar complexes is well known to those of ordinary skill in the art. An example of this oxidation-reduction reaction is illustrated below:

Formation of a nickel (II) complex:

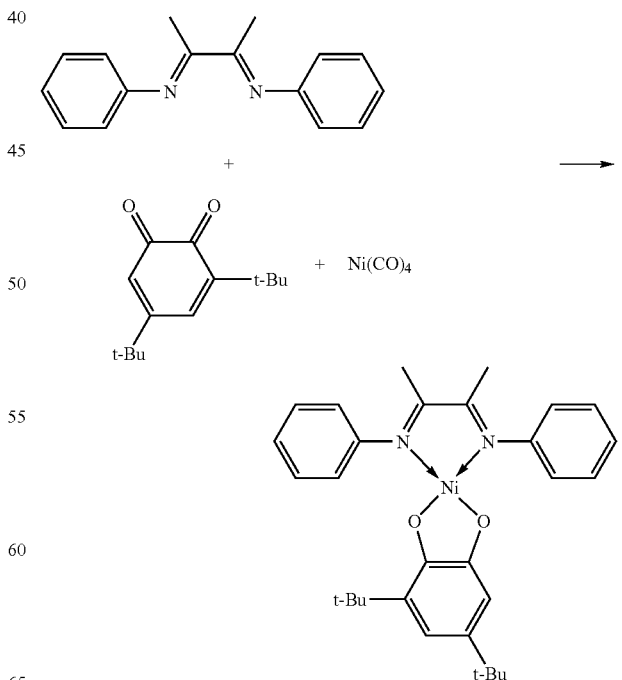

-continued

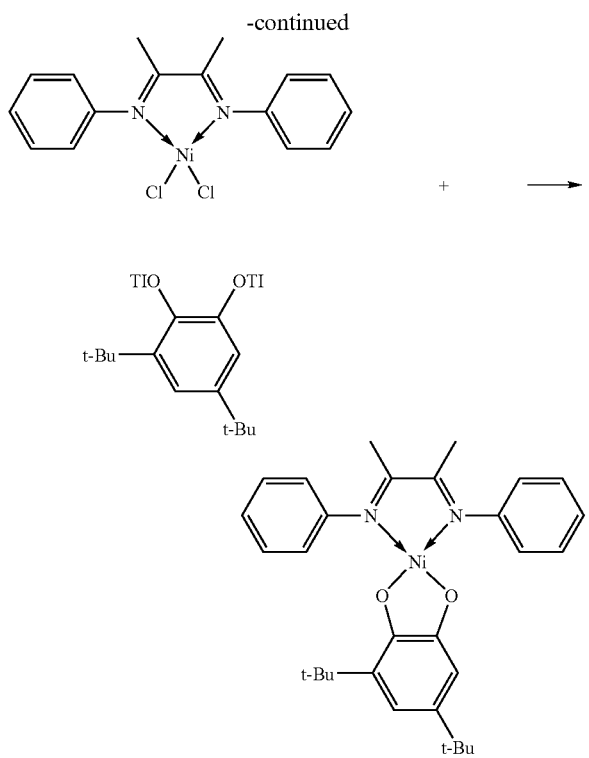

For purposes of this disclosure, the term activator is used interchangeably with cocatalyst. The activator functions to remove an abstractable ligand from the transition metal. After activation the transition metal is left with an empty coordination site at which incoming α-olefin can coordinate before it is incorporated into the oligomer or polymer. Any reagent that can so function without destroying the commercial viability of the oligomerization or polymerization process is suitable for use as an activator or cocatalyst in this invention. Exemplary cocatalysts are discussed below.

Common activators well known in the literature including alumoxanes, such as methylalumoxane, modified methylalumoxane, ethylalumoxane and the like; aluminum alkyls such as trimethyl aluminum, triethyl aluminum, triisopropyl aluminum and the like; alkyl aluminum halides such as diethyl aluminum chloride and the like; and alkylaluminum alkoxides are useful in the practice of this invention.

The alumoxane component useful as an activator typically is an oligomeric aluminum compound represented by the general formula $(R''—Al—O)_n$, which is a cyclic compound, or $R''(R''—Al—O)_nAlR''_2$, which is a linear compound. In the general alumoxane formula, R" is independently a $C_1$–$C_{20}$ alkyl radical, for example, methyl, ethyl, propyl, butyl, pentyl, isomers thereof, and the like, and "n" is an integer from 1–50. Most preferably, R" is methyl and "n" is at least 4. Methylalumoxane and modified methylalumoxanes are most preferred. For further descriptions see, EP 279586, EP 561476, WO94/10180 and U.S. Pat. Nos. 4,665,208, 4,908,463, 4,924,018, 4,952,540, 4,968,827, 5,041,584, 5,103,031, 5,157,137, 5,235,081, 5,248,801, 5,329,032, 5,391,793, and 5,416,229.

The aluminum alkyl component useful as an activator is represented by the general formula $R''AlZ_2$ where R" is defined above, and each Z is independently R" or a different univalent anionic ligand such as halogen (Cl, Br, I), alkoxide (OR") and the like. Most preferred aluminum alkyls include triethylaluminum, diethylaluminum chloride, triisobutylaluminum, tri-n-octylaluminum and the like.

When alumoxane or aluminum alkyl activators are used, the catalyst-precursor-to-activator molar ratio is from about 1:1000 to 10:1; alternatively, 1:500 to 1:1; or 1:300 to 1:10.

Additionally, discrete ionic activators such as $[Me_2PhNH]$ $[B(C_6F_5)_4]$, $[Bu_3NH][BF_4]$, $[NH_4][PF_6]$, $[NH_4][SbF_6]$, $[NH_4][AsF_6]$, $[NH_4][B(C_6H_5)_4]$ or Lewis acidic activators such as $B(C_6F_5)_3$ or $B(C_6H_5)_3$ can be used, Discrete ionic activators provide for an activated catalyst site and a relatively non-coordinating (or weakly coordinating) anion. Activators of this type are well known in the literature, see for instance W. Beck., et al., Chem. Rev., Vol. 88, p. 1405–1421 (1988); S. H. Strauss, Chem. Rev., Vol. 93, p. 927–942 (1993); U.S. Pat. Nos. 5,198,401, 5,278,119, 5,387, 568, 5,763,549, 5,807,939, 6,262,202, and WO93/14132, WO99/45042 WO01/30785 and WO01/42249.

When a discrete ionic activator is used, the catalyst-precursor-to-activator molar ratio is from: 1:10 to 1.2:1; 1:10 to 10:1; 1:10 to 2:1; 1:10 to 3:1; 1:10 to 5:1; 1:2 to 1.2:1; 1:2 to 10:1; 1:2 to 2:1; 1:2 to 3:1; 1:2 to 5:1; 1:3 to 1.2:1; 1:3 to 10:1; 1:3 to 2:1; 1:3 to 3:1; 1:3 to 5:1; 1:5 to 1.2:1; 1:5 to 10:1; 1:5 to 2:1; 1:5 to 3:1; 1:5 to 5:1.

The catalyst-precursor-to-alkylating-agent molar ratio is from: 1:10 to 10:1; 1:10 to 2:1; 1:10 to 25:1; 1:10 to 3:1; 1:10 to 5:1; 1:2 to 10:1; 1:2 to 2:1; 1:2 to 25:1; 1:2 to 3:1; 1:2 to 5:1; 1:25 to 10:1; 1:25 to 2:1; 1:25 to 25:1; 1:25 to 3:1; 1:25 to 5:1, 1:3 to 10:1; 1:3 to 2:1; 1:3 to 25:1; 1:3 to 3:1; 1:3 to 5:1; 1:5 to 10:1; 1:5 to 2:1; 1:5 to 25:1; 1:5 to 3:1; 1:5 to 5:1.

The catalyst systems of this invention can additionally be prepared by combining in any order, the bidentate ligand:

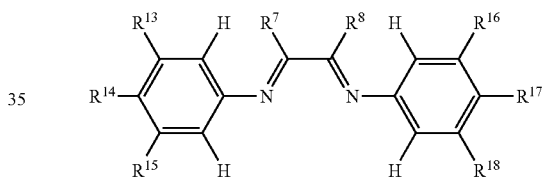

where N, H, $R^{13}$, $R^{14}$, $R^{15}$, $R^{16}$, $R^{17}$, $R^{18}$, $R^7$ and $R^8$ are as previously defined, with a Group-10 halide salt which may optionally be coordinated by solvent (for example $NiX_2$ or $NiX_2.MeOCH_2CH_2OMe$ where X=Cl, Br or I), and a 1,2-catecholate salt in a solvent, such as toluene, with dissolved activator compound (for example methylalumoxane). Similarly, the catalyst system can be prepared by combining in any order, the bidentate ligand, a neutral metal (such as $Ni(CO)_4$, $Ni(COD)_2$, Ni metal, Pd metal, $Pd(PPh_3)_4$, $Pd(Pcy_3)_2$, $Pd(t-Bu_3P)_2$), and an orthoquinone in a solvent, such as toluene, with dissolved activator compound (for example methylalumoxane). In either example, all reactants may be added in any order, or even essentially simultaneously. But some embodiments add the activator last.

The solubility of invention catalyst precursors allows for the ready preparation of supported catalysts. To prepare uniform supported catalysts, the catalyst precursor should significantly dissolve in the chosen solvent. The term "uniform supported catalyst" means that the catalyst precursor or the activated catalyst approach uniform distribution upon the support's accessible surface area, including the interior pore surfaces of porous supports.

Invention supported catalyst systems may be prepared by any method effective to support other coordination catalyst systems, effective meaning that the catalyst so prepared can be used for oligomerizing olefin in a heterogenous process. The catalyst precursor, activator, suitable solvent, and support may be added in any order or simultaneously. The activator, dissolved in an appropriate solvent such as toluene can be stirred with the support material for 1 minute to 10 hours. The total volume of the activation solution may be greater than the pore volume of the support, but some embodiments limit the total solution volume below that needed to form a gel or slurry (about 100–200% of the pore volume). The mixture is optionally heated from 30–200° C. during this time. The catalyst can be added to this mixture as a solid, if a suitable solvent is employed in the previous step, or as a solution. Or alternatively, this mixture can be filtered, and the resulting solid mixed with a catalyst precursor solution. Similarly, the mixture may be vacuum dried and mixed with a catalyst precursor solution. The resulting catalyst mixture is then stirred for 1 minute to 10 hours, and the catalyst is either filtered from the solution, and vacuum dried, or vacuum or evaporation alone removes the solvent.

The catalyst precursor and activator can be combined in solvent to form a solution. The support is then added to this solution and the mixture is stirred for 1 minute to 10 hours. The total volume of this solution may be greater than the pore volume of the support, but some embodiments limit the total solution volume below that needed to form a gel or slurry (about 100–200% pore volume). The residual solvent is then removed under vacuum, typically at ambient temperature and over 10–16 hours. But greater or lesser times are possible.

The catalyst precursor may also be supported in the absence of the activator, in which case the activator is added to the liquid phase of a slurry process. For example, a solution of catalyst precursor is mixed with a support material for a period of about 1 minute to 10 hours. The resulting pre-catalyst mixture is then filtered from the solution and dried under vacuum, or vacuum or evaporation alone removes the solvent. The total volume of the catalyst precursor solution may be greater than the pore volume of the support, but the total solution volume can be limited below that needed to form a gel or slurry (about 100–200% of the pore volume).

Additionally, two or more different catalyst precursors may be placed on the same support using any of the support methods disclosed above. Likewise, two or more activators may be placed on the same support.

Suitable solid particle supports typically comprise polymeric or refractory oxide materials. Porous supports (such as for example, talc, inorganic oxides, inorganic chlorides (magnesium chloride)) that have an average particle size greater than 10 µm can be used. Inorganic oxide materials as the support material including Group-2, -3, -4, -5, -13, or -14 metal or metalloid oxides also can be used. Catalyst support materials include silica, alumina, silica-alumina, and their mixtures. Other inorganic oxides may serve either alone or in combination with the silica, alumina, or silica-alumina. These are magnesia, titania, zirconia, and the like. Lewis acidic materials such as montmorillonite and similar clays may also serve as a support. In this case, the support can optionally double as the activator component. But additional activator may also be used.

As is well known in the art, the support material may be pretreated by any number of methods. For example, inorganic oxides may be calcined, chemically treated with dehydroxylating agents such as aluminum alkyls and the like, or both.

The carrier of invention catalysts can have a surface area of 10–700 m$^2$/g, or pore volume of 0.1–4.0 cc/g, and average particle size from 10–500 µm. But greater or lesser values may also be used.

Invention catalysts may generally be deposited on the support at a loading level of 10–100 micromoles of catalyst precursor per gram of solid support; alternately from 20–80 micromoles of catalyst precursor per gram of solid support; or from 40–60 micromoles of catalyst precursor per gram of support. But greater or lesser values may be used provided that the total amount of solid catalyst precursor does not exceed the support's pore volume.

Additionally, oxidizing agents may be added to the supported or unsupported catalyst as described in WO 01/68725.

Process

In the invention oligomerization processes, the process temperature may be −100° C. to 300° C., −20° C. to 200° C., or 0° C. to 150° C. Some embodiments select ethylene oligomerization pressures (gauge) from greater than 0 kPa up to 35 MPa or 500 kPa–15 MPa.

The preferred and primary feedstock for the oligomerization process is the α-olefin ethylene; however, other α-olefins including but not limited to propylene and 1-butene may also be used alone or in combination with ethylene.

Invention oligomerization processes may be run in the presence of various liquids, particularly aprotic organic liquids. The homogeneous catalyst system, ethylene, α-olefins, and product are soluble in these liquids. A supported (heterogeneous) catalyst system may also be used, but will form a slurry rather than a solution. Suitable liquids for both homo- and heterogeneous catalyst systems, include alkanes, alkenes, cycloalkanes, selected halogenated hydrocarbons, aromatic hydrocarbons, and in some cases, hydrofluorocarbons. Useful solvents specifically include hexane, toluene, cyclohexane, and benzene.

Also, under the correct conditions, mixtures of α-olefins containing desirable numbers of carbon atoms are obtained. Factor K from the Schulz-Flory theory (see for instance B. Elvers, et al., Ed. Ullmann's Encyclopedia of Industrial Chemistry, Vol. A13, VCH Verlagsgesellschaft mbH, Weinheim, 1989, p. 243–247 and 275–276) serves as a measure of these α-olefins' molecular weights. From this theory, $$K = n(C_{n+2} \text{ olefin})/n(C_n \text{ olefin})$$

where $n(C_n \text{ olefin})$ is the number of moles of olefin containing n carbon atoms, and $n(C_{n+2} \text{ olefin})$ is the number of moles of olefin containing n+2 carbon atoms, or in other words the next higher oligomer of $C_n$ olefin. From this can be determine the weight (mass) fractions of the various olefins in the resulting product. The ability to vary this factor provides the ability to obtain the desired olefins.

Invention-made α-olefins may be further polymerized with other olefins to form polyolefins, especially linear low-density polyethylenes, which are copolymers containing ethylene. They may also be homopolymerized. These polymers may be made by a number of known methods, such as Ziegler-Natta-type polymerization, metallocene catalyzed polymerization, and other methods, see for instance WO 96/23010, see for instance Angew. Chem., Int. Ed. Engl., vol. 34, p. 1143–1170 (1995); European Patent Application, 416,815; and U.S. Pat. No. 5,198,401 for information about metallocene-type catalysts, and J. Boor Jr., Ziegler-Natta Catalysts and Polymerizations, Academic Press, New York, 1979 and G. Allen, et al., Ed., Comprehensive Polymer Science, Vol. 4, Pergamon Press, Oxford, 1989, pp. 1–108, 409–412 and 533–584, for information about Ziegler-Natta-type catalysts, and H. Mark, et al., Ed., Encyclopedia of Polymer Science and Engineering, Vol. 6, John Wiley & Sons, New York, 1992, p. 383–522, for information about polyethylene.

Invention-made α-olefins may be converted to alcohols by known processes, these alcohols being useful for a variety of applications such as intermediates for detergents or plasticizers. The α-olefins may be converted to alcohols by a variety of processes, such as the oxo process followed by hydrogenation, or by a modified, single-step oxo process (the modified Shell process), see for instance B. Elvers, et al., Ed., Ullmann's Encyclopedia of Chemical Technology, 5th Ed., Vol. A18, VCH Verlagsgesellschaft mbH, Weinheim, 1991, p. 321–327.

A set of exemplary catalyst precursors is set out below. These are by way of example only and are not intended to list every catalyst precursor that is within the scope of the invention.

Several structures are shown along with their corresponding names to help define the nomenclature used in the precursor list.

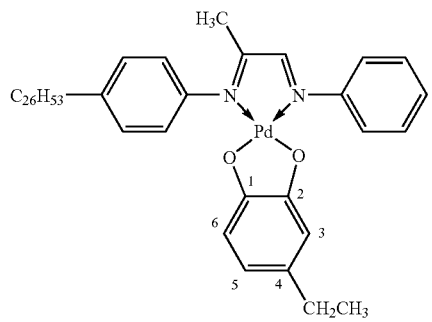

[1-(4-hexacosynyl phenyl)-2-(methyl)-3-(hydrido)-4-(phenyl)-1,4-diazabuta-1,3-diene]palladium[4-(ethyl)catecholate]

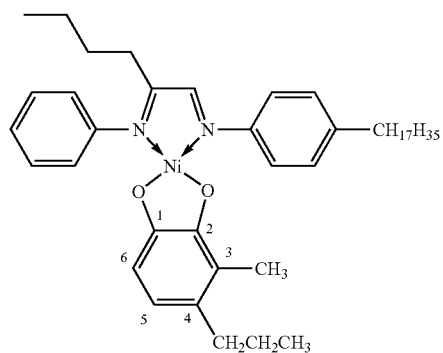

[1-(phenyl)-2-(butyl)-3-(hydrido)-4-(4-heptadecylphenyl)-1,4-diazabuta-1,3-diene]nickel[3-(methyl)-4-(propyl)catecholate]

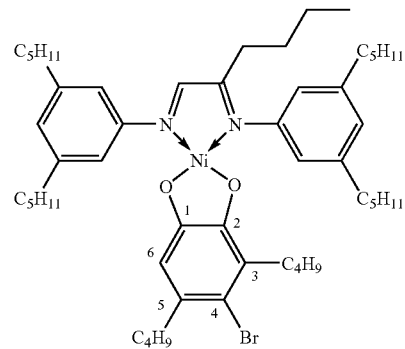

[1,4-bis{3,5-di(pentyl)phenyl}-2-(hydrido)-3-(butyl)-1,4-diazabuta-1,3-diene]nickel[3,5-di(butyl)-4-(bromo)catecholate]

[1,4-bis{phenyl}-2-(butyl)-3-(octyl)1,4-diazabuta-1,3-diene]nickel[3,5-di(ethyl)catecholate]; [1,4-bis{3,4-di(ethyl)phenyl}-2,3-(dibutyl)1,4-diazabuta-1,3-diene]nickel[4-(ethyl)-5-(butyl)catecholate]; [1,4-bis{3,4-di(propyl)phenyl}-2-(hydrido)-3-(butyl)1,4-diazabuta-1,3-diene]nickel[4-(propyl)catecholate]; [1,4-bis{phenyl}-2-(hexyl)-3-(pentyl)1,4-diazabuta-1,3-diene]nickel[3-(butyl)-4,6-di(methyl)catecholate]; [1,4-bis{3,5-di(ethyl)phenyl}-2-(pentadecyl)-3-(butyl)1,4-diazabuta-1,3-diene]nickel[3-(ethyl)catecholate]; [1,4-bis{4-dodecaphosphinophenyl}-2-(pentyl)-3-(dodecyl)1,4-diazabuta-1,3-diene]nickel[4-(butyl)catecholate]; [1,4-bis{3,4-di(pentyl)phenyl}-2-(hydrido)-3-(pentyl)1,4-diazabuta-1,3-diene]palladium[3-(butyl)catecholate]; [1,4-bis{3,5-di(ethyl)phenyl}-2-(pentyl)-3-(methyl)1,4-diazabuta-1,3-diene]nickel[3-(ethyl)-5-(pentyl)catecholate]; [1,4-bis{3-heptenylphenyl}-2-(hexyl)-3-(ethyl)1,4-diazabuta-1,3-diene nickel[3-(ethyl)-4-(methyl)catecholate]; [1,4-bis{3,4-di(proponyl)phenyl}-2-(pentyl)-3-(undecynyl)1,4-diazabuta-1,3-diene]nickel[3-(pentyl)-4-(butyl)catecholate]; [1,4-bis{phenyl}-2-(butyl)-3-(hexyl)1,4-diazabuta-1,3-diene]nickel[3-(propyl)-6-(ethyl)-catecholate]; [1,4-bis{phenyl}-2-(octyl)-3-(hydrido)1,4-diazabuta-1,3-diene]nickel[3,6-di(methyl)catecholate]; [1,4-bis{3,5-di(methyl)phenyl}-2-(octyl)-3-(butyl)1,4-diazabuta-1,3-diene]palladium[4-(methyl)-5-(pentyl)catecholate]; [1,4-bis{phenyl}-2-(butyl)-3-(pentyl)1,4-diazabuta-1,3-diene]nickel[4-(methyl)catecholate]; [1,4-bis{3,5-di(pentyl)-phenyl}-2-(hydrido)-3-(pentacosenyl)1,4-diazabuta-1,3-diene]palladium[3,4-di(ethyl)-6-(pentyl)catecholate]; [1,4-bis{3,4-di(propyl)phenyl}-2,3-(dibutyl)1,4-diazabuta-1,3-diene]nickel[3-(ethyl)-5-(butyl)catecholate]; [1,4-bis{phenyl}-2-(hydrido)-3-(octyl)1,4-diazabuta-1,3-diene]palladium[3,6-di(ethyl)catecholate]; [1,4-bis{phenyl}-2-(octyl)-3-(pentyl)1,4-diazabuta-1,3-diene]nickel[3,6-di(ethyl)catecholate]; [1,4-bis{phenyl}-2-(hydrido)-3-(butyl)1,4-diazabuta-1,3-diene]nickel[3-(pentyl)-6-(ethyl)catecholate]; [1,4-bis{3,5-di(butyl)phenyl}-2-(hydrido)-3-(hexyl)1,4-diazabuta-1,3-diene]nickel[4-(propyl)catecholate]; [1,4-bis{3-heneicosenylphenyl}-2,3-(dibutyl)1,4-diazabuta-1,3-diene]nickel[3-(propyl)catecholate]; [1,4-bis{4-undecenylphenyl}-2-(hydrido)-3-(butyl)-1,4-diazabuta-1,3-diene]nickel[3-(butyl)-4-(propyl)-6-(ethyl)catecholate]; [1,4-bis{phenyl}-2-(hydrido)-3-(butyl)1,4-diazabuta-1,3-diene]nickel[4-(ethyl)-5-(propyl)-catecholate]; [1,4-bis{3,5-di(pentyl)phenyl}-2,3-(dihydrido)1,4-diazabuta-1,3-diene]palladium[3-(pentyl)-4-(butyl)catecholate]; [1,4-bis{3,5-di(pentyl)phenyl}-2,3-(dibutyl)-1,4-diazabuta-1,3-diene]palladium[3-(propyl)-4-(butyl)catecholate]; [1,4-bis{3,5-di (pentyl)phenyl}-2-(butyl)-3-(hexyl)1,4-diazabuta-1,3-diene]nickel[3-(pentyl)-5-(ethyl)catecholate]; [1,4-bis{3,4-di(butyl)phenyl}-2,3-(dibutyl)1,4-diazabuta-1,3-diene]nickel[4-(ethyl)catecholate]; [1,4-bis{3,4-di(propyl)phenyl}-2-(butyl)-3-(pentyl)1,4-diazabuta-1,3-diene]nickel[3-(pentyl)-6-(methyl)catecholate]; [1,4-bis{phenyl}-2,3-(dibutyl)1,4-diazabuta-1,3-diene]nickel[3-(butyl)-6-(ethyl)catecholate]; [1,4-bis{phenyl}-2-(hexacosenyl)-3-(pentyl)1,4-diazabuta-1,3-diene]nickel[3-(pentyl)-6-(butyl)catecholate]; [1,4-bis{4-tridocosanalylphenyl}-2-(butyl)-3-(hexyl)1,4-diazabuta-1,3-diene]nickel[3-(ethyl)catecholate]; [1,4-bis{3,5-di(pentyl)phenyl}-2,3-(dibutyl)1,4-diazabuta-1,3-diene]nickel[3-(propyl)-4-(ethyl)-5-(pentyl)catecholate]; [1,4-bis{4-eicosynylphenyl}-2,3-(dipentyl)1,4-diazabuta-1,3-diene]palladium[3-(butyl)-5-(ethyl)-catecholate]; [1,4-bis{4-undecenylphenyl}-2-(octyl)-3-(butyl)1,4-diazabuta-1,3-diene]nickel[3-(butyl)-4-(methyl)-6-(ethyl)catecholate]; [1,4-bis{3,4-di(pentyl)phenyl}-2,3-(dibutyl)1,4-diazabuta-1,3-diene]nickel[3-(propyl)-4-(butyl)-5-(pentyl)catecholate]; [1,4-bis{3,5-di(pentyl)phenyl}-2-(hydrido)-3-(pentyl)1,4-diazabuta-1,3-diene]nickel[4-(ethyl)catecholate]; [1,4-bis{3,4-di(methyl)phenyl}-2-(butyl)-3-(hexyl)1,4-diazabuta-1,3-diene]palladium[3-(methyl)-4-(butyl)catecholate]; [1,4-bis{3,5-di(butyl)phenyl}-2-(octyl)-3-(butyl)1,4-diazabuta-1,3-diene]nickel[3-(propyl)-6-(butyl)catecholate]; [1,4-bis{phenyl}-2,3-(dibutyl)1,4-diazabuta-1,3-diene]nickel[4-(ethyl)catecholate]; [1,4-bis{phenyl}-2-(nonadecenyl)-3-(butyl)1,4-diazabuta-1,3-diene]nickel[3-(butyl)-catecholate]; [1,4-bis{3,5-di(pentyl)phenyl}-2,3-(dibutyl)1,4-diazabuta-1,3-diene]palladium[4-(ethyl)catecholate]; [1,4-bis{3-hexacosylphenyl}-2-(butyl)-3-(pentyl)1,4-diazabuta-1,3-diene]palladium[3-(ethyl)catecholate]; [1,4-bis{3,5-di(ethyl)phenyl}-2,3-(dibutyl)1,4-diazabuta-1,3-diene]nickel[4-(ethyl)catecholate]; [1,4-bis{3,5-di(propyl)-phenyl}-2-(methyl)-3-(butyl)1,4-diazabuta-1,3-diene]palladium[4-(propyl)-5-(pentyl)-catecholate]; [1,4-bis{3,5-di(propyl)phenyl}-2-(butyl)-3-(octyl)1,4-diazabuta-1,3-diene]nickel[3-(butyl)-6-(propyl)catecholate]; [1,4-bis{phenyl}-2-(methyl)-3-(pentyl)1,4-diazabuta-1,3-diene]palladium[3,4-di(propyl)catecholate]; [1,4-bis{phenyl}-2,3-(dihydrido)1,4-diazabuta-1,3-diene]nickel[3-(propyl)-4-(pentyl)catecholate]; [1,4-bis{phenyl}-2-(pentyl)-3-(hexyl)1,4-diazabuta-1,3-diene]nickel[3-(ethyl)-4-(pentyl)catecholate]; [1,4-bis{3-dodecynylphenyl}-2-(hydrido)-3-(octyl)1,4-diazabuta-1,3-diene]palladium[3-(methyl)-5-(butyl)catecholate]; [1,4-bis{3,4-di(propyl)phenyl}-2-(nonacosenyl)-3-(butyl)1,4-diazabuta-1,3-diene]nickel[3-(propyl)-5-(pentyl)-catecholate]; [1,4-bis{3,4-di(pentyl)phenyl}-2-(octyl)-3-(hydrido)1,4-diazabuta-1,3-diene]palladium[3-(methyl)-6-(butyl)catecholate]; [1,4-bis{3,5-di(pentyl)phenyl}-2-(docosyl)-3-(butyl)1,4-diazabuta-1,3-diene]palladium[3-(propyl)catecholate]; [1,4-bis{phenyl}-2-(octyl)-3-(butyl)1,4-diazabuta-1,3-diene]nickel[4-(ethyl)-5-(propyl)-catecholate]; [1,4-bis{4-heneicosenylphenyl}-2-(pentyl)-3-(hydrido)1,4-diazabuta-1,3-diene]nickel[3-(ethyl)catecholate]; [1,4-bis{4-octacosynyl}phenyl}-2,3-(dibutyl)1,4-diazabuta-1,3-diene]nickel[3-(butyl)-4-(pentyl)catecholate]; [1,4-bis{3,5-di(methyl)-phenyl}-2-(butyl)-3-(hydrido)1,4-diazabuta-1,3-diene]nickel[3,5-di(pentyl)catecholate];

[1,4-bis{3-pentadecylphenyl}-2-(butyl)-3-(hydrido)1,4-diazabuta-1,3-diene]palladium[4-(butyl)catecholate]; [1,4-bis{4-undecylphenyl}-2,3-(dibutyl)1,4-diazabuta-1,3-diene]palladium[4-(butyl)catecholate]; [1,4-bis{3,4-di(methyl)phenyl}-2-(hexyl)-3-(hydrido)1,4-diazabuta-1,3-diene]nickel[3-(propyl)catecholate]; [1,4-bis{4-tricosyl-phenyl}-2-(pentacosynyl)-3-(butyl)1,4-diazabuta-1,3-diene]nickel[4-(ethyl)catecholate]; [1,4-bis{3,4-di(proponyl)phenyl}-2-(hexyl)-3-(hydrido)1,4-diazabuta-1,3-diene]palladium[3-(propyl)catecholate]; [1,4-bis{3,4-di(butyl)phenyl}-2-(butyl)-3-(hydrido)1,4-diazabuta-1,3-diene]nickel[3-(butyl)-5-(pentyl)catecholate]; [1,4-bis{3,5-di(methyl)-phenyl}-2,3-(dibutyl)1,4-diazabuta-1,3-diene]nickel[3-(pentyl)-6-(propyl)catecholate]; [1,4-bis{phenyl}-2-(hexyl)-3-(octyl)1,4-diazabuta-1,3-diene]nickel[3-(pentyl)-5-(butyl)-catecholate]; [1,4-bis{3-heptacosenylphenyl}-2-(hydrido)-3-(methyl)1,4-diazabuta-1,3-diene]nickel[4-(ethyl)-5-(butyl)catecholate]; [1,4-bis{3,4-di(propyl)phenyl}-2-(butenyl)-3-(butyl)1,4-diazabuta-1,3-diene]nickel[3-(pentyl)catecholate]; [1,4-bis{3,5-di(pentyl)-phenyl}-2-(butyl)-3-(hexyl)1,4-diazabuta-1,3-diene]nickel[3-(methyl)catecholate]; [1,4-bis{3,4-di(methyl)phenyl}-2-(methyl)-3-(hydrido)1,4-diazabuta-1,3-diene]palladium[4,5-di(ethyl)catecholate]; [1,4-bis{phenyl}-2-(pentyl)-3-(butyl)1,4-diazabuta-1,3-diene]nickel[4-(butyl)-5-(pentyl)catecholate]; [1,4-bis{phenyl}-2-(hexyl)-3-(methyl)1,4-diazabuta-1,3-diene]nickel[4-(propyl)catecholate]; [1,4-bis{3,4-di(methyl)phenyl}-2-(methyl)-3-(pentyl)1,4-diazabuta-1,3-diene]nickel[3-(methyl)catecholate]; [1,4-bis{4-octylaminophenyl}-2-(butyl)-3-(pentyl)1,4-diazabuta-1,3-diene]nickel[3-(butyl)-5-(methyl)catecholate]; [1,4-bis{3,4-di(pentyl)phenyl}-2-(hydrido)-3-(pentyl)1,4-diazabuta-1,3-diene]palladium[3-(methyl)catecholate]; [1,4-bis{3,4-di(butonyl)phenyl}-2,3-(dioctyl)1,4-diazabuta-1,3-diene]nickel[3,4-di(propyl)-6-(pentyl)catecholate]; [1,4-bis{3-hexylphenyl}-2-(butyl)-3-(hydrido)1,4-diazabuta-1,3-diene]nickel[3-(butyl)-4-(propyl)catecholate]; [1,4-bis{3,4-di(methyl)phenyl}-2-(pentyl)-3-(hexyl)1,4-diazabuta-1,3-diene]nickel[3-(propyl)-5-(pentyl)catecholate]; [1,4-bis{phenyl}-2-(ethyl)-3-(butyl)-1,4-diazabuta-1,3-diene]palladium[4-(methyl)-5-(propyl)catecholate]; [1,4-bis{3,4-di(butyl)phenyl}-2-(octacosyl)-3-(hexyl)1,4-diazabuta-1,3-diene]nickel[3,4-di(propyl)-6-(hexyl)catecholate]; [1,4-bis{3,5-di(butyl)phenyl}-2-(hydrido)-3-(hexyl)1,4-diazabuta-1,3-diene]nickel[4-(butyl)catecholate]; [1,4-bis{3,4-di(butyl)phenyl}-2-(hexyl)-3-(butyl)1,4-diazabuta-1,3-diene]nickel[3,6-di(methyl)-4-(propyl)catecholate]; [1,4-bis{3,4-di(ethyl)phenyl}-2-(methyl)-3-(pentyl)1,4-diazabuta-1,3-diene]nickel[3-(butyl)-5-(pentyl)catecholate]; [1,4-bis{3,5-di(ethyl)phenyl}-2,3-(dibutyl)1,4-diazabuta-1,3-diene]nickel[3-(pentyl)catecholate]; [1,4-bis{3,5-di(ethyl)phenyl}-2-(pentyl)-3-(tetradecenyl)1,4-diazabuta-1,3-diene]nickel[4-(butyl)catecholate]; [1,4-bis{3,5-di(ethyl)phenyl}2-(octyl)-3-(butyl)1,4-diazabuta-1,3-diene]palladium[3-(ethyl)-catecholate]; [1,4-bis{3-butynylphenyl}-2-(octacosynyl)-3-(butyl)1,4-diazabuta-1,3-diene]palladium[3-(pentyl)-4-(methyl)catecholate]; [1,4-bis{3,4-di(pentyl)phenyl}-2-(tetracosynyl)-3-(hydrido)1,4-diazabuta-1,3-diene]palladium[4-(butyl)catecholate]; [1,4-bis{3,4-di(propyl)phenyl}-2,3-(dibutyl)1,4-diazabuta-1,3-diene]nickel[3-(ethyl)-4-(pentyl)-5-(methyl)catecholate]; [1,4-bis{3-propynylphenyl}-2-(butyl)-3-(heptyl)1,4-diazabuta-1,3-diene]nickel[3-(methyl)catecholate]; [1,4-bis{3,5-di(ethyl)phenyl}-2-(pentyl)-3-(hexyl)1,4-diazabuta-1,3-diene]palladium[3-(methyl)-6-(pentyl)catecholate]; [1,4-bis{3,4-di(butyl)phenyl}-2,3-(dibutyl)1,4-diazabuta-1,3-diene]palladium[4,5-di(ethyl)catecholate]; [1,4-bis{phenyl}-2-(hydrido)-3-(butyl)1,4-diazabuta-1,3-diene]nickel[3-(methyl)-6-(propyl)catecholate]; [1,4-bis{phenyl}-2-(hexyl)-3-(butyl)1,4-diazabuta-1,3-diene]nickel[4-(methyl)-5-(ethyl)catecholate]; [1,4-bis{phenyl}-2-(hexyl)-3-(butyl)1,4-diazabuta-1,3-diene]nickel[3,5-di(butyl)-4-(propyl)

catecholate]; [1,4-bis{3,4-di(methyl)phenyl}-2-(undecyl)-3-(hexyl)1,4-diazabuta-1,3-diene]palladium[3-(methyl)catecholate]; [1,4-bis{3,5-di(methyl)phenyl}-2,3-(dibutyl)1,4-diazabuta-1,3-diene]nickel[3-(methyl)-6-(ethyl)catecholate]; [1,4-bis{3-hexacosylphenyl}-2-(hexyl)-3-(butyl)1,4-diazabuta-1,3-diene]nickel[4-(methyl)-5-(pentyl)catecholate]; [1,4-bis{phenyl}-2-(pentyl)-3-(hydrido)1,4-diazabuta-1,3-diene]palladium[3-(butyl)-4-(pentyl)catecholate]; [1,4-bis{3,4-di(propyl)phenyl}-2,3-(dibutyl)1,4-diazabuta-1,3-diene]palladium[3-(propyl)-4-(pentyl)catecholate]; [1,4-bis{3,5-di(butyl)phenyl}-2-(pentyl)-3-(nonacosenyl)1,4-diazabuta-1,3-diene]palladium[3-(propyl)-4-(pentyl)-5-(butyl)catecholate]; [1,4-bis{3,5-di(propyl)phenyl}-2-(hydrido)-3-(hexyl)1,4-diazabuta-1,3-diene]nickel[3-(ethyl)-4-(pentyl)catecholate]; [1,4-bis{phenyl}-2-(hexyl)-3-(butyl)-1,4-diazabuta-1,3-diene]palladium[3-(pentyl)-5-(butyl)catecholate]; [1,4-bis{phenyl}-2-(butyl)-3-(hydrido)1,4-diazabuta-1,3-diene]palladium[4-(butyl)-5-(propyl)catecholate]; [1,4-bis{4-octadecynylphenyl}-2,3-(dibutyl)1,4-diazabuta-1,3-diene]nickel[3-(pentyl)-5-(butyl)catecholate]; [1,4-bis{phenyl}-2,3-(dibutyl)1,4-diazabuta-1,3-diene]palladium[4-(pentyl)catecholate]; [1,4-bis{3,5-di(pentyl)phenyl}-2-(hydrido)-3-(hexyl)1,4-diazabuta-1,3-diene]nickel[3-(butyl)catecholate]; [1,4-bis{3,4-di(ethyl)phenyl}-2,3-(dibutyl)1,4-diazabuta-1,3-diene]nickel[3-(ethyl)-4-(propyl)-5-(pentyl)catecholate]; [1,4-bis{3,4-di(proponyl)phenyl}-2-(butyl)-3-(undecenyl)1,4-diazabuta-1,3-diene]nickel[3-(propyl)-4-(butyl)catecholate]; [1,4-bis{3,5-di(ethyl)phenyl}-2-(hydrido)-3-(pentyl)1,4-diazabuta-1,3-diene]palladium[4-(ethyl)catecholate]; [1,4-bis{3,4-di(butyl)phenyl}-2,3-(dioctyl)-1,4-diazabuta-1,3-diene]nickel[3-(ethyl)-4-(propyl)-6-(butyl)catecholate]; [1,4-bis{3,5-di(pentyl)phenyl}-2-(butyl)-3-(tricosenyl)1,4-diazabuta-1,3-diene]nickel[4-(pentyl)-5-(ethyl)catecholate]; [1,4-bis{3,5-di(butyl)phenyl}-2-(pentyl)-3-(hexyl)1,4-diazabuta-1,3-diene]nickel[3-(butyl)-6-(pentyl)catecholate]; [1,4-bis{phenyl}-2-(octyl)-3-(hexyl)1,4-diazabuta-1,3-diene]palladium[4-(ethyl)catecholate]; [1,4-bis{3,5-di(butyl)phenyl}-2-(octyl)-3-(hexyl)1,4-diazabuta-1,3-diene]nickel[3-(methyl)-4-(butyl)catecholate]; [1,4-bis{3,4-di(propyl)phenyl}-2,3-(dibutyl)1,4-diazabuta-1,3-diene]nickel[3,6-di(ethyl)-4-(pentyl)catecholate]; [1,4-bis{3,4-di(methyl)phenyl}-2-(nonynyl)-3-(butyl)1,4-diazabuta-1,3-diene]nickel[3-(ethyl)-4-(propyl)catecholate]; [1,4-bis{4-nonylphenyl}-2-(butyl)-3-(hydrido)1,4-diazabuta-1,3-diene]nickel[3-(pentyl)-4,5-di(butyl)catecholate]; [1,4-bis{3,4-di(propyl)phenyl}-2-(butyl)-3-(hydrido)1,4-diazabuta-1,3-diene]nickel[3-(pentyl)-5-(ethyl)catecholate]; [1,4-bis{3,4-di(ethyl)phenyl}-2-(pentyl)-3-(hydrido)1,4-diazabuta-1,3-diene]nickel[3-(butyl)-5-(ethyl)catecholate]; [1,4-bis{3-heptacosynyl-phenyl}-2-(hexacosynyl)-3-(octyl)1,4-diazabuta-1,3-diene]palladium[4-(butyl)-catecholate]; [1,4-bis{3,5-di(propyl)phenyl}-2,3-(dihexyl)1,4-diazabuta-1,3-diene]nickel[4-(methyl)catecholate]; [1,4-bis{phenyl}-2-(octyl)-3-(hexyl)1,4-diazabuta-1,3-diene]nickel[3-(butyl)-6-(propyl)catecholate]; [1,4-bis{phenyl}-2-(hydrido)-3-(butyl)1,4-diazabuta-1,3-diene]nickel[4-(propyl)catecholate]; [1,4-bis{3,5-di(methyl)phenyl}-2-(butyl)-3-(hydrido)1,4-diazabuta-1,3-diene]nickel[3,6-di(butyl)-4-(proponyl)-catecholate]; [1,4-bis{3,5-di(ethyl)phenyl}-2-(butyl)-3-(pentyl)1,4-diazabuta-1,3-diene]nickel[3,4-di(propyl)-5-(ethyl)catecholate]; [1,4-bis{phenyl}-2-(butyl)-3-(octadecenyl)-1,4-diazabuta-1,3-diene]palladium[3-(methyl)-4-(pentyl)catecholate]; [1,4-bis{3,5-di(butyl)phenyl}-2-(nonadecynyl)-3-(hexyl)1,4-diazabuta-1,3-diene]palladium[4-(pentyl)-5-(propyl)catecholate]; [1,4-bis{phenyl}-2,3-(dibutyl)1,4-diazabuta-1,3-diene]nickel[4-(butyl)-5-(propyl)catecholate]; [1,4-bis{3,4-di(ethyl)phenyl}-2-(hydrido)-3-(butyl)1,4-diazabuta-1,3-diene]nickel[3-(butyl)-6-(propyl)catecholate]; [1,4-bis{3,5-di(propyl)phenyl}-2-(butyl)-3-(hydrido)1,4-diazabuta-1,3-diene]nickel[4-(pentyl)-5-(ethyl)catecholate]; [1,4-bis{phenyl}-2,3-(dibutyl)1,4-diazabuta-1,3-diene]nickel[3-(butyl)catecholate]; [1,4-bis{3,5-di(ethyl)phenyl}-2-(butyl)-3-(octyl)1,4-diazabuta-1,3-diene]nickel[3-(pentyl)-4-(butyl)catecholate]; [1,4-bis{3,4-di(diethylamino)phenyl}-2-(hexyl)-3-(decenyl)1,4-diazabuta-1,3-diene]nickel[3-(butyl)-5-(pentyl)catecholate]; [1,4-bis{3,4-di(methyl)phenyl}-2-(butyl)-3-(hydrido)1,4-diazabuta-1,3-diene]nickel[3-(propyl)catecholate]; [1,4-bis{phenyl}-2-(hexyl)-3-(pentyl)1,4-diazabuta-1,3-diene]nickel[3,4-di(ethyl)-5-(butyl)catecholate]; [1,4-bis{phenyl}-2-(butyl)-3-(hydrido)1,4-diazabuta-1,3-diene]palladium[3-(propyl)-6-(pentyl)catecholate]; [1,4-bis{3,5-di(ethyl)-phenyl}-2,3-(dibutyl)1,4-diazabuta-1,3-diene]nickel[3,5-di(ethyl)-4-(propyl)-catecholate]; [1,4-bis{phenyl}-2-(octyl)-3-(hexyl)1,4-diazabuta-1,3-diene]nickel[3-(pentyl)-5-(butyl)catecholate]; [1,4-bis{phenyl}-2-(butynyl)-3-(butyl)1,4-diazabuta-1,3-diene]nickel[3-(ethyl)catecholate]; [1,4-bis{3,4-di(propyl)phenyl}-2-(pentyl)-3-(butyl)-1,4-diazabuta-1,3-diene]nickel[3-(pentyl)catecholate]; [1,4-bis{3-heneicosynylphenyl}-2-(butyl)-3-(hexyl)1,4-diazabuta-1,3-diene]nickel[4-(propyl)-5-(pentyl)catecholate]; [1,4-bis{phenyl}-2-(pentyl)-3-(octyl)1,4-diazabuta-1,3-diene]nickel[3-(methyl)-catecholate]; [1,4-bis{3,5-di(ethyl)phenyl}-2-(methyl)-3-(octyl)1,4-diazabuta-1,3-diene]nickel[3-(methyl)-4-(butyl)-6-(propyl)catecholate]; [1,4-bis{3,5-di(ethyl)phenyl}-2-(butyl)-3-(hydrido)1,4-diazabuta-1,3-diene]nickel[3-(ethyl)catecholate]; [1,4-bis{3,5-di(methyl)phenyl}-2-(hydrido)-3-(pentyl)1,4-diazabuta-1,3-diene]palladium[3-(methyl)-4-(butyl)catecholate]; [1,4-bis{3,4-di(proponyl)phenyl}-2-(octyl)-3-(pentacosynyl)1,4-diazabuta-1,3-diene]palladium[4,5-di(propyl)catecholate]; [1,4-bis{3,5-di(methyl)-phenyl}-2-(octacosynyl)-3-(undecynyl)1,4-diazabuta-1,3-diene]palladium[3-(ethyl)-6-(butyl)catecholate]; [1,4-bis{phenyl}-2-(tetradecyl)-3-(butyl)1,4-diazabuta-1,3-diene]nickel[3-(butyl)catecholate]; [1,4-bis{3-tetradecynylphenyl}-2-(octyl)-3-(hexyl)1,4-diazabuta-1,3-diene]nickel[3-(methyl)catecholate]; [1,4-bis{3,5-di(dodecamino)-phenyl}-2-(ethyl)-3-(hexyl)1,4-diazabuta-1,3-diene]nickel[3-(butyl)catecholate]; [1,4-bis{3,4-di(pentyl)phenyl}-2-(pentyl)-3-(butyl)1,4-diazabuta-1,3-diene]nickel[4-(ethyl)-catecholate]; [1,4-bis{3,4-di(propyl)phenyl}-2,3-(dibutyl)1,4-diazabuta-1,3-diene]nickel[3,5-di(ethyl)-4-(propyl)catecholate]; [1,4-bis{3,5-di(butyl)phenyl}-2,3-(dihydrido)1,4-diazabuta-1,3-diene]nickel[4-(methyl)catecholate]; [1,4-bis{4-heptenylphenyl}-2-(pentyl)-3-(octyl)1,4-diazabuta-1,3-diene]palladium[3,4-di(pentyl)catecholate]; [1,4-bis{phenyl}-2-(pentyl)-3-(hydrido)1,4-diazabuta-1,3-diene]nickel[3-(ethyl)-6-(methyl)-catecholate]; [1,4-bis{phenyl}-2,3-(dibutyl)1,4-diazabuta-1,3-diene]nickel[3-(ethyl)-catecholate]; [1,4-bis{3,4-di(butyl)phenyl}-2,3-(dipentyl)1,4-diazabuta-1,3-diene]nickel[3-(methyl)catecholate]; [1,4-bis{phenyl}-2-(hexacosynyl)-3-(hydrido)1,4-diazabuta-1,3-diene]nickel[3-(ethyl)-4-(propyl)catecholate]; [1,4-bis{4-tetradecenylphenyl}-2-(hydrido)-3-(butyl)1,4-diazabuta-1,3-diene]palladium[3-(butyl)catecholate]; [1,4-bis{3,5-di(pentyl)phenyl}-2-(hydrido)-3-(butyl)1,4-diazabuta-1,3-diene]nickel[3-(ethyl)-4-(pentyl)-6-(methyl)catecholate]; [1,4-bis{4-tetradecynylphenyl}-2-(butyl)-3-(pentacosenyl)1,4-diazabuta-1,3-diene]nickel[4-(ethyl)-5-(propyl)

catecholate]; [1,4-bis{3,4-di(propyl)phenyl}-2-(butyl)-3-(methyl)1,4-diazabuta-1,3-diene]palladium[4-(butyl)catecholate]; [1,4-bis{phenyl}-2,3-(dibutyl)1,4-diazabuta-1,3-diene]nickel[3-(butyl)catecholate]; [1,4-bis{3,5-di(ethyl)phenyl}-2-(hydrido)-3-(butyl)1,4-diazabuta-1,3-diene]palladium[3-(ethyl)-4-(methyl)catecholate]; [1,4-bis{phenyl}-2-(pentadecynyl)-3-(methyl)1,4-diazabuta-1,3-diene]nickel[3-(propyl)-5-(methyl)catecholate]; [1,4-bis{phenyl}-2-(butyl)-3-(octacosenyl)1,4-diazabuta-1,3-diene]nickel[3-(propyl)-catecholate]; [1,4-bis{3,4-di(butyl)phenyl}-2-(hydrido)-3-(hexyl)1,4-diazabuta-1,3-diene]nickel[4-(butyl)catecholate]; [1,4-bis{4-ethylphenyl}-2-(hydrido)-3-(nonacosenyl)1,4-diazabuta-1,3-diene]nickel[3-(ethyl)-4-(propyl)-5-(pentyl)catecholate]; [1,4-bis{phenyl}-2-(hydrido)-3-(ethyl)1,4-diazabuta-1,3-diene]nickel[3-(propyl)catecholate]; [1,4-bis{4-(triethylsilylmethyl)phenyl}-2-(pentyl)-3-(heptadecyl)1,4-diazabuta-1,3-diene]nickel[4-(pentyl)catecholate]; [1,4-bis{phenyl}-2-(butyl)-3-(methyl)1,4-diazabuta-1,3-diene]nickel[3-(propyl)-5-(pentyl)catecholate]; [1,4-bis{3,5-di(pentyl)phenyl}-2,3-(dihexyl)1,4-diazabuta-1,3-diene]palladium[3-(ethyl)-5-(pentyl)catecholate]; [1,4-bis{3,4-di(methyl)phenyl}-2,3-(dibutyl)1,4-diazabuta-1,3-diene]nickel[4-(pentyl)-5-(ethyl)catecholate]; [1,4-bis{4-heptadecenylphenyl}-2-(undecyl)-3-(octyl)1,4-diazabuta-1,3-diene]nickel[3-(butyl)catecholate]; [1,4-bis{4-tetradecynylphenyl}-2,3-(dihydrido)-1,4-diazabuta-1,3-diene]nickel[4-(propyl)catecholate];

[1,4-bis{4-eicosylphenyl}-2-(butyl)-3-(octyl)1,4-diazabuta-1,3-diene]nickel[3-(trimethylsilylethyl)catecholate]; [1,4-bis{phenyl}-2-(butyl)-3-(hydrido)1,4-diazabuta-1,3-diene]nickel[4-(propyl)catecholate]; [1,4-bis{phenyl}-2-(pentacosenyl)-3-(ethyl)1,4-diazabuta-1,3-diene]palladium[3-(ethyl)-5-(butyl)catecholate]; [1,4-bis{phenyl}-2,3-(dihydrido)1,4-diazabuta-1,3-diene]nickel[3-(propyl)-5-(ethyl)catecholate]; [1,4-bis{3,5-di(butyl)phenyl}-2-(hydrido)-3-(pentyl)1,4-diazabuta-1,3-diene]nickel[4-(propyl)-catecholate]; [1,4-bis{phenyl}-2-(pentyl)-3-(hydrido)1,4-diazabuta-1,3-diene]palladium[4-(methyl)catecholate]; [1,4-bis{3,5-di(dodecamino)phenyl}-2-(methyl)-3-(hydrido)1,4-diazabuta-1,3-diene]nickel[3,4-di(propyl)catecholate]; [1,4-bis{3,4-di(propyl)phenyl}-2-(pentyl)-3-(hydrido)1,4-diazabuta-1,3-diene]palladium[4-(butyl)-5-(methyl)catecholate]; [1,4-bis{3,5-di(ethyl)phenyl}-2-(hydrido)-3-(butyl)1,4-diazabuta-1,3-diene]nickel[3-(methyl)catecholate]; [1,4-bis{3,4-di(butyl)phenyl}-2-(hydrido)-3-(methyl)1,4-diazabuta-1,3-diene]palladium[3,6-di(butyl)-4-(propyl)catecholate]; [1,4-bis{3,4-di(methyl)-phenyl}-2-(methyl)-3-(hydrido)1,4-diazabuta-1,3-diene]nickel[3-(trimethylsilylmethyl)-5-(butyl)catecholate]; [1,4-bis{3,5-di(butyl)phenyl}-2,3-(dioctyl)1,4-diazabuta-1,3-diene]palladium[4-(butyl)catecholate]; [1,4-bis{3-tetracosylphenyl}-2-(hydrido)-3-(butyl)1,4-diazabuta-1,3-diene]palladium[4-(pentyl)catecholate]; [1,4-bis{phenyl}-2-(butyl)-3-(hydrido)1,4-diazabuta-1,3-diene]palladium[4,5-di(propyl)catecholate]; [1,4-bis{3,5-di(pentyl)phenyl}-2-(pentadecynyl)-3-(hydrido)1,4-diazabuta-1,3-diene]nickel[4-(ethyl)catecholate]; [1,4-bis{3,4-di(propyl)phenyl}-2-(hydrido)-3-(butyl)1,4-diazabuta-1,3-diene]nickel[3-(ethyl)-6-(pentyl)catecholate]; [1,4-bis{4-methylethylaminophenyl}-2-(hexacosynyl)-3-(hydrido)1,4-diazabuta-1,3-diene]nickel[4-(pentyl)catecholate]; [1,4-bis{phenyl}-2-(butyl)-3-(hexyl)1,4-diazabuta-1,3-diene]nickel[3-(butyl)catecholate]; [1,4-bis{3-butanalylphenyl}-2-(propyl)-3-(nonadecynyl)1,4-diazabuta-1,3-diene]nickel[4-(ethyl)catecholate]; [1,4-bis{3,4-di(pentyl)phenyl}-2-(butyl)-3-(decynyl)1,4-diazabuta-1,3-diene]nickel[3-(ethyl)catecholate]; [1,4-bis{phenyl}-2-(hexyl)-3-(pentenyl)1,4-diazabuta-1,3-diene]nickel[4-(butyl)catecholate]; [1,4-bis{phenyl}-2-(hexyl)-3-(octyl)-1,4-diazabuta-1,3-diene]palladium[3-(pentyl)catecholate]; [1,4-bis{phenyl}-2-(butyl)-3-(hexyl)1,4-diazabuta-1,3-diene]palladium[3-(methyl)catecholate]; [1,4-bis{3,4-di(butonyl)phenyl}-2,3-(dibutyl)1,4-diazabuta-1,3-diene]palladium[3-(butyl)-4-(methyl)catecholate]; [1,4-bis{phenyl}-2-(hexyl)-3-(butyl)1,4-diazabuta-1,3-diene]palladium[3-(pentyl)-4-(methyl)-5-(ethyl)catecholate]; [1,4-bis{3,4-di(butyl)phenyl}-2-(octyl)-3-(hexyl)1,4-diazabuta-1,3-diene]nickel[3-(butyl)catecholate]; [1,4-bis{3,4-di(butyl)phenyl}-2-(octyl)-3-(hydrido)1,4-diazabuta-1,3-diene]nickel[3-(ethanalyl)-5-(pentyl)catecholate]; [1,4-bis{4-undecylphenyl}-2-(butyl)-3-(octyl)1,4-diazabuta-1,3-diene]nickel[3-(butyl)-4,6-di(ethyl)catecholate]; [1,4-bis{3,4-di(pentyl)phenyl}-2-(pentyl)-3-(butyl)1,4-diazabuta-1,3-diene]palladium[3-(butyl)-4-(propyl)-5-(pentyl)-catecholate]; [1,4-bis{4-trimethylsilylethylphenyl-}2-(butyl)-3-(hexacosyl)1,4-diazabuta-1,3-diene]palladium[3-(pentyl)catecholate]; [1,4-bis{3,5-di(methyl)phenyl}-2-(hexyl)-3-(propenyl)1,4-diazabuta-1,3-diene]nickel[3-(pentyl)catecholate]; [1,4-bis{phenyl}-2,3-(dioctyl)1,4-diazabuta-1,3-diene]nickel[3-(propyl)-6-(ethyl)catecholate]; [1,4-bis{3-nonacosenylphenyl}-2-(hydrido)-3-(butyl)1,4-diazabuta-1,3-diene]nickel[4-(methyl)-catecholate]; [1,4-bis{4-tridecylphenyl}-2-(butyl)-3-(hydrido)1,4-diazabuta-1,3-diene]nickel[3-(pentyl)-5-(ethyl)catecholate]; [1,4-bis{4-propynylphenyl}-2,3-(dibutyl)1,4-diazabuta-1,3-diene]nickel[3-(butyl)-5-(ethyl)catecholate]; [1,4-bis{3,5-di(butyl)-phenyl}-2,3-(dibutyl)1,4-diazabuta-1,3-diene]nickel[3-(butyl)-4-(pentyl)-6-(propyl)-catecholate]; [1,4-bis{3,4-di(dodecanonyl)phenyl}-2-(hydrido)-3-(butyl)1,4-diazabuta-1,3-diene]palladium[3-(ethyl)-5-(methyl)catecholate]; [1,4-bis{3-octylphenyl}-2,3-(dibutyl)1,4-diazabuta-1,3-diene]nickel[3-(butyl)catecholate]; [1,4-bis{4-tetradecynyl-phenyl}-2-(hexyl)-3-(pentyl)1,4-diazabuta-1,3-diene]nickel[4-(ethyl)catecholate]; [1,4-bis{3,4-di(methyl)phenyl}-2-(hexyl)-3-(tetradecynyl)1,4-diazabuta-1,3-diene]nickel[4-(butyl)catecholate]; [1,4-bis{3,4-di(dodecamino)phenyl}-2-(pentyl)-3-(methyl)1,4-diazabuta-1,3-diene]palladium[3-(ethyl)-4-(methyl)catecholate]; [1,4-bis{phenyl}-2-(octyl)-3-(ethyl)1,4-diazabuta-1,3-diene]palladium[3-(ethyl)-4-(methyl)catecholate]; [1,4-bis{phenyl}-2-(eicosyl)-3-(hydrido)1,4-diazabuta-1,3-diene]nickel[3,6-di(ethyl)-catecholate]; [1,4-bis{3,4-di(methyl)phenyl}-2,3-(dibutyl)1,4-diazabuta-1,3-diene]nickel[3-(butyl)-6-(pentyl)catecholate]; [1,4-bis{phenyl}-2,3-(dibutyl)1,4-diazabuta-1,3-diene]nickel[4-(propyl)-5-(ethyl)catecholate]; [1,4-bis{3,4-di(ethyl)phenyl}-2-(hexyl)-3-(butyl)1,4-diazabuta-1,3-diene]nickel[4-(pentyl)-5-(butyl)catecholate]; [1,4-bis{phenyl}-2,3-(dibutyl)1,4-diazabuta-1,3-diene]nickel[4-(pentyl)catecholate]; [1,4-bis{4-eicosynylphenyl}-2-(butyl)-3-(octyl)1,4-diazabuta-1,3-diene]palladium[3-(propyl)catecholate]; [1,4-bis{3-dodecaphosphinophenyl}-2-(ethyl)-3-(butyl)1,4-diazabuta-1,3-diene]nickel[3-(methyl)catecholate]; [1,4-bis{3,5-di(propyl)phenyl}-2-(hydrido)-3-(octyl)1,4-diazabuta-1,3-diene]palladium[3-(propyl)-4-(butyl)catecholate]; [1,4-bis{phenyl}-2-(hydrido)-3-(butyl)1,4-diazabuta-1,3-diene]nickel[3-(ethyl)-catecholate]; [1,4-bis{phenyl}-2-(ethyl)-3-(octyl)1,4-diazabuta-1,3-diene]nickel[3-(methyl)catecholate]; [1,4-bis{3,5-di(butyl)phenyl}-2-(hydrido)-3-(tetracosenyl)1,4-diazabuta-1,3-diene]nickel[3-(propyl)-6-(ethyl)catecholate]; [1,4-bis{3,5-di(methyl)-phenyl}-2-(pentyl)-3-(docosyl)1,4-diazabuta-1, 3-diene]palladium[3-(methyl)-4-(pentyl)-5-(propyl) catecholate]; [1,4-bis{3,5-di(pentyl)phenyl}-2-(butyl)-3-(hexyl)1,4-diazabuta-1,3-diene]nickel[4-(propyl) catecholate]; [1,4-bis{3,4-di(butyl)phenyl}-2-(pentyl)-3-(methyl)1,4-diazabuta-1,3-diene]nickel[4,5-di(methyl) catecholate]; [1,4-bis{4-heptynyl-phenyl}-2-(butyl)-3-(hydrido)1,4-diazabuta-1,3-diene]nickel[4-(ethyl) catecholate]; [1,4-bis{3,4-di(methyl)phenyl-}2-(hydrido-3-(nonacosenyl)1,4-diazabuta-1,3-diene]palladium[4-(ethyl) catecholate]; [1,4-bis{3,5-di(pentyl)phenyl}-2-(ethyl)-3-(hydrido)1,4-diazabuta-1,3-diene]nickel[3-((triethylsilylmethyl))catecholate]; [1,4-bis{phenyl}-2-(butyl)-3-(hexyl)1,4-diazabuta-1,3-diene]nickel[3-(pentyl)-4-(methyl)catecholate]; [1,4-bis{phenyl}-2,3-(dihydrido)1,4-diazabuta-1,3-diene]palladium[3-(propyl)-6-(methyl)-catecholate]; [1,4-bis{phenyl}-2-(triacontyl)-3-(butyl)1,4-diazabuta-1,3-diene]nickel[4-(butyl)catecholate]; [1,4-bis{4-trimethylsilylmethylphenyl}-2-(hydrido)-3-(nonadecynyl)-1,4-diazabuta-1,3-diene]palladium[3-(butyl)-6-(pentyl)catecholate]; [1,4-bis{phenyl}-2-(hydrido)-3-(methyl)1,4-diazabuta-1,3-diene]nickel[3,4-di(propyl)catecholate]; [1,4-bis{3,5-di(methyl)phenyl}-2-(butyl)-3-(hydrido)-1,4-diazabuta-1,3-diene]nickel[3-(butyl)-4-(propyl)-5-(pentyl)catecholate]; [1,4-bis{3,5-di(ethyl)phenyl}1-2-(pentyl)-3-(butyl)1,4-diazabuta-1,3-diene]palladium[3-(propyl)catecholate]; [1,4-bis{3,5-di(pentyl)phenyl}-2-(pentyl)-3-(butyl)1,4-diazabuta-1,3-diene]nickel[3-(butyl)-catecholate]; [1,4-bis{phenyl}-2-(butyl)-3-(octyl)1,4-diazabuta-1,3-diene]palladium[4-(methyl)catecholate]; [1,4-bis{phenyl}-2-(hydrido)-3-(hexyl)1,4-diazabuta-1,3-diene]nickel[3-(butyl) catecholate]; [1,4-bis{3,4-di(pentyl)phenyl}-2-(propyl)-3-(octyl)1,4-diazabuta-1,3-diene]nickel[3-(propyl)-5-(methyl) catecholate]; [1,4-bis{3,4-di(methyl)-phenyl}-2-(butyl)-3-(hydrido)1,4-diazabuta-1,3-diene]nickel[4-(ethyl) catecholate]; [1,4-bis{3,5-di(pentyl)phenyl}-2,3-(dihydrido)1,4-diazabuta-1,3-diene]nickel[3-(butyl)-catecholate]; [1,4-bis{phenyl}-2-(octyl)-3-(butyl)1,4-diazabuta-1,3-diene]nickel[3,5-di(butyl)catecholate]; [1,4-bis{4-tridecylphenyl}-2-(methyl)-3-(ethyl)1,4-diazabuta-1,3-diene]nickel[4-(methyl)catecholate]; [1,4-bis{3,4-di(methyl)phenyl}-2,3-(dihydrido)1,4-diazabuta-1,3-diene]nickel[3-(pentyl)-6-(propyl)catecholate]; [1,4-bis{4-tetracosenyl-phenyl}-2,3-(dihydrido)1,4-diazabuta-1,3-diene]nickel[3-(butyl)-4,6-di(methyl)-catecholate]; [1,4-bis{4-heptacosylphenyl}-2-(eicosenyl)-3-(hydrido)1,4-diazabuta-1,3-diene]nickel[4,5-di(propyl)catecholate]; [1,4-bis{phenyl}-2-(butyl)-3-(ethyl)1,4-diazabuta-1,3-diene]palladium[3-(butanalyl)-6-(ethyl)catecholate]; [1,4-bis{3-heptacosenylphenyl}-2-(hydrido)-3-(ethyl)1,4-diazabuta-1,3-diene]nickel[3,4-di(ethyl)-6-(pentyl)catecholate]; [1,4-bis{3,4-di(butyl)phenyl}-2,3-(dihydrido)1,4-diazabuta-1,3-diene]nickel[4-(butyl)catecholate]; [1,4-bis{3,4-di(methyl)phenyl}-2-(butyl)-3-(hydrido)1,4-diazabuta-1,3-diene]nickel[3-(butyl)-4-(propyl)-6-(ethyl)catecholate]; [1,4-bis{phenyl}-2-(pentyl)-3-(butyl)1,4-diazabuta-1,3-diene]palladium[4-(pentyl)-5-(propyl)catecholate]; [1,4-bis{3,5-di(ethyl)phenyl}-2-(hexyl)-3-(butyl)1,4-diazabuta-1,3-diene]nickel[3-(pentyl)-5-(butyl)catecholate]; [1,4-bis{phenyl}-2-(methyl)-3-(butyl)1,4-diazabuta-1,3-diene]nickel[4,5-di(methyl)catecholate]; [1,4-bis{phenyl}-2,3-(dibutyl)-1,4-diazabuta-1,3-diene]nickel[3-(hexonyl)-5-(pentyl) catecholate]; [1,4-bis{3,5-di(ethyl)phenyl}-2-(octyl)-3-(hexyl)1,4-diazabuta-1,3-diene]nickel[4-(propyl)-5-(methyl)catecholate]; [1,4-bis{4-butanalylphenyl}-2-(methyl)-3-(hexyl)1,4-diazabuta-1,3-diene]nickel[3-(ethyl) catecholate]; [1,4-bis{3,5-di(pentyl)phenyl}-2,3-(dibutyl)1,4-diazabuta-1,3-diene]nickel[3-(pentyl)-4-(methyl)-5-(ethyl)catecholate]; [1,4-bis{phenyl}-2-(ethyl)-3-(butyl)1,4-diazabuta-1,3-diene]palladium[3-(propyl)-4-(pentyl)-catecholate]; [1,4-bis{3,4-di(pentyl)phenyl}-2,3-(dihydrido)1,4-diazabuta-1,3-diene]palladium[3-(propyl) catecholate]; [1,4-bis{3,4-di(dodecanonyl)phenyl}-2-(hydrido)-3-(butyl)1,4-diazabuta-1,3-diene]nickel[3-(methyl)-4-(butyl)catecholate]; [1,4-bis{3,5-di(pentyl) phenyl}-2-(methyl)-3-(butyl)1,4-diazabuta-1,3-diene]nickel[4-(butyl)-catecholate]; [1,4-bis{phenyl}-2-(hydrido)-3-(butyl)1,4-diazabuta-1,3-diene]nickel[3-(pentyl)-5-(ethyl) catecholate]; [1,4-bis{phenyl}-2-(butyl)-3-(hydrido)1,4-diazabuta-1,3-diene]nickel[3-(propyl)-6-(methyl) catecholate]; [1,4-bis{4-octadecenylphenyl}-2,3-(dibutyl)1,4-diazabuta-1,3-diene]palladium[3-(ethyl)catecholate]; [1,4-bis{3-pentacosyl-phenyl}-2-(pentyl)-3-(octyl)1,4-diazabuta-1,3-diene]nickel[3-(methyl)-4-(ethyl)-catecholate]; [1,4-bis{3-dodecaphosphinophenyl}-2-(hydrido)-3-(octyl)1,4-diazabuta-1,3-diene]palladium[4-(methyl)catecholate]; [1,4-bis{phenyl}-2-(butyl)-3-(ethyl)1,4-diazabuta-1,3-diene]nickel[4-(propyl)catecholate]; [1,4-bis{3,5-di(pentyl)phenyl}-2-(octyl)-3-(hydrido)1,4-diazabuta-1,3-diene]nickel[3-(ethanalyl)catecholate]; [1,4-bis{phenyl}-2-(butyl)-3-(pentyl)1,4-diazabuta-1,3-diene] palladium[3-(methyl)-catecholate]; [1,4-bis{3,5-di(propyl) phenyl}-2,3-(dibutyl)1,4-diazabuta-1,3-diene]nickel[3-(pentyl)-6-(methyl)catecholate]; [1,4-bis{4-diethylaminophenyl}-2-(butyl)-3-(hydrido)1,4-diazabuta-1,3-diene]palladium[4-(ethyl)catecholate]; [1,4-bis{3,5-di(methyl)phenyl}-2-(docosenyl)-3-(butyl)1,4-diazabuta-1,3-diene]palladium[3-(ethanalyl)-4,5-di(butyl)catecholate]; [1,4-bis{phenyl}-2,3-(dibutyl)1,4-diazabuta-1,3-diene]palladium[4-(methyl)catecholate]; [1,4-bis{phenyl}-2-(butyl)-3-(hexyl)1,4-diazabuta-1,3-diene]nickel[4-(butyl) catecholate]; [1,4-bis{4-nonacosylphenyl}-2-(pentyl)-3-(tetradecynyl)1,4-diazabuta-1,3-diene]nickel[3-(methyl)-4-(ethyl)-5-(pentyl)-catecholate]; [1,4-bis{3,4-di(methyl) phenyl}-2-(hydrido)-3-(butyl)1,4-diazabuta-1,3-diene] nickel[3-(butyl)-6-(methyl)catecholate]; [1,4-bis{phenyl}-2,3-(dihydrido)1,4-diazabuta-1,3-diene]palladium[3-(methyl)-4-(pentyl)catecholate]; [1,4-bis{phenyl}-2-(butyl)-3-(octyl)1,4-diazabuta-1,3-diene]nickel[3-(ethyl)-4-(methyl)-6-(pentyl)-catecholate]; [1,4-bis{3,5-di(butyl) phenyl}-2-(butyl)-3-(pentyl)1,4-diazabuta-1,3-diene]nickel [3-(methyl)catecholate]; [1,4-bis{3,5-di(dodecamino) phenyl}-2-(hexyl)-3-(butyl)-1,4-diazabuta-1,3-diene]nickel [4-(propyl)-5-(ethyl)catecholate]; [1,4-bis{4-butyl-phenyl}-2-(hydrido)-3-(butyl)1,4-diazabuta-1,3-diene]nickel[3-(ethyl)-4-(propyl)-catecholate]; [1,4-bis{3,5-di(pentyl) phenyl}-2-(butyl)-3-(octyl)1,4-diazabuta-1,3-diene] palladium[3-(butyl)-5-(propyl)catecholate]; [1,4-bis{4-propynylphenyl}-2-(tetradecyl)-3-(octyl)1,4-diazabuta-1,3-diene]nickel[4-(ethyl)catecholate]; [1,4-bis{4-dodecenyl-phenyl}-2-(pentadecyl)-3-(octyl)1,4-diazabuta-1,3-diene] nickel[3-(butyl)-4-(propyl)-5-(methyl)catecholate]; [1,4-bis{4-octacosynylphenyl}-2-(hexyl)-3-(hydrido)1,4-diazabuta-1,3-diene]palladium[3-(methyl)catecholate]; [1,4-bis{3-heptacosenylphenyl}-2-(pentadecyl)-3-(butyl)1,4-diazabuta-1,3-diene]palladium[3,6-di(pentyl) catecholate]; [1,4-bis{3-pentynylphenyl}-2-(decynyl)-3-(hydrido)1,4-diazabuta-1,3-diene]nickel[3-(propyl)-5-(pentyl)catecholate]; [1,4-bis{3,5-di(butyl)phenyl}-2-(butyl)-3-(octenyl)1,4-diazabuta-1,3-diene]nickel[3-(methyl)catecholate]; [1,4-bis{4-nonacosenylphenyl}-2-(decynyl)-3-(butyl)1,4-diazabuta-1,3-diene]palladium[3-(propyl)-4-(butanalyl)-5-(methyl)catecholate]; [1,4-bis{3,4-di(propyl)phenyl}-2-(hexyl)-3-(butyl)1,4-diazabuta-1,3- diene]nickel[3-(pentyl)-5-(methyl)catecholate]; [1,4-bis{phenyl}-2-(hydrido)-3-(butyl)1,4-diazabuta-1,3-diene]palladium[3-(propyl)-5-(pentyl)catecholate]; [1,4-bis{phenyl}-2,3-(dibutyl)1,4-diazabuta-1,3-diene]nickel[4,5-di(propyl)catecholate]; [1,4-bis{3,5-di(propyl)phenyl}-2-(butyl)-3-(hydrido)1,4-diazabuta-1,3-diene]palladium[4-(methyl)catecholate]; [1,4-bis{phenyl}-2-(butyl)-3-(undecenyl)1,4-diazabuta-1,3-diene]palladium[3-(pentyl)-4-(methyl)catecholate]; [1,4-bis{3-hexonylphenyl}-2-(butyl)-3-(hydrido)1,4-diazabuta-1,3-diene]nickel[3-(butyl)catecholate]; [1,4-bis{3,5-di(pentyl)phenyl}-2,3-(dibutyl)1,4-diazabuta-1,3-diene]nickel[4-(propyl)catecholate]; [1,4-bis{3,4-di(propyl)phenyl}-2-(hydrido)-3-(butyl)1,4-diazabuta-1,3-diene]nickel[4-(methyl)catecholate]; [1,4-bis{3,5-di(ethyl)phenyl}-2,3-(dibutyl)1,4-diazabuta-1,3-diene]nickel[3-(propyl)-5-(ethyl)catecholate]; [1,4-bis{3,4-di(ethyl)phenyl}-2-(nonacosyl)-3-(octyl)1,4-diazabuta-1,3-diene]nickel[3-(propyl)-4-(methyl)-5-(pentyl)catecholate]; [1,4-bis{phenyl}-2-(pentyl)-3-(ethyl)1,4-diazabuta-1,3-diene]nickel[3-(propyl)catecholate]; [1,4-bis{3,4-di(ethyl)phenyl}-2-(ethyl)-3-(pentyl)1,4-diazabuta-1,3-diene]nickel[4-(pentyl)catecholate]; [1,4-bis{3,5-di(methyl)phenyl}-2,3-(dihexyl)1,4-diazabuta-1,3-diene]nickel[3-(pentyl)catecholate]; [1,4-bis{3,4-di(butyl)phenyl}-2-(hydrido)-3-(butyl)1,4-diazabuta-1,3-diene]nickel[3-(ethyl)catecholate]; [1,4-bis{phenyl}-2-(dodecyl)-3-(hexyl)1,4-diazabuta-1,3-diene]nickel[4-(pentyl)catecholate]; [1,4-bis{3,4-di(ethyl)phenyl}-2-(hydrido)-3-(butyl)1,4-diazabuta-1,3-diene]nickel[3-(propyl)-4,6-di(butyl)catecholate]; [1,4-bis{3,5-di(methyl)phenyl}-2-(octyl)-3-(butyl)1,4-diazabuta-1,3-diene]palladium[3-(methyl)catecliolate]; [1,4-bis{3-hexylphenyl}-2-(hydrido)-3-(octyl)1,4-diazabuta-1,3-diene]nickel[3-(methyl)-5-(ethyl)catecholate]; [1,4-bis{3,4-di(methyl)phenyl}-2-(butyl)-3-(pentyl)1,4-diazabuta-1,3-diene]nickel[4-(propyl)-catecholate]; [1,4-bis{3,5-di(pentyl)phenyl}-2-(butyl)-3-(hexyl)1,4-diazabuta-1,3-diene]nickel[3-(pentyl)-5-(ethyl)catecholate]; [1,4-bi s{3,4-di(proponyl)phenyl}-2,3-(dimethyl)-1,4-diazabuta-1,3-diene]nickel[3-(propyl)-5-(ethyl)catecholate]; [1,4-bis{3,5-di(pentyl)-phenyl}-2-(butyl)-3-(hydrido)1,4-diazabuta-1,3-diene]nickel[3,6-di(methyl)catecholate]; [1,4-bis{3,4-di(ethyl)phenyl}-2-(dodecyl)-3-(butyl)1,4-diazabuta-1,3-diene]nickel[4-(methyl)catecholate]; [1,4-bis{3,5-di(ethyl)phenyl}-2-(butyl)-3-(pentyl)1,4-diazabuta-1,3-diene]nickel[4-(ethyl)catecholate]; [1,4-bis{3-docosylphenyl}-2-(butyl)-3-(hexacosynyl)1,4-diazabuta-1,3-diene]nickel[4-(methyl)catecholate]; [1,4-bis{3-nonyl-phenyl}-2-(pentyl)-3-(hydrido)1,4-diazabuta-1,3-diene]nickel[4-(butyl)catecholate];

[1,4-bis{3,5-di(methyl)phenyl}-2-(hydrido)-3-(octyl)1,4-diazabuta-1,3-diene]nickel[3-(methyl)-4-(ethyl)catecholate]; [1,4-bis{3,4-di(ethyl)phenyl}-2-(butyl)-3-(pentyl)1,4-diazabuta-1,3-diene]nickel[3-(ethyl)-4-(butyl)catecholate]; [1,4-bis{3,5-di(ethyl)phenyl}-2-(pentyl)-3-(hydrido)1,4-diazabuta-1,3-diene]nickel[4-(butyl)catecholate]; [1,4-bis{phenyl}-2-(heptacosyl)-3-(butyl)1,4-diazabuta-1,3-diene]nickel[3-(pentyl)-4-(butyl)-6-(methyl)catecholate]; [1,4-bis{3,4-di(butyl)phenyl}-2-(butyl)-3-(pentyl)1,4-diazabuta-1,3-diene]nickel[3-(propyl)-6-(ethyl)catecholate]; [1,4-bis{3,4-di(ethyl)phenyl}-2,3-(dibutyl)1,4-diazabuta-1,3-diene]nickel[3-(ethyl)-4-(pentyl)-6-(butyl)catecholate]; [1,4-bis{4-heptacosylphenyl}-2-(pentyl)-3-(butyl)1,4-diazabuta-1,3-diene]nickel[3-(ethyl)-6-(propyl)catecholate]; [1,4-bis{3,4-di(propyl)phenyl}-2-(hydrido)-3-(butyl)1,4-diazabuta-1,3-diene]nickel[3-(propyl)-4-(pentyl)-5-(ethyl)-catecholate]; [1,4-bis{3-pentadecynylphenyl}-2-(pentyl)-3-(heptadecyl)1,4-diazabuta-1,3-diene]palladium[3-(methyl)-6-(pentyl)catecholate]; [1,4-bis{phenyl}-2,3-(dioctyl)1,4-diazabuta-1,3-diene]nickel[4-(methyl)-5-(ethyl)catecholate]; [1,4-bis{4-methyldiethylsilylmethyl)phenyl}-2,3-(dipentyl)1,4-diazabuta-1,3-diene]nickel[3-(butyl)catecholate]; [1,4-bis{3,4-di(propyl)phenyl}-2-(tetradecyl)-3-(butyl)1,4-diazabuta-1,3-diene]nickel[4-(propyl)catecholate]; [1,4-bis{4-pentylphenyl}-2-(hydrido)-3-(octyl)-1,4-diazabuta-1,3-diene]nickel[3-(butyl)-4,6-di(propyl)catecholate]; [1,4-bis{3,4-di(methyl)phenyl}-2-(ethyl)-3-(octyl)1,4-diazabuta-1,3-diene]nickel[3-(methyl)-5-(pentyl)catecholate]; [1,4-bis{3,5-di(propyl)phenyl}-2-(butyl)-3-(octyl)1,4-diazabuta-1,3-diene]nickel[4-(dodecanonyl)catecholate]; [1,4-bis{phenyl}-2-(hexyl)-3-(butyl)1,4-diazabuta-1,3-diene]nickel[4-(ethyl)catecholate]; [1,4-bis{3,5-di(butyl)phenyl}-2-(butyl)-3-(ethyl)1,4-diazabuta-1,3-diene]palladium[3-(propyl)-5-(butyl)catecholate]; [1,4-bis{4-pentacosenylphenyl}-2-(butyl)-3-(hexyl)1,4-diazabuta-1,3-diene]palladium [3-(butyl)-4-(ethyl)-6-(methyl)catecholate]; [1,4-bis{4-ethylphenyl}-2-(hexyl)-3-(butyl)-1,4-diazabuta-1,3-diene]nickel[3-(ethyl)catecholate]; [1,4-bis{3,4-di(ethyl)phenyl}-2-(pentyl)-3-(butyl)1,4-diazabuta-1,3-diene]nickel[3-(methyl)-4-(propyl)catecholate]; [1,4-bis{phenyl}-2-(octyl)-3-(butyl)1,4-diazabuta-1,3-diene]palladium[4-(methyl)-catecholate]; [1,4-bis{3,5-di(methyl)phenyl}-2-(butyl)-3-(hexyl)1,4-diazabuta-1,3-diene]nickel[3,4-di(pentyl)catecholate]; [1,4-bis{3,5-di(ethyl)phenyl}-2,3-(dihydrido)1,4-diazabuta-1,3-diene]palladium[4-(ethyl)catecholate]; [1,4-bis{3,4-di(pentyl)phenyl}-2-(heptacosyl)-3-(hydrido)1,4-diazabuta-1,3-diene]nickel[3-(pentyl)-6-(ethyl)catecholate]; [1,4-bis{phenyl}-2-(pentyl)-3-(butyl)1,4-diazabuta-1,3-diene]nickel[3-(propyl)-4-(butyl)catecholate]; [1,4-bis{3,4-di(pentyl)phenyl}-2-(hydrido)-3-(pentyl)1,4-diazabuta-1,3-diene]nickel[3-(ethyl)-4-(butyl)catecholate]; [1,4-bis{4-octylphenyl}-2-(butyl)-3-(ethyl)1,4-diazabuta-1,3-diene]palladium[4-(methyl)-5-(butyl)catecholate]; [1,4-bis{4-nonadecynylphenyl}-2-(methyl)-3-(octyl)1,4-diazabuta-1,3-diene]nickel[3-(methyl)-catecholate]; [1,4-bis{phenyl}-2-(hydrido)-3-(dodecyl)1,4-diazabuta-1,3-diene]nickel[3-(methyl)-5-(butyl)catecholate]; [1,4-bis{3,5-di(butyl)phenyl}-2-(octyl)-3-(hydrido)1,4-diazabuta-1,3-diene]nickel[3-(methyl)-4-(propyl)catecholate]; [1,4-bis{3,4-di(butyl)-phenyl}-2-(hydrido)-3-(pentyl)1,4-diazabuta-1,3-diene]palladium[4-(propyl)-catecholate]; [1,4-bis{3,5-di(butyl)phenyl}-2-(octyl)-3-(nonacosenyl)1,4-diazabuta-1,3-diene]nickel[3-(pentyl)catecholate]; [1,4-bis{3,4-di(ethyl)phenyl}-2-(pentyl)-3-(hydrido)1,4-diazabuta-1,3-diene]nickel[3-(propyl)-6-(pentyl)catecholate]; [1,4-bis{phenyl}-2-(propyl)-3-(butyl)1,4-diazabuta-1,3-diene]nickel[3-(pentyl)-6-(ethyl)-catecholate]; [1,4-bis{3,5-di(ethyl)phenyl}-2-(hydrido)-3-(heneicosyl)1,4-diazabuta-1,3-diene]palladium[3-(methyl)catecholate]; [1,4-bis{4-pentacosenylphenyl}-2-(octyl)-3-(butyl)-1,4-diazabuta-1,3-diene]palladium[3-(ethyl)-4-(pentyl)-5-(hexonyl)catecholate]; [1,4-bis{3,4-di(methyl)phenyl}-2,3-(dibutyl)1,4-diazabuta-1,3-diene]nickel[3-(trimethylsilylmethyl)-5-(butyl)catecholate]; [1,4-bis{3,5-di(propyl)phenyl}-2,3-(dibutyl)1,4-diazabuta-1,3-diene]nickel[4-(butyl)catecholate]; [1,4-bis{phenyl}-2-(hydrido)-3-(butyl)1,4-diazabuta-1,3-diene]nickel[3-(propyl)-4-(butyl)catecholate]; [1,4-bis{3,5-di(methyl)phenyl}-2,3-(dibutyl)1,4-diazabuta-1,3-diene]palladium[4-(propyl)-5-(methyl)catecholate]; [1,4-bis{phenyl}-2,3-(dibutyl)1,4-diazabuta-1,3-diene]nickel[4-(butyl)-catecholate]; [1,4-bis{phenyl}-2-(octyl)-3-(heptacosyl)1,4-diazabuta-1,3-diene]nickel[3-(butyl)-5-(pentyl)catecholate]; [1,4-bis{3,5-di(ethyl)

phenyl}-2-(hydrido)-3-(butyl)1,4-diazabuta-1,3-diene]
palladium[3,4-di(pentyl)-6-(pentyl)catecholate]; [1,4-bis{3,4-di(pentyl)phenyl}-2-(octyl)-3-(hydrido)1,4-diazabuta-1,3-diene]nickel[3-(ethyl)-catecholate]; [1,4-bis{3,4-di(ethyl)phenyl}-2-(butyl)-3-(pentyl)1,4-diazabuta-1,3-diene]palladium[3-(pentyl)-4-(butyl)-6-(methyl)catecholate]; [1,4-bis{3,4-di(pentyl)phenyl}-2-(pentyl)-3-(butyl)1,4-diazabuta-1,3-diene]palladium[3,4-di(ethyl)-6-(pentyl)-catecholate]; [1,4-bis{4-heptadecenylphenyl}-2-(butyl)-3-(hexynyl)1,4-diazabuta-1,3-diene]nickel[3,5-di(methyl)catecholate]; [1,4-bis{phenyl}-2-(octyl)-3-(butyl)1,4-diazabuta-1,3-diene]nickel[3-(ethyl)-4-(propyl)catecholate]; [1,4-bis{phenyl}-2-(butyl)-3-(octyl)1,4-diazabuta-1,3-diene]nickel[3-(ethyl)-5-(methyl)catecholate]; [1,4-bis{3,4-di(propyl)phenyl}-2-(octyl)-3-(pentacosyl)1,4-diazabuta-1,3-diene]nickel[3-(ethyl)-4-(butyl)catecholate]; [1,4-bis{phenyl}-2-(hydrido)-3-(hexyl)1,4-diazabuta-1,3-diene]nickel[4-(butyl)catecholate]; [1,4-bis{3-heptadecylphenyl}-2-(butyl)-3-(octyl)1,4-diazabuta-1,3-diene]nickel[4-(butyl)-5-(ethyl)catecholate]; [1,4-bis{3-triacontylphenyl}-2-(pentyl)-3-(butyl)1,4-diazabuta-1,3-diene]nickel[4-(propyl)-5-(methyl)catecholate]; [1,4-bis{3,4-di(butyl)phenyl}-2-(pentyl)-3-(butyl)1,4-diazabuta-1,3-diene]palladium[3-(ethyl)-4-(propyl)-5-(pentyl)catecholate]; [1,4-bis{3-heptacosenylphenyl}-2,3-(dihydrido)1,4-diazabuta-1,3-diene]nickel[3-(pentyl)catecholate]; [1,4-bis{3,4-di(butyl)-phenyl}-2,3-(dibutyl)1,4-diazabuta-1,3-diene]nickel[3,5-di(pentyl)-4-(butyl)-catecholate]; [1,4-bis{4-docosenylphenyl}-2-(ethyl)-3-(pentyl)1,4-diazabuta-1,3-diene]nickel[3-(bromo)-4-(pentyl)catecholate]; [1,4-bis{3,4-di(butyl)phenyl}-2-(pentacosynyl)-3-(tricosenyl)1,4-diazabuta-1,3-diene]nickel[4-(butyl)catecholate]; [1,4-bis{3-heptadecylphenyl}-2,3-(dibutyl)1,4-diazabuta-1,3-diene]palladium[3-(trimethylsilylethyl)catecholate]; [1,4-bis{3,4-di(ethyl)phenyl}-2-(tricosyl)-3-(hydrido)-1,4-diazabuta-1,3-diene]palladium[4-(ethyl)catecholate]; [1,4-bis{3,5-di(ethyl)phenyl}-2-(methyl)-3-(hydrido)1,4-diazabuta-1,3-diene]palladium[3-(propyl)-6-(methyl)-catecholate]; 1,4-bis{3,5-di(ethyl)phenyl}-2,3-(dioctyl)1,4-diazabuta-1,3-diene]nickel[3-(methyl)catecholate]; [1,4-bis{3-butanalylphenyl}-2,3-(dihydrido)1,4-diazabuta-1,3-diene]nickel[3-(pentyl)-5-(butyl)catecholate]; [1,4-bis{3-tricosynylphenyl}-2,3-(dibutyl)1,4-diazabuta-1,3-diene]nickel[4-(ethyl)catecholate]; [1,4-bis{phenyl}-2-(butyl)-3-(hydrido)1,4-diazabuta-1,3-diene]palladium[3-((triethylsilylmethyl))-4-(butyl)-5-(propyl)catecholate]; [1,4-bis{phenyl}-2,3-(dibutyl)1,4-diazabuta-1,3-diene]nickel[3-(propyl)-5-(pentyl)catecholate];

[1,4-bis{3,4-di(pentyl)phenyl}-2-(methyl)-3-(hydrido)1,4-diazabuta-1,3-diene]nickel[4-(propyl)catecholate]; [1,4-bis{phenyl}-2,3-(dibutyl)1,4-diazabuta-1,3-diene]nickel[3-(ethyl)-4-(pentyl)catecholate]; [1,4-bis{3-undecynylphenyl}-2,3-(dihydrido)1,4-diazabuta-1,3-diene]nickel[4,5-di(butyl)catecholate]; [1,4-bis{phenyl}-2-(butyl)-3-(octyl)1,4-diazabuta-1,3-diene]palladium[3-(pentyl)catecholate]; [1,4-bis{3-dodecanonylphenyl}-2-(hexyl)-3-(hydrido)1,4-diazabuta-1,3-diene]nickel[4-(butyl)-catecholate]; [1,4-bis{3,5-di(methyl)phenyl}-2-(butyl)-3-(hydrido)1,4-diazabuta-1,3-diene]nickel[4-(methyl)catecholate]; [1,4-bis{3,5-di(methyl)phenyl}-2-(pentyl)-3-(hydrido)1,4-diazabuta-1,3-diene]palladium[4,5-di(methyl)catecholate]; [1,4-bis{3,4-di(butyl)phenyl}-2-(hydrido)-3-(octyl)1,4-diazabuta-1,3-diene]nickel[4-(butyl)-5-(propyl)catecholate]; [1,4-bis{phenyl}-2-(hexyl)-3-(butyl)1,4-diazabuta-1,3-diene]palladium[3-(ethyl)catecholate]; [1,4-bis{3,5-di(pentyl)phenyl}-2-(butyl)-3-(pentyl)1,4-diazabuta-1,3-diene]nickel[3-(butyl)-4-(propyl)catecholate];[1,4-bis{phenyl}-2-(hexyl)-3-(hydrido)1,4-diazabuta-1,3-diene]nickel[4-(ethyl)catecholate];[1,4-bis{4-butenyl-phenyl}-2,3-(dibutyl)1,4-diazabuta-1,3-diene]nickel[3,4-di(ethyl)-6-(pentyl)-catecholate]; [1,4-bis{phenyl}-2-(pentyl)-3-(butyl)1,4-diazabuta-1,3-diene]nickel[3-(pentyl)-4-(butyl)catecholate]; [1,4-bis{3-undecylphenyl}-2-(hexyl)-3-(pentyl)1,4-diazabuta-1,3-diene]nickel[4-(ethyl)catecholate]; [1,4-bis{4-nonacosenylphenyl}-2-(tetracosenyl)-3-(butyl)1,4-diazabuta-1,3-diene]nickel[3-(butyl)-5-(pentyl)catecholate]; [1,4-bis{3,4-di(ethyl)phenyl}-2-(butynyl)-3-(butyl)1,4-diazabuta-1,3-diene]nickel[3-(butyl)catecholate]; [1,4-bis{3,5-di(pentyl)phenyl}-2-(docosynyl)-3-(heptacosynyl)1,4-diazabuta-1,3-diene]nickel[4-(methyl)-5-(ethyl)catecholate]; [1,4-bis{phenyl}-2-(hydrido)-3-(butyl)1,4-diazabuta-1,3-diene]palladium[4-(ethyl)catecholate]; [1,4-bis{3,4-di(propyl)phenyl}-2,3-(dibutyl)1,4-diazabuta-1,3-diene]nickel[3-(ethyl)-catecholate]; [1,4-bis{phenyl}-2-(octyl)-3-(butyl)1,4-diazabuta-1,3-diene]nickel[4-(ethyl)catecholate]; [1,4-bis{phenyl}-2-(pentyl)-3-(octacosenyl)1,4-diazabuta-1,3-diene]nickel[3-(propyl)-5-(methyl)catecholate]; [1,4-bis{3,4-di(pentyl)phenyl}-2,3-(dibutyl)-1,4-diazabuta-1,3-diene]palladium[4-(butyl)-5-(ethyl)catecholate]; [1,4-bis{3,4-di(propyl)phenyl}-2-(pentacosenyl)-3-(butyl)1,4-diazabuta-1,3-diene]nickel[4-(methyl)-catecholate]; [1,4-bis{3-heptadecylphenyl}-2-(hydrido)-3-(pentyl)1,4-diazabuta-1,3-diene]nickel[4-(ethyl)-5-(propyl)catecholate]; [1,4-bis{phenyl}-2-(octyl)-3-(pentyl)1,4-diazabuta-1,3-diene]palladium[4,5-di(propyl)catecholate]; [1,4-bis{3,4-di(ethyl)-phenyl}-2-(hydrido)-3-(octyl)1,4-diazabuta-1,3-diene]palladium[3-(butyl)catecholate]; [1,4-bis{3,5-di(methyl)phenyl}-2-(butyl)-3-(hydrido)1,4-diazabuta-1,3-diene]palladium[4-(propyl)catecholate]; [1,4-bis{3,5-di(pentyl)phenyl}-2-(butyl)-3-(octyl)1,4-diazabuta-1,3-diene]nickel[3-(methylethylamino)-4-(propyl)-5-(methyl)catecholate]; [1,4-bis{3,4-di(methyl)phenyl}-2-(octyl)-3-(butyl)1,4-diazabuta-1,3-diene]nickel[3-(butyl)-6-(pentyl)catecholate]; [1,4-bis{3,5-di(pentyl)phenyl}-2-(docosenyl)-3-(hydrido)1,4-diazabuta-1,3-diene]nickel[3-(methyl)-4-(propyl)catecholate]; [1,4-bis{3,4-di(propyl)-phenyl}-2-(nonacosyl)-3-(tetradecynyl)1,4-diazabuta-1,3-diene]nickel[4-(pentyl)-catecholate]; [1,4-bis{phenyl}-2-(octyl)-3-(hydrido)1,4-diazabuta-1,3-diene]nickel[4-(propyl)catecholate]; [1,4-bis{3,4-di(butyl)phenyl}-2-(pentyl)-3-(butyl)1,4-diazabuta-1,3-diene]nickel[3-(methyl)-4-(butyl)-6-(pentyl)catecholate]; [1,4-bis{3-eicosenylphenyl}-2-(pentyl)-3-(octyl)1,4-diazabuta-1,3-diene]nickel[4-(butyl)catecholate]; [1,4-bis{3,5-di(methyl)phenyl}-2-(butyl)-3-(octyl)1,4-diazabuta-1,3-diene]nickel[3-(pentyl)-6-(propyl)catecholate]; [1,4-bis{phenyl}-2,3-(dihydrido)1,4-diazabuta-1,3-diene]palladium[4-(propanalyl)-5-(propyl)catecholate]; [1,4-bis{3-hexenylphenyl}-2-(hydrido)-3-(butyl)-1,4-diazabuta-1,3-diene]nickel[4-(ethyl)catecholate]; [1,4-bis{3-nonacosynylphenyl}-2-(hydrido)-3-(nonadecynyl)1,4-diazabuta-1,3-diene]nickel[4-(propyl)catecholate]; [1,4-bis{3,5-di(pentyl)phenyl}-2,3-(dibutyl)1,4-diazabuta-1,3-diene]palladium[4-(butyl)-5-(propyl)catecholate]; [1,4-bis{phenyl}-2-(butyl)-3-(hydrido)1,4-diazabuta-1,3-diene]palladium[4-(pentyl)catecholate]; [1,4-bis{3,5-di(ethyl)phenyl}-2-(octyl)-3-(butyl)1,4-diazabuta-1,3-diene]nickel[3-(butyl)-6-(methyl)catecholate]; [1,4-bis{3,4-di(methyl)-phenyl}-2-(heptacosyl)-3-(pentyl)1,4-diazabuta-1,3-diene]palladium[3-(pentyl)-5-(butyl)catecholate]; [1,4-bis{3,4-di(dodecanonyl)phenyl}-2-(hydrido)-3-(methyl)1,4-diazabuta-1,3-diene]nickel[3-

(butyl)catecholate]; [1,4-bis{4-nonacosylphenyl}-2-(octyl)-3-(butenyl)1,4-diazabuta-1,3-diene]nickel[3-(propanalyl)-5-(propyl)catecholate]; [1,4-bis{phenyl}-2-(butyl)-3-(hexyl)1,4-diazabuta-1,3-diene]palladium[3-(pentyl)-catecholate]; [1,4-bis{3-tetradecenylphenyl}-2-(methyl)-3-(butyl)1,4-diazabuta-1,3-diene]nickel[4,5-di(ethyl)catecholate]; [1,4-bis{4-hexadecenylphenyl}-2-(butyl)-3-(hexyl)1,4-diazabuta-1,3-diene]nickel[3-(butyl)-4-(hexonyl)catecholate]; [1,4-bis{3,4-di(propyl)phenyl}-2-(butynyl)-3-(butyl)1,4-diazabuta-1,3-diene]nickel[3-(pentyl)-4-(butyl)catecholate]; [1,4-bis{3,4-di(pentyl)phenyl}-2-(hydrido)-3-(butyl)1,4-diazabuta-1,3-diene]nickel[3-(methyl)-4-(pentyl)-5-(propyl)catecholate]; [1,4-bis{3-tricosenyl-phenyl}-2-(hexadecyl)-3-(nonenyl)1,4-diazabuta-1,3-diene]nickel[3,5-di(methyl)-catecholate]; [1,4-bis{3-docosylphenyl}-2-(hydrido)-3-(octyl)1,4-diazabuta-1,3-diene]nickel[3-(ethyl)catecholate]; [1,4-bis{3,4-di(proponyl)phenyl}-2-(hexyl)-3-(pentyl)1,4-diazabuta-1,3-diene]nickel[3-(trimethylsilylmethyl)-4-(propyl)catecholate]; [1,4-bis{phenyl}-2-(octyl)-3-(hydrido)1,4-diazabuta-1,3-diene]nickel[3-(pentyl)-4-(butyl)-catecholate]; [1,4-bis{phenyl}-2-(methyl)-3-(hexyl)1,4-diazabuta-1,3-diene]nickel[3-(methyl)-4-(pentyl)catecholate]; [1,4-bis{phenyl}-2-(hydrido)-3-(octyl)1,4-diazabuta-1,3-diene]palladium[3-(methyl)-6-(butyl)catecholate]; [1,4-bis{3,5-di(butyl)phenyl}-2-(pentyl)-3-(undecyl)1,4-diazabuta-1,3-diene]nickel[4-(pentyl)catecholate]; [1,4-bis{3,5-di(ethyl)phenyl}-2-(butyl)-3-(pentyl)1,4-diazabuta-1,3-diene]nickel[4-(pentyl)-catecholate]; [1,4-bis{phenyl}-2,3-(dibutyl)1,4-diazabuta-1,3-diene]nickel[3-(methyl)-5-(butyl)catecholate]; [1,4-bis{phenyl}-2-(butyl)-3-(tetracosenyl)1,4-diazabuta-1,3-diene]nickel[4-(methyl)-5-(butyl)catecholate]; [1,4-bis{phenyl}-2-(dodecenyl)-3-(butyl)1,4-diazabuta-1,3-diene]nickel[3-(propyl)catecholate]; [1,4-bis{3-hexylphenyl}-2-(undecynyl)-3-(hydrido)1,4-diazabuta-1,3-diene]nickel[3-(butyl)catecholate]; [1,4-bis{phenyl}-2-(ethyl)-3-(heneicosenyl)1,4-diazabuta-1,3-diene]nickel[3-(ethyl)-4-(methyl)catecholate]; [1,4-bis{3,5-di(methyl)phenyl}-2-(butyl)-3-(hydrido)1,4-diazabuta-1,3-diene]palladium[3,4-di(ethyl)catecholate]; [1,4-bis{phenyl}-2,3-(dibutyl)1,4-diazabuta-1,3-diene]palladium[3-(pentyl)-4,5-di(methyl)catecholate]; [1,4-bis{4-octylaminophenyl}-2-(hexyl)-3-(pentyl)1,4-diazabuta-1,3-diene]nickel[3-(propyl)-5-(pentyl)catecholate]; [1,4-bis{3,5-di(propyl)phenyl}-2-(tetradecenyl)-3-(methyl)1,4-diazabuta-1,3-diene]palladium[4-(propyl)catecholate]; [1,4-bis{3,5-di(butyl)phenyl}-2-(butyl)-3-(octyl)1,4-diazabuta-1,3-diene]palladium[3-(methyl)-4-(butyl)-6-(ethyl)-catecholate]; [1,4-bis{3,4-di(methylethylamino)phenyl}-2-(methyl)-3-(heneicosenyl)1,4-diazabuta-1,3-diene]palladium[4-(butyl)-5-(pentyl)catecholate]; [1,4-bis{3,5-di(ethyl)-phenyl}-2-(hydrido)-3-(butyl)1,4-diazabuta-1,3-diene]nickel[3-(methyl)catecholate]; [1,4-bis{3,5-di(methyl)phenyl}-2-(butyl)-3-(hexyl)1,4-diazabuta-1,3-diene]nickel[3,6-di(propyl)catecholate]; [1,4-bis{3,4-di(pentyl)phenyl}-2,3-(dibutyl)1,4-diazabuta-1,3-diene]palladium[4-(butyl)catecholate]; [1,4-bis{3,4-di(pentyl)phenyl}-2,3-(dioctyl)1,4-diazabuta-1,3-diene]palladium[3,5-di(methyl)-4-(ethyl)catecholate]; [1,4-bis{3-dodecynylphenyl}-2-(hydrido)-3-(butyl)1,4-diazabuta-1,3-diene]palladium[3,6-di(ethyl)catecholate]; [1,4-bis{phenyl}-2,3-(dibutyl)1,4-diazabuta-1,3-diene]nickel[3-(ethyl)-4-(propyl)catecholate]; [1,4-bis{phenyl}-2-(butyl)-3-(octyl)1,4-diazabuta-1,3-diene]nickel[3-(dodecanonyl)-5-(butyl)catecholate]; [1,4-bis{3-pentacosynylphenyl}-2-(hydrido)-3-(pentyl)1,4-diazabuta-1,3-diene]nickel[3-(pentyl)-6-(methyl)catecholate]; [1,4-bis{4-hexadecylphenyl}-2,3-(dibutyl)1,4-diazabuta-1,3-diene]palladium[3-(butyl)-5-(methyl)catecholate]; [1,4-bis{4-pentonylphenyl-}2-(eicosenyl)-3-(heptacosyl)1,4-diazabuta-1,3-diene]nickel[3,4-di(methyl)-6-(methyl)catecholate]; [1,4-bis{3,4-di(butyl)phenyl}2-(hydrido)-3-(hexyl)1,4-diazabuta-1,3-diene]nickel[3-(butyl)-5-(methyl)catecholate]; [1,4-bis{phenyl}-2-(butyl)-3-(pentyl)1,4-diazabuta-1,3-diene]palladium[4-(methyl)-5-(propyl)catecholate]; [1,4-bis{3-heptenylphenyl}-2,3-(dihexyl)-1,4-diazabuta-1,3-diene]nickel[3-(pentyl)-4-(butyl)catecholate]; [1,4-bis{3,5-di(pentyl)-phenyl}-2,3-(dibutyl)1,4-diazabuta-1,3-diene]nickel[4-(methyl)catecholate]; [1,4-bis{phenyl}-2-(hydrido)-3-(pentyl)1,4-diazabuta-1,3-diene]nickel[4-(propyl)-catecholate]; [1,4-bis{phenyl}-2-(methyl)-3-(butyl)1,4-diazabuta-1,3-diene]palladium[3,5-di(methyl)catecholate]; [1,4-bis{3-pentacosylphenyl}-2-(butyl)-3-(pentyl)1,4-diazabuta-1,3-diene]nickel[4-(ethyl)catecholate]; [1,4-bis{3,5-di(ethyl)phenyl}-2-(butyl)-3-(hydrido)1,4-diazabuta-1,3-diene]nickel[4-(butyl)-5-(propyl)catecholate]; [1,4-bis{phenyl}-2-(pentacosenyl)-3-(butyl)1,4-diazabuta-1,3-diene]nickel[3-(diethylamino)-catecholate]; [1,4-bis{3,4-di(butonyl)phenyl}-2-(butyl)-3-(hexyl)1,4-diazabuta-1,3-diene]nickel[4-(propyl)-5-(ethyl)catecholate]; [1,4-bis{phenyl}-2-(hexyl)-3-(butyl)1,4-diazabuta-1,3-diene]nickel[3-(methyl)catecholate]; [1,4-bis{phenyl}-2-(butyl)-3-(octyl)-1,4-diazabuta-1,3-diene]palladium[3-(propyl)catecholate]; [1,4-bis{4-dodecanonyl-phenyl}-2,3-(dibutyl)1,4-diazabuta-1,3-diene]nickel[3-(methyl)catecholate]; [1,4-bis{3,5-di(methyl)phenyl}-2-(heptynyl)-3-(methyl)1,4-diazabuta-1,3-diene]palladium[3-(butyl)catecholate]; [1,4-bis{3,4-di(ethyl)phenyl}-2,3-(dibutyl)1,4-diazabuta-1,3-diene]nickel[3-(ethyl)catecholate]; [1,4-bis{phenyl}-2-(hexyl)-3-(pentynyl)1,4-diazabuta-1,3-diene]nickel[4-(pentyl)catecholate]; [1,4-bis{4-dodecylphenyl}-2-(butyl)-3-(nonenyl)-1,4-diazabuta-1,3-diene]palladium[3-(propyl)catecholate]; [1,4-bis{phenyl}-2-(hexyl)-3-(hydrido)1,4-diazabuta-1,3-diene]nickel[3-(ethyl)-5-(butyl)catecholate]; [1,4-bis{phenyl}-2,3-(dihydrido)1,4-diazabuta-1,3-diene]nickel[3,4-di(methyl)catecholate]; [1,4-bis{3,4-di(propyl)phenyl}-2,3-(dibutyl)1,4-diazabuta-1,3-diene]palladium[3-(propyl)-4,5-di(ethyl)catecholate]; [1,4-bis{3,5-di(butyl)phenyl}-2-(hydrido)-3-(pentyl)-1,4-diazabuta-1,3-diene]palladium[3,6-di(ethyl)catecholate]; [1,4-bis{4-dodecaphosphinophenyl}-2-(hydrido)-3-(octacosenyl)1,4-diazabuta-1,3-diene]palladium[3-(ethyl)catecholate]; [1,4-bis{3,5-di(methyl)phenyl}-2-(butyl)-3-(octyl)1,4-diazabuta-1,3-diene]palladium[3-(methyl)-5-(ethyl)catecholate]; [1,4-bis{3,4-di(butyl)phenyl}-2-(pentyl)-3-(propenyl)1,4-diazabuta-1,3-diene]nickel[3-(methyl)-4-(pentyl)-5-(butonyl)-catecholate]; [1,4-bis{3,4-di(methyl)phenyl}-2-(octyl)-3-(hexyl)1,4-diazabuta-1,3-diene]nickel[3-(butyl)-6-(methyl)catecholate]; [1,4-bis{3,5-di(pentyl)phenyl}-2-(hexyl)-3-(butyl)1,4-diazabuta-1,3-diene]nickel[3-(butyl)catecholate]; [1,4-bis{3,5-di(methyl)-phenyl}-2-(butyl)-3-(pentynyl)1,4-diazabuta-1,3-diene]nickel[4,5-di(propyl)-catecholate]; [1,4-bis{3,5-di(propyl)phenyl}-2-(hydrido)-3-(butyl)1,4-diazabuta-1,3-diene]palladium[3-(methyl)-6-(pentyl)catecholate]; [1,4-bis{3,5-di(methyl)phenyl}-2-(methyl)-3-(hexyl)1,4-diazabuta-1,3-diene]nickel[4-(ethyl)catecholate]; [1,4-bis{3,5-di(pentyl)phenyl}-2-(butyl)-3-(hexyl)1,4-diazabuta-1,3-diene]palladium[3-(butyl)-4-(propyl)catecholate]; [1,4-bis{3,5-di(propyl)phenyl}-2-(hydrido)-3-(undecenyl)1,4-diazabuta-1,3-diene]nickel[3-(ethyl)-6-(propyl)catecholate]; [1,4-bis{3,4-di(propyl)-phenyl}-2-(hydrido)-3-(triacontenyl)1,4-diazabuta-1,3-diene]palladium[3-(pentyl)-4-(butyl)-6-(methyl)

catecholate]; [1,4-bis{4-butanalylphenyl}-2-(ethyl)-3-(butyl)1,4-diazabuta-1,3-diene]nickel[4-(methyl)-5-(ethyl)catecholate]; [1,4-bis{3,5-di(methyl)-phenyl}-2-(butyl)-3-(hydrido)1,4-diazabuta-1,3-diene]nickel[3-(methyl)-4-(hexyl)-5-(propyl)catecholate]; [1,4-bis{3,5-di(butyl)phenyl}-2-(butyl)-3-(hydrido)1,4-diazabuta-1,3-diene]palladium[3-(butyl)-4-(pentyl)-5-(methyl)catecholate]; [1,4-bis{4-hexadecynylphenyl}-2-(pentyl)-3-(methyl)1,4-diazabuta-1,3-diene]nickel[3-(pentyl)-catecholate]; [1,4-bis{3-tetracosylphenyl}-2-(butyl)-3-(hydrido)1,4-diazabuta-1,3-diene]nickel[4-(propyl)catecholate]; [1,4-bis{phenyl}-2-(butyl)-3-(nonadecyl)1,4-diazabuta-1,3-diene]palladium[4-(pentyl)catecholate]; [1,4-bis{3,5-di(ethyl)phenyl}-2-(hexyl)-3-(octyl)1,4-diazabuta-1,3-diene]nickel[3-(methyl)-4-(pentyl)catecholate]; [1,4-bis{3,4-di(butyl)phenyl}-2-(undecenyl)-3-(hexyl)1,4-diazabuta-1,3-diene]nickel[3-(propyl)-4-(butonyl)-5-(ethyl)catecholate]; [1,4-bis{phenyl}-2-(pentenyl)-3-(butyl)1,4-diazabuta-1,3-diene]palladium[3-(ethyl)-5-(pentyl)catecholate]; [1,4-bis{3,4-di(ethyl)phenyl}-2-(ethyl)-3-(methyl)1,4-diazabuta-1,3-diene]nickel[3-(propyl)-5-(ethyl)catecholate]; [1,4-bis{3,5-di(methyl)phenyl}-2-(hydrido)-3-(tricosyl)1,4-diazabuta-1,3-diene]nickel[3-(butyl)-5-(propyl)catecholate]; [1,4-bis{phenyl}-2-(ethyl)-3-(butyl)1,4-diazabuta-1,3-diene]nickel[3-(pentyl)-6-(ethyl)catecholate]; [1,4-bis{4-propanalylphenyl}-2-(butyl)-3-(hydrido)1,4-diazabuta-1,3-diene]nickel[3-(butyl)-4,6-di(methyl)catecholate]; [1,4-bis{phenyl}-2-(butyl)-3-(hydrido)1,4-diazabuta-1,3-diene]nickel[3-(methyl)-catecholate]; [1,4-bis{phenyl}-2,3-(dibutyl)1,4-diazabuta-1,3-diene]nickel[3-(propyl)-4-(pentyl)-5-(butyl)catecholate]; [1,4-bis{phenyl}-2-(hydrido)-3-(butyl)1,4-diazabuta-1,3-diene]nickel[3,6-di(pentyl)catecholate]; [1,4-bis{3,4-di(tridocosanalyl)phenyl}-2-(butyl)-3-(undecynyl)1,4-diazabuta-1,3-diene]nickel[3-(methyl)-4-(butyl)catecholate]; [1,4-bis{3,4-di(propyl)phenyl}-2-(hydrido)-3-(docosyl)1,4-diazabuta-1,3-diene]nickel[3-(propyl)-4-(ethyl)catecholate]; [1,4-bis{3,4-di(butyl)phenyl}-2-(butyl)-3-(pentyl)1,4-diazabuta-1,3-diene]nickel[3-(propyl)-6-(butyl)catecholate]; [1,4-bis{3,4-di(methyl)-phenyl}-2-(pentyl)-3-(octyl)1,4-diazabuta-1,3-diene]palladium[4-(methyl)-5-(ethyl)-catecholate]; [1,4-bis{phenyl}-2-(butyl)-3-(butynyl)1,4-diazabuta-1,3-diene]nickel[3-(pentyl)-4-(ethyl)catecholate]; [1,4-bis{3-ethylphenyl}-2-(butyl)-3-(methyl)1,4-diazabuta-1,3-diene]palladium[3-(butyl)catecholate]; [1,4-bis{3,5-di(methyl)phenyl}-2,3-(dihydrido)1,4-diazabuta-1,3-diene]nickel[4-(pentyl)-5-(methyl)catecholate]; [1,4-bis{3,4-di(pentyl)phenyl}-2-(hydrido)-3-(butyl)1,4-diazabuta-1,3-diene]nickel[3-(propyl)-4-(butyl)catecholate]; [1,4-bis{4-octynylphenyl}-2-(butyl)-3-(ethyl)1,4-diazabuta-1,3-diene]palladium[4-(ethyl)catecholate]; [1,4-bis{phenyl}-2-(butyl)-3-(octyl)1,4-diazabuta-1,3-diene]nickel[4-(ethyl)catecholate]; [1,4-bis{3-proponyl-phenyl}-2-(hexyl)-3-(heneicosynyl)1,4-diazabuta-1,3-diene]nickel[3-(pentyl)-6-(propyl)catecholate]; [1,4-bis{3-heptacosynylphenyl}-2-(pentyl)-3-(hydrido)1,4-diazabuta-1,3-diene]palladium[4-(pentyl)catecholate]; [1,4-bis{3-hexadecynylphenyl}-2-(hexyl)-3-(hexadecynyl)1,4-diazabuta-1,3-diene]nickel[3-(butyl)-4-(ethyl)-catecholate]; [1,4-bis{3-triacontenylphenyl}-2-(pentyl)-3-(undecyl)1,4-diazabuta-1,3-diene]nickel[3-(butyl)catecholate]; [1,4-bis{3,4-di(methyl)phenyl}-2-(undecenyl)-3-(butyl)1,4-diazabuta-1,3-diene]nickel[3,4-di(ethyl)catecholate]; [1,4-bis{4-nonacosynyl-phenyl}-2-(hydrido)-3-(butyl)1,4-diazabuta-1,3-diene]nickel[3-(ethyl)catecholate]; [1,4-bis{4-octadecynylphenyl}-2-(butyl)-3-(hydrido)1,4-diazabuta-1,3-diene]nickel[3,6-di(ethyl)-4-(pentyl)catecholate]; [1,4-bis{phenyl}-2-(butyl)-3-(hexyl)1,4-diazabuta-1,3-diene]palladium[3-(butyl)catecholate]; [1,4-bis{3,4-di(butyl)phenyl}-2-(pentyl)-3-(hydrido)1,4-diazabuta-1,3-diene]nickel[3-(methyl)catecholate]; [1,4-bis{3,5-di(methyl)phenyl}-2-(eicosenyl)-3-(octyl)1,4-diazabuta-1,3-diene]nickel[3-(ethyl)-4,6-di(methyl)catecholate]; [1,4-bis{phenyl}-2-(pentyl)-3-(butyl)1,4-diazabuta-1,3-diene]palladium[3-(butyl)catecholate]; [1,4-bis{3,4-di(propyl)phenyl}-2,3-(dioctyl)1,4-diazabuta-1,3-diene]nickel[3-(dodecamino)-6-(propyl)catecholate]; [1,4-bis{phenyl}-2-(hydrido)-3-(butyl)1,4-diazabuta-1,3-diene]nickel[4-(propyl)catecholate]; [1,4-bis{3,5-di(butonyl)phenyl}-2-(hexyl)-3-(butyl)1,4-diazabuta-1,3-diene]nickel[3-(butyl)-catecholate]; [1,4-bis{3-dodecylphenyl}-2-(butyl)-3-(hydrido)1,4-diazabuta-1,3-diene]nickel[3-(methyl)catecholate]; [1,4-bis{4-octacosenylphenyl}-2-(octyl)-3-(tetracosenyl)-1,4-diazabuta-1,3-diene]nickel[4-(dodecanonyl)catecholate]; [1,4-bis{3,5-di(ethyl)-phenyl}-2-(hydrido)-3-(octadecyl)1,4-diazabuta-1,3-diene]nickel[3,5-di(ethyl)-catecholate]; [1,4-bis{phenyl}-2-(hydrido)-3-(butyl)1,4-diazabuta-1,3-diene]nickel[3-(methyl)catecholate]; [1,4-bis{4-decylphenyl}-2-(pentyl)-3-(hydrido)1,4-diazabuta-1,3-diene]nickel[3-(butyl)-5-(pentyl)catecholate]; [1,4-bis{4-octynylphenyl}-2-(docosenyl)-3-(hexyl)1,4-diazabuta-1,3-diene]nickel[3,4-di(ethyl)catecholate]; [1,4-bis{phenyl}-2,3-(dibutyl)1,4-diazabuta-1,3-diene]nickel[4-(hexonyl)catecholate]; [1,4-bis{3,5-di(ethyl)-phenyl}-2-(hydrido)-3-(butyl)1,4-diazabuta-1,3-diene]nickel[3-(propyl)-5-(ethyl)-catecholate]; [1,4-bis{3,5-di(butyl)phenyl}-2-(hexyl)-3-(hydrido)1,4-diazabuta-1,3-diene]nickel[3-(butyl)-4-(propyl)catecholate]; [1,4-bis{3,5-di(butyl)phenyl}-2-(pentyl)-3-(ethyl)1,4-diazabuta-1,3-diene]nickel[3-(butyl)-4-(ethyl)catecholate]; [1,4-bis{4-ethanalylphenyl}-2-(butenyl)-3-(butyl)1,4-diazabuta-1,3-diene]nickel[4-(methyl)-5-(pentyl)catecholate]; [1,4-bis{3,4-di(pentyl)phenyl}-2,3-(dibutyl)1,4-diazabuta-1,3-diene]palladium[3-(methyl)-4-(butyl)catecholate]; [1,4-bis{phenyl}-2-(hydrido)-3-(butyl)1,4-diazabuta-1,3-diene]nickel[4-(propyl)catecholate]; [1,4-bis{phenyl}-2-(ethyl)-3-(hydrido)1,4-diazabuta-1,3-diene]palladium[3-(ethyl)-5-(butyl)catecholate]; [1,4-bis{3,4-di(ethyl)phenyl}-2-(butyl)-3-(octyl)1,4-diazabuta-1,3-diene]palladium[4-(butyl)catecholate]; [1,4-bis{3,4-di(pentyl)phenyl}-2-(hexyl)-3-(butyl)1,4-diazabuta-1,3-diene]nickel[3-(pentyl)-4-(ethyl)catecholate]; [1,4-bis{3,5-di(butonyl)phenyl}-2-(pentyl)-3-(butyl)1,4-diazabuta-1,3-diene]nickel[3-(butyl)-5-(pentyl)catecholate]; [1,4-bis{3,4-di(propyl)phenyl}-2,3-(dibutyl)1,4-diazabuta-1,3-diene]nickel[4-(methyl)-catecholate]; [1,4-bis{3,4-di(propyl)phenyl}-2-(hexynyl)-3-(tricosyl)1,4-diazabuta-1,3-diene]nickel[3-(pentyl)catecholate]; [1,4-bis{3,5-di(butyl)phenyl}-2-(hexyl)-3-(docosenyl)1,4-diazabuta-1,3-diene]nickel[4-(methyl)-5-(ethyl)catecholate]; [1,4-bis{3,5-di(pentyl)phenyl}-2,3-(dibutyl)1,4-diazabuta-1,3-diene]palladium[3-(pentyl)catecholate]; [1,4-bis{3,5-di(pentyl)phenyl}-2-(hexyl)-3-(butyl)1,4-diazabuta-1,3-diene]palladium[3-(methyl)catecholate]; [1,4-bis{phenyl}-2-(octacosenyl)-3-(butyl)1,4-diazabuta-1,3-diene]palladium[3-(butyl)-5-(ethyl)catecholate]; [1,4-bis{phenyl}-2,3-(dihydrido)1,4-diazabuta-1,3-diene]nickel[4-(pentyl)catecholate]; [1,4-bis{3-pentadecynylphenyl}-2-(hexyl)-3-(pentyl)1,4-diazabuta-1,3-diene]nickel[3-(pentyl)-catecholate]; [1,4-bis{phenyl}-2,3-(dibutyl)1,4-diazabuta-1,3-diene]palladium[3-(propyl)catecholate]; (propyl)catecholate]; [1,4-bis{phenyl}-2-(methyl)-3-(butyl)1,4-diazabuta-1,3- diene]nickel[3-(diethylamino)-6-(propyl)catecholate]; [1,4-bis{phenyl}-2-(hexyl)-3-(hydrido)-1,4-diazabuta-1,3-diene]nickel[4-(ethyl)catecholate]; [1,4-bis{3,4-di(pentyl)phenyl}-2-(ethyl)-3-(butyl)1,4-diazabuta-1,3-diene]nickel[3-(pentyl)-6-(ethyl)catecholate]; [1,4-bis{phenyl}-2-(butyl)-3-(pentyl)1,4-diazabuta-1,3-diene]nickel[3,6-di(ethyl)-catecholate]; [1,4-bis{3,4-di(ethyl)phenyl}-2-(docosyl)-3-(butyl)1,4-diazabuta-1,3-diene]nickel[3-(methyl)-4-(pentyl)catecholate]; [1,4-bis{3-heptylphenyl}-2,3-(dibutyl)1,4-diazabuta-1,3-diene]nickel[4-(butyl)-5-(propyl)catecholate]; [1,4-bis{phenyl}-2,3-(dibutyl)1,4-diazabuta-1,3-diene]palladium[3-(pentyl)-4-(butyl)-6-(methyl)catecholate]; [1,4-bis{phenyl}-2-(butyl)-3-(hexyl)1,4-diazabuta-1,3-diene]nickel[4-(methyl)-catecholate]; [1,4-bis{3,4-di(ethyl)phenyl}-2-(octyl)-3-(butyl)1,4-diazabuta-1,3-diene]nickel[3-(ethyl)catecholate]; [1,4-bis{3,4-di(methyl)phenyl}-2,3-(dipentyl)1,4-diazabuta-1,3-diene]nickel[3-(ethyl)-5-(butyl)catecholate]; [1,4-bis{phenyl}-2-(butyl)-3-(ethyl)-1,4-diazabuta-1,3-diene]nickel[3-(propyl)-6-(methyl)catecholate]; [1,4-bis{3,4-di(ethyl)-phenyl}-2-(methyl)-3-(butyl)1,4-diazabuta-1,3-diene]palladium[3,4-di(ethyl)-6-(pentyl)-catecholate]; [1,4-bis{phenyl}-2-(hydrido)-3-(butyl)1,4-diazabuta-1,3-diene]palladium[3-(propyl)-4-(pentyl)catecholate]; [1,4-bis{3,4-di(dodecamino)phenyl}-2-(hexyl)-3-(tricosyl)1,4-diazabuta-1,3-diene]palladium[4-(methyl)catecholate]; [1,4-bis{3,5-di(pentyl)phenyl}-2,3-(dioctyl)1,4-diazabuta-1,3-diene]nickel[4-(methyl)-5-(ethyl)-catecholate]; [1,4-bis{phenyl}-2,3-(dihydrido)1,4-diazabuta-1,3-diene]nickel[4-(propyl)-5-(pentyl)catecholate]; [1,4-bis{phenyl}-2,3-(dibutyl)1,4-diazabuta-1,3-diene]palladium[4-(methyl)catecholate]; [1,4-bis{3,5-di(pentyl)phenyl}2-(octyl)-3-(butyl)1,4-diazabuta-1,3-diene]nickel[3-(methyl)-4-(pentyl)catecholate]; [1,4-bis{3,4-di(ethyl)-phenyl}-2-(butyl)-3-(pentyl)1,4-diazabuta-1,3-diene]palladium[3-(butyl)-6-(pentyl)-catecholate]; [1,4-bis{3,5-di(pentyl)phenyl}-2-(hydrido)-3-(hexyl)1,4-diazabuta-1,3-diene]palladium[3,4-di(propyl)catecholate]; [1,4-bis{phenyl}-2,3-(dibutyl)1,4-diazabuta-1,3-diene]nickel[4-(butyl)-5-(methyl)catecholate]; [1,4-bis{phenyl}-2-(butyl)-3-(hydrido)1,4-diazabuta-1,3-diene]nickel[4-(pentyl)-5-(dodecamino)catecholate]; [1,4-bis{3,4-di(propyl)phenyl}-2-(butyl)-3-(hydrido)1,4-diazabuta-1,3-diene]nickel[3-(ethyl)catecholate]; [1,4-bis{phenyl}-2,3-(dibutyl)1,4-diazabuta-1,3-diene]nickel[3,5-di(methyl)catecholate]; [1,4-bis{3-dodecaphosphinophenyl}-2,3-(dibutyl)1,4-diazabuta-1,3-diene]palladium[4-(propyl)-5-(pentyl)catecholate]; [1,4-bis{phenyl}-2-(nonyl)-3-(butyl)1,4-diazabuta-1,3-diene]palladium[3-(octylamino)catecholate]; [1,4-bis{3-nonynylphenyl}-2-(octynyl)-3-(butyl)1,4-diazabuta-1,3-diene]nickel[4-(ethyl)-catecholate]; [1,4-bis{phenyl}-2-(butyl)-3-(hexyl)1,4-diazabuta-1,3-diene]nickel[3-(methyl)-5-(butyl)catecholate]; [1,4-bis{phenyl}-2-(octyl)-3-(hydrido)1,4-diazabuta-1,3-diene]nickel[4-(ethyl)catecholate]; [1,4-bis{phenyl}-2-(hydrido)-3-(hexyl)1,4-diazabuta-1,3-diene]nickel[4-(ethyl)catecholate]; [1,4-bis{3,5-di(methyl)phenyl}-2,3-(dibutyl)1,4-diazabuta-1,3-diene]palladium[3-(propyl)-4-(methyl)catecholate]; [1,4-bis{3,4-di(butyl)phenyl}-2,3-(dibutyl)1,4-diazabuta-1,3-diene]nickel[4-(pentyl)-catecholate]; [1,4-bis{3,5-di(methyl)phenyl}-2-(butyl)-3-(hydrido)1,4-diazabuta-1,3-diene]nickel[3,6-di(propyl)catecholate]; [1,4-bis{3,4-di(ethyl)phenyl}-2-(butyl)-3-(pentacosynyl)1,4-diazabuta-1,3-diene]nickel[3-(pentyl)catecholate]; [1,4-bis{3,5-di(methyl)phenyl}-2-(pentyl)1,4-diazabuta-1,3-diene]nickel[4-(methyl)-catecholate]; [1,4-bis{3,4-di(butyl)phenyl}-2-(hexadecynyl)-3-(butyl)1,4-diazabuta-1,3-diene]nickel[3-(butyl)catecholate]; [1,4-bis{phenyl}-2-(hydrido)-3-(pentyl)1,4-diazabuta-1,3-diene]nickel[3-(pentyl)catecholate]; [1,4-bis{3,5-di(ethyl)phenyl}-2-(butyl)-3-(hydrido)1,4-diazabuta-1,3-diene]nickel[4-(butyl)catecholate]; [1,4-bis{3,5-di(pentyl)phenyl}-2-(butyl)-3-(hydrido)1,4-diazabuta-1,3-diene]nickel[3-(ethyl)-4-(butyl)-5-(pentyl)catecholate]; [1,4-bis{phenyl}-2-(butyl)-3-(hexyl)1,4-diazabuta-1,3-diene]nickel[4-(propyl)-5-(ethyl)catecholate]; [1,4-bis{3-tetradecylphenyl}-2,3-(dibutyl)1,4-diazabuta-1,3-diene]palladium[4-(pentyl)-5-(dodecamino)catecholate]; [1,4-bis{3,4-di(ethyl)phenyl}-2-(butyl)-3-(octyl)1,4-diazabuta-1,3-diene]nickel[3-(butyl)-4-(propyl)catecholate]; [1,4-bis{3,5-di(methyl)phenyl}-2-(methyl)-3-(butyl)1,4-diazabuta-1,3-diene]nickel[4-(butyl)-5-(methyl)catecholate]; [1,4-bis{3,4-di(pentyl)-phenyl}-2-(pentyl)-3-(triacontyl)1,4-diazabuta-1,3-diene]palladium[3-(butyl)-catecholate]; [1,4-bis{3,5-di(pentyl)phenyl}-2-(decyl)-3-(hexyl)1,4-diazabuta-1,3-diene]nickel[3-(propyl)-4-(ethyl)-5-(butyl)catecholate]; [1,4-bis{3,5-di(butyl)phenyl}-2,3-(dibutyl)1,4-diazabuta-1,3-diene]palladium[3-(ethyl)-5-(propyl)catecholate]; [1,4-bis{3,5-di(butyl)phenyl}-2,3-(dibutyl)1,4-diazabuta-1,3-diene]nickel[3-(propyl)-4-(ethyl)catecholate]; [1,4-bis{3,5-di(pentyl)phenyl}-2-(butyl)-3-(hydrido)1,4-diazabuta-1,3-diene]nickel[4-(ethyl)-5-(pentyl)catecholate]; [1,4-bis{3-trimethylsilylethylphenyl}-2,3-(dibutyl)1,4-diazabuta-1,3-diene]nickel[3-(pentyl)-4-(propyl)-6-(methyl)-catecholate]; [1,4-bis{3,5-di(propyl)phenyl}-2-(ethyl)-3-(octyl)1,4-diazabuta-1,3-diene]palladium[3-(methyl)-6-(pentyl)catecholate]; [1,4-bis{3-nonylphenyl}-2,3-(dibutyl)1,4-diazabuta-1,3-diene]nickel[3-(ethyl)-5-(methyl)catecholate]; [1,4-bis{4-heptenyl-phenyl}-2-(octyl)-3-(hydrido)1,4-diazabuta-1,3-diene]nickel[4-(propyl)catecholate]; [1,4-bis{phenyl}-2-(methyl)-3-(hydrido)1,4-diazabuta-1,3-diene]palladium[3-(pentyl)-5-(butyl)catecholate]; [1,4-bis{3,5-di(pentyl)phenyl}-2-(methyl)-3-(hexyl)1,4-diazabuta-1,3-diene]nickel[3-(propyl)-5-(ethyl)catecholate];

[1,4-bis{3-octadecynylphenyl}-2-(butyl)-3-(pentyl)1,4-diazabuta-1,3-diene]nickel[4-(ethyl)catecholate]; [1,4-bis{3,5-di(propyl)phenyl}-2-(butyl)-3-(hexyl)1,4-diazabuta-1,3-diene]nickel[3-(ethyl)-4,5-di(pentyl)catecholate]; [1,4-bis{phenyl}-2-(hydrido)-3-(butyl)1,4-diazabuta-1,3-diene]palladium[3-(ethyl)-5-(methyl)catecholate]; [1,4-bis{3-heptadecynylphenyl}-2-(hexyl)-3-(butyl)1,4-diazabuta-1,3-diene]nickel[3-(butyl)-5-(methyl)catecholate]; [1,4-bis{3,5-di(propyl)phenyl}-2-(hydrido)-3-(butyl)1,4-diazabuta-1,3-diene]nickel[4-(pentyl)-5-(hexyl)catecholate]; [1,4-bis{phenyl}-2-(hexyl)-3-(butyl)1,4-diazabuta-1,3-diene]nickel[3-(pentyl)-4-(propyl)catecholate]; [1,4-bis{3-heptylphenyl}-2-(octyl)-3-(hexyl)1,4-diazabuta-1,3-diene]nickel[3,4-di(ethyl)-5-(methyl)catecholate]; [1,4-bis{phenyl}-2-(butyl)-3-(pentyl)1,4-diazabuta-1,3-diene]palladium[3-(butyl)catecholate]; [1,4-bis{phenyl}-2-(octyl)-3-(hexyl)1,4-diazabuta-1,3-diene]nickel[3-(methyl)-4-(butyl)-6-(pentyl)catecholate]; [1,4-bis{phenyl}-2-(butyl)-3-(octyl)1,4-diazabuta-1,3-diene]nickel[4-(methyl)catecholate]; [1,4-bis{3-docosenyl-phenyl}-2-(butyl)-3-(octyl)1,4-diazabuta-1,3-diene]nickel[4,5-di(methyl)catecholate]; [1,4-bis{3,5-di(methyl)phenyl}-2-(hydrido)-3-(ethyl)1,4-diazabuta-1,3-diene]nickel[3-(ethyl)-4-(butyl)catecholate]; [1,4-bis{3,5-di(dodecamino)phenyl}-2-(hexacosynyl)-3-(pentyl)1,4-diazabuta-1,3-diene]nickel[3-(propyl)-6-(ethyl)catecholate]; [1,4-bis{3,5-di(butyl)phenyl}-2-(heptadecenyl)-3-(methyl)1,4-diazabuta-1,3-diene]nickel[4-(butyl)-catecholate]; [1,4-bis{3,4-di(methyl)phenyl}-2,3-

(dibutyl)1,4-diazabuta-1,3-diene]nickel[3-(butyl)-6-(pentyl) catecholate]; [1,4-bis{3,4-di(pentyl)phenyl}-2-(butyl)-3-(hydrido)-1,4-diazabuta-1,3-diene]nickel[4-(butyl) catecholate]; [1,4-bis{3-trimethylsilylethyl-phenyl}-2-(hydrido)-3-(octyl)1,4-diazabuta-1,3-diene]nickel[3-(propyl)-5-(pentyl)-catecholate]; [1,4-bis{3,4-di(butyl) phenyl}-2-(heptadecyl)-3-(octyl)1,4-diazabuta-1,3-diene] nickel[3-(butyl)-4-(methyl)catecholate]; [1,4-bis{4-pentacosylphenyl}-2-(ethyl)-3-(octadecynyl)1,4-diazabuta-1,3-diene]nickel[3-(ethyl)catecholate]; [1,4-bis{3,4-di (butyl)phenyl}-2,3-(dibutyl)1,4-diazabuta-1,3-diene]nickel [3-(ethyl)catecholate]; [1,4-bis{phenyl}-2-(hydrido)-3-(butyl)1,4-diazabuta-1,3-diene]palladium[3,4-di(ethyl)-6-(pentyl)catecholate]; [1,4-bis{3,5-di(propyl)phenyl}-2-(butyl)-3-(octyl)1,4-diazabuta-1,3-diene]nickel[4-(ethyl)-5-(pentyl)catecholate]; [1,4-bis{phenyl}-2-(hydrido)-3-(butyl)-1,4-diazabuta-1,3-diene]nickel[4-(propanalyl)-5-(propyl)catecholate]; [1,4-bis{3,5-di(methyl)phenyl}-2-(butyl)-3-(methyl)1,4-diazabuta-1,3-diene]nickel[3-(butyl)-catecholate]; [1,4-bis{phenyl}-2-(methyl)-3-(butyl)1,4-diazabuta-1,3-diene]nickel[3-(propyl)catecholate]; [1,4-bis{3,5-di(pentyl)phenyl}-2-(hydrido)-3-(butyl)1,4-diazabuta-1,3-diene]nickel[4-(ethyl)catecholate]; [1,4-bis{3,5-di(butyl)phenyl}-2,3-(dihydrido)1,4-diazabuta-1,3-diene]palladium[4-(ethyl)catecholate]; [1,4-bis{phenyl}-2-(butyl)-3-(hexyl)1,4-diazabuta-1,3-diene]nickel[3,6-di (ethyl)catecholate]; [1,4-bis{3,4-di(pentyl)-phenyl}-2-(butyl)-3-(octyl)1,4-diazabuta-1,3-diene]palladium[3-(methyl)catecholate]; [1,4-bis{4-hexadecynylphenyl}-2,3-(dioctyl)1,4-diazabuta-1,3-diene]nickel[4-(methyl)-5-(butyl)catecholate]; [1,4-bis{3,5-di(methyl)phenyl}-2-(butyl)-3-(hexyl)1,4-diazabuta-1,3-diene]nickel[3-(pentyl)-5-(butyl)catecholate]; [1,4-bis{3,5-di(ethyl)phenyl}-2-(hydrido)-3-(butyl)1,4-diazabuta-1,3-diene]nickel[3-(propyl)catecholate]; [1,4-bis{phenyl}-2-(hexyl)-3-(pentyl) 1,4-diazabuta-1,3-diene]nickel[4-(propyl)-5-(ethyl)-catecholate]; [1,4-bis{3-dodecylphenyl}-2-(butyl)-3-(hexadecyl)1,4-diazabuta-1,3-diene]palladium[4-(propyl) catecholate]; [1,4-bis{phenyl}-2-(hexyl)-3-(butyl)1,4-diazabuta-1,3-diene]palladium[3-(ethyl)catecholate]; [1,4-bis{3,5-di(ethyl)phenyl}-2-(butyl)-3-(hydrido)1,4-diazabuta-1,3-diene]palladium[3-(ethyl)-4-(butyl) catecholate]; [1,4-bis{4-heptacosylphenyl}-2-(butyl)-3-(hydrido)1,4-diazabuta-1,3-diene]nickel[3-(propyl)-catecholate]; [1,4-bis{3,5-di(pentyl)phenyl}-2-(hydrido)-3-(butyl)1,4-diazabuta-1,3-diene]palladium[3-(butyl)-6-(ethyl)catecholate]; [1,4-bis{3,4-di(propyl)phenyl}-2-(pentyl)-3-(hydrido)1,4-diazabuta-1,3-diene]nickel[3-(pentyl)-5-(butyl)catecholate]; [1,4-bis{4-tridecenylphenyl}-2-(heneicosyl)-3-(hexyl)1,4-diazabuta-1,3-diene]palladium[3,4-di(methyl)-6-(methyl)catecholate]; [1,4-bis{phenyl}-2,3-(dibutyl)1,4-diazabuta-1,3-diene] palladium[4-(methyl)-5-(pentyl)catecholate]; [1,4-bis{phenyl}-2-(butyl)-3-(pentyl)1,4-diazabuta-1,3-diene] palladium[4-(ethyl)-5-(methyl)catecholate]; [1,4-bis{3,5-di (ethyl)phenyl}-2-(butyl)-3-(hexenyl)1,4-diazabuta-1,3-diene]nickel[3-(methyl)catecholate]; [1,4-bis{3,4-di(pentyl) phenyl}-2-(tetracosenyl)-3-(heptadecynyl)-1,4-diazabuta-1, 3-diene]nickel[3-(ethyl)-5-(pentyl)catecholate]; [1,4-bis{3, 5-di(propyl)-phenyl}-2,3-(dioctyl)1,4-diazabuta-1,3-diene] nickel[3-(propyl)-5-(pentyl)catecholate]; [1,4-bis{3,4-di (propyl)phenyl}-2,3-(dihydrido)1,4-diazabuta-1,3-diene] nickel[4-(pentyl)catecholate]; [1,4-bis{3,5-di(ethyl) phenyl}-2-(hydrido)-3-(butyl)1,4-diazabuta-1,3-diene] nickel[3-(butyl)-4-(methyl)-5-(ethyl)catecholate]; [1,4-bis{3-hexacosynyl-phenyl}-2-(pentyl)-3-(butyl)1,4-diazabuta-1,3-diene]nickel[3-(propyl)-6-(butyl)-catecholate]; [1,4-bis{4-hexadecenylphenyl}-2-(pentyl)-3-(butyl),4-diazabuta-1,3-diene]nickel[3-(methyl)-4-(ethyl) catecholate]; [1,4-bis{phenyl}-2,3-(dibutyl)1,4-diazabuta-1, 3-diene]nickel[3-(pentyl)catecholate]; [1,4-bis{3-tetradecylphenyl}-2-(nonadecyl)-3-(hexyl)-1,4-diazabuta-1, 3-diene]nickel[3-(butyl)-6-(methyl)catecholate]; [1,4-bis{3, 4-di(ethyl)phenyl}-2-(butyl)-3-(hydrido)1,4-diazabuta-1,3-diene]nickel[3-(propyl)-4-(pentyl)-6-(butyl)catecholate]; [1,4-bis{phenyl}-2,3-(dibutyl)1,4-diazabuta-1,3-diene] nickel[3-(propyl)-6-(ethyl)catecholate]; [1,4-bis{3,4-di (ethyl)phenyl}-2,3-(dibutyl)1,4-diazabuta-1,3-diene]nickel [4-(methyl)catecholate]; [1,4-bis{3,5-di(methyl)phenyl}-2-(pentyl)-3-(hexyl)1,4-diazabuta-1,3-diene]nickel[3,5-di (butyl)-4-(propyl)catecholate]; [1,4-bis{3,4-di(butyl) phenyl}-2,3-(dihydrido)1,4-diazabuta-1,3-diene]palladium [4-(methyl)catecholate]; [1,4-bis{phenyl}-2-(octyl)-3-(pentadecenyl)1,4-diazabuta-1,3-diene]palladium[4-(methyl)-5-(ethyl)catecholate]; [1,4-bis{3,5-di (dodecamino)phenyl}-2-(octyl)-3-(hydrido)1,4-diazabuta-1,3-diene]nickel[3,4-di(methyl)-6-(methyl)-catecholate]; [1,4-bis{3-eicosynylphenyl}-2-(pentacosenyl)-3-(hydrido) 1,4-diazabuta-1,3-diene]; nickel[4-(methyl)catecholate]; [1,4-bis{3,5-di(pentyl)phenyl}-2-(butyl)-3-(ethyl)-1,4-diazabuta-1,3-diene]nickel[3-(methyl)-4-(propyl)-5-(butyl) catecholate]; [1,4-bis{4-trimethylsilylethylphenyl}-2-(hexyl)-3-(octyl)1,4-diazabuta-1,3-diene]palladium[3-(propyl)-5-(butyl)catecholate]; [1,4-bis{4-butenylphenyl}-2-(butyl)-3-(hydrido)1,4-diazabuta-1,3-diene]palladium[3, 6-di(ethyl)catecholate]; [1,4-bis{phenyl}-2,3-(dipentyl)1,4-diazabuta-1,3-diene]palladium[3-(methyl)-5-(propyl) catecholate]; [1,4-bis{3-tricosenylphenyl}-2-(butyl)-3-(hydrido)1,4-diazabuta-1,3-diene]nickel[3-(ethyl)-catecholate]; [1,4-bis{3-nonadecylphenyl}-2-(heneicosyl)-3-(butyl)1,4-diazabuta-1,3-diene]palladium[3-(methyl) catecholate]; [1,4-bis{phenyl}-2-(ethyl)-3-(octyl)1,4-diazabuta-1,3-diene]nickel[3-(ethyl)catecholate]; [1,4-bis{phenyl}-2-(hydrido)-3-(butyl)1,4-diazabuta-1,3-diene] nickel[3-(ethyl)-4-(methyl)-6-(pentyl)catecholate]; [1,4-bis{3,4-di(ethyl)phenyl}-2(butyl)-3-(octacosynyl1,4-diazabuta-1,3-diene]nickel[3,4-di(ethyl)-5-(methyl) catecholate]; [1,4-bis{3,5-di(pentyl)phenyl}-2-(hydrido)-3-(butyl)1,4-diazabuta-1,3-diene]nickel[4-(pentyl)-5-(methyl) catecholate]; [1,4-bis{3,5-di(pentyl)-phenyl}-2-(pentyl)-3-(hydrido)1,4-diazabuta-1,3-diene]nickel[3-(ethyl)-4-(butyl)-6-(pentyl)catecholate]; [1,4-bis{3,4-di(butyl) phenyl}-2,3-(dibutyl)1,4-diazabuta-1,3-diene]nickel[3-(propyl)-6-(pentyl)catecholate]; [1,4-bis{3,4-di(propyl) phenyl}-2-(pentadecynyl)-3-(methyl)1,4-diazabuta-1,3-diene]nickel[3-(propyl)-4-(butanalyl)-5-(methyl) catecholate]; [1,4-bis{phenyl}-2-(butyl)-3-(pentyl)1,4-diazabuta-1,3-diene]palladium[3-(propyl)-6-(pentyl) catecholate]; [1,4-bis{3,5-di(pentyl)phenyl}-2-(ethyl)-3-(hydrido)1,4-diazabuta-1,3-diene]nickel[4-(methyl) catecholate]; [1,4-bis{phenyl}-2,3-(dihydrido)1,4-diazabuta-1,3-diene]nickel[4-(propyl)catecholate]; [1,4-bis{phenyl}-2-(octyl)-3-(pentyl)1,4-diazabuta-1,3-diene] nickel[3-(methyl)-5-(propyl)catecholate]; [1,4-bis{4-propenylphenyl}-2,3-(dihydrido)1,4-diazabuta-1,3-diene] palladium[4-(butyl)-5-(ethyl)catecholate]; [1,4-bis{3,4-di (ethyl)phenyl}-2-(ethyl)-3-(butyl)1,4-diazabuta-1,3-diene] nickel[3-(ethyl)-5-(pentyl)catecholate]; [1,4-bis{4-eicosynylphenyl}-2,3-(dibutyl)1,4-diazabuta-1,3-diene] nickel[3-(butyl)catecholate]; [1,4-bis{3,5-di(ethyl)-phenyl}-2-(tridecenyl)-3-(pentyl)1,4-diazabuta-1,3-diene] nickel[4,5-di(methyl)-catecholate]; [1,4-bis{phenyl}-2-(tricosyl)-3-(octyl)1,4-diazabuta-1,3-diene]nickel[3-(butyl) catecholate]; [1,4-bis{3-methylethylaminophenyl}-2,3-

(dibutyl)1,4-diazabuta-1,3-diene]nickel[3-(pentyl)catecholate]; [1,4-bis{phenyl}-2-(pentyl)-3-(ethyl)1,4-diazabuta-1,3-diene]nickel[3,4-di(propyl)catecholate]; [1,4-bis{3,4-di(methyl)phenyl}-2-(hexyl)-3-(butyl)1,4-diazabuta-1,3-diene]nickel[4-(ethyl)catecholate]; [1,4-bis{4-hexadecynyl-phenyl}-2-(butyl)-3-(pentyl)1,4-diazabuta-1,3-diene]nickel[3-(octylamino)catecholate]; [1,4-bis{4-nonacosenylphenyl}-2-(octenyl)-3-(hydrido)1,4-diazabuta-1,3-diene]nickel [3-(butyl)catecholate]; [1,4-bis{3,5-di(ethyl)phenyl}-2-(butyl)-3-(pentyl)1,4-diazabuta-1,3-diene]nickel[3-(ethyl)catecholate]; [1,4-bis{3,5-di(butyl)phenyl}-2-(pentyl)-3-(butyl)1,4-diazabuta-1,3-diene]nickel[3-(ethyl)catecholate]; [1,4-bis{3-octacosynylphenyl}-2-(butyl)-3-(tricosenyl)1,4-diazabuta-1,3-diene]nickel[4-(ethyl)catecholate]; [1,4-bis{phenyl}-2-(hydrido)-3-(butyl)1,4-diazabuta-1,3-diene]palladium[4-(methyl)-5-(ethyl)catecholate]; [1,4-bis{3-octadecynylphenyl}-2-(pentyl)-3-(hydrido)1,4-diazabuta-1,3-diene]nickel[4-(ethyl)catecholate]; [1,4-bis{4-butanalylphenyl}-2-(pentyl)-3-(methyl)1,4-diazabuta-1,3-diene]nickel[3-(butyl)-5-(methyl)catecholate]; [1,4-bis{3,5-di(methyl)phenyl}-2-(butyl)-3-(hexyl)1,4-diazabuta-1,3-diene]palladium[4-(ethyl)-catecholate]; [1,4-bis{3,4-di(pentyl)phenyl}-2-(octyl)-3-(nonadecenyl)1,4-diazabuta-1,3-diene]nickel[3,6-di(pentyl)catecholate]; [1,4-bis{phenyl}-2-(propynyl)-3-(hydrido)1,4-diazabuta-1,3-diene]nickel[4-(methyl)catecholate]; [1,4-bis{phenyl}-2-(hydrido)-3-(butyl)1,4-diazabuta-1,3-diene]palladium[3-(butyl)catecholate]; [1,4-bis{phenyl}-2-(hexyl)-3-(propenyl)1,4-diazabuta-1,3-diene]nickel[3-(butyl)-4-(pentyl)catecholate]; [1,4-bis{phenyl}-2,3-(dibutyl)1,4-diazabuta-1,3-diene]palladium[3-(propyl)catecholate]; [1,4-bis{phenyl}-2,3-(dibutyl)1,4-diazabuta-1,3-diene]palladium[4-(butyl)catecholate]; [1,4-bis{3,5-di(ethyl)phenyl}-2,3-(dibutyl)1,4-diazabuta-1,3-diene]nickel[3-(butyl)-4-(propyl)catecholate]; [1,4-bis{3,4-di(propyl)phenyl}-2-(pentyl)-3-(butyl)1,4-diazabuta-1,3-diene]palladium[3-(propyl)-5-(pentyl)catecholate]; [1,4-bis{3,4-di(ethyl)phenyl}-2-(octyl)-3-(hydrido)1,4-diazabuta-1,3-diene]nickel[4-(methyl)-5-(butyl)catecholate]; [1,4-bis{phenyl}-2-(butyl)-3-(ethyl)1,4-diazabuta-1,3-diene]nickel[4-(propyl)-catecholate]; [1,4-bis{3,5-di(methyl)phenyl}-2-(butyl)-3-(hydrido)1,4-diazabuta-1,3-diene]nickel[3-(ethyl)-4-(propyl)catecholate]; [1,4-bis{phenyl}-2,3-(dihydrido)1,4-diazabuta-1,3-diene]palladium[4-(pentyl)-5-(ethyl)catecholate]; [1,4-bis{3,5-di(methyl)-phenyl}-2-(butyl)-3-(octyl)1,4-diazabuta-1,3-diene]palladium[4-(pentyl)catecholate]; [1,4-bis{phenyl}-2-(butyl)-3-(hydrido)1,4-diazabuta-1,3-diene]palladium[3,5-di(pentyl)-catecholate]; [1,4-bis{3,4-di(butyl)phenyl}-2-(octyl)-3-(eicosyl)1,4-diazabuta-1,3-diene]nickel[3-(ethyl)-4-(methyl)catecholate]; [1,4-bis{3,5-di(butyl)phenyl}-2-(butyl)-3-(methyl)1,4-diazabuta-1,3-diene]palladium[4,5-di(butyl)catecholate]; [1,4-bis{3,4-di(ethyl)phenyl}-2-(hydrido)-3-(butyl)1,4-diazabuta-1,3-diene]nickel[3-(butyl)-4-(pentyl)-5-(methyl)catecholate]; [1,4-bis{3-hexacosylphenyl}-2-(methyl)-3-(butyl)1,4-diazabuta-1,3-diene]palladium[4-(propyl)-5-(methyl)catecholate]; [1,4-bis{phenyl}-2-(undecynyl)-3-(hydrido)1,4-diazabuta-1,3-diene]nickel[3-(propyl)catecholate]; [1,4-bis{phenyl}-2-(hydrido)-3-(methyl)1,4-diazabuta-1,3-diene]nickel[3-(methyl)-catecholate]; [1,4-bis{3,5-di(pentyl)phenyl}-2-(hydrido)-3-(butyl)1,4-diazabuta-1,3-diene]palladium[3,4-di(pentyl)-5-(ethyl)catecholate]; [1,4-bis{phenyl}-2-(nonadecyl)-3-(hydrido)1,4-diazabuta-1,3-diene]nickel[3-(butyl)-4-(pentyl)catecholate]; [1,4-bis{3,4-di(methyl)phenyl}-2-(hydrido)-3-(butyl)1,4-diazabuta-1,3-diene]nickel[3-(propyl)-catecholate]; [1,4-bis{3,5-di(butyl)phenyl}-2-(dodecynyl)-3-(hexyl)1,4-diazabuta-1,3-diene]nickel[4,5-di(butyl)catecholate]; [1,4-bis{phenyl}-2,3-(dihydrido)1,4-diazabuta-1,3-diene]palladium[4,5-di(ethyl)catecholate]; [1,4-bis{3,5-di(methyl)phenyl}-2-(ethyl)-3-(butyl)1,4-diazabuta-1,3-diene]palladium[3-(pentyl)-6-(ethyl)catecholate]; [1,4-bis{phenyl}-2-(pentyl)-3-(butyl)1,4-diazabuta-1,3-diene]nickel[4-(butyl)catecholate]; [1,4-bis{3,5-di(pentyl)phenyl}-2-(decynyl)-3-(hexyl)1,4-diazabuta-1,3-diene]nickel[3-(butyl)-6-(pentyl)catecholate]; [1,4-bis{3,4-di(pentyl)phenyl}-2-(hexynyl)-3-(butyl)1,4-diazabuta-1,3-diene]palladium[4-(propyl)catecholate]; [1,4-bis{3-(triethylsilylmethyl)-phenyl}-2,3-(dihydrido)1,4-diazabuta-1,3-diene]nickel[4-(pentyl)-5-(propyl)-catecholate]; [1,4-bis{phenyl}-2-(butyl)-3-(hydrido)1,4-diazabuta-1,3-diene]palladium[3-(methyl)catecholate]; [1,4-bis{3,4-di(pentyl)phenyl}-2,3-(dibutyl)1,4-diazabuta-1,3-diene]nickel[4-(propyl)catecholate]; [1,4-bis{3,4-di(methyl)phenyl}-2-(hexyl)-3-(butyl)-1,4-diazabuta-1,3-diene]palladium[3-(propyl)-6-(methyl)catecholate]; [1,4-bis{phenyl}-2-(pentyl)-3-(octyl)1,4-diazabuta-1,3-diene]nickel[4-(butyl)catecholate]; [1,4-bis{3,5-di(ethyl)phenyl}-2,3-(dihexyl)1,4-diazabuta-1,3-diene]palladium[3-(pentyl)-5-(butyl)-catecholate]; [1,4-bis{3,5-di(ethyl)phenyl}-2,3-(dibutyl)1,4-diazabuta-1,3-diene]palladium[4-(ethyl)catecholate]; [1,4-bis{3,4-di(methylethylamino)phenyl}-2-(butyl)-3-(nonadecyl)1,4-diazabuta-1,3-diene]palladium[3-(methyl)-4-(ethyl)catecholate]; [1,4-bis{phenyl}-2,3-(dihydrido)1,4-diazabuta-1,3-diene]nickel[3-(butyl)catecholate]; [1,4-bis{phenyl}-2-(octyl)-3-(hydrido)1,4-diazabuta-1,3-diene]nickel[4-(methyl)catecholate]; [1,4-bis{3,4-di(ethyl)phenyl}-2-(hydrido)-3-(hexyl)1,4-diazabuta-1,3-diene]palladium[3,4-di(pentyl)-6-(butyl)catecholate]; [1,4-bis{phenyl}-2-(butyl)-3-(hydrido)1,4-diazabuta-1,3-diene]nickel[4-(ethyl)-5-(pentyl)catecholate]; [1,4-bis{3,4-di(butyl)-phenyl}-2-(hydrido)-3-(dodecyl)1,4-diazabuta-1,3-diene]nickel[4-(pentyl)catecholate]; [1,4-bis{3,5-di(ethyl)phenyl}-2-(butyl)-3-(octyl)1,4-diazabuta-1,3-diene]nickel [3-methyl-5-(butyl)catecholate]; [1,4-bis{3,4-di(methyl)phenyl}-2-(butyl)-3-(ethyl)1,4-diazabuta-1,3-diene]nickel [3,6-di(butyl)-4-(propyl)catecholate]; [1,4-bis{phenyl}-2-(ethyl)-3-(pentyl)1,4-diazabuta-1,3-diene]nickel[3-(methyl)-6-(pentyl)catecholate]; [1,4-bis{3,4-di(propyl)phenyl}-2-(butyl)-3-(heneicosyl)1,4-diazabuta-1,3-diene]nickel[4-(pentyl)catecholate]; [1,4-bis{3,5-di(butyl)phenyl}-2-(eicosynyl)-3-(butyl)1,4-diazabuta-1,3-diene]palladium[4-(methyl)-5-(ethyl)catecholate]; [1,4-bis{3,4-di(ethyl)phenyl}-2,3-(dipentyl)1,4-diazabuta-1,3-diene]nickel [4-(methyl)catecholate]; [1,4-bis{3,4-di(pentyl)-phenyl}-2-(undecenyl)-3-(undecyl)1,4-diazabuta-1,3-diene]nickel[3-(propyl)-4,5-di(ethyl)catecholate]; [1,4-bis{3,4-di(pentyl)phenyl}-2-(pentyl)-3-(hexyl)1,4-diazabuta-1,3-diene]nickel [3,4-di(butyl)-5-(methyl)catecholate]; [1,4-bis{4-octenylphenyl}-2-(butyl)-3-(pentyl)1,4-diazabuta-1,3-diene]palladium[3-(pentyl)-4-(butyl)catecholate]; [1,4-bis{phenyl}-2-(methyl)-3-(butyl)1,4-diazabuta-1,3-diene]nickel[4-(methyl)-catecholate]; [1,4-bis{phenyl}-2-(hydrido)-3-(nonacosenyl)1,4-diazabuta-1,3-diene]nickel [4-(ethyl)-5-(propyl)catecholate]; [1,4-bis{3,5-di(pentyl)phenyl}-2-(butyl)-3-(hydrido)1,4-diazabuta-1,3-diene]nickel[3-(ethyl)-4-(propyl)catecholate]; [1,4-bis{3,4-di(butyl)phenyl}-2-(pentadecyl)-3-(tetracosynyl)1,4-diazabuta-1,3-diene]nickel[3,5-di(pentyl)catecholate]; [1,4-bis{phenyl}-2-(hexyl)-3-(butyl)1,4-diazabuta-1,3-diene]nickel[4-(trimethylsilylethyl)-5-(ethyl)catecholate]; [1,4-bis{3,4-di(ethyl)phenyl}-2-(hydrido)-3-(butyl)1,4- diazabuta-1,3-diene]nickel[3-(butyl)-5-(pentyl)catecholate]; [1,4-bis{3,5-di(methyl)phenyl}-2,3-(dibutyl)1,4-diazabuta-1,3-diene]nickel[3-(methyl)-catecholate]; [1,4-bis{3,4-di(propyl)phenyl}-2-(hexyl)-3-(docosyl)1,4-diazabuta-1,3-diene]nickel[3-(methyl)-6-(propyl)catecholate]; [1,4-bis{3,4-di(propyl)phenyl}-2-(pentyl)-3-(butyl)1,4-diazabuta-1,3-diene]nickel[3-((triethylsilylmethyl))-5-(methyl)-catecholate]; [1,4-bis{3,5-di(methyl)phenyl}-2-(butyl)-3-(pentyl)1,4-diazabuta-1,3-diene]palladium[4-(propyl)catecholate]; [1,4-bis{3,5-di(propyl)phenyl}-2-(butyl)-3-(hydrido)-1,4-diazabuta-1,3-diene]nickel[4-(methyl)catecholate]; [1,4-bis{4-triacontynylphenyl}-2-(hydrido)-3-(undecynyl)1,4-diazabuta-1,3-diene]palladium[3-(butyl)-4-(propyl)-6-(ethyl)catecholate]; [1,4-bis{3,4-di(ethyl)phenyl}-2-(hydrido)-3-(butyl)1,4-diazabuta-1,3-diene]nickel[3-(ethyl)catecholate]; [1,4-bis{3,5-di(methyl)phenyl}-2-(butyl)-3-(hexyl)-1,4-diazabuta-1,3-diene]palladium[3,5-di(propyl)catecholate]; [1,4-bis{3,4-di(pentyl)-phenyl}-2-(hexyl)-3-(hydrido)1,4-diazabuta-1,3-diene]nickel[3-(pentyl)catecholate]; [1,4-bis{3,5-di(methyl)phenyl}-2-(ethyl)-3-(hexyl)1,4-diazabuta-1,3-diene]nickel[3-(pentyl)-5-(butyl)catecholate]; [1,4-bis{3,4-di(propyl)phenyl}-2-(butyl)-3-(ethyl)1,4-diazabuta-1,3-diene]nickel[3,4-di(pentyl)-5-(ethyl)catecholate]; [1,4-bis{3-nonadecynyl-phenyl}-2-(nonyl)-3-(hexyl)1,4-diazabuta-1,3-diene]nickel[3-(ethyl)catecholate]; [1,4-bis{3,5-di(butyl)phenyl}-2-(hydrido)-3-(butyl)1,4-diazabuta-1,3-diene]nickel[3-(pentyl)-5-(propyl)catecholate]; [1,4-bis{phenyl}-2-(butyl)-3-(pentyl)1,4-diazabuta-1,3-diene]nickel[3-(butyl)-4-(ethyl)-6-(methyl)catecholate]; [1,4-bis{phenyl}-2-(butyl)-3-(hydrido)1,4-diazabuta-1,3-diene]nickel[3-(pentyl)-4-(methyl)catecholate]; [1,4-bis{3-heptaconsenylphenyl}-2-(methyl)-3-(ethyl)1,4-diazabuta-1,3-diene]nickel[3-(methyl)-catecholate]; [1,4-bis{3-eicosylphenyl}-2,3-(dihydrido)1,4-diazabuta-1,3-diene]nickel [4-(butyl)-5-(ethyl)catecholate]; [1,4-bis{3,4-di(ethyl)phenyl}-2-(pentyl)-3-(butyl)1,4-diazabuta-1,3-diene]nickel[3,5-di(butyl)catecholate]; [1,4-bis{3,4-di(methyl)phenyl}-2-(hexyl)-3-(pentyl)1,4-diazabuta-1,3-diene]nickel[3,5-di(methyl)catecholate]; [1,4-bis{phenyl}-2-(butyl)-3-(pentyl)1,4-diazabuta-1,3-diene]nickel[3-(methyl)catecholate]; [1,4-bis{3,4-di(propyl)phenyl}-2,3-(dibutyl)1,4-diazabuta-1,3-diene]palladium[4-(pentyl)catecholate]; [1,4-bis{phenyl}-2-(butyl)-3-(hexyl)-1,4-diazabuta-1,3-diene]nickel[3-(pentyl)-6-(ethyl)catecholate]; [1,4-bis{phenyl}-2,3-(dibutyl)1,4-diazabuta-1,3-diene]nickel[3-(ethyl)-5-(butyl)catecholate]; [1,4-bis{3,4-di(pentyl)phenyl}-2-(pentyl)-3-(butyl)1,4-diazabuta-1,3-diene]nickel[3-(ethyl)catecholate]; [1,4-bis{4-heptacosynyl-phenyl}-2-(nonynyl)-3-(butyl)1,4-diazabuta-1,3-diene]nickel[3-(pentyl)catecholate]; [1,4-bis{4-methylphenyl}-2-(butyl)-3-(hydrido)1,4-diazabuta-1,3-diene]nickel[3-(butyl)-6-(pentyl)catecholate]; [1,4-bis{phenyl}-2,3-(dihydrido)1,4-diazabuta-1,3-diene]nickel[1,3-(butyl)-6-(methyl)catecholate]; [1,4-bis{phenyl}-2-(butyl)-3-(hydrido)1,4-diazabuta-1,3-diene]nickel[3-(propyl)-5-(ethyl)catecholate]; [1,4-bis{3,4-di(ethyl)-phenyl}-2-(hexyl)-3-(butyl)1,4-diazabuta-1,3-diene]nickel[3-(propyl)-4-(butyl)-5-(pentyl)catecholate]; [1,4-bis{3,4-di(ethyl)phenyl}-2-(eicosynyl)-3-(ethyl)1,4-diazabuta-1,3-diene]nickel[3-(propyl)-4-(methyl)catecholate]; [1,4-bis{4-docosylphenyl}-2-(butyl)-3-(pentyl)1,4-diazabuta-1,3-diene]palladium[3-(ethyl)catecholate]; [1,4-bis{3,5-di(ethyl)phenyl}-2-(hydrido)-3-(hexyl)1,4-diazabuta-1,3-diene]nickel[4-(propyl)-5-(ethyl)catecholate]; [1,4-bis{3,5-di(methyl)phenyl}-2-(hydrido)-3-(butyl)1,4-diazabuta-1,3-diene]nickel[4-(methyl)-5-(butyl)catecholate]; [1,4-bis{3,4-di(propyl)phenyl}-2-(hexyl)-3-(hydrido)1,4-diazabuta-1,3-diene]nickel[3-(propyl)-4-(pentyl)-5-(butyl)-catecholate]; [1,4-bis{3-pentynylphenyl}-2-(pentyl)-3-(butyl)1,4-diazabuta-1,3-diene]nickel[4-(pentyl)catecholate]; [1,4-bis{4-propenylphenyl}-2-(butyl)-3-(hydrido)1,4-diazabuta-1,3-diene]nickel[4-(trimethylsilylethyl)-5-(ethyl)catecholate]; [1,4-bis{3,4-di(ethyl)phenyl}-2-(hydrido)-3-(pentyl)1,4-diazabuta-1,3-diene]nickel[3-(methyl)-4-(propyl)-5-(ethyl)catecholate]; [1,4-bis{4-hexacosenylphenyl}-2-(butyl)-3-(hydrido)1,4-diazabuta-1,3-diene]nickel[3-(propyl)catecholate]; [1,4-bis{3,4-di(pentyl)phenyl}-2-(hexyl)-3-(butyl)1,4-diazabuta-1,3-diene]nickel[3,4-di(methyl)-5-(ethyl)catecholate]; [1,4-bis{3,5-di(pentyl)phenyl}-2-(octyl)-3-(butyl)1,4-diazabuta-1,3-diene]nickel[3-(propyl)-4-(butyl)catecholate]; [1,4-bis{phenyl}-2-(octacosynyl)-3-(octyl)1,4-diazabuta-1,3-diene]nickel[3-(methyl)-6-(propyl)catecholate]; [1,4-bis{phenyl}-2-(octyl)-3-(butyl)1,4-diazabuta-1,3-diene]nickel[3-(ethyl)-4-(propyl)catecholate]; [1,4-bis{3,4-di(methyl)phenyl}-2,3-(dihydrido)1,4-diazabuta-1,3-diene]nickel[3-(methyl)-5-(propyl)-catecholate]; [1,4-bis{3,4-di(butyl)phenyl}-2-(undecenyl)-3-(hexyl)1,4-diazabuta-1,3-diene]palladium[3-(methyl)catecholate]; [1,4-bis{3,5-di(pentyl)phenyl}-2-(pentyl)-3-(butyl)1,4-diazabuta-1,3-diene]palladium[3-(pentyl)-6-(methyl)catecholate]; [1,4-bis{3,4-di(butyl)phenyl}-2-(butyl)-3-(hydrido)1,4-diazabuta-1,3-diene]palladium[3-(pentyl)catecholate]; [1,4-bis{4-methylethylaminophenyl}-2-(octyl)-3-(hydrido)1,4-diazabuta-1,3-diene]nickel[3-(methyl)-5-((triethylsilylmethyl))catecholate]; [1,4-bis{phenyl}-2-(octyl)-3-(methyl)1,4-diazabuta-1,3-diene]nickel[3-(ethyl)-4-(propyl)-catecholate]; [1,4-bis{4-propenylphenyl}-2-(hydrido)-3-(pentyl)1,4-diazabuta-1,3-diene]nickel[3-(butyl)-4-(methyl)-6-(ethyl)catecholate]; [1,4-bis{3-propynylphenyl}-2-(pentyl)-3-(butyl)1,4-diazabuta-1,3-diene]palladium[3,4-di(methyl)-5-(ethyl)-catecholate]; [1,4-bis{4-pentenylphenyl}-2-(tricosynyl)-3-(pentadecynyl)1,4-diazabuta-1,3-diene]nickel[3-(trimethylsilylmethyl)-4-(propyl)catecholate]; [1,4-bis{3-octenyl-phenyl}-2,3-(dihydrido)1,4-diazabuta-1,3-diene]nickel[3-(ethyl)-4-(methyl)-6-(pentyl)-catecholate]; [1,4-bis{3,5-di(butyl)phenyl}-2-(butyl)-3-(pentyl)1,4-diazabuta-1,3-diene]nickel[3-(propanalyl)-5-(propyl)catecholate]; [1,4-bis{3,4-di(methyl)phenyl}-2-hexadecenyl-3-(butyl)1,4-diazabuta-1,3-diene]palladium[4-(butyl)-5-(pentyl)-catecholate]; [1,4-bis{4-methylethylaminophenyl}-2-(ethyl)-3-(hydrido)1,4-diazabuta-1,3-diene]nickel[3-(methyl)-6-(propyl)catecholate]; [1,4-bis{3,4-di(butyl)phenyl}-2-(methyl)-3-(butyl)1,4-diazabuta-1,3-diene]palladium[3-(ethyl)catecholate]; [1,4-bis{3,5-di(propyl)phenyl}-2-(hydrido)-3-(tridecyl)1,4-diazabuta-1,3-diene]nickel[3-(pentyl)-4-(butyl)catecholate]; [1,4-bis{4-heptadecylphenyl}-2,3-(dibutyl)1,4-diazabuta-1,3-diene]nickel[3,4-di(methyl)catecholate]; [1,4-bis{3-proponylphenyl}-2-(octyl)-3-(butynyl)1,4-diazabuta-1,3-diene]nickel[3,6-di(methyl)-4-(hexonyl)catecholate]; [1,4-bis{phenyl}-2,3-(dioctyl)1,4-diazabuta-1,3-diene]nickel[3-(methyl)catecholate]; [1,4-bis{3-tridocosanalylphenyl}-2-(hydrido)-3-(butyl)1,4-diazabuta-1,3-diene]palladium[3-(butyl)catecholate]; [1,4-bis{3,4-di(ethyl)phenyl}-2-(pentyl)-3-(octyl)1,4-diazabuta-1,3-diene]palladium[4-(butyl)catecholate]; [1,4-bis{3,5-di(methyl)phenyl}-2-(hydrido)-3-(methyl)1,4-diazabuta-1,3-diene]nickel[4-(butyl)catecholate]; [1,4-bis{phenyl}-2-(butyl)-3-(hydrido)1,4-diazabuta-1,3-diene]nickel[4-(propyl)-5-(ethyl)catecholate]; [1,4-bis{3,4-di(methyl)phenyl}-2-(ethyl)-3-(hydrido)1,4-diazabuta-1,3-diene]palladium[3-(methyl)-4-

(propyl)catecholate]; [1,4-bis{3,5-di(ethyl)phenyl}-2,3-(dibutyl)1,4-diazabuta-1,3-diene]nickel[4,5-di(propyl)catecholate]; [1,4-bis{phenyl}-2-(octyl)-3-(hydrido)1,4-diazabuta-1,3-diene]nickel[4-(pentyl)catecholate]; [1,4-bis{3,5-di(butyl)-phenyl}-2-(pentyl)-3-(butyl)1,4-diazabuta-1,3-diene]palladium[3-(butyl)-6-(methyldiethylsilylmethyl))catecholate]; [1,4-bis{3,5-di(butyl)phenyl}-2-(butyl)-3-(hexyl)1,4-diazabuta-1,3-diene]palladium[3-(butyl)-5-(pentyl)catecholate]; [1,4-bis{3,5-di(methyl)phenyl}-2-(propyl)-3-(butyl)1,4-diazabuta-1,3-diene]nickel[3-(pentyl)-catecholate]; [1,4-bis{3,4-di(methyl)phenyl}-2-(butyl)-3-(hexyl)1,4-diazabuta-1,3-diene]palladium[4-(propyl)catecholate]; [1,4-bis{4-undecenylphenyl}-2-(methyl)-3-(butyl)1,4-diazabuta-1,3-diene]nickel[4-(butonyl)-5-(butyl)catecholate]; [1,4-bis{phenyl}-2-(triacontynyl)-3-(hydrido)1,4-diazabuta-1,3-diene]nickel[4-(methyl)catecholate]; [1,4-bis{3,4-di(ethyl)phenyl}-2-(hexyl)-3-(hydrido)1,4-diazabuta-1,3-diene]nickel[3-(propyl)-4,6-di(butyl)catecholate]; [1,4-bis{3-tetradecylphenyl}-2-(butyl)-3-(hydrido)1,4-diazabuta-1,3-diene]palladium[3-(methyl)-6-(butyl)catecholate]; [1,4-bis{3,4-di(propyl)phenyl}-2-(octyl)-3-(hydrido)1,4-diazabuta-1,3-diene]nickel[3-(propyl)-4,5-di(ethyl)catecholate]; [1,4-bis{3,5-di(methyl)phenyl}-2-(pentyl)-3-(octyl)1,4-diazabuta-1,3-diene]nickel[3-(ethyl)-4-(propyl)catecholate]; [1,4-bis{phenyl}-2-(pentyl)-3-(octyl)-1,4-diazabuta-1,3-diene]nickel[4-(pentyl)catecholate]; [1,4-bis{3,4-di(proponyl)-phenyl}-2-(butyl)-3-(octyl)1,4-diazabuta-1,3-diene]palladium[3-(propyl)catecholate]; [1,4-bis{3,5-di(ethyl)phenyl}-2-(hydrido)-3-(hexyl)1,4-diazabuta-1,3-diene]nickel[4-(ethyl) catecholate]; [1,4-bis{3,4-di(pentyl)phenyl}-2,3-(dihydrido)1,4-diazabuta-1,3-diene]nickel[3-(methyl)-6-(ethyl)catecholate]; [1,4-bis{3,5-di(methyl)phenyl}-2-(butyl)-3-(hydrido)1,4-diazabuta-1,3-diene]palladium[3-(propyl)catecholate]; [1,4-bis{phenyl}-2-(pentyl)-3-(butyl)-1,4-diazabuta-1,3-diene]nickel[3-(propyl)-4-(ethyl)-5-(pentyl)-catecholate]; [1,4-bis{3,4-di(propyl)phenyl}-2-(pentyl)-3-(butyl)1,4-diazabuta-1,3-diene]nickel[4-(propyl)catecholate]; [1,4-bis{3-decynylphenyl}-2-(ethyl)-3-(butyl)1,4-diazabuta-1,3-diene]palladium[3,5-di(ethyl)catecholate]; [1,4-bis{4-dodecaminophenyl}-2-(butyl)-3-(hydrido)1,4-diazabuta-1,3-diene]nickel[3,6-di(butyl)-4-(proponyl)catecholate]; [1,4-bis{3,5-di(ethyl)phenyl}-2-(pentyl)-3-(butyl)1,4-diazabuta-1,3-diene]nickel[4,5-di(ethyl)catecholate]; [1,4-bis{3,4-di(pentyl)phenyl}-2-(pentyl)-3-(pentynyl)1,4-diazabuta-1,3-diene]palladium[4-(pentyl)catecholate]; [1,4-bis{4-butonylphenyl}-2,3-(dibutyl)1,4-diazabuta-1,3-diene]nickel[4-(ethyl)-5-(pentyl)-catecholate]; [1,4-bis{3-nonadecylphenyl}-2,3-(dibutyl)1,4-diazabuta-1,3-diene]nickel [3-(butyl)catecholate]; [1,4-bis{phenyl}-2-(octyl)-3-(butyl)1,4-diazabuta-1,3-diene]palladium[3-(propyl)-4-(butyl)-6-(ethyl)catecholate]; [1,4-bis{4-octacosynylphenyl}-2-(hexyl)-3-(butyl)1,4-diazabuta-1,3-diene]nickel[3-(butyl)catecholate]; [1,4-bis{4-diethylaminophenyl}-2-(butyl)-3-(hexyl)1,4-diazabuta-1,3-diene]nickel[4-(pentyl)-catecholate]; [1,4-bis{phenyl}-2-(butyl)-3-(pentyl)1,4-diazabuta-1,3-diene]nickel[4-(pentyl)-5-(methyl)catecholate]; [1,4-bis{3,5-di(propyl)phenyl}-2,3-(dibutyl)1,4-diazabuta-1,3-diene]nickel[3-(propyl) catecholate]; [1,4-bis{3,4-di(ethyl)phenyl}-2,3-(dibutyl)1,4-diazabuta-1,3-diene]nickel[3-(butyl)catecholate]; [1,4-bis{3,4-di(butyl)-phenyl}-2-(pentyl)-3-(hydrido)1,4-diazabuta-1,3-diene]nickel[4-(ethyl)catecholate]; [1,4-bis{4-decylphenyl}-2-(hydrido)-3-(butyl)1,4-diazabuta-1,3-diene]nickel[3-(propyl)-4-(methyl)-6-(ethyl)catecholate]; [1,4-bis{3,4-di(butyl)phenyl}-2-(hexyl)-3-(hydrido)1,4-diazabuta-1,3-diene]nickel[3-(propyl)-4-(pentyl)catecholate]; [1,4-bis{3-pentenylphenyl}-2-(octynyl)-3-(octyl)1,4-diazabuta-1,3-diene]nickel[3-(propyl)-5-(pentyl)catecholate]; [1,4-bis{4-tridecylphenyl}-2,3-(dibutyl)1,4-diazabuta-1,3-diene]nickel[3-(methyl)catecholate]; [1,4-bis{4-tetracosylphenyl}-2-(ethyl)-3-(butyl)1,4-diazabuta-1,3-diene]nickel[3,4-di(propyl)catecholate]; [1,4-bis{3,4-di(pentyl)phenyl}-2-(hexyl)-3-(butyl)1,4-diazabuta-1,3-diene]nickel[3-(propyl)-4-(pentyl)-6-(butyl)-catecholate]; [1,4-bis{3,4-di(pentyl)phenyl}-2-(hydrido)-3-(tricosyl)1,4-diazabuta-1,3-diene]nickel[3-(pentyl)catecholate]; [1,4-bis{phenyl}-2,3-(dihydrido)1,4-diazabuta-1,3-diene]nickel[3-(methyl)-4,5-di(propyl)catecholate]; [1,4-bis{4-heptenylphenyl}-2-(butyl)-3-(tridecynyl)1,4-diazabuta-1,3-diene]nickel[3-(ethyl)catecholate]; [1,4-bis{3,4-di(butyl)phenyl}-2,3-(dibutyl)1,4-diazabuta-1,3-diene]nickel[3,4-di(propyl)-5-(ethyl)-catecholate]; [1,4-bis{4-hexadecylphenyl}-2,3-(dibutyl)1,4-diazabuta-1,3-diene]palladium[4-(pentyl)catecholate]; [1,4-bis{3,5-di(dodecamino)phenyl}-2-(hydrido)-3-(tricosyl)1,4-diazabuta-1,3-diene]nickel[3-(butyl)-4-(propyl)catecholate]; [1,4-bis{phenyl}-2,3-(dibutyl)1,4-diazabuta-1,3-diene]palladium[4-(dodecamino)-catecholate]; [1,4-bis{3,5-di(pentyl)phenyl}-2-(pentynyl)-3-(butyl)1,4-diazabuta-1,3-diene]nickel[3-(methyldiethylsilylmethyl))catecholate]; [1,4-bis{3,4-di(methyl)phenyl}-2-(hydrido)-3-(pentyl)1,4-diazabuta-1,3-diene]nickel[3-(propyl)-6-(pentyl)catecholate]; [1,4-bis{3,5-di(pentyl)phenyl}-2-(hydrido)-3-(hexyl)1,4-diazabuta-1,3-diene]nickel[4-(propyl)catecholate]; [1,4-bis{phenyl}-2-(hydrido)-3-(propenyl)1,4-diazabuta-1,3-diene]nickel[3-(pentyl)-4-(propyl)catecholate]; [1,4-bis{4-hexacosylphenyl}-2,3-(dihydrido)-1,4-diazabuta-1,3-diene]nickel[3-(propyl)-6-(butyl)catecholate]; [1,4-bis{3,5-di(ethyl)-phenyl}-2-(hexyl)-3-(butyl)1,4-diazabuta-1,3-diene]nickel[3-(butyl)-4-(methyl)-6-(ethyl)catecholate]; [1,4-bis{3-butynylphenyl}-2-(pentadecenyl)-3-(ethyl)1,4-diazabuta-1,3-diene]nickel[3-(hexyl)-5-(butyl)catecholate]; [1,4-bis{3-dodecynylphenyl}-2-(heptynyl)-3-(pentacosyl)1,4-diazabuta-1,3-diene]nickel[3-(methyl)catecholate]; [1,4-bis{4-nonylphenyl}-2,3-(dibutyl)1,4-diazabuta-1,3-diene]nickel[3-(ethyl)-4-(propyl)-catecholate]; [1,4-bis{phenyl}-2-(hydrido)-3-(hexadecynyl)1,4-diazabuta-1,3-diene]nickel[3-(pentyl)catecholate]; [1,4-bis{3,4-di(methyl)phenyl}-2-(hydrido)-3-(hexyl)1,4-diazabuta-1,3-diene]palladium[4-(pentyl)-5-(ethyl)catecholate]; [1,4-bis{4-butyl-phenyl}-2,3-(dibutyl)1,4-diazabuta-1,3-diene]nickel[3,4-di(pentyl)-6-(propyl)-catecholate]; [1,4-bis{3,5-di(pentyl)phenyl}-2-(octyl)-3-(heneicosynyl)1,4-diazabuta-1,3-diene]nickel[4-(propyl)catecholate]; [1,4-bis{3-docosylphenyl}-2-(hexyl)-3-(pentyl)1,4-diazabuta-1,3-diene]palladium[4,5-di(methyl)catecholate]; [1,4-bis{3,5-di(pentyl)-phenyl}-2-(hydrido)-3-(butyl)1,4-diazabuta-1,3-diene]palladium[3-(methyl)catecholate]; [1,4-bis{3-heptacosynylphenyl}-2-(butyl)-3-(hydrido)1,4-diazabuta-1,3-diene]nickel[4-(ethyl)catecholate]; [1,4-bis{3,5-di(butyl)phenyl}-2,3-(dibutyl)1,4-diazabuta-1,3-diene]nickel[3-(pentyl)catecholate]; [1,4-bis{3,5-di(methyl)phenyl}-2-(octacosynyl)-3-(butyl)-1,4-diazabuta-1,3-diene]nickel[4-(butyl)catecholate]; [1,4-bis{3,4-di(methyl)phenyl}-2-(butyl)-3-(hexyl)1,4-diazabuta-1,3-diene]nickel[4-(ethyl)-5-(propyl)catecholate]; [1,4-bis{3,4-di(pentyl)phenyl}-2-(butyl)-3-(hydrido)1,4-diazabuta-1,3-diene]nickel[3-(pentyl)-5-(methyl)catecholate]; [1,4-bis{phenyl}-2-(hexacosyl)-3-(pentyl)-1,4-diazabuta-1,3-diene]nickel[4-(ethyl)catecholate]; [1,4-bis{3,4-di(butyl)phenyl}-2-(butyl)-3-(ethyl)-1,4-diazabuta-1,3-diene]nickel[3-(methyl)-4-(butyl)

catecholate]; [1,4-bis{3-pentacosenylphenyl}-2-(butyl)-3-(hexyl)1,4-diazabuta-1,3-diene]nickel[3-(methyl)-5-(butanalyl)catecholate]; [1,4-bis{phenyl}-2-(butyl)-3-(hydrido)1,4-diazabuta-1,3-diene]nickel[3,6-di(ethyl)catecholate]; [1,4-bis{3,5-di(methyl)phenyl}-2-(propynyl)-3-(butyl)-1,4-diazabuta-1,3-diene]nickel[3,5-di(butyl)-4-(bromo)catecholate]; [1,4-bis{3,5-di(ethyl)phenyl}-2,3-(dibutyl)1,4-diazabuta-1,3-diene]nickel[3-(ethyl)-6-(pentyl)-catecholate]; [1,4-bis{4-hexacosynylphenyl}-2-(butyl)-3-(hydrido)1,4-diazabuta-1,3-diene]nickel[4-(methyl)catecholate]; [1,4-bis{phenyl}-2,3-(dibutyl)1,4-diazabuta-1,3-diene]palladium[3-(methyl)-6-(propyl)catecholate]; [1,4-bis{phenyl}-2-(hydrido)-3-(octyl)1,4-diazabuta-1,3-diene]nickel[4-(methyl)-5-(propyl)catecholate]; [1,4-bis{3,4-di(butyl)phenyl}-2-(hexyl)-3-(hydrido)1,4-diazabuta-1,3-diene]palladium[3-(methyl)-catecholate]; [1,4-bis{3-nonadecylphenyl}-2-(methyl)-3-(ethyl)1,4-diazabuta-1,3-diene]palladium[3-(dodecamino)-5-(butyl)catecholate]; [1,4-bis{3,5-di(ethyl)phenyl}-2-(octyl)-3-(hydrido)1,4-diazabuta-1,3-diene]nickel[3-(butyl)-4-(methyl)catecholate]; [1,4-bis{3,5-di(methyl)phenyl}-2-(methyl)-3-(octadecenyl)1,4-diazabuta-1,3-diene]nickel[3-(ethyl)-4-(methyl)-5-(propyl)catecholate]; [1,4-bis{3,4-di(propyl)phenyl}-2-(hexyl)-3-(hydrido)1,4-diazabuta-1,3-diene]nickel[3,5-di(pentyl)catecholate]; [1,4-bis{3,4-di(methyl)phenyl}-2-(butyl)-3-(pentyl)1,4-diazabuta-1,3-diene]nickel[3-(butyl)-4-(pentyl)-5-(methyl)catecholate]; [1,4-bis{3,4-di(pentyl)phenyl}-2,3-(dihydrido)1,4-diazabuta-1,3-diene]nickel[3-(methyl)catecholate]; [1,4-bis{3,5-di(butyl)phenyl}-2-(eicosenyl)-3-(octyl)1,4-diazabuta-1,3-diene]nickel[4,5-di(propyl)catecholate]; [1,4-bis{3,4-di(ethyl)phenyl}-2-(pentyl)-3-(butyl)1,4-diazabuta-1,3-diene]nickel[4-(propyl)-catecholate]; [1,4-bis{3,4-di(ethyl)phenyl}-2-(methyl)-3-(octyl)1,4-diazabuta-1,3-diene]nickel[4-(ethyl)catecholate]; [1,4-bis{3,4-di(propyl)phenyl}-2-(hydrido)-3-(butyl)1,4-diazabuta-1,3-diene]nickel[3,4-di(ethyl)-6-(methyl)catecholate]; [1,4-bis{3,5-di(pentyl)-phenyl}-2-(butyl)-3-(butenyl)1,4-diazabuta-1,3-diene]palladium[3-(methyl)catecholate]; [1,4-bis{phenyl}-2-(hexyl)-3-(pentyl)1,4-diazabuta-1,3-diene]nickel[4,5-di(propyl)-catecholate]; [1,4-bis{phenyl}-2-(ethyl)-3-(butyl)1,4-diazabuta-1,3-diene]nickel[3-(ethyl)-4-(methyl)catecholate]; [1,4-bis{3,4-di(propyl)phenyl}-2-(butyl)-3-(pentyl)1,4-diazabuta-1,3-diene]nickel[3-(pentyl)-4-(methyl)catecholate]; [1,4-bis{4-nonadecynyl-phenyl}-2,3-(dibutyl)1,4-diazabuta-1,3-diene]nickel[4-(propyl)catecholate]; [1,4-bis{phenyl}-2,3-(dibutyl)1,4-diazabuta-1,3-diene]palladium[3-(methyl)-5-((triethylsilylmethyl))catecholate]; [1,4-bis{phenyl}-2-(hexyl)-3-(butyl)1,4-diazabuta-1,3-diene]palladium[3-(propyl)catecholate]; [1,4-bis{4-undecylphenyl}-2-(hydrido)-3-(hexyl)1,4-diazabuta-1,3-diene]nickel[4-(pentyl)-5-(propyl)catecholate]; [1,4-bis{3,5-di(pentyl)phenyl}-2-(undecynyl)-3-(hydrido),4-diazabuta-1,3-diene]nickel[3,4-di(methyl)-6-(methyl)catecholate]; [1,4-bis{3,4-di(propyl)phenyl}-2-(octyl)-3-(butyl)1,4-diazabuta-1,3-diene]nickel[3,4-di(propyl)catecholate]; [1,4-bis{3,5-di(propyl)phenyl}-2-(butyl)-3-(hexyl)1,4-diazabuta-1,3-diene]nickel[3-(pentyl)-4-(methyl)catecholate]; [1,4-bis{3,4-di(ethyl)phenyl}-2,3-(dibutyl)1,4-diazabuta-1,3-diene]palladium[4-(methyl)-catecholate]; [1,4-bis{phenyl}-2-(hydrido)-3-(octyl)1,4-diazabuta-1,3-diene]nickel[3-(ethyl)-4-(butyl)catecholate]; [1,4-bis{3-tetradecynylphenyl}-2-(hydrido)-3-(butyl)1,4-diazabuta-1,3-diene]nickel[3,5-di(pentyl)catecholate]; [1,4-bis{4-propanalylphenyl}-2-(butyl)-3-(methyl)1,4-diazabuta-1,3-diene]nickel[3,5-di(ethyl)catecholate]; [1,4-bis{phenyl}-2-(butyl)-3-(hexyl)1,4-diazabuta-1,3-diene]nickel[4-(propyl)catecholate]; [1,4-bis{3-heptenylphenyl}-2-(hydrido)-3-(butyl)1,4-diazabuta-1,3-diene]palladium[3,4-di(methyl)catecholate]; [1,4-bis{phenyl}-2-(butyl)-3-(hydrido)1,4-diazabuta-1,3-diene]palladium[4-(ethyl)catecholate]; [1,4-bis{4-nonadecynylphenyl}-2-(butyl)-3-(octadecenyl)1,4-diazabuta-1,3-diene]nickel[3-(dodecamino)-6-(propyl)catecholate]; [1,4-bis{3-docosynylphenyl}-2-(octyl)-3-(butyl)1,4-diazabuta-1,3-diene]palladium[3-(propyl)-6-(methyl)catecholate]; [1,4-bis{phenyl}-2-(hydrido)-3-(octadecyl)1,4-diazabuta-1,3-diene]nickel[4-(methyl)catecholate]; [1,4-bis{phenyl}-2-(butyl)-3-(hydrido)1,4-diazabuta-1,3-diene]nickel[3,5-di(pentyl)catecholate]; [1,4-bis{3-propynyl-phenyl}-2-(propenyl)-3-(pentyl)1,4-diazabuta-1,3-diene]nickel[3-(butanalyl)-4-(ethyl)-6-(methyl)catecholate]; [1,4-bis{phenyl}-2-(hexyl)-3-(butyl)1,4-diazabuta-1,3-diene]palladium[3-(methyl)catecholate]; [1,4-bis{3,4-di(propyl)phenyl}-2-(pentyl)-3-(octyl)-1,4-diazabuta-1,3-diene]nickel[3-(methyl)-6-(butyl)catecholate]; [1,4-bis{3,4-di(ethyl)-phenyl}-2,3-(dibutyl)1,4-diazabuta-1,3-diene]nickel[4-(pentyl)-5-(ethyl)catecholate]; [1,4-bis{4-hexadecynylphenyl}-2-(pentyl)-3-(hydrido)1,4-diazabuta-1,3-diene]palladium[3-(ethyl)-6-(butyl)catecholate]; [1,4-bis{3,4-di(ethyl)phenyl}-2,3-(dibutyl)1,4-diazabuta-1,3-diene]nickel[3-(butyl)-4-(pentyl)catecholate]; [1,4-bis{3,5-di(ethyl)phenyl}-2-(hexyl)-3-(butyl)1,4-diazabuta-1,3-diene]palladium[3-(propyl)-5-(ethyl)catecholate]; [1,4-bis{3,4-di(ethyl)phenyl}-2-(butyl)-3-(octyl)1,4-diazabuta-1,3-diene]nickel[4-(propyl)catecholate]; [1,4-bis{3,4-di(propyl)phenyl}-2-(pentyl)-3-(heptadecynyl)1,4-diazabuta-1,3-diene]nickel[3-(methyl)catecholate]; [1,4-bis{phenyl}-2-(hydrido)-3-(docosenyl)1,4-diazabuta-1,3-diene]nickel[4-(ethyl)catecholate]; [1,4-bis{phenyl}-2-(nonadecynyl)-3-(pentyl)1,4-diazabuta-1,3-diene]palladium[3-(butyl)-4-(propyl)-catecholate]; [1,4-bis{3-nonacosenylphenyl}-2-(dodecyl)-3-(butyl)1,4-diazabuta-1,3-diene]palladium[4-(methyl)catecholate]; [1,4-bis{phenyl}-2-(heptacosyl)-3-(butyl)1,4-diazabuta-1,3-diene]nickel[3,4-di(propyl)-6-(propyl)catecholate]; [1,4-bis{phenyl}-2-(hydrido)-3-(butyl)1,4-diazabuta-1,3-diene]nickel[3-(ethyl)-6-(butyl)catecholate]; [1,4-bis{phenyl}-2-(octyl)-3-(heneicosyl)1,4-diazabuta-1,3-diene]palladium[3-(trimethylsilylethyl)-5-(trimethylsilylmethyl)catecholate]; [1,4-bis{phenyl}-2-(methyl)-3-(hydrido)1,4-diazabuta-1,3-diene]nickel[4-(propyl)catecholate]; [1,4-bis{3,4-di(propyl)-phenyl}-2-(eicosyl)-3-(hexyl)-1,4-diazabuta-1,3-diene]nickel[3,5-di(pentyl)catecholate]; [1,4-bis{3-pentylphenyl}-2-(methyl)-3-(hydrido)1,4-diazabuta-1,3-diene]nickel[3,4-di(propyl)-5-(ethyl)catecholate]; [1,4-bis{3,4-di(propyl)phenyl}-2-(butyl)-3-(hydrido)1,4-diazabuta-1,3-diene]palladium[4-(pentyl)-5-(butyl)catecholate]; [1,4-bis{3-undecyl-phenyl}-2-(pentyl)-3-(hexyl)l,4-diazabuta-1,3-diene]nickel[4,5-di(propyl)catecholate]; [1,4-bis{3-tridecylphenyl}-2-(tetradecynyl)-3-(hydrido)1,4-diazabuta-,3-diene]nickel[3-(ethyl)catecholate]; [1,4-bis{3,4-di(pentyl)phenyl}-2-(hydrido)-3-(butyl)1,4-diazabuta-1,3-diene]nickel[3-(butyl)catecholate]; [1,4-bis{phenyl}-2-(pentyl)-3-(hydrido)1,4-diazabuta-1,3-diene]palladium[4-(methyl)-5-(propyl)catecholate]; [1,4-bis{phenyl}-2,3-(dibutyl)1,4-diazabuta-1,3-diene]palladium[3-(propyl)catecholate]; [1,4-bis{3,4-di(ethyl)phenyl}-2-(heneicosyl)-3-(butyl)1,4-diazabuta-1,3-diene]nickel[3,4-di(ethyl)-5-(pentyl)catecholate]; [1,4-bis{3-dodecylphenyl}-2-(butyl)-3-(octyl)1,4-diazabuta-1,3-diene]nickel[3-(ethyl)catecholate]; [1,4-bis{phenyl}-2-(hydrido)-3-(pentyl)1,4-diazabuta-1,3-diene]nickel[3-(pentyl)catecholate]; [1,4-bis{4-dodecylphenyl}-2,3-(dibutyl)1,4- diazabuta-1,3-diene]nickel[3-(methyl)-4-(pentyl) catecholate]; [1,4-bis{3,4-di(propyl)phenyl}-2,3-(dibutyl)1,4-diazabuta-1,3-diene]nickel[4-(butyl)catecholate]; [1,4-bis{3,4-di(ethyl)phenyl}-2-(hydrido)-3-(octyl)1,4-diazabuta-1,3-diene]nickel[3-(butyl)-6-(pentyl) catecholate]; [1,4-bis{phenyl}2,3-(dibutyl)1,4-diazabuta-1,3-diene]nickel[3-(propyl)-5-(pentyl)catecholate]; [1,4-bis{3-dodecynylphenyl}-2-(tetracosenyl)-3-(triacontyl)1,4-diazabuta-1,3-diene]nickel[3-(butyl)catecholate]; [1,4-bis{4-tridecenyl-phenyl}-2,3-(dibutyl)1,4-diazabuta-1,3-diene]nickel[3-(methyl)catecholate]; [1,4-bis{3,5-di(pentyl)phenyl}-2,3-(dibutyl)1,4-diazabuta-1,3-diene]nickel[3-(butyl)-4-(pentyl)catecholate]; [1,4-bis{phenyl}-2-(triacontyl)-3-(butyl)1,4-diazabuta-1,3-diene]palladium[4-(pentyl)-5-(butyl)catecholate]; [1,4-bis{phenyl}-2-(butyl)-3-(octyl)1,4-diazabuta-1,3-diene]nickel[3-(butyl)-4-(propyl)catecholate]; [1,4-bis{3,4-di(butyl)-phenyl}-2-(hydrido)-3-(octyl)1,4-diazabuta-1,3-diene]nickel[3-(methyl)-5-(pentyl)-catecholate]; [1,4-bis{phenyl}-2-(hexyl)-3-(pentyl)1,4-diazabuta-1,3-diene]nickel[3-(propyl)-4-(pentyl)-5-(methyl)catecholate]; [1,4-bis{3,5-di(pentyl)phenyl}-2,3-(dihydrido)1,4-diazabuta-1,3-diene]nickel[3-(ethyl)catecholate]; [1,4-bis{3,4-di(methyl)phenyl}-2-(butyl)-3-(nonacosyl)1,4-diazabuta-1,3-diene]nickel[3,4-di(pentyl)catecholate]; [1,4-bis{3,5-di(pentyl)phenyl}-2-(hydrido)-3-(octadecyl)1,4-diazabuta-1,3-diene]nickel[4,5-di(ethyl)catecholate]; [1,4-bis{phenyl}-2-(decenyl)-3-(nonenyl)1,4-diazabuta-1,3-diene]palladium[3-(propyl)-4-(methyl)catecholate]; [1,4-bis{3,4-di(propyl)phenyl}-2,3-(dihexyl)1,4-diazabuta-1,3-diene]palladium[3-(ethyl)-5-(pentyl)catecholate]; [1,4-bis{3,4-di(butyl)phenyl}-2-(butyl)-3-(hydrido)1,4-diazabuta-1,3-diene]nickel[4-(methyl)-5-(ethyl)catecholate]; [1,4-bis{phenyl}-2,3-(dihexyl)1,4-diazabuta-1,3-diene]nickel[3-(ethyl)catecholate];

[1,4-bis{3,4-di(methyl)phenyl}-2-(pentyl)-3-(hydrido)1,4-diazabuta-1,3-diene]nickel[3-(ethyl)-6-(butyl)catecholate]; [1,4-bis{3-octenylphenyl}-2-(butyl)-3-(hydrido)-1,4-diazabuta-1,3-diene]nickel[3,6-di(ethyl)catecholate]; [1,4-bis{phenyl}-2-(hydrido)-3-(octyl)1,4-diazabuta-1,3-diene]nickel[3-(propyl)catecholate]; [1,4-bis{3,5-di(ethyl)-phenyl}-2-(hydrido)-3-(ethyl)1,4-diazabuta-1,3-diene]palladium[3-(methyl)-6-(pentyl)catecholate]; [1,4-bis{phenyl}-2-(butyl)-3-(hydrido)1,4-diazabuta-1,3-diene]nickel[3-(butyl)-6-(ethyl)catecholate]; [1,4-bis{3,4-di(pentyl)phenyl}-2-(hexyl)-3-(hexacosenyl)-1,4-diazabuta-1,3-diene]palladium[4-(propyl)catecholate]; [1,4-bis{3,5-di(methyl)-phenyl}-2-(tetradecyl)-3-(butyl)1,4-diazabuta-1,3-diene]nickel[3-(ethyl)-6-(butyl)-catecholate]; [1,4-bis{3-propanalylphenyl}-2-(hydrido)-3-(butyl)1,4-diazabuta-1,3-diene]nickel[3-(butyl)-4-(propyl)catecholate]; [1,4-bis{3,5-di(propyl)phenyl}-2,3-(dihydrido)-1,4-diazabuta-1,3-diene]nickel[3-(butyl)-4-(pentyl)catecholate]; [1,4-bis{3,4-di(propyl)-phenyl}-2-(butyl)-3-(pentyl)1,4-diazabuta-1,3-diene]nickel[3-(pentyl)-6-(propyl)-catecholate]; [1,4-bis{3,4-di(ethyl)phenyl}-2-(hydrido)-3-(butyl)1,4-diazabuta-1,3-diene]nickel[3-(propyl)catecholate]; [1,4-bis{3,5-di(methyl)phenyl}-2-(heptacosenyl)-3-(butyl)1,4-diazabuta-1,3-diene]nickel[3-(butyl)-4-(methyl)-5-(propyl)catecholate]; [1,4-bis{3,4-di(proponyl)phenyl}-2-(hydrido)-3-(butyl)1,4-diazabuta-1,3-diene]nickel[3-(methyl)-5-(pentyl)catecholate]; [1,4-bis{4-nonacosenylphenyl}-2-(pentyl)-3-(methyl)-1,4-diazabuta-1,3-diene]nickel[3-(pentyl)-4-(ethyl)catecholate]; [1,4-bis{3,4-di(pentyl)-phenyl}-2,3-(dibutyl)-1,4-diazabuta-1,3-diene]nickel[3-(pentyl)-4-(propyl)-6-(methyl)-catecholate]; [1,4-bis{phenyl}-2-(octyl)-3-(eicosenyl)1,4-diazabuta-1,3-diene]nickel[3-(butyl)-4-(methyl)catecholate]; [1,4-bis{phenyl}-2-(butyl)-3-(ethyl)1,4-diazabuta-1,3-diene]nickel[4-(methyl)catecholate]; [1,4-bis{phenyl}-2,3-(dibutyl)1,4-diazabuta-1,3-diene]nickel[3-(methyl)-5-(ethyl)catecholate]; [1,4-bis{3,5-di(pentyl)phenyl}-2-(octyl)-3-(tridecynyl)1,4-diazabuta-1,3-diene]nickel[4-(pentyl)-5-(butyl)catecholate]; [1,4-bis{3,4-di(ethyl)phenyl}-2,3-(dibutyl)1,4-diazabuta-1,3-diene]nickel[4-(propyl)-catecholate]; [1,4-bis{3,4-di(butyl)phenyl}-2-(hydrido)-3-(hexacosyl)1,4-diazabuta-1,3-diene]nickel[3-(pentyl)-4-(ethyl)catecholate]; [1,4-bis{3,5-di(butyl)phenyl}-2-(ethyl)-3-(butyl)-1,4-diazabuta-1,3-diene]nickel[3,4-di(ethyl)catecholate]; [1,4-bis{phenyl}-2-(ethyl)-3-(hexyl)1,4-diazabuta-1,3-diene]nickel[4-(pentyl)-5-(ethyl)catecholate]; [1,4-bis{3,4-di(butyl)phenyl}-2-(pentyl)-3-(butyl)1,4-diazabuta-1,3-diene]nickel[4-(propanalyl)-5-(propyl)catecholate]; [1,4-bis{3-decylphenyl}-2-(butyl)-3-(butenyl)1,4-diazabuta-1,3-diene]nickel[3,4-di(ethyl)-5-(pentyl)catecholate]; [1,4-bis{3,4-di(propyl)-phenyl}-2-(pentyl)-3-(octyl)1,4-diazabuta-1,3-diene]palladium[4-(methyl)-5-(ethyl)-catecholate]; [1,4-bis{phenyl}-2-(butyl)-3-(hexyl)1,4-diazabuta-1,3-diene]nickel[3-(ethyl)-4,5-di(methyl)catecholate]; [1,4-bis{3-triacontylphenyl}-2-(butyl)-3-(methyl)1,4-diazabuta-1,3-diene]nickel[3,6-di(pentyl)catecholate]; [1,4-bis{3-ethanalylphenyl}-2-(butyl)-3-(octyl)1,4-diazabuta-1,3-diene]palladium[3-(ethyl)-6-(propyl)catecholate]; [1,4-bis{3,4-di(methyl)phenyl}-2-(octyl)-3-(hydrido)1,4-diazabuta-1,3-diene]nickel[3-(butyl)-5-(methyl)catecholate]; [1,4-bis{3,5-di(methyl)phenyl}-2-(butyl)-3-(hexynyl)1,4-diazabuta-1,3-diene]nickel[3,4-di(pentyl)-6-(ethyl)catecholate]; [1,4-bis{phenyl}-2-(hydrido)-3-(butyl)1,4-diazabuta-1,3-diene]nickel[3-(propyl)-5-(pentyl)catecholate]; [1,4-bis{phenyl}-2-(hydrido)-3-(octyl)1,4-diazabuta-1,3-diene]nickel[4,5-di(methyl)-catecholate]; [1,4-bis{3-octadecylphenyl}-2-(hydrido)-3-(octyl)1,4-diazabuta-1,3-diene]nickel[3-(ethyl)-6-(propyl)catecholate]; [1,4-bis{4-tridecylphenyl}-2-(butyl)-3-(octenyl)-1,4-diazabuta-1,3-diene]nickel[3-(octylamino)catecholate]; [1,4-bis{4-octynylphenyl}-2-(octyl)-3-(butyl)1,4-diazabuta-1,3-diene]nickel[4-(propyl)catecholate]; [1,4-bis{3,4-di(propyl)phenyl}-2,3-(dihydrido)1,4-diazabuta-1,3-diene]nickel[3-(diethylamino)-catecholate]; [1,4-bis{3,4-di(propyl)phenyl}-2-(butyl)-3-(pentadecenyl)1,4-diazabuta-1,3-diene]palladium[3-(pentyl)-5-(ethyl)catecholate]; [1,4-bis{3,5-di(methyl)phenyl}-2-(nonacosynyl)-3-(octadecenyl)1,4-diazabuta-1,3-diene]palladium[4-(ethyl)catecholate]; [1,4-bis{phenyl}-2-(butyl)-3-(hydrido)1,4-diazabuta-1,3-diene]nickel[4-(ethyl)-5-(methyl)catecholate]; [1,4-bis{3,5-di(pentyl)phenyl}-2-(pentyl)-3-(butyl)1,4-diazabuta-1,3-diene]nickel[3-(butyl)-5-(pentyl)catecholate]; [1,4-bis{3,5-di(methyl)phenyl}-2-(butyl)-3-(hexyl)1,4-diazabuta-1,3-diene]nickel[3-(ethyl)-4-(pentyl)catecholate]; [1,4-bis{3,5-di(methyl)phenyl}-2-(butyl)-3-(ethyl)1,4-diazabuta-1,3-diene]nickel[3-(butyl)-4-(dodecanonyl)-6-(ethyl)catecholate]; [1,4-bis{3,4-di(butyl)phenyl}-2-(hexyl)-3-(methyl)1,4-diazabuta-1,3-diene]nickel[4-(butyl)catecholate]; [1,4-bis{phenyl}-2,3-(dibutyl)1,4-diazabuta-1,3-diene]palladium[4-(methyl)-5-(pentyl)catecholate]; [1,4-bis{3,5-di(butyl)phenyl}-2-(butyl)-3-(ethyl)1,4-diazabuta-1,3-diene]palladium[3-(pentyl)-6-(ethyl)catecholate]; [1,4-bis{3,5-di(methyl)phenyl}-2-(pentyl)-3-(hexyl)1,4-diazabuta-1,3-diene]nickel[3-(butyl)-5-(heptyl)catecholate]; [1,4-bis{3-nonacosynyl-phenyl}-2-(heptynyl)-3-(butyl)1,4-diazabuta-1,3-diene]nickel[3-(methyl)catecholate]; [1,4-bis{phenyl}-2,3-(dipentyl)1,4-diazabuta-1,3-diene]palladium[4-(butyl)catecholate][1,4- bis{4-nonylphenyl}-2-(hexyl)-3-(ethyl)1,4-diazabuta-1,3-diene]nickel[3-(pentyl)-4-(butyl)-5-(ethyl)catecholate]; [1,4-bis{3,4-di(methyl)phenyl}-2-(hydrido)-3-(butyl)1,4-diazabuta-1,3-diene]nickel[3-(methyl)-6-(ethyl) catecholate]; [1,4-bis{3-octadecyl-phenyl}-2-(butyl)-3-(octyl)1,4-diazabuta-1,3-diene]nickel[3-(trimethylsilylethyl)-catecholate]; [1,4-bis{3,5-di(propyl) phenyl}-2-(methyl)-3-(butyl)1,4-diazabuta-1,3-diene]nickel[3,5-di(butyl)-4-(methyl)catecholate]; [1,4-bis{3,5-di(methyl)phenyl}-2,3-(dibutyl)1,4-diazabuta-1,3-diene]nickel[3,5-di(butyl)-4-(ethyl)catecholate]; [1,4-bis{3,4-di(pentyl)phenyl}-2-(hydrido)-3-(hexyl)1,4-diazabuta-1,3-diene]nickel[4-(methyl)-5-(butyl)catecholate]; [1,4-bis{3-pentadecenylphenyl}-2-(hydrido)-3-(butyl)1,4-diazabuta-1,3-diene]nickel[3-(ethyl)catecholate]; [1,4-bis{phenyl}-2-(hydrido)-3-(octyl)1,4-diazabuta-1,3-diene]palladium[4-(propyl)catecholate]; [1,4-bis{4-heptadecylphenyl}-2-(decynyl)-3-(octyl)1,4-diazabuta-1,3-diene]nickel[3-(propyl)catecholate]; [1,4-bis{3,5-di(methyl)phenyl}-2-(hexyl)-3-(butyl)1,4-diazabuta-,3-diene]palladium[3-(ethyl)-4,5-di(pentyl)catecholate]; [1,4-bis{phenyl}-2-(hydrido)-3-(butyl)1,4-diazabuta-1,3-diene]palladium[3-(propyl)-4-(pentyl)catecholate]; [1,4-bis{3-tetracosylphenyl}-2-(butyl)-3-(pentyl)1,4-diazabuta-1,3-diene]nickel[3-(pentyl)-6-(propyl)catecholate]; [1,4-bis{3,4-di(propyl)phenyl}-2-(butyl)-3-(octyl)1,4-diazabuta-1,3-diene]nickel[4-(ethyl)-5-(methyl)catecholate]; [1,4-bis{3-pentenylphenyl}-2-(pentynyl)-3-(butyl)1,4-diazabuta-1,3-diene]nickel[4-(methyl)-5-((triethylsilylmethyl)) catecholate]; [1,4-bis{3,4-di(pentyl)phenyl}-2-(octyl)-3-(butyl)1,4-diazabuta-1,3-diene]palladium[3,4-di(propyl)-5-(methyl)catecholate]; [1,4-bis{3,5-di(methyl)phenyl}-2-(hydrido)-3-(methyl)1,4-diazabuta-1,3-diene]nickel[3-(propyl)catecholate]; [1,4-bis{4-hexacosenylphenyl}-2,3-(dihexyl)1,4-diazabuta-1,3-diene]nickel[3-(methyl)-4-(ethyl)-5-(propyl)catecholate]; [1,4-bis{3,4-di(butyl) phenyl}-2-(hydrido)-3-(methyl)1,4-diazabuta-1,3-diene] nickel[3-(propyl)catecholate]; [1,4-bis{phenyl}-2-(butyl)-3-(ethyl)1,4-diazabuta-1,3-diene]nickel[4-(ethyl) catecholate]; [1,4-bis{4-hexadecynylphenyl}-2,3-(dibutyl) 1,4-diazabuta-1,3-diene]nickel[3-(octylamino)catecholate]; [1,4-bis{3,5-di(butyl)phenyl}-2-(butyl)-3-(hexyl)1,4-diazabuta-1,3-diene]nickel[4-(methyl)catecholate]; [1,4-bis{3,5-di(propyl)-phenyl}-2-(butyl)-3-(heptenyl)1,4-diazabuta-1,3-diene]nickel[3-(ethyl)catecholate]; [1,4-bis{4-tetradecenylphenyl}-2-(butyl)-3-(hexacosenyl)1,4-diazabuta-1,3-diene]palladium[3-(pentyl)catecholate]; [1,4-bis{3-butanalylphenyl}-2-(hydrido)-3-(butyl)1,4-diazabuta-1,3-diene]nickel[3-(butyl)-4-(pentyl)-6-(methyl) catecholate]; [1,4-bis{3,5-di(methyl)phenyl}-2-(octyl)-3-(hydrido)1,4-diazabuta-1,3-diene]nickel[3-(methyl)-catecholate]; [1,4-bis{3,4-di(propyl)phenyl}-2,3-(diethyl)1,4-diazabuta-1,3-diene]nickel[3-(butyl)catecholate]; [1,4-bis{phenyl}-2,3-(dibutyl)1,4-diazabuta-1,3-diene]nickel[3-(pentyl)catecholate]; [1,4-bis{3-heptynylphenyl}-2,3-(dibutyl)1,4-diazabuta-1,3-diene]palladium[4-(trimethylsilylethyl)-5-(ethyl)catecholate]; [1,4-bis{3,5-di(propyl)phenyl}-2-(octyl)-3-(hydrido)1,4-diazabuta-1,3-diene]nickel[3-(hexyl)-5-(butyl)catecholate]; [1,4-bis{4-heneicosylphenyl}-2-(butyl)-3-(methyl)1,4-diazabuta-1,3-diene]nickel[3-(butyl)-6-(pentyl)catecholate]; [1,4-bis{3,4-di(ethyl)phenyl}-2-(octyl)-3-(hexyl)1,4-diazabuta-1,3-diene]nickel[3-(octylamino)-6-(pentyl)catecholate]; [1,4-bis{3,5-di(pentyl)phenyl}-2-(butyl)-3-(hexyl)1,4-diazabuta-1,3-diene]nickel[3-(butyl)-6-(methyl) catecholate]; [1,4-bis{phenyl}-2-(hexyl)-3-(butyl)1,4-diazabuta-1,3-diene]palladium[3-(methyl)-4-(propyl) catecholate]; [1,4-bis{phenyl}-2-(heneicosyl)-3-(butyl)-1,4-diazabuta-1,3-diene]nickel[3-(butyl)-5-(methyl) catecholate]; [1,4-bis{3,4-di(propyl)phenyl}-2-(pentyl)-3-(hydrido)1,4-diazabuta-1,3-diene]nickel[3,5-di(methyl)-catecholate]; [1,4-bis{3,4-di(propyl)phenyl}-2-(octyl)-3-(pentyl)1,4-diazabuta-1,3-diene]nickel[4-(ethyl) catecholate]; [1,4-bis{3,4-di(pentyl)phenyl}-2-(hexyl)-3-(methyl)1,4-diazabuta-1,3-diene]palladium[3-(methyl)-4-(butyl)catecholate]; [1,4-bis{3,5-di(methyl)phenyl}-2-(butenyl)-3-(butyl)1,4-diazabuta-1,3-diene]nickel[3-(butyl)-6-(methyl)catecholate]; [1,4-bis{3,5-di(ethyl) phenyl}-2-(ethyl)-3-(hexyl)1,4-diazabuta-1,3-diene]nickel [3-(butyl)-6-(pentyl)catecholate]; [1,4-bis{phenyl}-2,3-(dibutyl)1,4-diazabuta-1,3-diene]nickel[4-(ethyl)-5-(butyl) catecholate]; [1,4-bis{3,5-di(methyl)-phenyl}-2-(ethyl)-3-(methyl)1,4-diazabuta-1,3-diene]nickel[3-(methyl)-4-(ethyl)-catecholate]; [1,4-bis{phenyl}-2-(butyl)-3-(tetracosynyl)1,4-diazabuta-1,3-diene]nickel[3-(methyl)-4-(ethyl)catecholate]; [1,4-bis{3,4-di(propyl)phenyl}-2-(butyl)-3-(hexyl)1,4-diazabuta-1,3-diene]nickel[4-(methyl)-5-(pentyl)catecholate]; [1,4-bis{phenyl}-2-(hydrido)-3-(hexyl)1,4-diazabuta-1,3-diene]nickel[3-(ethyl)-4-(butyl) catecholate]; [1,4-bis{phenyl}-2-(butyl)-3-(hydrido)1,4-diazabuta-1,3-diene]nickel[3-(butyl)catecholate]; [1,4-bis{phenyl}-2-(dodecenyl)-3-(hydrido)1,4-diazabuta-1,3-diene]palladium[3-(ethyl)-6-(butyl)catecholate]; [1,4-bis{phenyl}-2-(hydrido)-3-(butyl)1,4-diazabuta-1,3-diene] nickel[3,4-di(methyl)-6-(propyl)catecholate]; [1,4-bis{phenyl}-2,3-(dibutyl)1,4-diazabuta-1,3-diene]nickel[3-(methyl)catecholate]; [1,4-bis{3,5-di(propyl)phenyl}-2-(ethyl)-3-(butyl)1,4-diazabuta-1,3-diene]nickel[3-(dodecamino)-6-(propyl)catecholate]; [1,4-bis{phenyl}-2-(hydrido)-3-(pentyl)1,4-diazabuta-1,3-diene]palladium[3-(butyl-6(pentyl)catecholate]; [1,4-bis{phenyl}-2-(pentyl)-3-(ethyl)1,4-diazabuta-1,3-diene]nickel[4-(ethyl)catecholate]; [1,4-bis{3-proponylphenyl}-2-(butyl)-3-(ethyl)1,4-diazabuta-1,3-diene]nickel[3-(ethyl)-6-(pentyl)catecholate]; [1,4-bis{3-nonacosenylphenyl}-2-(pentyl)-3-(butynyl)1,4-diazabuta-1,3-diene]nickel[3-(methyl)-4-(propyl) catecholate]; [1,4-bis{phenyl}-2,3-(dibutyl)1,4-diazabuta-1,3-diene]palladium[4-(propyl)catecholate]; [1,4-bis{4-methyidiethylsilylmethyl)phenyl}-2,3-(dihydrido)1,4-diazabuta-1,3-diene]palladium[3-(trimethylsilylethyl)-5-(trimethylsilylmethyl)catecholate]; [1,4-bis{4-hexadecynylphenyl}-2,3-(dibutyl)1,4-diazabuta-1,3-diene] nickel[3,6-di(methyl)-4-(ethyl)catecholate]; [1,4-bis{4-octadecenylphenyl}-2-(hydrido)-3-(butyl)1,4-diazabuta-1,3-diene]palladium[4-(propyl)catecholate]; [1,4-bis{4-octylaminophenyl}-2-(hydrido)-3-(pentyl)1,4-diazabuta-1,3-diene]palladium[3-(butyl)catecholate]; [1,4-bis{3,5-di(methyl)phenyl}-2-(butyl)-3-(hexyl)1,4-diazabuta-1,3-diene]nickel[4-(methyl)-catecholate]; [1,4-bis{phenyl}-2-(hydrido)-3-(butyl)1,4-diazabuta-1,3-diene]nickel[3-(butyl) catecholate]; [1,4-bis{3,4-di(methylethylamino)phenyl}-2-(hydrido)-3-(butyl)1,4-diazabuta-1,3-diene]nickel[3,5-di (ethyl)-4-(propyl)catecholate]; [1,4-bis{phenyl}-2-(butyl)-3-(pentyl)1,4-diazabuta-1,3-diene]nickel[3-(propyl)-6-(butyl)catecholate]; [1,4-bis{phenyl}-2-(butyl)-3-(tetracosynyl)1,4-diazabuta-1,3-diene]nickel[3-(methyl)-5-(propyl)catecholate]; [1,4-bis{phenyl}-2-(hexyl)-3-(hydrido)1,4-diazabuta-1,3-diene]nickel[3-(ethyl)-4-(methyl)catecholate]; [1,4-bis{3-hexacosenylphenyl}-2-(hydrido)-3-(octyl)1,4-diazabuta-1,3-diene]palladium[3-(propyl)-4-(butonyl)-5-(ethyl)catecholate]; [1,4-bis{phenyl}-2,3-(dihydrido)1,4-diazabuta-1,3-diene]nickel [3-(ethyl)-5-(propyl)-catecholate]; [1,4-bis{phenyl}-2,3-(dibutyl)1,4-diazabuta-1,3-diene]palladium[3-(ethyl)- catecholate]; [1,4-bis{3,4-di(propyl)phenyl}-2,3-(dibutyl)1,4-diazabuta-1,3-diene]palladium[3-(pentyl)-5-(ethyl)catecholate]; [1,4-bis{3,5-di(butyl)phenyl}-2-(tetracosyl)-3-(hydrido)1,4-diazabuta-1,3-diene]palladium[4-(propyl)catecholate]; [1,4-bis{4-heptadecylphenyl}-2-(propenyl)-3-(octyl)1,4-diazabuta-1,3-diene]nickel[3-(propyl)-5-(methyl)catecholate]; [1,4-bis{3,4-di(butyl)phenyl}-2-(hydrido)-3-(hexyl)1,4-diazabuta-1,3-diene]palladium[3-(ethyl)-6-(butyl)catecholate]; [1,4-bis{3,5-di(ethyl)phenyl}-2-(hydrido)-3-(butyl)1,4-diazabuta-1,3-diene]nickel[3-(methyl)-5-(ethyl)catecholate]; [1,4-bis{phenyl}-2-(pentyl)-3-(hydrido)1,4-diazabuta-1,3-diene]nickel[4-(butyl)-5-(pentyl)catecholate]; [1,4-bis{3,5-di(ethyl)phenyl}-2-(butyl)-3-(pentyl)1,4-diazabuta-1,3-diene]nickel[3-(ethyl)-6-(pentyl)catecholate]; [1,4-bis{3,5-di(pentyl)phenyl}-2-(butyl)-3-(octyl)1,4-diazabuta-1,3-diene]nickel[3-(pentyl)catecholate]; [1,4-bis{4-tricosyl-phenyl}-2,3-(dibutyl)1,4-diazabuta-1,3-diene]nickel[3-(methyl)-5-(pentyl)catecholate]; [1,4-bis{phenyl}-2,3-(dibutyl)1,4-diazabuta-1,3-diene]palladium[3-(methyl)-5-(propyl)-catecholate]; [1,4-bis{3,5-di(methyl)phenyl}-2-(butyl)-3-(hexyl)1,4-diazabuta-1,3-diene]nickel[3-(butyl)-5-(propyl)catecholate]; [1,4-bis{3,5-di(pentyl)phenyl}-2-(heptacosyl)-3-(pentenyl)1,4-diazabuta-1,3-diene]nickel[3,4-di(propyl)-6-(propyl)catecholate]; [1,4-bis{3,4-di(proponyl)phenyl}-2-(hexyl)-3-(nonacosenyl)1,4-diazabuta-1,3-diene]palladium[3-(propyl)-6-(ethyl)catecholate]; [1,4-bis{phenyl}-2,3-(dibutyl)1,4-diazabuta-1,3-diene]palladium[3-(methyl)catecholate]; [1,4-bis{3,5-di(dodecamino)phenyl}-2-(tetracosyl)-3-(pentyl)1,4-diazabuta-1,3-diene]palladium[4-(propyl)catecholate]; [1,4-bis{3,4-di(ethyl)phenyl}-2-(octacosyl)-3-(octyl)1,4-diazabuta-1,3-diene]nickel[3-(methyl)-5-(propyl)catecholate]; [1,4-bis{phenyl}-2,3-(dibutyl)1,4-diazabuta-1,3-diene]palladium[3-(butyl)-4-(ethyl)catecholate]; [1,4-bis{3,4-di(butyl)phenyl}-2-(pentyl)-3-(hexyl)1,4-diazabuta-1,3-diene]nickel[3-(butyl)catecholate]; [1,4-bis{3,4-di(methyl)-phenyl}-2-(pentyl)-3-(butyl)1,4-diazabuta-1,3-diene]palladium[3-(ethyl)-5-(butyl)-catecholate]; [1,4-bis{3,5-di(propyl)phenyl}-2-(octyl)-3-(butyl)1,4-diazabuta-1,3-diene]nickel[3,6-di(methyl)catecholate]; [1,4-bis{phenyl}-2-(octyl)-3-(butyl)1,4-diazabuta-1,3-diene]nickel[3-(ethyl)-4-(pentyl)catecholate]; [1,4-bis{3,4-di(butyl)phenyl}-2,3-(dibutyl)1,4-diazabuta-1,3-diene]nickel[3-(methyl)-5-(ethyl)catecholate]; [1,4-bis{phenyl}-2-(hydrido)-3-(hexyl)1,4-diazabuta-1,3-diene]nickel[3-(pentyl)-4-(butyl)-6-(methyl)catecholate]; [1,4-bis{4-heptacosylphenyl}-2-(butyl)-3-(hydrido)1,4-diazabuta-1,3-diene]nickel[4-(ethyl)catecholate]; [1,4-bis{phenyl}-2,3-(dihydrido)1,4-diazabuta-1,3-diene]nickel[3-(hexonyl)catecholate]; [1,4-bis{3,5-di(ethyl)phenyl}-2-(hexyl)-3-(hydrido)1,4-diazabuta-1,3-diene]nickel[3-(methyl)-5-(butyl)catecholate]; [1,4-bis{3,5-di(methyl)phenyl}-2-(hydrido)-3-(butyl)1,4-diazabuta-1,3-diene]nickel[3-(ethyl)-4-(pentyl)catecholate]; [1,4-bis{3,4-di(methyl)phenyl}-2-(pentyl)-3-(nonadecynyl)1,4-diazabuta-1,3-diene]nickel[3-(propyl)catecholate]; [1,4-bis{phenyl}-2-(octyl)-3-(butyl)-1,4-diazabuta-1,3-diene]palladium[3,6-di(propyl)-4-(pentyl)catecholate]; [1,4-bis{3,4-di(butyl)phenyl}-2-(pentyl)-3-(hydrido)1,4-diazabuta-1,3-diene]nickel[4-(ethyl)-catecholate]; [1,4-bis{3,4-di(butyl)phenyl}-2-(hydrido)-3-(butenyl)1,4-diazabuta-1,3-diene]palladium[3-(butyl)-5-(propyl)catecholate]; [1,4-bis{3,5-di(butyl)phenyl}-2-(hydrido)-3-(octyl)1,4-diazabuta-1,3-diene]palladium[3-(butyl)-4-(methyl)-5-(propyl)-catecholate]; [1,4-bis{4-hexynylphenyl}-2-(octyl)-3-(butyl)1,4-diazabuta-1,3-diene]nickel[4-(methyl)catecholate]; [1,4-bis{4-methyldiethylsilylmethyl)phenyl}-2,3-(dibutyl)1,4-diazabuta-1,3-diene]palladium[3-(ethyl)-6-(butyl)catecholate]; [1,4-bis{phenyl}-2-(butyl)-3-(hexyl)1,4-diazabuta-1,3-diene]nickel[3-(pentyl)catecholate]; [1,4-bis{3,5-di(ethyl)phenyl}-2-(dodecyl)-3-(pentyl)1,4-diazabuta-1,3-diene]palladium[3-(pentyl)-4-(butyl)catecholate]; [1,4-bis{3-triacontenylphenyl}-2-(hydrido)-3-(butyl)-1,4-diazabuta-1,3-diene]nickel[4-(propyl)catecholate]; [1,4-bis{4-proponylphenyl}-2,3,-(dihydrido)1,4-diazabuta-1,3-diene]nickel[4-(methyl)catecholate]; [1,4-bis{3,5-di(pentyl)phenyl}-2,3-(dihydrido)1,4-diazabuta-1,3-diene]nickel[3,4-di(ethyl)-5-(butyl)-catecholate]; [1,4-bis{3,4-di(propyl)phenyl}-2-(pentyl)-3-(hydrido)1,4-diazabuta-1,3-diene]nickel[3-(pentyl)-6-(methyl)catecholate]; [1,4-bis{3,5-di(methyl)phenyl}-2-(hexyl)-3-(hydrido),4-diazabuta-1,3-diene]palladium[3,6-di(propyl)-4-(methyldiethylsilylmethyl))catecholate]; [1,4-bis{3,4-di(methyl)phenyl}-2-(butyl)-3-(pentyl)1,4-diazabuta-1,3-diene]palladium[4,5-di(pentyl)catecholate]; [1,4-bis{4-propanalylphenyl}-2-(heneicosyl)-3-(pentyl)1,4-diazabuta-1,3-diene]nickel[4-(methyl)-5-(pentyl)catecholate]; [1,4-bis{4-docosynylphenyl}-2-(pentyl)-3-(butyl)1,4-diazabuta-1,3-diene]nickel[3-(methyl)-5-(ethyl)catecholate]; [1,4-bis{3-octylaminophenyl}-2,3-(dihydrido)1,4-diazabuta-1,3-diene]nickel[3-(ethyl)-4,6-di(methyl)catecholate]; [1,4-bis{3,4-di(propyl)phenyl-}2-(hydrido)-3-(pentyl)1,4-diazabuta-1,3-diene]nickel[3-(pentyl)-6-(butyl)catecholate]; [1,4-bis{4-octynylphenyl}-2-(hexyl)-3-(hydrido)1,4-diazabuta-1,3-diene]nickel[3-(methyl)-6-(methylethylamino)catecholate]; [1,4-bis{phenyl}-2,3-(dihexyl)1,4-diazabuta-1,3-diene]nickel[3,4-di(butyl)catecholate]; [1,4-bis{3,5-di(methyl)phenyl}-2,3-(dihydrido)1,4-diazabuta-1,3-diene]nickel[3-(ethyl)-catecholate]; [1,4-bis{3,4-di(pentyl)phenyl}-2-(ethyl)-3-(butyl)1,4-diazabuta-1,3-diene]nickel[3-(pentyl)-4-(butyl)catecholate]; [1,4-bis{4-octadecynylphenyl}-2-(butyl)-3-(hexyl)1,4-diazabuta-1,3-diene]nickel[3-((triethylsilylmethyl))-4-(butyl)-5-(propyl)-catecholate]; [1,4-bis{3,5-di(pentyl)phenyl}-2-(hydrido)-3-(octyl)1,4-diazabuta-1,3-diene]nickel[4-(ethyl)-5-(propyl)catecholate]; [1,4-bis{3-pentacosenylphenyl}-2,3-(dibutyl)1,4-diazabuta-1,3-diene]nickel[3-(pentyl)-4-(butyl)catecholate]; [1,4-bis{3,4-di(butyl)phenyl}-2-(butyl)-3-(ethyl)1,4-diazabuta-1,3-diene]nickel[3-(methyl)-4-(hexyl)-5-(propyl)catecholate]; [1,4-bis{4-docosenylphenyl}-2-(tetracosenyl)-3-(hydrido)1,4-diazabuta-1,3-diene]nickel[4-(ethyl)catecholate]; [1,4-bis{phenyl}-2-(hydrido)-3-(butyl)1,4-diazabuta-1,3-diene]palladium[3-(ethyl)catecholate]; [1,4-bis{3-eicosynylphenyl}-2,3-(dibutyl)1,4-diazabuta-1,3-diene]nickel[4-(pentyl)catecholate]; [1,4-bis{3,4-di(dodecanoyl)phenyl}-2-(heneicosenyl)-3-(ethyl)1,4-diazabuta-1,3-diene]nickel[4-(propyl)catecholate]; [1,4-bis{3,4-di(propyl)phenyl}-2-(butyl)-3-(octadecyl)1,4-diazabuta-1,3-diene]nickel[4,5-di(ethyl)catecholate]; [1,4-bis{phenyl}-2,3-(dibutyl)1,4-diazabuta-1,3-diene]nickel[3-(butyl)-6-(pentyl)catecholate]; [1,4-bis{phenyl}-2,3-(dibutyl)1,4-diazabuta-1,3-diene]nickel[4-(methyl)catecholate]; [1,4-bis{3,5-di(propyl)-phenyl}-2-(octyl)-3-(butyl)1,4-diazabuta-1,3-diene]nickel[3,6-di(butyl)catecholate]; [1,4-bis{3,5-di(methyl)phenyl}-2,3-(dibutyl)1,4-diazabuta-1,3-diene]palladium[4-(pentyl)-5-(ethyl)catecholate]; [1,4-bis{3,4-di(methyl)phenyl}-2-(octyl)-3-(pentyl)1,4-diazabuta-1,3-diene]nickel[4-(ethyl)catecholate]; [1,4-bis{phenyl}-2-(butyl)-3–1,4-diazabuta-1,3-diene]nickel[3-(butyl)-4-(propyl)catecholate]; [1,4-bis{phenyl}-2-(ethyl)-3-(butyl)1,4-diazabuta-1,3-diene]nickel[4-(pentyl)-5-((triethylsilylmethyl))-catecholate];

[1,4-bis{phenyl}-2,3-(dibutyl)1,4-diazabuta-1,3-diene]nickel[4-(ethyl)-(propyl)catecholate]; [1,4-bis{phenyl}-2-(butyl)-3-(hydrido)1,4-diazabuta-1,3-diene]palladium[4-(methyl)catecholate]; [1,4-bis{3,4-di(methyl)phenyl}-2-(butyl)-3-(pentacosyl)1,4-diazabuta-1,3-diene]palladium[3-(pentyl)-6-(ethyl)catecholate]; [1,4-bis{3,4-di(pentyl)phenyl}-2-(hydrido)-3-(butyl)1,4-diazabuta-1,3-diene]palladium[3-(butyl)catecholate]; [1,4-bis{3,5-di(pentyl)phenyl}-2-(hydrido)-3-(hexacosenyl)1,4-diazabuta-1,3-diene]palladium[3-(propyl)-5-(pentyl)catecholate]; [1,4-bis{3,5-di(butyl)-phenyl}-2-(heptadecyl)-3-(butyl)1,4-diazabuta-1,3-diene]palladium[3-(ethyl)-5-(methyl)catecholate]; [1,4-bis{3,4-di(pentyl)phenyl}-2-(hexyl)-3-(butyl)1,4-diazabuta-1,3-diene]nickel[3-(butyl)-5-(ethyl)catecholate]; [1,4-bis{3,5-di(propyl)phenyl}-2-(hexadecynyl)-3-(butyl)1,4-diazabuta-1,3-diene]nickel[4-(methyl)-5-(pentyl)-catecholate]; [1,4-bis{phenyl}-2-(butyl)-3-(hydrido)1,4-diazabuta-1,3-diene]nickel[4,5-di(methyl)catecholate]; [1,4-bis{phenyl}-2-(ethyl)-3-(methyl)1,4-diazabuta-1,3-diene]nickel[4-(methyl)-5-(pentyl)catecholate]; [1,4-bis{phenyl}-2-(hydrido)-3-(pentyl)1,4-diazabuta-1,3-diene]palladium[3-(ethyl)-4-(pentyl)catecholate]; [1,4-bis{phenyl}-2-(pentyl)-3-(butyl)1,4-diazabuta-1,3-diene]nickel[4-(pentyl)-5-(methyl)catecholate]; [1,4-bis{3,4-di(propyl)phenyl}-2-(octyl)-3-(pentyl)1,4-diazabuta-1,3-diene]nickel[3,6-di(methyl)-4-(butyl)catecholate]; [1,4-bis{3,5-di(propyl)phenyl}-2,3-(dibutyl)1,4-diazabuta-1,3-diene]palladium[3-(pentyl)catecholate]; [1,4-bis{3,4-di(methyl)phenyl}-2-(ethyl)-3-(hexyl)1,4-diazabuta-1,3-diene]nickel[4-(pentyl)-5-(propyl)catecholate]; [1,4-bis{3,5-di(pentyl)phenyl}-2-(hexyl)-3-(octyl)1,4-diazabuta-1,3-diene]nickel[4-(pentyl)-5-(butyl)catecholate]; [1,4-bis{3-propanalylphenyl}-2-(hexyl)-3-(hydrido)1,4-diazabuta-1,3-diene]palladium[4-(pentyl)-5-(butyl)catecholate]; [1,4-bis{3,4-di(ethyl)-phenyl}-2-(octyl)-3-(ethyl)1,4-diazabuta-1,3-diene]palladium[3-(butyl)-4-(octylamino)-catecholate]; [1,4-bis{3,4-di(methyl)phenyl}-2-(hydrido)-3-(butyl)1,4-diazabuta-1,3-diene]nickel[4-(ethyl)-5-(pentyl)catecholate]; [1,4-bis{3,4-di(propyl)phenyl}-2-(hydrido)-3-(pentyl)1,4-diazabuta-1,3-diene]palladium[3,6-di(pentyl)catecholate]; [1,4-bis{3,5-di(butyl)phenyl}-2-(pentadecyl)-3-(octyl)1,4-diazabuta-1,3-diene]nickel[4-(pentyl)catecholate]; [1,4-bis{phenyl}-2,3-(dihydrido)1,4-diazabuta-1,3-diene]nickel[4-(butyl)catecholate]; [1,4-bis{4-methyldiethylsilylmethyl)phenyl}-2-(heptadecenyl)-3-(hydrido)1,4-diazabuta-1,3-diene]nickel[3-(ethyl)-5-(pentyl)catecholate]; [1,4-bis{3,4-di(butyl)phenyl}-2-(octyl)-3-(pentyl)1,4-diazabuta-1,3-diene]palladium[3-(ethyl)-6-(butyl)catecholate]; [1,4-bis{4-decylphenyl}-2,3-(dihydrido)1,4-diazabuta-1,3-diene]nickel[3-(methyl)-4-(propyl)catecholate]; [1,4-bis{3,4-di(ethyl)phenyl}-2,3-(dibutyl)1,4-diazabuta-1,3-diene]palladium[4-(methyl)-5-(ethyl)catecholate]; [1,4-bis{3,5-di(methyl)phenyl}-2-(octyl)-3-(butyl)1,4-diazabuta-1,3-diene]nickel[3-(trimethylsilylmethyl)-5-(butyl)catecholate]; [1,4-bis{4-dodecylphenyl}-2-(ethyl)-3-(hexyl)1,4-diazabuta-1,3-diene]nickel[3,4-di(propyl)-5-(ethyl)catecholate]; [1,4-bis{4-tridecynylphenyl}-2-(hydrido)-3-(butyl)1,4-diazabuta-1,3-diene]nickel[3-(propanalyl)-6-(propyl)catecholate]; [1,4-bis{3,5-di(propyl)phenyl}-2-(butyl)-3-(triacontynyl)1,4-diazabuta-1,3-diene]nickel[4-(ethyl)catecholate]; [1,4-bis{4-propynylphenyl}-2-(nonynyl)-3-(hydrido)1,4-diazabuta-1,3-diene]nickel[4-(pentyl)catecholate]; [1,4-bis{3,4-di(pentyl)phenyl}-2-(methyl)-3-(octadecynyl)1,4-diazabuta-1,3-diene]nickel[4-(ethyl)-5-(methyl)catecholate]; [1,4-bis{4-dodecenylphenyl}-2-(hexyl)-3-(butyl)1,4-diazabuta-1,3-diene]palladium[4-(methyl)-5-(butyl)catecholate]; [1,4-bis{3,5-di(propyl)phenyl}-2-(ethyl)-3-(butyl)1,4-diazabuta-1,3-diene]nickel[4-(propyl)-catecholate]; [1,4-bis{phenyl}-2-(octyl)-3-(butyl)1,4-diazabuta-1,3-diene]palladium[4-(methyl)-5-(ethyl)catecholate]; [1,4-bis{3,4-di(pentyl)phenyl}-2-(hexyl)-3-(hydrido)1,4-diazabuta-1,3-diene]nickel[3,4-di(pentyl)-5-(ethyl)catecholate]; [1,4-bis{3,4-di(propyl)-phenyl}-2-(pentadecenyl)-3-(butyl)1,4-diazabuta-1,3-diene]palladium[3-(ethyl)-5-(methyl)catecholate]; [1,4-bis{3,4-di(methyl)phenyl}-2,3-(dioctyl)1,4-diazabuta-1,3-diene]nickel[3-(propyl)-6-(ethyl)catecholate]; [1,4-bis{3,4-di(butyl)phenyl}-2-(butyl)-3-(hydrido)1,4-diazabuta-1,3-diene]palladium[3-(propyl)-4-(pentyl)catecholate]; [1,4-bis{4-heptadecylphenyl}-2-(hydrido)-3-(hexyl)1,4-diazabuta-1,3-diene]nickel[3-(butyl)-6-(methyl)catecholate]; [1,4-bis{phenyl}-2,3-(dibutyl)1,4-diazabuta-1,3-diene]nickel[4-(methyl)catecholate]; [1,4-bis{4-hexacosynylphenyl}-2-(hydrido)-3-(pentyl)1,4-diazabuta-1,3-diene]nickel[3,5-di(pentyl)catecholate]; [1,4-bis{phenyl}-2-(pentyl)-3-(butyl)1,4-diazabuta-1,3-diene]palladium[4-(methyl)-5-(pentyl)catecholate]; [1,4-bis{phenyl}-2,3-(dibutyl)1,4-diazabuta-1,3-diene]nickel[4-(pentyl)-5-(ethyl)-catecholate]; [1,4-bis{3,5-di(dodecamino)phenyl}-2-(hexyl)-3-(hydrido)1,4-diazabuta-1,3-diene]nickel[3-(ethyl)-4-(methyl)-5-(pentyl)catecholate]; [1,4-bis{3,4-di(ethyl)-phenyl}-2-(butyl)-3-(pentyl)1,4-diazabuta-1,3-diene]nickel[4-(butyl)-5-(pentyl)-catecholate]; [1,4-bis{3,4-di(methyl)phenyl}-2-(butyl)-3-(hydrido)1,4-diazabuta-1,3-diene]nickel[4-(propyl)catecholate]; [1,4-bis{3,4-di(ethyl)phenyl}-2-(tricosyl)-3-(pentyl)1,4-diazabuta-1,3-diene]nickel[4-(methyl)-5-(butyl)catecholate]; [1,4-bis{3-ethanalylphenyl}-2-(hydrido)-3-(ethyl)1,4-diazabuta-1,3-diene]palladium[3-(propyl)-4-(methyl)-6-(ethyl)catecholate]; [1,4-bis{3,5-di(hexonyl)phenyl}-2-(pentyl)-3-(hydrido)-1,4-diazabuta-1,3-diene]palladium[3-(dodecanonyl)catecholate]; [1,4-bis{phenyl}-2-(tetradecenyl)-3-(pentyl)1,4-diazabuta-1,3-diene]nickel[4-(ethyl)catecholate]; [1,4-bis{phenyl}-2-(butyl)-3-(hexyl)1,4-diazabuta-1,3-diene]nickel[3-(methyl)-6-(propyl)-catecholate]; [1,4-bis{3,5-di(methyl)phenyl}-2-(hydrido)-3-(octyl)1,4-diazabuta-1,3-diene]palladium[3,5-di(ethyl)catecholate]; [1,4-bis{phenyl}-2-(hexyl)-3-(butyl)1,4-diazabuta-1,3-diene]nickel[3-(propyl)-4-(butyl)-5-(methyl)catecholate]; [1,4-bis{phenyl}-2-(hydrido)-3-(butyl)1,4-diazabuta-1,3-diene]nickel[3-(methyl)catecholate]; [1,4-bis{3,4-di(butyl)phenyl}-2-(ethyl)-3-(pentyl)1,4-diazabuta-1,3-diene]nickel[3-(hexonyl)catecholate]; [1,4-bis{3,4-di(butyl)phenyl}-2,3-(dibutyl)1,4-diazabuta-1,3-diene]palladium[3,4-di(pentyl)-6-(propyl)catecholate]; [1,4-bis{3-tetracosenyl-phenyl}-2,3-(dibutyl)1,4-diazabuta-1,3-diene]palladium[3-(methyl)-5-(propyl)-catecholate]; [1,4-bis{phenyl}-2-(pentyl)-3-(octyl)1,4-diazabuta-1,3-diene]palladium[3-(butyl)-5-(propyl)catecholate]; [1,4-bis{4-hexadecenylphenyl}-2-(eicosynyl)-3-(butyl)-1,4-diazabuta-1,3-diene]nickel[4-(ethyl)catecholate]; [1,4-bis{3,4-di(propyl)phenyl}-2-(hexyl)-3-(pentyl)1,4-diazabuta-1,3-diene]nickel[3-(propyl)catecholate]; [1,4-bis{phenyl}-2-(heptacosyl)-3-(hydrido)1,4-diazabuta-1,3-diene]nickel[3-(methyl)-catecholate]; [1,4-bis{phenyl}-2,3-(dihydrido)1,4-diazabuta-1,3-diene]palladium[4,5-di(ethyl)catecholate]; [1,4-bis{3,5-di(butyl)phenyl}-2-(ethyl)-3-(dodecenyl)1,4-diazabuta-1,3-diene]palladium[3-(methyl)-4-(ethyl)catecholate]; [1,4-bis{4-heptenyl-phenyl}-2-(octyl)-3-(hydrido)1,4-diazabuta-1,3-diene]nickel[3,4-di(propyl)catecholate]; [1,4-bis{3,5-di(methyl)phenyl}-2-(butyl)-3-(hexyl)1,4-diazabuta-1,3-diene]palladium[3-(ethyl)-4-(pentyl)catecholate]; [1,4-bis{3,5-di(methyl)phenyl}-2,3-

(dioctyl)1,4-diazabuta-1,3-diene]nickel[4-(pentyl)-5-(butyl) catecholate]; [1,4-bis{3,5-di(ethyl)phenyl}-2-(butyl)-3-(pentyl)1,4-diazabuta-1,3-diene]nickel[4-(ethyl) catecholate]; [1,4-bis{3-butyl-phenyl}-2-(hydrido)-3-(octyl)1,4-diazabuta-1,3-diene]nickel[3-(methyl)-4-(butyl)-catecholate]; [1,4-bis{4-hexacosynylphenyl}-2-(methyl)-3-(butyl)1,4-diazabuta-1,3-diene]nickel[4-(pentyl)-5-(butyl) catecholate]; [1,4-bis{phenyl}-2-(hexyl)-3-(butyl)1,4-diazabuta-1,3-diene]nickel[3-(pentyl)catecholate]; [1,4-bis{3,4-di(pentyl)phenyl}-2-(methyl)-3-(hydrido)1,4-diazabuta-1,3-diene]nickel[4-(ethyl)-5-(butyl)catecholate]; [1,4-bis{3,5-di(propyl)phenyl}-2-(butyl)-3-(hydrido)1,4-diazabuta-1,3-diene]palladium[4-(ethyl)-5-(propyl) catecholate]; [1,4-bis{3,4-di(propyl)phenyl}-2,3-(dipentyl) 1,4-diazabuta-1,3-diene]nickel[3,4-di(methyl)-5-(ethyl) catecholate]; [1,4-bis{phenyl}-2-(hexyl)-3-(pentyl)1,4-diazabuta-1,3-diene]nickel[3-(propyl)-6-(methyl) catecholate]; [1,4-bis{3,4-di(methyl)phenyl}-2,3-(dihydrido)1,4-diazabuta-1,3-diene]palladium[3-(methyl)-6-(ethyl)catecholate]; [1,4-bis{phenyl}-2-(hydrido)-3-(heptacosenyl)1,4-diazabuta-1,3-diene]nickel[3-(methyl)-5-(ethyl)catecholate]; [1,4-bis{phenyl}-2-(hydrido)-3-octyl) 1,4-diazabuta-1,3-diene]palladium[4-(methyl)catecholate]; [1,4-bis{4-heptadecylphenyl}-2-(pentyl)-3-(butyl)1,4-diazabuta-1,3-diene]palladium[3-(propyl)catecholate]; [1,4-bis{3,5-di(butanalyl)phenyl}-2-(hexyl)-3-(butyl)1,4-diazabuta-1,3-diene]nickel[3-(methyl)-4-(butyl)-5-(pentyl) catecholate]; [1,4-bis{3,4-di(pentyl)-phenyl}-2-(octyl)-3-(hexyl)1,4-diazabuta-1,3-diene]nickel[3-(pentyl)-4-(propyl)-5-methyl catecholate]; [1,4-bis{4-undecylphenyl}-2-(butyl)-3-(hydrido)1,4-diazabuta-1,3-diene]nickel[3-(butyl)catecholate]; [1,4-bis{3-methylethylaminophenyl}-2-(hydrido)-3-(butyl)1,4-diazabuta-1,3-diene]palladium[4-(pentyl)-5-(ethyl)catecholate]; [1,4-bis{phenyl}-2,3-(dipentyl)1,4-diazabuta-1,3-diene]nickel[4-(methyl)-5-(pentyl)-catecholate]; [1,4-bis{3,5-di(methyl)phenyl}-2-(nonadecynyl)-3-(butyl)1,4-diazabuta-1,3-diene]palladium [4-(methyl)-5-(pentyl)catecholate]; [1,4-bis{4-eicosenylphenyl}-2-(butyl)-3-(hydrido)1,4-diazabuta-1,3-diene]nickel[3-(pentyl)-4-(butyl)catecholate]; [1,4-bis{phenyl}-2-(hydrido)-3-(ethyl)1,4-diazabuta-1,3-diene] nickel[4-(propyl)catecholate]; [1,4-bis{phenyl}-2-(undecynyl)-3-(butyl)1,4-diazabuta-1,3-diene]palladium[3-(propyl)-6-(methyl)catecholate]; [1,4-bis{3-tetradecenylphenyl}-2-(octyl)-3-(hydrido)1,4-diazabuta-1, 3-diene]nickel[4-(butyl)catecholate]; [1,4-bis{phenyl}-2-(tricosenyl)-3-(octyl)1,4-diazabuta-1,3-diene]nickel[3-(butyl)-5-(pentyl)catecholate]; [1,4-bis{phenyl}-2-(hydrido)-3-(pentyl)1,4-diazabuta-1,3-diene]nickel[4-(hexonyl)catecholate]; [1,4-bis{phenyl}-2-(butyl)-3-(hydrido)1,4-diazabuta-1,3-diene]nickel[4,5-di(methyl)-catecholate]; [1,4-bis{3,5-di(ethyl)phenyl}-2,3-(dioctyl)1, 4-diazabuta-1,3-diene]palladium[4,5-di(ethyl)catecholate]; [1,4-bis{phenyl}-2-(pentyl)-3-(butyl)1,4-diazabuta-1,3-diene]nickel[3-(methyl)-6-(pentyl)catecholate]; [1,4-bis{3, 5-di(butyl)phenyl}-2-(hydrido)-3-(butyl)1,4-diazabuta-1,3-diene]nickel[3,5-di(propyl)-4-(methyl)catecholate]; [1,4-bis{3-undecynylphenyl}-2-(hydrido)-3-(octyl)1,4-diazabuta-1,3-diene]palladium[4,5-di(pentyl)catecholate]; [1,4-bis{3-heneicosenylphenyl}-2-(butyl)-3-(hydrido)1,4-diazabuta-1,3-diene]nickel[4-(butyl)catecholate]; [1,4-bis{3,5-di(pentyl)phenyl}-2-(ethyl)-3-(butyl)1,4-diazabuta-1,3-diene]nickel[4,5-di(propyl)catecholate]; [1,4-bis{3-ethanalylphenyl}-2,3-(dibutyl)1,4-diazabuta-1,3-diene] nickel[3-(methyl)-4-(propyl)-catecholate]; [1,4-bis{3-undecenylphenyl}-2-(hydrido)-3-(butyl)1,4-diazabuta-1,3-diene]nickel[4-(butyl)catecholate]; [1,4-bis{phenyl}-2-(pentyl)-3-(heneicosynyl)1,4-diazabuta-1,3-diene]nickel[4-(butyl)catecholate]; [1,4-bis{3,5-di(pentyl)phenyl}-2-(octyl)-3-(butyl)1,4-diazabuta-1,3-diene]palladium[4-(ethyl)-5-(pentyl)catecholate]; [1,4-bis{4-nonylphenyl}-2, 3-(dihydrido)1,4-diazabuta-1,3-diene]nickel[3-(methyl)-5-(pentyl)-catecholate]; [1,4-bis{3,4-di(ethyl)phenyl}-2-(hexadecynyl)-3-(nonadecyl)1,4-diazabuta-1,3-diene]nickel [3-(pentyl)catecholate]; [1,4-bis{3-octadecynylphenyl}-2,3-(dibutyl)-1,4-diazabuta-1,3-diene]nickel[3-(ethyl)-6-(pentyl)catecholate]; [1,4-bis{4-nonacosynyl-phenyl}-2-(hydrido)-3-(butyl)1,4-diazabuta-1,3-diene]nickel[4-(methyl)catecholate]; [1,4-bis{phenyl}-2-(methyl)-3-(hydrido)1,4-diazabuta-1,3-diene]nickel[4-(propyl)-catecholate]; [1,4-bis{3,4-di(butyl)phenyl}-2-(hydrido)-3-(butyl)1,4-diazabuta-1,3-diene]nickel[3-(propyl)-6-(pentyl) catecholate]; [1,4-bis{3-octacosynylphenyl}-2,3-(dihydrido)-1,4-diazabuta-1,3-diene]nickel[3-(propyl) catecholate]; [1,4-bis{3,5-di(pentyl)phenyl}-2-(butyl)-3-(triacontyl)1,4-diazabuta-1,3-diene]nickel[3-(propyl)-6-(butyl)catecholate]; [1,4-bis{phenyl}-2,3-(dibutyl)1,4-diazabuta-1,3-diene]nickel[4-(methyl)catecholate]; [1,4-bis{phenyl}-2-(octadecyl)-3-(butyl)1,4-diazabuta-1,3-diene]nickel[3-(ethyl)-catecholate]; [1,4-bis{phenyl}-2-(butyl)-3-(octyl)1,4-diazabuta-1,3-diene]nickel[3-(propyl)-4-(butyl)-5-(pentyl)catecholate]; [1,4-bis{4-dodecylphenyl}-2-(octyl)-3-(hexyl)-1,4-diazabuta-1,3-diene]palladium[3-(butyl)catecholate]; [1,4-bis{3-octacosenyl-phenyl}-2-(hexyl)-3-(ethyl)1,4-diazabuta-1,3-diene]nickel[4-(ethyl)-5-(pentyl)-catecholate]; [1,4-bis{3,4-di(propyl)phenyl}-2-(octyl)-3-(hexyl),4-diazabuta-1,3-diene]nickel[4-(butyl)-5-(pentyl)catecholate]; [1,4-bis{3,5-di(ethyl)phenyl}-2-(hydrido)-3-(butenyl)1,4-diazabuta-1,3-diene]nickel[3-(pentyl)-5-(butyl)catecholate]; [1,4-bis{4-triacontenylphenyl}-2-(butyl)-3-(hexyl)1,4-diazabuta-1,3-diene]nickel[4,5-di(methyl)-catecholate]; [1,4-bis{3,4-di (pentyl)phenyl}-2,3-(dibutyl)1,4-diazabuta-1,3-diene] palladium[3-(pentyl)-4-(propyl)catecholate]; [1,4-bis{3-heptynylphenyl}-2-(butyl)-3-(ethyl)1,4-diazabuta-1,3-diene]nickel[4-(propyl)catecholate]; [1,4-bis{phenyl}-2-(undecynyl)-3-(butyl)1,4-diazabuta-1,3-diene]palladium[4-(pentyl)-5-(ethyl)-catecholate]; [1,4-bis{3,5-di(methyl) phenyl}-2,3-(dibutyl)1,4-diazabuta-1,3-diene]palladium[3-(pentyl)catecholate]; [1,4-bis{3,4-di(pentyl)phenyl}-2-(tetracosenyl)-3-(hydrido)1,4-diazabuta-1,3-diene]nickel[3-(methyl)-6-(butyl)catecholate]; [1,4-bis{4-diethylaminophenyl}-2-(hexyl)-3-(octacosyl)-1,4-diazabuta-1,3-diene]nickel[4-(methyl)-5-(butyl)catecholate]; [1,4-bis{3,5-di(butyl)phenyl}-2-(hexyl)-3-(butyl)1,4-diazabuta-1,3-diene]nickel[3-(butyl)-6-(ethyl)catecholate]; [1,4-bis{3, 5-di(ethyl)phenyl}-2-(butyl)-3-(ethyl)1,4-diazabuta-1,3-diene]nickel[3-(pentyl)-4-(butyl)-5-(ethyl)catecholate]; [1,4-bis{3,5-di(pentyl)phenyl}-2-(hydrido)-3-(butyl)1,4-diazabuta-1,3-diene]nickel[3,5-di(butyl)-4-(bromo) catecholate]; [1,4-bis{3,4-di(propyl)phenyl}-2-(butyl)-3-(hexyl)1,4-diazabuta-1,3-diene]palladium[4-(propyl) catecholate]; [1,4-bis{phenyl}-2,3-(dipentyl)-1,4-diazabuta-1,3-diene]nickel[3-(propyl)-4-(butyl) catecholate]; [1,4-bis{3,4-di(butyl)-phenyl}-2-(hexyl)-3-(butyl)1,4-diazabuta-1,3-diene]palladium[4-(ethyl) catecholate]; [1,4-bis{phenyl}-2-(butyl)-3-(hexyl)1,4-diazabuta-1,3-diene]nickel[3-(methyl)-4-(propyl) catecholate]; [1,4-bis{phenyl}-2-(hydrido)-3-(butyl)1,4-diazabuta-1,3-diene]nickel[3,4-di(methyl)-6-(propyl) catecholate]; [1,4-bis{4-heneicosylphenyl}-2-(butyl)-3-(hexyl)1,4-diazabuta-1,3-diene]nickel[3,4-di(propyl)-6-(methyl)catecholate]; [1,4-bis{phenyl}-2-(ethyl)-3-(methyl) 1,4-diazabuta-1,3-diene]nickel[3-(methyl)-6-(butyl)- catecholate]; [1,4-bis{4-tridocosanalylphenyl}-2-(docosyl)-3-(butyl)1,4-diazabuta-1,3-diene]nickel[4-(ethyl)catecholate]; [1,4-bis{3,4-di(butyl)phenyl}-2-(butyl)-3-(octyl)1,4-diazabuta-1,3-diene]nickel[3-(methyl)-4-(pentyl)catecholate]; [1,4-bis{3,4-di(pentyl)-phenyl}-2-(butyl)-3-(hydrido)1,4-diazabuta-1,3-diene]nickel[3-(propyl)catecholate]; [1,4-bis{3,5-di(propyl)phenyl}-2-(butyl)-3-(pentyl)1,4-diazabuta-1,3-diene]nickel[3-(propyl)catecholate]; [1,4-bis{3,5-di(methyl)phenyl}-2-(butyl)-3-(hydrido)1,4-diazabuta-1,3-diene]palladium[3-(ethyl)-4,5-di(butyl)catecholate]; [1,4-bis{3,4-di(methyl)phenyl}-2-(pentyl)-3-(hydrido)1,4-diazabuta-1,3-diene]nickel[3-(butyl)-4-(ethyl)-6-(methyl)-catecholate]; [1,4-bis{3,5-di(methyl)phenyl}-2-(butyl)-3-(docosyl)1,4-diazabuta-1,3-diene]nickel[4-(pentyl)catecholate]; [1,4-bis{4-methyldiethylsilylmethyl)phenyl}-2-(butyl)-3-(octyl)1,4-diazabuta-1,3-diene]palladium[4-(methyl)catecholate]; [1,4-bis{3,4-di(pentyl)phenyl}-2-(hydrido)-3-(nonacosynyl)1,4-diazabuta-1,3-diene]nickel[3-(methyl)-6-(butyl)catecholate]; [1,4-bis{3-butylphenyl}-2,3-(dihydrido)1,4-diazabuta-1,3-diene]nickel[3-(methyl)-4-(butyl)-5-(ethyl)catecholate]; [1,4-bis{3,5-di(propyl)-phenyl}-2-(hydrido)-3-(butyl)1,4-diazabuta-1,3-diene]nickel[3-(butyl)-4-(propyl)-6-(ethyl)catecholate]; [1,4-bis{3-heptadecylphenyl}-2,3-(dihydrido)1,4-diazabuta-1,3-diene]nickel[4-(methyl)-5-(pentyl)catecholate]; [1,4-bis{3,4-di(ethyl)phenyl}-2,3-(dibutyl)1,4-diazabuta-1,3-diene]nickel[4-(ethyl)catecholate]; [1,4-bis{3,4-di(butyl)-phenyl}-2-(methyl)-3-(hydrido)1,4-diazabuta-1,3-diene]nickel[3-(ethyl)catecholate]; [1,4-bis{4-undecynylphenyl}-2-(hydrido)-3-(butyl)1,4-diazabuta-1,3-diene]palladium[3-(pentyl)catecholate]; [1,4-bis{3,4-di(pentyl)phenyl}-2-(pentyl)-3-(butyl)1,4-diazabuta-1,3-diene]nickel[3-(hexonyl)catecholate]; [1,4-bis{3,5-di(propyl)phenyl}-2,3-(dioctyl)-1,4-diazabuta-1,3-diene]palladium[4-(pentyl)catecholate]; [1,4-bis{phenyl}-2-(ethyl)-3(hexyl)1,4-diazabuta-1,3-diene]palladium[4-(ethyl)-5-(methyl)catecholate]; [1,4-bis{3,4-di(butyl)phenyl}-2-(hydrido)-3-(butyl)1,4-diazabuta-1,3-diene]nickel[3-(butyl)-6-(ethyl)catecholate]; [1,4-bis{phenyl}-2-(butyl)-3-(hydrido)1,4-diazabuta-1,3-diene]nickel[4-(pentyl)-5-(propyl)catecholate]; [1,4-bis{4-heneicosenylphenyl}-2-(butyl)-3-(octynyl)1,4-diazabuta-1,3-diene]palladium[4-(ethyl)catecholate]; [1,4-bis{phenyl}-2-(heneicosyl)-3-(decynyl),4-diazabuta-1,3-diene]nickel[3-(pentyl)-4-(butyl)catecholate]; [1,4-bis{4-nonacosenylphenyl}-2-(ethyl)-3-(hydrido)1,4-diazabuta-1,3-diene]nickel[3-(propyl)catecholate]; [1,4-bis{phenyl}-2-(hexyl)-3-(butyl)1,4-diazabuta-1,3-diene]nickel[3-(butyl)catecholate]; [1,4-bis{3,5-di(pentyl)phenyl}-2-(hydrido)-3-(butyl),4-diazabuta-1,3-diene]nickel[3-(ethyl)-4-(propyl)catecholate]; [1,4-bis{phenyl}-2-(octyl)-3-(butyl)-1,4-diazabuta-1,3-diene]nickel[3-(ethyl)catecholate]; [1,4-bis{3,5-di(pentyl)phenyl}-2-(pentacosyl)-3-(pentyl)1,4-diazabuta-1,3-diene]nickel[3-(ethyl)-5-(pentyl)catecholate]; [1,4-bis{3-octylaminophenyl}-2-(hydrido)-3-(butyl),4-diazabuta-1,3-diene]nickel[3,5-di(ethyl)catecholate]; [1,4-bis{phenyl}-2-(butyl)-3-(pentyl)1,4-diazabuta-1,3-diene]nickel[3-(propyl)-6-(butyl)catecholate]; [1,4-bis{3,5-di(pentyl)phenyl}-2,3-(dibutyl)1,4-diazabuta-1,3-diene]palladium[4,5-di(propyl)catecholate]; [1,4-bis{3-heptynylphenyl}-2-(octyl)-3-(butyl)1,4-diazabuta-1,3-diene]nickel[3-(methyl)catecholate]; [1,4-bis{3-octylaminophenyl}-2-(pentyl)-3-(butyl)1,4-diazabuta-1,3-diene]nickel[3-(propyl)catecholate]; [1,4-bis{3,5-di(methyl)phenyl}-2-(butyl)-3-(nonadecynyl)1,4-diazabuta-1,3-diene]palladium[4-(ethyl)-5-(ethanalyl)catecholate]; [1,4-bis{phenyl}-2,3-(dihydrido)-1,4-diazabuta-1,3-diene]nickel[3-(ethyl)-5-(methyl)catecholate]; [1,4-bis{4-methyldiethylsilylmethyl)phenyl}-2-(hydrido)-3-(butyl)1,4-diazabuta-1,3-diene]nickel[3-(methyl)-4-(ethyl)-6-(pentyl)catecholate]; [1,4-bis{3,4-di(ethyl)phenyl}-2-(pentyl)-3-(methyl)1,4-diazabuta-1,3-diene]nickel[4-(pentyl)catecholate]; [1,4-bis{3,5-di(propyl)-phenyl}-2,3-(dibutyl)1,4-diazabuta-1,3-diene]nickel[3-(pentyl)catecholate]; [1,4-bis{3-heptacosynylphenyl}-2-(nonacosynyl)-3-(nonynyl)1,4-diazabuta-1,3-diene]nickel[3-(butyl)catecholate]; [1,4-bis{phenyl}-2-(hydrido)-3-(pentyl)1,4-diazabuta-1,3-diene]nickel[3-(ethyl)-5-(methyl)catecholate]; [1,4-bis{phenyl}-2-(nonacosyl)-3-(hexyl)1,4-diazabuta-1,3-diene]nickel[3-(butyl)catecholate]; [1,4-bis{3,5-di(butyl)phenyl}-2-(octyl)-3-(heptenyl)1,4-diazabuta-1,3-diene]palladium[4,5-di(methyl)catecholate]; [1,4-bis{3,4-di(ethyl)phenyl}-2-(hydrido)-3-(butyl)1,4-diazabuta-1,3-diene]nickel[3-(pentyl)catecholate]; [1,4-bis{3,4-di(pentyl)phenyl}-2-(nonacosyl)-3-(butyl)1,4-diazabuta-1,3-diene]palladium[3,6-di(propyl)catecholate]; [1,4-bis{4-tricosylphenyl}-2-(butyl)-3-(octyl)1,4-diazabuta-1,3-diene]nickel[3-(methyl)-4-(propyl)catecholate]; [1,4-bis{phenyl}-2-(octyl)-3-(ethyl)1,4-diazabuta-1,3-diene]nickel[3-(methyl)-4-(hexyl)-5-(propyl)catecholate]; [1,4-bis{4-undecenylphenyl}-2-(pentyl)-3-(methyl)1,4-diazabuta-1,3-diene]nickel[4-(butyl)-5-(propyl)catecholate]; [1,4-bis{3-pentynylphenyl}-2-(hydrido)-3-(tridecyl)1,4-diazabuta-1,3-diene]nickel[3-(propyl)catecholate]; [1,4-bis{3,5-di(pentyl)phenyl}-2-(pentyl)-3-(propenyl)1,4-diazabuta-1,3-diene]nickel[4-(ethyl)catecholate]; [1,4-bis{3,4-di(butyl)phenyl}-2-(hexyl)-3-(hydrido)1,4-diazabuta-1,3-diene]nickel[4-(methyl)catecholate]; [1,4-bis{3,5-di(butyl)phenyl}-2,3-(dibutyl)1,4-diazabuta-1,3-diene]nickel[3-(pentyl)catecholate]; [1,4-bis{3,5-di(methyl)phenyl}-2-(hydrido)-3-(butyl)1,4-diazabuta-1,3-diene]nickel[4-(butyl)-5-(propyl)catecholate]; [1,4-bis{phenyl}-2-(hexyl)-3-(pentyl)1,4-diazabuta-1,3-diene]nickel[3-(propyl)-6-(methyl)-catecholate]; [1,4-bis{phenyl}-2-(hexadecenyl)-3-(octyl)1,4-diazabuta-1,3-diene]nickel[3-(butyl)catecholate]; [1,4-bis{3,4-di(pentyl)phenyl}-2-(hydrido)-3-(octyl)1,4-diazabuta-1,3-diene]palladium[4-(trimethylsilylmethyl)-5-(butyl)catecholate]; [1,4-bis{3,5-di(pentyl)phenyl}-2-(dodecenyl)-3-(butyl)1,4-diazabuta-1,3-diene]nickel[3-(ethyl)-catecholate]; [1,4-bis{3-nonylphenyl}-2-(heneicosynyl)-3-(nonynyl)1,4-diazabuta-1,3-diene]nickel[3-(butyl)-6-(methyl)catecholate]; [1,4-bis{phenyl}-2-(decenyl)-3-(hexyl)-1,4-diazabuta-1,3-diene]nickel[3-(trimethylsilylmethyl)-4,5-di(methyl)catecholate]; [1,4-bis{3,5-di(methyl)phenyl}-2-(octyl)-3-(hydrido)1,4-diazabuta-1,3-diene]palladium[3-(propyl)catecholate]; [1,4-bis{phenyl}-2-(octyl)-3-(docosenyl)1,4-diazabuta-1,3-diene]nickel[3-(propyl)catecholate]; [1,4-bis{3,4-di(ethyl)phenyl}-2,3-(dihydrido)1,4-diazabuta-1,3-diene]nickel[4-(pentyl)catecholate]; [1,4-bis{3,5-di(propyl)phenyl}-2-(hexyl)-3-(pentyl)1,4-diazabuta-1,3-diene]nickel[3-(butyl)catecholate]; [1,4-bis{phenyl}-2-(hydrido)-3-(butyl)1,4-diazabuta-1,3-diene]nickel[3,4-di(propyl)-catecholate]; [1,4-bis{3,5-di(methyl)phenyl}-2-(hydrido)-3-(butyl)1,4-diazabuta-1,3-diene]palladium[4-(butanalyl)catecholate]; [1,4-bis{phenyl}-2-(butyl)-3-(heptynyl)1,4-diazabuta-1,3-diene]nickel[4-(propyl)catecholate]; [1,4-bis{phenyl}-2,3-(dihydrido)1,4-diazabuta-1,3-diene]palladium[3-(pentyl)-5-(methyl)catecholate]; [1,4-bis{phenyl}-2-(butyl)-3-(hydrido)1,4-diazabuta-1,3-diene]nickel[3-(ethyl)-4-(butyl)-6-(pentyl)-catecholate]; [1,4-bis{3,4-di(pentyl)phenyl}-2,3-(dibutyl)1,4-diazabuta-1,3-diene]palladium[3-(methyl)-4-(propyl)-5-(ethyl)catecholate]; [1,4- bis{phenyl}-2,3-(dibutyl)-1,4-diazabuta-1,3-diene]nickel[4,5-di(methyl)catecholate]; [1,4-bis{phenyl}-2-(butyl)-3-(pentyl)1,4-diazabuta-1,3-diene]palladium[3-(pentyl)catecholate]; [1,4-bis{4-hexadecyl-phenyl}-2-(butyl)-3-(octyl)1,4-diazabuta-1,3-diene]palladium[4-(ethyl)-5-(propyl)-catecholate]; [1,4-bis{4-butanalylphenyl}-2-(methyl)-3-(butyl)1,4-diazabuta-1,3-diene]palladium[3-(methyl)-6-(pentyl)catecholate]; [1,4-bis{3,4-di(methyl)phenyl}-2-(hydrido)-3-(ethyl)1,4-diazabuta-1,3-diene]nickel[3-(methyl)-6-(pentyl)catecholate]; [1,4-bis{phenyl}-2-(butyl)-3-(hexyl)1,4-diazabuta-1,3-diene]palladium[3-(butyl)-catecholate]; [1,4-bis{phenyl}-2-(nonynyl)-3-(octyl)1,4-diazabuta-1,3-diene]palladium [3-(hexyl)-6-(methyl)catecholate]; [1,4-bis{phenyl}-2-(butyl)-3-(ethyl)1,4-diazabuta-1,3-diene]palladium[3-(ethyl)-6-(butyl)catecholate]; [1,4-bis{3,5-di(ethyl)phenyl}-2,3-(dibutyl)1,4-diazabuta-1,3-diene]nickel[4-(methyl)catecholate]; [1,4-bis{3,4-di(pentyl)-phenyl}-2-(propenyl)-3-(pentyl)1,4-diazabuta-1,3-diene]nickel[3,5-di(methyl)-catecholate]; [1,4-bis{phenyl}-2-(pentyl)-3-(pentenyl)1,4-diazabuta-1,3-diene]nickel[3,4-di(propyl)-6-(pentyl)catecholate]; [1,4-bis{3,4-di(methyl)phenyl}-2-(pentyl)-3-(heptacosyl)1,4-diazabuta-1,3-diene]nickel[4,5-di(pentyl)catecholate]; [1,4-bis{3,5-di(pentyl)phenyl}-2-(butyl)-3-(hexyl),4-diazabuta-1,3-diene]nickel[3,5-di(pentyl)-catecholate]; [1,4-bis{3,4-di(pentyl)phenyl}-2-(triacontynyl)-3-(pentyl),4-diazabuta-1,3-diene]nickel[3-(ethyl)-6-(propyl)catecholate]; [1,4-bis{3-tridecylphenyl}-2-(hydrido)-3-(heptynyl)1,4-diazabuta-1,3-diene]nickel[4-(pentyl)-5-(butyl)catecholate]; [1,4-bis{3-octadecynylphenyl}-2-(octyl)-3-(hydrido)1,4-diazabuta-1,3-diene]nickel[3-(methyl)-catecholate]; [1,4-bis{3,5-di(ethyl)phenyl}-2-(hydrido)-3-(methyl)1,4-diazabuta-1,3-diene]palladium[4-(pentyl)catecholate]; [1,4-bis{3,5-di(pentyl)phenyl}-2-(tetradecynyl)-3-(octenyl)1,4-diazabuta-1,3-diene]nickel[3-(butyl)catecholate]; [1,4-bis{3,4-di(pentyl)-phenyl}-2,3-(dibutyl)1,4-diazabuta-1,3-diene]nickel[4-(pentyl)catecholate]; [1,4-bis{phenyl}-2-(octyl)-3-(butyl)1,4-diazabuta-1,3-diene]nickel[3-(ethyl)catecholate]; [1,4-bis{phenyl}-2-(pentyl)-3-(butyl)1,4-diazabuta-1,3-diene]nickel[3-(methyl)-6-(pentyl)catecholate]; [1,4-bis{3,4-di(propyl)phenyl}-2-(hydrido)-3-(pentyl)1,4-diazabuta-1,3-diene]nickel[4-(butyl)-5-(methyl)catecholate]; [1,4-bis{phenyl}-2-(octyl)-3-(butyl)-1,4-diazabuta-1,3-diene]nickel[3-(methyl)-5-(ethyl)catecholate]; [1,4-bis{3-heptacosenylphenyl}-2,3-(dibutyl)1,4-diazabuta-1,3-diene]palladium[3-(methyl)-4-(ethyl)catecholate]; [1,4-bis{phenyl}-2-(hydrido)-3-(butyl)1,4-diazabuta-1,3-diene]palladium[3-(ethyl)-6-(pentyl)catecholate]; [1,4-bis{3,4-di(methylethylamino)phenyl}-2-(methyl)-3-(octyl)1,4-diazabuta-1,3-diene]nickel[3-(butyl)-4-(propyl)catecholate]; [1,4-bis{4-octenylphenyl}-2-(butyl)-3-(heneicosyl)1,4-diazabuta-1,3-diene]nickel[3-(propyl)-4-(butyl)-5-(pentyl)catecholate]; [1,4-bis{phenyl}-2-(butyl)-3-(hydrido)1,4-diazabuta-1,3-diene]nickel[4-(ethyl)catecholate]; [1,4-bis{phenyl}-2-(eicosynyl)-3-(butyl)1,4-diazabuta-1,3-diene]nickel[3-(propyl)catecholate]; [1,4-bis{3,4-di(ethyl)-phenyl}-2-(butyl)-3-(tridecenyl)1,4-diazabuta-1,3-diene]palladium[3-(propyl)-catecholate]; [1,4-bis{3,5-di(propyl)phenyl}-2,3-(dihydrido)1,4-diazabuta-1,3-diene]nickel[3-(ethyl)-4-(methyl)-6-(butyl)catecholate]; [1,4-bis{3-tetradecylphenyl}-2-(hydrido)-3-(nonynyl)1,4-diazabuta-1,3-diene]nickel[3-(butyl)-6-(pentyl)catecholate]; [1,4-bis{3,5-di(butyl)phenyl}-2-(hexyl)-3-(triacontenyl)1,4-diazabuta-1,3-diene]nickel[4-(ethyl)catecholate]; [1,4-bis{phenyl}-2,3-(dihydrido),4-diazabuta-1,3-diene]nickel[3-(ethyl)-5-(octyl)catecholate]; [1,4-bis{phenyl-}2-(butyl)-3-(octyl)1,4-diazabuta-1,3-diene]nickel[3-(propyl)-4-(pentyl)-5-(butyl)catecholate]; [1,4-bis{3,5-di(ethyl)phenyl}-2,3-(dibutyl)1,4-diazabuta-1,3-diene]nickel[3-(dodecanonyl)-5-(butyl)catecholate]; [1,4-bis{3-tridocosanalylphenyl}-2-(hexyl)-3-(butyl)1,4-diazabuta-1,3-diene]palladium[3-(butyl)catecholate]; [1,4-bis{3-dodecenylphenyl}-2-(octyl)-3-(butyl)1,4-diazabuta-1,3-diene]palladium[3-(methyl)catecholate]; [1,4-bis{3,5-di(butyl)phenyl}-2-(hydrido)-3-(butyl)1,4-diazabuta-1,3-diene]nickel[3-(methyl)catecholate]; [1,4-bis{phenyl}-2-(pentyl)-3-(hydrido)1,4-diazabuta-1,3-diene]palladium[3,6-di(methyl)catecholate]; [1,4-bis{3,4-di(butyl)phenyl}-2-(butyl)-3-(methyl)1,4-diazabuta-1,3-diene]nickel[4-(methyl)catecholate]; [1,4-bis{3,5-di(methyl)phenyl}-2,3-(dibutyl)1,4-diazabuta-1,3-diene]nickel[3,5-di(methyl)catecholate]; [1,4-bis{3,5-di(ethyl)phenyl}-2-(hydrido)-3-(pentynyl)1,4-diazabuta-1,3-diene]palladium[3-(butyl)-5-(propyl)catecholate]; [1,4-bis{phenyl}-2-(octyl)-3-(hexyl)1,4-diazabuta-1,3-diene]nickel[3-(pentyl)catecholate]; [1,4-bis{4-octylphenyl}-2-(pentyl)-3-(butyl)1,4-diazabuta-1,3-diene]nickel[3-(pentyl)-6-(ethyl)catecholate]; [1,4-bis{3,4-di(methyl)phenyl}-2-(undecenyl)-3-(dodecynyl)1,4-diazabuta-1,3-diene]nickel[3-(ethyl)-5-(butyl)catecholate]; [1,4-bis{3,5-di(pentyl)-phenyl}-2-(hydrido)-3-(nonenyl)1,4-diazabuta-1,3-diene]palladium[4-(ethyl)-catecholate]; [1,4-bis{3,4-di(methyl)phenyl}-2-(butyl)-3-(methyl)1,4-diazabuta-1,3-diene]nickel[3-(butyl)catecholate]; [1,4-bis{3,4-di(ethyl)phenyl}-2-(butyl)-3-(pentyl)-1,4-diazabuta-1,3-diene]nickel[3-(butyl)catecholate]; [1,4-bis{phenyl}-2-(butyl)-3-(hydrido)1,4-diazabuta-1,3-diene]nickel[3-(propyl)catecholate]; [1,4-bis{3,5-di(methyl)-phenyl}-2-(butyl)-3-(ethyl)1,4-diazabuta-1,3-diene]nickel[4-(ethyl)catecholate]; [1,4-bis{3,4-di(pentyl)phenyl}-2-(pentyl)-3-(butyl)1,4-diazabuta-1,3-diene]nickel[3-(propyl)catecholate]; [1,4-bis{3,5-di(butyl)phenyl}-2-(tricosynyl)-3-(butyl)1,4-diazabuta-1,3-diene]nickel[3-(pentyl)catecholate]; [1,4-bis{phenyl}-2-(butyl)-3-(octyl)1,4-diazabuta-1,3-diene]nickel[3-(ethyl)catecholate]; [1,4-bis{3-pentenylphenyl}-2-(butyl)-3-(methyl)1,4-diazabuta-1,3-diene]nickel[4-(pentyl)catecholate]; [1,4-bis{3,5-di(ethyl)-phenyl}-2-(ethyl)-3-(methyl)1,4-diazabuta-1,3-diene]nickel[3-(pentyl)-6-(ethyl)-catecholate]; [1,4-bis{3,5-di(pentyl)phenyl}-2,3-(dibutyl)1,4-diazabuta-1,3-diene]nickel[3-(propyl)-5-(pentyl)catecholate]; [1,4-bis{phenyl}-2-(butyl)-3-(hydrido)1,4-diazabuta-1,3-diene]nickel[3-(ethyl)-4-(methyl)-5-(pentyl)catecholate]; [1,4-bis{phenyl}-2-(butynyl)-3-(butyl)1,4-diazabuta-1,3-diene]nickel[3-(ethyl)-4-(butyl)catecholate]; [1,4-bis{3-tetradecylphenyl}-2-(butyl)-3-(hydrido)1,4-diazabuta-1,3-diene]palladium[3-(propyl)catecholate]; [1,4-bis{3,4-di(ethyl)phenyl}-2-(hydrido)-3-(butyl)1,4-diazabuta-1,3-diene]nickel[4-(methyl)catecholate]; [1,4-bis{3,5-di(methyl)phenyl}-2,3-(dibutyl)-1,4-diazabuta-1,3-diene]palladium[4-(propyl)-5-(ethyl)catecholate]; [1,4-bis{3,4-di(propyl)phenyl}-2-(octyl)-3-(butyl)1,4-diazabuta-1,3-diene]nickel[3-(propyl)-catecholate]; [1,4-bis{3,4-di(propyl)phenyl}-2-(pentyl)-3-(hexyl)1,4-diazabuta-1,3-diene]nickel[3,4-di(methyl)-5-(diethylamino)catecholate]; [1,4-bis{3,5-di(pentyl)phenyl}-2-(methyl)-3-(butyl)1,4-diazabuta-1,3-diene]nickel[3-(pentyl)-6-(ethyl)catecholate]; [1,4-bis{3-undecylphenyl}-2-(docosyl)-3-(butyl)1,4-diazabuta-1,3-diene]nickel[3-(ethyl)-catecholate]; [1,4-bis{3,4-di(pentyl)phenyl}-2-(octyl)-3-(hydrido)1,4-diazabuta-1,3-diene]palladium[4-(pentyl)catecholate]; [1,4-bis{phenyl}-2-(heptenyl)-3-(hydrido)1,4-diazabuta-1,3-diene]nickel[3-(methyl)-4-(diethylamino)catecholate]; [1,4-bis{3,5-di(ethyl)phenyl}-2-(butyl)-3-(hydrido)1,4-diazabuta-1,3-diene]nickel[3-(methyl)-4-(propyl)

catecholate]; [1,4-bis{phenyl}-2-(hydrido)-3-(butyl)1,4-diazabuta-1,3-diene]nickel[3-(methyl)-6-(propyl)catecholate]; [1,4-bis{3,5-di(pentyl)phenyl}-2-(hexyl)-3-(methyl)1,4-diazabuta-1,3-diene]nickel[3-(ethyl)-4-(pentyl)-6-(butyl)catecholate]; [1,4-bis{3,4-di(pentyl)phenyl}-2-(hexyl)-3-(butyl)1,4-diazabuta-1,3-diene]nickel[4-(pentyl)-catecholate]; [1,4-bis{4-docosylphenyl}-2-(eicosenyl)-3-(butyl)1,4-diazabuta-1,3-diene]nickel[3-(pentyl)-5-(propyl)catecholate]; [1,4-bis{3,5-di(methyl)phenyl}-2-(octyl)-3-(hexyl)1,4-diazabuta-1,3-diene]nickel[3,4-di(pentyl)-6-(propyl)catecholate]; [1,4-bis{phenyl}-2-(methyl)-3-(hydrido)1,4-diazabuta-1,3-diene]nickel[3-(propyl)-6-(methyl)catecholate]; [1,4-bis{phenyl}-2-(octyl)-3-(hydrido)1,4-diazabuta-1,3-diene]nickel[3-(methyl)-4-(propyl)-5-(ethyl)catecholate]; [1,4-bis{3-heptacosenylphenyl}-2-(butynyl)-3-(hydrido)1,4-diazabuta-1,3-diene]nickel[3-(methyl)-5-(butyl)catecholate]; [1,4-bis{4-butylphenyl}-2-(tricosynyl)-3-(pentyl)1,4-diazabuta-1,3-diene]nickel[3-(ethyl)catecholate]; [1,4-bis{3-heptacosynylphenyl}-2-(ethyl)-3-(hexyl)1,4-diazabuta-1,3-diene]nickel[3,6-di(pentyl)catecholate]; [1,4-bis{phenyl}-2,3-(dibutyl)1,4-diazabuta-1,3-diene]nickel[3-(methyl)catecholate]; [1,4-bis{3,4-di(ethyl)phenyl}-2-(butyl)-3-(hydrido)1,4-diazabuta-1,3-diene]nickel[3-(pentyl)catecholate]; [1,4-bis{3,5-di(pentyl)-phenyl}-2-(butyl)-3-(ethyl)1,4-diazabuta-1,3-diene]nickel[4,5-di(butyl)catecholate]; [1,4-bis{4-tetracosynylphenyl}-2-(hydrido)-3-(butyl)1,4-diazabuta-1,3-diene]palladium[4-(methyl)catecholate]; [1,4-bis{phenyl}-2-(butyl)-3-(hexyl)1,4-diazabuta-1,3-diene]nickel[4,5-di(ethyl)catecholate]; [1,4-bis{3-eicosynylphenyl}-2-(butyl)-3-(hydrido)1,4-diazabuta-1,3-diene]palladium[3,6-di(propyl)-4-(butyl)catecholate]; [1,4-bis{phenyl}-2,3-(dibutyl)1,4-diazabuta-1,3-diene]nickel[4-(butyl)-5-(ethyl)catecholate]; [1,4-bis{3,5-di(pentyl)phenyl}-2-(undecenyl)-3-(octynyl)1,4-diazabuta-1,3-diene]nickel[4-(ethyl)-catecholate]; [1,4-bis{phenyl}-2-(hydrido)-3-(methyl)1,4-diazabuta-1,3-diene]nickel[4-(methyl)catecholate]; [1,4-bis{3,5-di(pentyl)phenyl}-2-(hydrido)-3-(butyl)1,4-diazabuta-1,3-diene]nickel[4-(methyl)catecholate]; [1,4-bis{3,4-di(pentyl)phenyl}-2-(hydrido)-3-(butyl)1,4-diazabuta-1,3-diene]nickel[3-(propyl)catecholate]; [1,4-bis{phenyl}-2-(octyl)-3-(pentyl)1,4-diazabuta-1,3-diene]nickel[4-(ethyl)catecholate]; [1,4-bis{3,5-di(methyl)phenyl}-2-(butyl)-3-(hydrido)1,4-diazabuta-1,3-diene]nickel[3-(ethyl)-catecholate]; [1,4-bis{phenyl}-2-(pentyl)-3-(butyl)1,4-diazabuta-1,3-diene]nickel[3,5-di(pentyl)catecholate]; [1,4-bis{phenyl}-2,3-(dihydrido)1,4-diazabuta-1,3-diene]nickel[4-(butyl)-5-(methyl)catecholate]; [1,4-bis{4-nonacosenylphenyl}-2-(octyl)-3-(nonacosenyl)1,4-diazabuta-1,3-diene]palladium[3-(propyl)catecholate]; [1,4-bis{phenyl}-2-(hexyl)-3-(octyl)1,4-diazabuta-1,3-diene]nickel[3-(butyl)-4-(pentyl)-(methyl)catecholate]; [1,4-bis{3,5-di(pentyl)phenyl}-2-(pentyl)-3-(butyl)1,4-diazabuta-1,3-diene]palladium[4-(pentyl)-5-(dodecamino)catecholate]; [1,4-bis{3-tetradecenyl-phenyl}-2-(butyl)-3-(hydrido)1,4-diazabuta-1,3-diene]palladium[3-(butyl)catecholate]; [1,4-bis{phenyl}-2,3-(dibutyl)1,4-diazabuta-1,3-diene]nickel[4-(tridocosanalyl)-5-(ethyl)catecholate]; [1,4-bis{phenyl}-2-(tetracosyl)-3-(butyl)1,4-diazabuta-1,3-diene]nickel[3-(pentyl)-6-(methyl)catecholate]; [1,4-bis{3,5-di(methyl)phenyl}-2,3-(dihydrido)1,4-diazabuta-1,3-diene]nickel [3-(propyl)-4-(methyl)-5-(pentyl)catecholate]; [1,4-bis{3,5-di(methyl)phenyl}-2-(hexyl)-3-(butyl)1,4-diazabuta-1,3-diene]nickel[4-(pentyl)catecholate]; [1,4-bis{3,5-di(butyl)phenyl}-2,3-(dihydrido)1,4-diazabuta-1,3-diene]nickel[4-(ethyl)catecholate]; [1,4-bis{phenyl}-2-(butyl)-3-(hexyl)1,4-diazabuta-1,3-diene]palladium[3-(butyl)-6-(methyl)catecholate]; [1,4-bis{3,5-di(methyl)phenyl}-2-(hydrido)-3-(ethyl)1,4-diazabuta-1,3-diene]nickel[3-(butyl)-6-(pentyl)catecholate]; [1,4-bis{4-dodecenylphenyl}-2-(hydrido)-3-(butyl)1,4-diazabuta-1,3-diene]nickel[3-(pentyl)catecholate]; [1,4-bis{phenyl}-2-(hydrido)-3-(butyl)1,4-diazabuta-1,3-diene]nickel[3-(propyl)-5-(pentyl)catecholate]; [1,4-bis{3,5-di(ethyl)phenyl}-2-(eicosyl)-3-(pentadecenyl)1,4-diazabuta-1,3-diene]nickel[3-(propyl)-4-(ethyl)catecholate]; [1,4-bis{3,4-di(propyl)phenyl}-2,3-(dibutyl)1,4-diazabuta-1,3-diene]nickel[4-(tridocosanalyl)catecholate]; [1,4-bis{3-tetradecylphenyl}-2-(butyl)-3-(ethyl)1,4-diazabuta-1,3-diene]nickel[4-(butyl)-5-(ethyl)catecholate]; [1,4-bis{phenyl}-2,3-(dibutyl)1,4-diazabuta-1,3-diene]nickel[3-(propyl)catecholate]; [1,4-bis{4-butanalyl-phenyl}-2-(hydrido)-3-(butyl)1,4-diazabuta-1,3-diene]nickel[4-(methyl)-5-(ethyl)-catecholate]; [1,4-bis{4-propylphenyl}-2,3-(dihydrido)1,4-diazabuta-1,3-diene]nickel[3-(propyl)catecholate]; [1,4-bis{phenyl}-2-(butyl)-3-(methyl)1,4-diazabuta-1,3-diene]nickel[3-(butyl)-4-(methyl)-5-(ethyl)catecholate]; [1,4-bis{phenyl}-2,3-(dibutyl)1,4-diazabuta-1,3-diene]nickel[3,4-di(ethyl)catecholate]; [1,4-bis{3-hexenylphenyl}-2-(hydrido)-3-(hexyl)1,4-diazabuta-1,3-diene]nickel[3-(bromo)-4-(pentyl)catecholate]; [1,4-bis{3,4-di(propyl)phenyl}-2-(butyl)-3-(octyl)1,4-diazabuta-1,3-diene]palladium[3,4-di(pentyl)-5-(ethyl)catecholate]; [1,4-bis{3,5-di(ethyl)phenyl}-2-(butyl)-3-(triacontynyl)1,4-diazabuta-1,3-diene]nickel[4-(propyl)catecholate]; [1,4-bis{3,4-di(butyl)phenyl}-2-(butyl)-3-(hydrido)1,4-diazabuta-1,3-diene]nickel[3-(ethyl)-catecholate]; [1,4-bis{phenyl}-2-(butyl)-3-(pentyl)1,4-diazabuta-1,3-diene]nickel[4,5-di(ethyl)catecholate]; [1,4-bis{phenyl}-2-(octyl)-3-(butyl)1,4-diazabuta-1,3-diene]nickel[3-(ethyl)catecholate]; [1,4-bis{3-heptacosenylphenyl}-2-(hexyl)-3-(butyl)1,4-diazabuta-1,3-diene]palladium[3-(pentyl)catecholate]; [1,4-bis{3,4-di(ethyl)phenyl}-2-(octyl)-3-(butyl)1,4-diazabuta-1,3-diene]palladium[4-(ethyl)catecholate]; [1,4-bis{3,5-di(butyl)-phenyl}-2-(octyl)-3-(butyl)1,4-diazabuta-1,3-diene]palladium[3-(butyl)catecholate]; [1,4-bis{3,5-di(pentyl)phenyl}-2-(hexyl)-3-(butyl)1,4-diazabuta-1,3-diene]nickel[4-(propyl)-5-(methyl)catecholate]; [1,4-bis{3,5-di(propyl)phenyl}-2-(hydrido)-3-(butyl)1,4-diazabuta-1,3-diene]palladium[3-(pentyl)catecholate]; [1,4-bis{3-eicosenylphenyl}-2-(butyl)-3-(pentyl)1,4-diazabuta-1,3-diene]palladium[3-(pentyl)-6-(methyl)catecholate]; [1,4-bis{3,5-di(ethyl)phenyl}-2-(tridecynyl)-3-(butyl)1,4-diazabuta-1,3-diene]palladium[3-(methyl)-4-(pentyl)catecholate]; [1,4-bis{phenyl}-2-(octyl)-3-(ethyl)1,4-diazabuta-1,3-diene]nickel[3-(methyl)catecholate]; [1,4-bis{3,5-di(butyl)phenyl}-2,3-(dibutyl)1,4-diazabuta-1,3-diene]nickel[3-(methyl)catecholate]; [1,4-bis{phenyl}-2,3-(dibutyl)1,4-diazabuta-1,3-diene]nickel[3,6-di(propyl)catecholate]; [1,4-bis{4-propylphenyl}-2-(butyl)-3-(hydrido)1,4-diazabuta-1,3-diene]palladium[3-(methyl)-4-(ethyl)-6-(butyl)-catecholate]; [1,4-bis{phenyl}-2-(octyl)-3-(hexyl)1,4-diazabuta-1,3-diene]nickel[3-(methyldiethylsilylmethyl))-4-(butyl)catecholate]; [1,4-bis{3,5-di(butyl)phenyl}-2-(butyl)-3-(octyl)1,4-diazabuta-1,3-diene]nickel[3-(propyl)-4-(ethyl)catecholate]; [1,4-bis{phenyl}-2-(butyl)-3-(hexyl)1,4-diazabuta-1,3-diene]nickel[3-(butyl)-5-(ethyl)-catecholate]; [1,4-bis{phenyl}-2,3-(dihydrido)1,4-diazabuta-1,3-diene]nickel[3-(propyl)-4-(pentyl)catecholate]; [1,4-bis{phenyl}-2-(hydrido)-3-(butyl)1,4-diazabuta-1,3-diene]nickel[3-(propyl)catecholate]; [1,4-bis{3,4-di(propyl)phenyl}-2-(octyl)-3-(methyl)1,4-diazabuta-1,3-diene]palladium[3-(ethyl)-6-

(propyl)catecholate]; [1,4-bis{4-heptylphenyl}-2-(hydrido)-3-(pentacosenyl)1,4-diazabuta-1,3-diene]nickel[4-(butyl)-5-(ethyl)catecholate]; [1,4-bis{3,4-di(pentyl)phenyl}-2-(hexyl)-3-(tricosyl)1,4-diazabuta-1,3-diene]nickel[3-(ethyl) catecholate]; [1,4-bis{4-dodecaphosphinophenyl}2-(hexyl)-3-(hydrido)1,4-diazabuta-1,3-diene]nickel[4-(ethyl) catecholate]; [1,4-bis{3,5-di(propyl)-phenyl}-2-(hexenyl)-3-(butyl)1,4-diazabuta-1,3-diene]palladium[4-(dodecamino)-catecholate]; [1,4-bis{3,5-di(pentyl)phenyl}-2-(butyl)-3-(octadecyl)1,4-diazabuta-1,3-diene]nickel[3-(ethyl)-6-(methyl)catecholate]; [1,4-bis{3,5-di(methyl) phenyl}-2-(hexyl)-3-(ethyl)1,4-diazabuta-1,3-diene]nickel [3-(pentyl)-6-(propyl)catecholate]; [1,4-bis{phenyl}-2-(ethyl)-3-(hydrido)1,4-diazabuta-1,3-diene]palladium[4-(pentyl)-catecholate]; [1,4-bis{3,4-di(ethyl)phenyl}-2-(hydrido)-3-(butyl)1,4-diazabuta-1,3-diene]nickel[3,6-di (methyl)-4-(hexonyl)catecholate]; [1,4-bis{3,5-di(ethyl) phenyl}-2-(octyl)-3-(triacontyl)1,4-diazabuta-1,3-diene] nickel[3-(pentyl)-4-(butyl)catecholate]; [1,4-bis{3,4-di (pentyl)phenyl}-2-(octyl)-3-(butyl)1,4-diazabuta-1,3-diene] palladium[3-(propyl)-4-(methyl)catecholate]; [1,4-bis{phenyl}-2-(butyl)-3-(pentyl)1,4-diazabuta-1,3-diene] palladium[3-(propyl)catecholate]; [1,4-bis{3,4-di(pentyl) phenyl}-2-(butyl)-3-(tridecyl)-1,4-diazabuta-1,3-diene] palladium[4-(pentyl)-5-(butyl)catecholate]; [1,4-bis{phenyl}-2,3-(dibutyl)1,4-diazabuta-1,3-diene]nickel[3-(butyl)-5-(propyl)catecholate]; [1,4-bis{4-tetracosynylphenyl}-2-(octyl)-3-(butyl)1,4-diazabuta-1,3-diene]nickel[3-(methyl)-6-(butyl)catecholate]; [1,4-bis{3,4-di(propyl)phenyl}-2-(nonyl)-3-(butyl)1,4-diazabuta-1,3-diene]nickel[4-(methyl)-5-propyl)catecholate]; [1,4-bis{3,5-di(ethyl)phenyl}-2-(tridecenyl)-3-(octyl)1,4-diazabuta-1,3-diene]nickel[3-(methyl)-5-(ethyl)catecholate]; [1,4-bis{phenyl}-2-(butyl)-3-(octyl)1,4-diazabuta-1,3-diene] palladium[4-(methyl)-5-(pentyl)catecholate]; [1,4-bis{phenyl}-2-(hydrido)-3-(hexyl)1,4-diazabuta-1,3-diene] palladium[3,4-di(methyl)-5-(ethyl)catecholate]; [1,4-bis{3,5-di(pentyl)phenyl}-2-(undecynyl)-3-(methyl)1,4-diazabuta-1,3-diene]nickel[3-(propyl)catecholate]; [1,4-bis{4-pentadecylphenyl}-2-(butyl)-3-(methyl)1,4-diazabuta-1,3-diene]nickel[3-(methyl)catecholate]; [1,4-bis{4-tridecynylphenyl}-2-(butyl)-3-(hydrido)1,4-diazabuta-1,3-diene]nickel[3-(pentyl)-4-(propyl) catecholate]; [1,4-bis{3,5-di(ethyl)phenyl}-2-(pentyl)-3-(butyl)1,4-diazabuta-1,3-diene]palladium[3-(dodecanonyl)-5-(butyl)-catecholate]; [1,4-bis{3,4-di(methyl)phenyl}-2-(butyl)-3-(methyl)1,4-diazabuta-1,3-diene]palladium[4-(ethyl)catecholate]; [1,4-bis{phenyl}-2-(octyl)-3-(hydrido) 1,4-diazabuta-1,3-diene]nickel[4-(methyl)catecholate]; [1,4-bis{3,5-di(propyl)phenyl}-2-(docosenyl)-3-(pentacosynyl)1,4-diazabuta-1,3-diene]nickel[3,4-di (propyl)-5-(methyl)-catecholate]; [1,4-bis{4-tridocosanalylphenyl}-2-(butyl)-3-(hydrido)1,4-diazabuta-1,3-diene]nickel[3-(ethyl)-4-(methyl)catecholate]; [1,4-bis{phenyl}-2,3-(dibutyl)1,4-diazabuta-1,3-diene]nickel[3-(pentyl)-5-(ethyl)catecholate]; [1,4-bis{3,4-di(butyl)-phenyl}-2-(octyl)-3-(pentyl)1,4-diazabuta-1,3-diene] palladium[4-(methyl)catecholate]; [1,4-bis{3-ethylphenyl}-2-(pentyl)-3-(tetradecyl)1,4-diazabuta-1,3-diene]nickel[4,5-di(pentyl)catecholate]; [1,4-bis{phenyl}-2-(hexyl)-3-(hydrido)1,4-diazabuta-1,3-diene]nickel[4-(pentyl) catecholate]; [1,4-bis{phenyl}-2-(octyl)-3-(pentyl)1,4-diazabuta-1,3-diene]nickel[3-(propyl)catecholate]; [1,4-bis{3,4-di(propyl)phenyl}-2-(hexyl)-3-(heneicosenyl)1,4-diazabuta-1,3-diene]nickel[3-(propyl)catecholate]; [1,4-bis{3,4-di(proponyl)phenyl}-2-(octyl)-3-(octyl)1,4-diazabuta-1,3-diene]nickel[3-(hexonyl)-5-(pentyl) catecholate]; [1,4-bis{3,5-di(pentyl)phenyl}-2-(butyl)-3-(hydrido)1,4-diazabuta-1,3-diene]nickel[3-(diethylamino)-6-(butyl)catecholate]; [1,4-bis{3-heneicosylphenyl}-2,3-(dihydrido)1,4-diazabuta-1,3-diene]nickel[3,4-di(butyl) catecholate]; [1,4-bis{3,4-di(methyl)phenyl}-2,3-(dibutyl) 1,4-diazabuta-1,3-diene]nickel[3-(ethyl)-6-(methyl)-catecholate]; [1,4-bis{3,4-di(propyl)phenyl}-2-(pentyl)-3-(butyl)1,4-diazabuta-1,3-diene]nickel[3-(diethylamino) catecholate]; [1,4-bis{3,4-di(pentyl)phenyl}-2,3-(dibutyl)1,4-diazabuta-1,3-diene]nickel[3-(butyl)-5-(ethyl) catecholate]; [1,4-bis{3,4-di(ethyl)-phenyl}-2-(hydrido)-3-(butyl)1,4-diazabuta-1,3-diene]nickel[3-(methyl) catecholate]; [1,4-bis{3,4-di(methyl)phenyl}-2,3-(dihydrido)1,4-diazabuta-1,3-diene]nickel[3-(ethyl)-4-(methyl)-5-(pentyl)catecholate]; [1,4-bis{3,5-di(ethyl) phenyl}-2-(hexyl)-3-(butyl)1,4-diazabuta-1,3-diene]nickel [4-(butyl)-5-(methyl)catecholate]; [1,4-bis{3-heptacosynyl-phenyl}-2,3-(dihydrido)1,4-diazabuta-1,3-diene]nickel[3-(butyl)catecholate]; [1,4-bis{3,4-di(propyl)phenyl}-2-(hexyl)-3-(hydrido)1,4-diazabuta-1,3-diene]palladium[4-(methyl)catecholate]; [1,4-bis{phenyl}-2-(ethyl)-3-(butyl)1, 4-diazabuta-1,3-diene]nickel[3-(propyl)-6-(ethyl) catecholate]; [1,4-bis{3,5-di(pentyl)phenyl}-2-(pentadecyl)-3-(ethyl)1,4-diazabuta-1,3-diene]nickel[3-(pentyl)catecholate]; [1,4-bis{3,4-di(butyl)-phenyl}-2,3-(dibutyl)1,4-diazabuta-1,3-diene]nickel[3-(ethyl) catecholate];

[1,4-bis{3,4-di(methyl)phenyl}-2-(butyl)-3-(octyl)1,4-diazabuta-1,3-diene]nickel[4-(butyl)catecholate]; [1,4-bis{4-dodecaphosphinophenyl}-2-(pentyl)-3-(butyl)1,4-diazabuta-1,3-diene]nickel[3-(methyl)catecholate]; [1,4-bis{3,4-di(pentyl)phenyl}-2-(butyl)-3-(pentyl)1,4-diazabuta-1,3-diene]palladium[3-(propyl)-4-(pentyl)-5-(butyl)-catecholate]; [1,4-bis{4-pentacosenylphenyl}-2-(octacosynyl)-3-(hydrido)1,4-diazabuta-1,3-diene]nickel[4-(methyl)catecholate]; [1,4-bis{3,5-di(pentyl)phenyl}-2,3-(dihydrido)-1,4-diazabuta-1,3-diene]nickel[3-(methyl)-4-(butyl)-6-(pentyl)catecholate]; [1,4-bis{3,4-di(propyl) phenyl}-2-(butyl)-3-(hydrido)1,4-diazabuta-1,3-diene] palladium[3,5-di(ethyl)-4-(methylethylamino)catecholate]; [1,4-bis{4-heptadecylphenyl}-2-(hydrido)-3-(nonenyl)1,4-diazabuta-1,3-diene]nickel[3,4-di(propyl)-6-(pentyl) catecholate]; [1,4-bis{3,5-di(ethyl)phenyl}-2-(pentyl)-3-(heptacenyl)1,4-diazabuta-1,3-diene]nickel[3,5-di(butyl)-4-(methyl)catecholate]; [1,4-bis{3,5-di(pentyl)phenyl}-2-(pentadecyl)-(hexyl)1,4-diazabuta-1,3-diene]nickel[3-(butyl)-4,5-di(propyl)catecholate]; [1,4-bis{3,4-di(butyl) phenyl}-2-(pentyl)-3-(octyl)1,4-diazabuta-1,3-diene]nickel [3-(ethyl)-6-(butyl)-catecholate]; [1,4-bis{3-ethylphenyl}-2-(butyl)-3-(hydrido)1,4-diazabuta-1,3-diene]nickel[3-(butyl)-6-(ethyl)catecholate]; [1,4-bis{3,4-di (tridocosanalyl)phenyl}-2-(hexyl)-3-(pentenyl)1,4-diazabuta-1,3-diene]nickel[3-(propyl)-6-(methyl) catecholate]; [1,4-bis{3,4-di(methyl)phenyl}-2-(hydrido)-3-(hexyl)1,4-diazabuta-1,3-diene]nickel[4-(butyl)-5-(methyl)catecholate]; [1,4-bis{phenyl}-2,3-(dioctyl)1,4-diazabuta-1,3-diene]palladium[4-(methyl)-5-(ethyl)catecholate]; [1,4-bis{3,4-di(pentyl)phenyl}-2-(butyl)-3-(pentyl)1,4-diazabuta-1,3-diene]nickel[3-(propyl)-4-(butyl)-5-(ethyl) catecholate]; [1,4-bis{phenyl}-2-(butyl)-3-(hydrido)1,4-diazabuta-1,3-diene]nickel[4-(butyl)catecholate]; [1,4-bis{3,5-di(propyl)phenyl}-2,3-(dibutyl)1,4-diazabuta-1,3-diene]nickel[4,5-di(ethyl)catecholate]; [1,4-bis{phenyl}-2-(pentyl)-3-(butyl)1,4-diazabuta-1,3-diene]nickel[4-(methyl)-5-(ethyl)catecholate]; [1,4-bis{4-octadecenylphenyl}-2-(hexyl)-3-(hydrido)1,4-diazabuta-1,3-diene]palladium[3-(ethyl)-5-(pentyl)catecholate]; [1,4- bis{3,4-di(propyl)phenyl}-2-(octacosyl)-3-(hydrido)1,4-diazabuta-1,3-diene]nickel[3-(propanalyl)-6-(propyl) catecholate]; [1,4-bis{4-octylphenyl}-2-(butyl)-3-(hexyl)1,4-diazabuta-1,3-diene]nickel[3-(ethyl)-6(pentyl) catecholate]; [1,4-bis{4-tetracosenyl-phenyl}-2-(butyl)-3-(pentyl)1,4-diazabuta-1,3-diene]nickel[4-(pentyl)-5-(ethyl)catecholate]; [1,4-bis{4-tridocosanalylphenyl}-2-(nonacosyl)-3-(butyl)1,4-diazabuta-1,3-diene]nickel[3-(methyl)-6-(propyl)catecholate]; [1,4-bis{3-docosynylphenyl}-2-(hexyl)-3-(butyl)1,4-diazabuta-1,3-diene]nickel[3-(pentyl)catecholate]; [1,4-bis{3,4-di(propyl)-phenyl}-2,3-(dibutyl)1,4-diazabuta-1,3-diene] nickel[3-(ethyl)catecholate]; [1,4-bis{3,5-di(pentyl) phenyl}-2-(tetradecynyl)-3-(hydrido)1,4-diazabuta-1,3-diene]nickel[4-(propyl)catecholate]; [1,4-bis{3,5-di(ethyl) phenyl}-2-(butyl)-3-(hexyl)1,4-diazabuta-1,3-diene] palladium[3-(ethyl)-4,5-di(pentyl)catecholate]; [1,4-bis{3,4-di(methyl)phenyl}-2,3-(dihydrido)1,4-diazabuta-1,3-diene]nickel[3-(propyl)-4-(butyl)-5-(pentyl)-catecholate]; [1,4-bis{3,5-di(methyl)phenyl}-2,3-(dibutyl)1,4-diazabuta-1,3-diene]nickel[4-(butyl)-5-(propyl)catecholate]; [1,4-bis{3,5-di(pentyl)phenyl}-2-(octyl)-3-(hydrido)-1,4-diazabuta-1,3-diene]nickel[4-(pentyl)-5-(butyl) catecholate]; [1,4-bis{3,5-di(butyl)-phenyl}-2-(octyl)-3-(hydrido)1,4-diazabuta-1,3-diene]nickel[4-(ethyl) catecholate]; [1,4-bis{3,4-di(propyl)phenyl}-2-(docosyl)-3-(hydrido)1,4-diazabuta-1,3-diene]nickel[3-(butyl)-5-(pentyl)catecholate]; [1,4-bis{3,5-di(ethyl)phenyl}-2-(hydrido)-3-(butyl)1,4-diazabuta-1,3-diene]nickel[4-(ethyl) catecholate]; [1,4-bis{3,5-di(pentyl)phenyl}-2-(hexyl)-3-(butyl)1,4-diazabuta-1,3-diene]nickel[3-(propyl)-4,6-di (methyl)catecholate]; [1,4-bis{phenyl}-2,3-(dibutyl)1,4-diazabuta-1,3-diene]palladium[3-(pentyl)-4-(methyl)-6-(propyl)catecholate]; [1,4-bis{3,5-di(pentyl)phenyl}-2-(hydrido)-3-(hexyl)1,4-diazabuta-1,3-diene]palladium [3,4-di(butyl)-6-(pentyl)catecholate]; [1,4-bis{3,5-di(pentyl) phenyl}-2-(hexyl)-3-(butyl)1,4-diazabuta-1,3-diene]nickel [3-(ethyl)-6-(pentyl)catecholate]; [1,4-bis{phenyl}-2-(butyl)-3-(pentyl)1,4-diazabuta-1,3-diene]palladium[3-(butyl)catecholate]; [1,4-bis{3,4-di(ethyl)phenyl}-2,3-(dibutyl)1,4-diazabuta-1,3-diene]palladium[4-(methyl) catecholate]; [1,4-bis{3-tetradecynylphenyl}-2-(pentyl)-3-(hydrido)1,4-diazabuta-1,3-diene]nickel[3-(butyl)-5-(methyl)catecholate]; [1,4-bis{4-nonadecenylphenyl}-2,3-(dimethyl)1,4-diazabuta-1,3-diene]nickel[4-(propyl)-5-(pentyl)catecholate]; [1,4-bis{phenyl}-2-(hydrido)-3-(butyl)1,4-diazabuta-1,3-diene]nickel[4-(propyl)-5-(methyl)catecholate]; [1,4-bis{3,5-di(pentyl)phenyl}-2-(hydrido)-3-(octyl)1,4-diazabuta-1,3-diene]nickel[4-(butyl)-5-(pentyl)catecholate]; [1,4bis{3,4-di(ethyl) phenyl}-2-(docosenyl)-3-(hexyl)1,4-diazabuta-1,3-diene] nickel[3-(butyl)-6-(pentyl)catecholate]; [-1,4-bis{3-hexadecynylphenyl}-2,3-(dipentyl)1,4-diazabuta-1,3-diene] nickel[3-(bromo)-4-(pentyl)catecholate]; [1,4-bis{4-nonadecenyl-phenyl}-2-(butyl)-3-(pentyl)1,4-diazabuta-1, 3-diene]nickel[3,4-di(butyl)catecholate]; [1,4-bis{3,4-di (propyl)phenyl}-2-(octyl)-3-(undecyl)1,4-diazabuta-1,3-diene]nickel[3,5-di(methyl)catecholate]; [1,4-bis{4-hexadecylphenyl}-2-(hexyl)-3-(butyl)1,4-diazabuta-1,3-diene]nickel[3-(ethyl)catecholate]; [1,4-bis{4-dodecanonylphenyl}-2-(pentyl)-3-(hexyl)1,4-diazabuta-1, 3-diene]nickel[3-(pentyl)-4,6-di(ethyl)catecholate]; [1,4-bis{3-hexacosynylphenyl}-2-(octyl)-3-(butyl)1,4-diazabuta-1,3-diene]nickel[3,4-di(propyl)-5-(methyl) catecholate]; [1,4-bis{4-tetracosynylphenyl}-2-(butyl)-3-(octyl)1,4-diazabuta-1,3-diene]palladium[4-(dodecanonyl) catecholate]; [1,4-bis{4-decenylphenyl}-2-(ethyl)-3-(butyl) 1,4-diazabuta-1,3-diene]nickel[3-(ethyl)-4-(butyl) catecholate]; [1,4-bis{phenyl}-2-(butyl)-3-(octyl)1,4-diazabuta-1,3-diene]nickel[4-(propyl)-5-(methyl)-catecholate]; [1,4-bis{4-octacosynylphenyl}-2-(butyl)-3-(pentyl)1,4-diazabuta-1,3-diene]nickel[3-((triethylsilylmethyl))catecholate]; [1,4-bis{3,5-di(methyl) phenyl}-2-(hexyl)-3-(butyl)1,4-diazabuta-1,3-diene]nickel [3-(bromo)-4-(octylamino)-5-(ethyl)catecholate]; [1,4-bis{3,5-di(butyl)phenyl}-2-(butyl)-3-(hydrido)1,4-diazabuta-1,3-diene]palladium[4-(propyl)catecholate]; [1,4-bis{3,5-di(methyl)phenyl}-2,3-(dibutyl)1,4-diazabuta-1,3-diene]nickel[4-(ethyl)catecholate]; [1,4-bis{3,5-di(butyl) phenyl}-2,3-(dihydrido)1,4-diazabuta-1,3-diene]nickel[4-(ethyl)catecholate]; [1,4-bis{3,5-di(pentyl)phenyl}-2-(pentyl)-3-(butyl)1,4-diazabuta-1,3-diene]nickel[4-(butyl)-5-(propyl)catecholate]; [1,4-bis{3,5-di(ethyl)phenyl}-2-(nonacosenyl)-3-(hydrido)1,4-diazabuta-1,3-diene]nickel [4-(ethyl)catecholate]; [1,4-bis{3,4-di(butyl)phenyl}-2-(hydrido)-3-(methyl)1,4-diazabuta-1,3-diene]palladium[3-(pentyl)catecholate]; [1,4-bis{3,4-di(propyl)phenyl}-2-(hydrido)-3-(nonacosenyl)1,4-diazabuta-1,3-diene] palladium[3-(ethyl)catecholate]; [1,4-bis{3-butenylphenyl}-2-(butyl)-3-(pentyl)1,4-diazabuta-1,3-diene]palladium[3-(ethyl)-catecholate]; [1,4-bis{3,4-di (methyl)phenyl}-2-(butyl)-3-(tetradecynyl)1,4-diazabuta-1, 3-diene]nickel[3-(propyl)-4-(pentyl)-6-(butyl)catecholate]; [1,4-bis{4-dodecaminophenyl}-2-(butyl)-3-(hydrido)1,4-diazabuta-1,3-diene]nickel[4-(propyl)-catecholate]; [1,4-bis{phenyl}-2-(hydrido)-3-(butyl)1,4-diazabuta-1,3-diene] nickel[3-(ethyl)catecholate]; [1,4-bis{3-tricosenylphenyl}-2-(octadecenyl)-3-(heptadecyl)1,4-diazabuta-1,3-diene] nickel[3-(ethyl)catecholate]; [1,4-bis{3,4-di(methyl) phenyl}-2-(butyl)-3-(hexyl)1,4-diazabuta-1,3-diene]nickel [3-(ethyl)catecholate]; [1,4-bis{3-undecenylphenyl}-2,3-(dibutyl)1,4-diazabuta-1,3-diene]nickel[3-(butyl) catecholate]; [1,4-bis{phenyl}-2-(butyl)-3-(ethyl)1,4-diazabuta-1,3-diene]nickel[3,6-di(methyl)-4-(propyl) catecholate]; [1,4-bis{4-butonylphenyl}-2-(methyl)-3-(butyl)1,4-diazabuta-1,3-diene]nickel[3-(methyl) catecholate]; [1,4-bis{3,4-di(ethyl)phenyl}-2-(methyl)-3-(pentyl)1,4-diazabuta-1,3-diene]nickel[3-(pentyl)-5-(butyl) catecholate]; [1,4-bis{3,5-di(propyl)phenyl}-2-(butyl)-3-(hydrido)1,4-diazabuta-1,3-diene]nickel[3-(ethyl)-4-(butyl) catecholate]; [1,4-bis{3,5-di(pentyl)phenyl}-2-(butyl)-3-(hydrido)1,4-diazabuta-1,3-diene]nickel[4(methyl) catecholate]; [1,4-bis{3,5-di(methyl)phenyl}-2-(butyl)-3-(hydrido)1,4-diazabuta-1,3-diene]palladium[3-(propyl)-5-(methyl)catecholate]; [1,4-bis{phenyl}-2,3-(dibutyl)1,4-diazabuta-1,3-diene]nickel[4-(ethyl)catecholate]; [1,4-bis{phenyl}-2-(pentyl)-3-(hydrido)1,4-diazabuta-1,3-diene] nickel[3-(pentyl)-6-(butyl)-catecholate]; [1,4-bis{phenyl}-2-(hydrido)-3-(butyl)1,4-diazabuta-1,3-diene]nickel [(pentyl)-4-(ethyl)catecholate]; [1,4-bis{3,4-di(propyl) phenyl}-2-(butyl)-3-(hydrido)1,4-diazabuta-1,3-diene] nickel[3-(methyl)catecholate]; [1,4-bis{3,5-di(butyl) phenyl}-2-(butyl)-3-(hydrido)1,4-diazabuta-1,3-diene] palladium[3-(ethanalyl)catecholate]; [1,4-bis{phenyl}-2-(undecynyl)-3-(butyl)1,4-diazabuta-1,3-diene]nickel[4-(propyl)-catecholate]; [1,4-bis{3-triacontylphenyl}-2-(butyl)-3-(hexyl)1,4-diazabuta-1,3-diene]nickel[4-(methyl)-5-(pentyl)catecholate]; [1,4-bis{phenyl}-2-(butyl)-3-(methyl)1,4-diazabuta-1,3-diene]nickel[4-(ethyl) catecholate]; [1,4-bis{phenyl}-2-(butyl)-3-(methyl)-1,4-diazabuta-1,3-diene]nickel[3,5-di(butyl)-4-(bromo) catecholate]; [1,4-bis{phenyl}-2-(butyl)-3-(tridecyl)1,4-diazabuta-1,3-diene]nickel[3,5-di(butyl)catecholate]; [1,4-bis{phenyl}-2,3-(dibutyl)1,4-diazabuta-1,3-diene]nickel[4-

(butyl)catecholate]; [1,4-bis{phenyl}-2-(tridecenyl)-3-(ethyl)1,4-diazabuta-1,3-diene]palladium[3-(butyl)-catecholate]; [1,4-bis{3,5-di(butyl)phenyl}-2-(octyl)-3-(butyl)1,4-diazabuta-1,3-diene]nickel[3-(ethyl)-4-(methyl)catecholate]; [1,4-bis{4-docosynylphenyl}-2-(hydrido)-3-(pentyl)1,4-diazabuta-1,3-diene]palladium[3-(methyl)-5-(propyl)catecholate]; [1,4-bis{3,4-di(pentyl)phenyl}-2-(methyl)-3-(octadecyl)1,4-diazabuta-1,3-diene]palladium[3,4-di(propyl)-6-(propyl)catecholate]; [1,4-bis{3,5-di(pentyl)phenyl}-2-(methyl)-3-(hydrido)1,4-diazabuta-1,3-diene]palladium[4,5-di(propyl)catecholate]; [1,4-bis{3,4-di(butonyl)phenyl}-2-(butyl)-3-(hydrido)1,4-diazabuta-1,3-diene]nickel[4-(methyl)-catecholate]; [1,4-bis{phenyl}-2-(methyl)-3-(hydrido)1,4-diazabuta-1,3-diene]palladium[3-(propyl)-4-(pentyl)-5-(butyl)catecholate]; [1,4-bis{3,5-di(butyl)phenyl}-2,3-(dibutyl)-1,4-diazabuta-1,3-diene]nickel[3,4-di(methyl)-5-(pentyl)catecholate]; [1,4-bis{3,4-di(ethyl)phenyl}-2,3-(dioctyl)1,4-diazabuta-1,3-diene]nickel[4-(methyl)-5-(butyl)-catecholate]; [1,4-bis{3-tetracosenylphenyl}-2-(hexyl)-3-(butyl)1,4-diazabuta-1,3-diene]nickel[3-(butyl)catecholate]; [1,4-bis{3-tridocosanalylphenyl}-2-(pentyl)-3-(pentenyl)-1,4-diazabuta-1,3-diene]nickel[4-(propyl)catecholate]; [1,4-bis{4-pentenylphenyl}-2-(butyl)-3-(hydrido)1,4-diazabuta-1,3-diene]nickel[4-(ethyl)catecholate]; [1,4-bis{phenyl}-2-(hexyl)-3-(tetradecenyl)1,4-diazabuta-1,3-diene]nickel[3-(propyl)-catecholate]; [1,4-bis{phenyl}-2,3-(dibutyl)1,4-diazabuta-1,3-diene]nickel[3-(butyl)-4-(propyl)catecholate]; [1,4-bis{3,4-di(methyl)phenyl}-2,3-(dihydrido)1,4-diazabuta-1,3-diene]nickel[3-(pentyl)-5-(butyl)catecholate]; [1,4-bis{3,4-di(propyl)phenyl}-2-(methyl)-3-(pentyl)1,4-diazabuta-1,3-diene]palladium[4-(pentyl)-5-(propyl)catecholate]; [1,4-bis{phenyl}-2,3-(dihydrido)1,4-diazabuta-1,3-diene]nickel[3-(methyldiethylsilylmethyl))-4-(butyl)catecholate]; [1,4-bis{phenyl}-2-(hydrido)-3-(butyl)1,4-diazabuta-1,3-diene]palladium[3-(butyl)-4-(ethyl)-6-(methyl)catecholate]; [1,4-bis{3,4-di(pentyl)phenyl}-2-(pentyl)-3-(octyl)1,4-diazabuta-1,3-diene]nickel[3,4-di(propyl)catecholate]; [1,4-bis{phenyl}-2-(butyl)-3-(hexyl)1,4-diazabuta-1,3-diene]palladium[3-(ethyl)catecholate]; [1,4-bis{3,5-di(propyl)phenyl}-2-(hydrido)-3-(butyl)-1,4-diazabuta-1,3-diene]nickel[4-(butyl)-5-(pentyl)catecholate]; [1,4-bis{phenyl}-2-(butyl)-3-(hydrido)1,4-diazabuta-1,3-diene]nickel[3-(ethyl)-5-(pentyl)catecholate]; [1,4-bis{3-dodecynylphenyl}-2-(ethyl)-3-(hydrido)1,4-diazabuta-1,3-diene]palladium[4-(ethyl)catecholate]; [1,4-bis{3,5-di(butyl)phenyl}-2-(butyl)-3-(heptacosenyl)1,4-diazabuta-1,3-diene]nickel[3-(ethyl)-4-(propyl)-6-(butyl)catecholate]; [1,4-bis{3,4-di(ethyl)phenyl}-2-(octyl)-3-(butyl)1,4-diazabuta-1,3-diene]nickel[3-(butyl)-4-(bromo)-catecholate]; [1,4-bis{3,5-di(propyl)phenyl}-2,3-(dibutyl)1,4-diazabuta-1,3-diene]nickel[4,5-di(ethyl)catecholate]; [1,4-bis{3-heneicosynylphenyl}-2,3-(dihydrido)1,4-diazabuta-1,3-diene]nickel[3-(ethyl)-5-(butyl)catecholate]; [1,4-bis{4-nonacosenylphenyl}-2-(hydrido)-3-(butyl)1,4-diazabuta-1,3-diene]nickel[3-(ethyl)-5-(pentyl)catecholate]; [1,4-bis{3,5-di(ethyl)phenyl}-2-(hydrido)-3-(ethyl)1,4-diazabuta-1,3-diene]nickel[3-(ethyl)-4,6-di(methyl)catecholate]; [1,4-bis{3,5-di(pentyl)phenyl}-2-(butyl)-3-(hydrido)1,4-diazabuta-1,3-diene]nickel[3-(propyl)catecholate]; [1,4-bis{4-pentylphenyl}-2-(butyl)-3-(hydrido)1,4-diazabuta-1,3-diene]nickel[3-(diethylamino)catecholate]; [1,4-bis{3,5-di(methyl)phenyl}-2-(pentyl)-3-(butyl)1,4-diazabuta-1,3-diene]nickel[3-(propyl)-6-(methyl)catecholate]; [1,4-bis{phenyl}-2-(hexyl)-3-(butyl)1,4-diazabuta-1,3-diene]nickel[4-(pentyl)catecholate]; [1,4-bis{3,5-di(butyl)phenyl}-2-(butyl)-3-(pentyl)1,4-diazabuta-1,3-diene]nickel[4-(ethyl)catecholate]; [1,4-bis{3,5-di(methyl)phenyl}-2-(nonacosenyl)-3-(ethyl)1,4-diazabuta-1,3-diene]nickel[4-(propyl)catecholate]; [1,4-bis{phenyl}-2-(butyl)-3-(pentyl)1,4-diazabuta-1,3-diene]nickel[3-(butyl)-6-(propyl)catecholate]; [1,4-bis{3,5-di(butyl)phenyl}-2-(hydrido)-3-(ethyl)1,4-diazabuta-1,3-diene]nickel[3-(pentyl)catecholate]; [1,4-bis{4-tridecenylphenyl}-2-(eicosynyl)-3-(hydrido)1,4-diazabuta-1,3-diene]palladium[4-(methyl)catecholate]; [1,4-bis{3-docosenylphenyl}-2-(hydrido)-3-(butyl)1,4-diazabuta-1,3-diene]palladium[4-(tridocosanalyl)catecholate]; [1,4-bis{3,4-di(propyl)phenyl}-2-(hexyl)-3-(octyl)1,4-diazabuta-1,3-diene]nickel[3-(methyl)-6-(butyl)catecholate]; [1,4-bis{4-nonenylphenyl}-2-(heptenyl)-3-(pentyl)1,4-diazabuta-1,3-diene]palladium[3-(pentyl)-6-(methyl)catecholate]; [1,4-bis{4-tricosenyl-phenyl}-2-(butyl)-3-(eicosynyl)1,4-diazabuta-1,3-diene]palladium[4-(butyl)-5-(methyl)-catecholate]; [1,4-bis{3,4-di(butyl)phenyl}-2-(decyl)-3-(butyl)1,4-diazabuta-1,3-diene]nickel[4-(butyl)catecholate]; [1,4-bis{4-tetracosylphenyl}-2-(butyl)-3-(octyl)1,4-diazabuta-1,3-diene]nickel[3,6-di(methyl)catecholate]; [1,4-bis{3,5-di(propyl)phenyl}-2-(nonadecenyl)-3-(methyl)1,4-diazabuta-1,3-diene]palladium[3-(methyl)-6-(propyl)-catecholate]; [1,4-bis{3,5-di(pentyl)phenyl}-2-(triacontenyl)-3-(ethyl)1,4-diazabuta-1,3-diene]palladium[3-(pentyl)catecholate]; [1,4-bis{3-pentylphenyl}-2-(butyl)-3-(hexadecenyl)1,4-diazabuta-1,3-diene]nickel[3-(ethyl)-4-(methyl)catecholate]; [1,4-bis{3,4-di(butyl)phenyl}-2,3-(dibutyl)1,4-diazabuta-1,3-diene]nickel[3,4-di(propyl)-catecholate]; [1,4-bis{phenyl}-2-(hydrido)-3-(butyl)1,4-diazabuta-1,3-diene]nickel[(ethyl)catecholate]; [1,4-bis{4-tetracosenylphenyl}-2-(butyl)-3-(hydrido)1,4-diazabuta-1,3-diene]nickel[3,5-di(ethyl)-4-(propyl)catecholate]; [1,4-bis{3-undecylphenyl}-2-(pentenyl)-3-(hydrido)1,4-diazabuta-1,3-diene]nickel[3-(propyl)-5-(pentyl)catecholate]; [1,4-bis{3,4-di(ethyl)phenyl}-2-(pentyl)-3-(hydrido)1,4-diazabuta-1,3-diene]nickel[3-(butyl)-4-(methyl)-5-(ethyl)catecholate]; [1,4-bis{phenyl}-2-(butyl)-3-(pentenyl)1,4-diazabuta-1,3-diene]palladium[3-(butyl)-4-(pentyl)-5-(methyl)catecholate]; [1,4-bis{3-nonadecylphenyl}-2-(butyl)-3-(hydrido)1,4-diazabuta-1,3-diene]nickel[3-(methyl)-6-(pentyl)catecholate]; [1,4-bis{3,5-di(pentyl)phenyl}-2-(hydrido)-3-(butyl)1,4-diazabuta-1,3-diene]palladium[4,5-di(methyl)catecholate]; [1,4-bis{3,5-di(butyl)phenyl}-2-(tricosenyl)-3-(octyl)1,4-diazabuta-1,3-diene]nickel[3-(methyl)-5-(propyl)catecholate]; [1,4-bis{4-octacosynylphenyl}-2-(butyl)-3-(pentyl)1,4-diazabuta-1,3-diene]nickel[3-(methyl)-5-(ethyl)catecholate]; [1,4-bis{3,4-di(propyl)phenyl}-2,3-(dibutyl)1,4-diazabuta-1,3-diene]nickel[3-(ethyl)-4-(methyl)catecholate]; [1,4-bis{3,4-di(propyl)-phenyl}-2-(octyl)-3-(butyl)1,4-diazabuta-1,3-diene]palladium[3-(pentyl)catecholate]; [1,4-bis{phenyl}-2-(hydrido)-3-(butyl)1,4-diazabuta-1,3-diene]nickel[3-(ethyl)-4,5-di(pentyl)catecholate]; [1,4-bis{3,4-di(pentyl)phenyl}-2,3-(dihydrido)1,4-diazabuta-1,3-diene]nickel[3,5-di(methyl)-4-(pentyl)catecholate]; [1,4-bis{3,5-di(butyl)phenyl}-2-(hexyl)-3-(eicosynyl)1,4-diazabuta-1,3-diene]nickel[3,6-di(butyl)catecholate]; [1,4-bis{3,5-di(pentyl)phenyl}-2-(butyl)-3-(methyl)1,4-diazabuta-1,3-diene]nickel[3-(pentyl)-4-(propyl)catecholate]; [1,4-bis{phenyl}-2-(butyl)-3-(heptyl)1,4-diazabuta-1,3-diene]nickel[4-(butyl)catecholate]; [1,4-bis{phenyl}-2-(hydrido)-3-(undecynyl)1,4-diazabuta-1,3-diene]nickel[4-(pentyl)-5-(propyl)catecholate]; [1,4-bis{4-docosynyl-phenyl}-2,3-(dibutyl)1,4-diazabuta-1,3-diene]nickel[4-(methyl)catecholate]; [1,4-bis{3-triacontenylphenyl}-2,3-(dibutyl)1,4-diazabuta-1,3- diene]nickel[4-(pentyl)catecholate]; [1,4-bis{3,4-di(pentyl)phenyl}-2-(hydrido)-3-(undecenyl)1,4-diazabuta-1,3-diene]nickel[4,5-di(pentyl)catecholate]; [1,4-bis{3-undecenylphenyl}-2-(hydrido)-3-(propenyl)1,4-diazabuta-1,3-diene]nickel[4-(butyl)catecholate]; [1,4-bis{3,5-di(methyl)phenyl}-2-(butyl)-3-(pentyl)1,4-diazabuta-1,3-diene]palladium[3-(butyl)catecholate]; [1,4-bis{3-tetracosenylphenyl}-2,3-(dibutyl)1,4-diazabuta-1,3-diene]nickel[4-(ethyl)catecholate]; [1,4-bis{3,5-di(ethyl)phenyl}-2-(hydrido)-3-(octyl)1,4-diazabuta-1,3-diene]nickel[3-(pentyl)-4,6-di(ethyl)catecholate]; [1,4-bis{phenyl}-2-(methyl)-3-(butyl)1,4-diazabuta-1,3-diene]nickel[3-(pentyl)-5-(methyl)catecholate]; [1,4-bis{3,4-di(butyl)phenyl}-2-(butyl)-3-(hydrido)1,4-diazabuta-1,3-diene]nickel[3-(propyl)-4-(butyl)catecholate]; [1,4-bis{3,4-di(pentyl)phenyl}-2,3-(dibutyl)1,4-diazabuta-1,3-diene]nickel[3-(pentyl)-catecholate]; [1,4-bis{phenyl}-2-(octynyl)-3-(butyl)1,4-diazabuta-1,3-diene]nickel[3-(methyl)-4-(propyl)catecholate]; [1,4-bis{phenyl}-2-(butyl)-3-(octyl)1,4-diazabuta-1,3-diene]nickel[3-(ethyl)catecholate]; [1,4-bis{phenyl}-2-(pentyl)-3-(octyl)1,4-diazabuta-1,3-diene]palladium[4-(propyl)-5-(methyl)catecholate]; [1,4-bis{phenyl}-2,3-(dihydrido)1,4-diazabuta-1,3-diene]nickel[3,6-di(ethyl)catecholate]; [1,4-bis{3,4-di(butyl)phenyl}-2-(butyl)-3-(hydrido)1,4-diazabuta-1,3-diene]nickel[3-(methyl)-catecholate]; [1,4-bis{phenyl}-2-(hydrido)-3-(pentyl)1,4-diazabuta-1,3-diene]nickel[3-(dodecamino)-6-(propyl)catecholate]; [1,4-bis{3,4-di(butyl)phenyl}-2-(butyl)-3-(hydrido)1,4-diazabuta-1,3-diene]nickel[4-(methyl)catecholate]; [1,4-bis{phenyl}-2,3-(dibutyl)1,4-diazabuta-1,3-diene]nickel[4-(butyl)catecholate]; [1,4-bis{4-undecyl-phenyl}-2-(hydrido)-3-(hexyl)1,4-diazabuta-1,3-diene]palladium[4-(propyl)catecholate]; [1,4-bis{3-hexylphenyl}-2-(octyl)-3-(butyl)1,4-diazabuta-1,3-diene]nickel[3-(propyl)-6-(ethyl)catecholate]; [1,4-bis{4-propylphenyl}-2-(hydrido)-3-(pentyl)1,4-diazabuta-1,3-diene]palladium[4,5-di(ethyl)catecholate]; [1,4-bis{phenyl}-2-(heptadecenyl)-3-(butyl)-1,4-diazabuta-1,3-diene]nickel[3-(ethyl)-4-(pentyl)-5-(butyl)catecholate]; [1,4-bis{4-undecynylphenyl}-2-(butyl)-3-(hydrido)1,4-diazabuta-1,3-diene]nickel[3-(propyl)-5-(butyl)catecholate]; [1,4-bis{3,5-di(pentyl)phenyl}-2-(pentyl)-3-(hydrido)1,4-diazabuta-1,3-diene]nickel[4-(propyl)-5-(methyl)catecholate]; [1,4-bis{3,4-di(butyl)phenyl}-2,3-(dibutyl)1,4-diazabuta-1,3-diene]nickel[3-(ethyl)-6-(butyl)catecholate]; [1,4-bis{3,5-di(butyl)phenyl}-2-(hydrido)-3-(hexyl)1,4-diazabuta-1,3-diene]nickel[3-(methyl)-catecholate]; [1,4-bis{phenyl}-2-(hexyl)-3-(nonynyl)1,4-diazabuta-1,3-diene]nickel[3-(ethyl)-4-(butyl)catecholate]; [1,4-bis{4-pentacosenylphenyl}-2-(butyl)-3-(hydrido)1,4-diazabuta-1,3-diene]nickel[4-(ethyl)catecholate]; [1,4-bis{3-trimethylsilylmethyl-phenyl}-2,3-(dibutyl)1,4-diazabuta-1,3-diene]nickel[4-(methyl)-5-(pentyl)catecholate]; [1,4-bis{3,5-di(ethyl)phenyl}-2-(butyl)-3-(octyl)1,4-diazabuta-1,3-diene]nickel[3-(methyl)-4-(butyl)-5-(pentyl)catecholate]; [1,4-bis{phenyl}-2-(pentyl)-3-(hydrido)1,4-diazabuta-1,3-diene]nickel[3-(ethyl)catecholate]; [1,4-bis{3,4-di(butyl)phenyl}-2-(butyl)-3-(triacontynyl)1,4-diazabuta-1,3-diene]palladium[3-(propyl)catecholate]; [1,4-bis{phenyl}-2-(pentyl)-3-(hydrido)1,4-diazabuta-1,3-diene]nickel[3-(pentyl)-4,5-di(methyl)catecholate]; [1,4-bis{3,4-di(pentyl)phenyl}-2-(butyl)-3-(pentyl)1,4-diazabuta-1,3-diene]nickel[4-(ethyl)-5-(butyl)catecholate]; [1,4-bis{phenyl}-2-(butyl)-3-(tridecyl)1,4-diazabuta-1,3-diene]nickel[3-(pentyl)catecholate]; [1,4-bis{phenyl}-2-(butyl)1,4-diazabuta-1,3-diene]nickel[3-(methyl)catecholate]; [1,4-bis{phenyl}-2-(hexyl)-3-(butyl)1,4-diazabuta-1,3-diene]nickel[3-(propyl)-5-(ethyl)-catecholate]; [1,4-bis{phenyl}-2,3-(dibutyl)1,4-diazabuta-1,3-diene]nickel[4-(ethyl)-catecholate]; [1,4-bis{3,5-di(ethyl)phenyl}-2-(butyl)-3-(ethyl)1,4-diazabuta-1,3-diene]palladium[3-(methyl)-5-(pentyl)catecholate]; [1,4-bis{3,5-di(methyl)phenyl}-2-(nonenyl)-3-(octyl)1,4-diazabuta-1,3-diene]nickel[3-(propyl)-5-(pentyl)catecholate]; [1,4-bis{3,5-di(pentyl)phenyl}-2-(butyl)-3-(heptacosynyl)1,4-diazabuta-1,3-diene]nickel[3-(butyl)-4-(pentyl)-5-(propyl)catecholate]; [1,4-bis{phenyl}-2-(butyl)-3-(octyl)1,4-diazabuta-1,3-diene]nickel[3-(pentyl)-4-(propyl)catecholate]; [1,4-bis{3,5-di(propyl)-phenyl}-2-(octyl)-3-(hydrido)1,4-diazabuta-1,3-diene]nickel[3-(ethyl)-4-(methyl)-5-(propyl)catecholate]; [1,4-bis{3,4-di(ethyl)phenyl}-2,3-(dibutyl)1,4-diazabuta-1,3-diene]nickel[3-(methyl)-4-(butyl)catecholate]; [1,4-bis{3,5-di(butyl)phenyl}-2-(heneicosyl)-3-(butyl)1,4-diazabuta-1,3-diene]nickel[4-(pentyl)-5-(methyl)catecholate]; [1,4-bis{3,5-di(ethyl)phenyl}-2-(pentyl)-3-(octyl)1,4-diazabuta-1,3-diene]palladium[4-(ethyl)-5-(propyl)catecholate]; [1,4-bis{3-octacosenylphenyl}-2-(butynyl)-3-(methyl)1,4-diazabuta-1,3-diene]nickel[3-(methyl)-4-(methyl)catecholate]; [1,4-bis{phenyl}-2-(hydrido)-3-(hexyl)1,4-diazabuta-1,3-diene]nickel[3-(ethyl)-4-(methyl)catecholate]; [1,4-bis{3,4-di(methyl)phenyl}-2-(octacosyl)-3-(butyl)1,4-diazabuta-1,3-diene]nickel[3-(methyl)-4-(butyl)-5-(hexonyl)catecholate]; [1,4-bis{3,5-di(methyl)phenyl}-2-(pentyl)-3-(tridecenyl)1,4-diazabuta-1,3-diene]nickel[3-(propyl)catecholate]; [1,4-bis{phenyl}-2,3-(dibutyl)1,4-diazabuta-1,3-diene]nickel[3,6-di(propyl)catecholate]; [1,4-bis{phenyl}-2-(hexyl)-3-(octyl)1,4-diazabuta-1,3-diene]nickel[3,6-di(butyl)catecholate]; [1,4-bis{phenyl}-2-(hydrido)-3-(butyl)1,4-diazabuta-1,3-diene]nickel[3-(pentyl)catecholate]; [1,4-bis{3,4-di(propyl)phenyl}-2-(octacosenyl)-3-(butyl)1,4-diazabuta-1,3-diene]palladium[3-(butyl)catecholate]; [1,4-bis{phenyl}-2-(hydrido)-3-(pentyl)1,4-diazabuta-1,3-diene]palladium[3,5-di(butyl)-4-(propyl)catecholate]; [1,4-bis{4-nonadecenyl-phenyl}-2,3-(dibutyl)1,4-diazabuta-1,3-diene]nickel[3-(hexyl)-5-(butyl)catecholate]; [1,4-bis{phenyl}-2,3-(dihydrido)1,4-diazabuta-1,3-diene]nickel[3,4-di(ethyl)-5-(methyl)catecholate]; [1,4-bis{3,4-di(ethyl)phenyl}-2-(octyl)-3-(nonadecyl)1,4-diazabuta-1,3-diene]nickel[3,4-di(methyl)catecholate]; [1,4-bis{phenyl}-2,3-(dibutyl)1,4-diazabuta-1,3-diene]nickel[3-(butyl)catecholate]; [1,4-bis{3,5-di(methyl)phenyl}-2-(butyl)-3-(hydrido)1,4-diazabuta-1,3-diene]nickel[3-(butyl)catecholate]; [1,4-bis{3,4-di(pentyl)phenyl}-2,3-(dihexyl)1,4-diazabuta-1,3-diene]nickel[3-(ethyl)-5-(propyl)-catecholate]; [1,4-bis{3,5-di(pentyl)phenyl}-2,3-(dihydrido)1,4-diazabuta-1,3-diene]nickel[3-(butyl)catecholate]; [1,4-bis{phenyl}-2-(octyl)-3-(butyl)1,4-diazabuta-1,3-diene]nickel[3-(propyl)catecholate]; [1,4-bis{3,4-di(butyl)phenyl}-2-(butyl)-3-(hydrido)1,4-diazabuta-1,3-diene]nickel[3-(ethyl)-5-(methyl)catecholate]; [1,4-bis{3,4-di(propyl)phenyl}-2-(butyl)-3-(pentyl)1,4-diazabuta-1,3-diene]nickel[3,6-di(butyl)-catecholate]; [1,4-bis{4-hexacosylphenyl}-2-(hydrido)-3-(octyl)1,4-diazabuta-1,3-dien]nickel[3-(methyl)-5-(pentyl)catecholate]; [1,4-bis{4-octenylphenyl}-2,3-(dipentyl)1,4-diazabuta-1,3-diene]nickel[3,5-di(butyl)-4-(bromo)catecholate]; [1,4-bis{3-heptenyl-phenyl}-2-(octyl)-3-(hydrido)1,4-diazabuta-1,3-diene]palladium[3-(butyl)catecholate]; [1,4-bis{3-propanalylphenyl}-2-(octyl)-3-(propenyl)1,4-diazabuta-1,3-diene]nickel[3-(propyl)-4-(ethyl)-5-(butyl)catecholate]; [1,4-bis{phenyl}-2-(hydrido)-3-(pentyl)1,4-diazabuta-1,3-diene]nickel[3-(butyl)-6-(methyl)catecholate]; [1,4-bis{phenyl}-2,3-

(dibutyl)1,4-diazabuta-1,3-diene]palladium[3-(butyl)-4-(propyl)catecholate]; [1,4-bis{phenyl}-2-(butyl)-3-(octyl)1,4-diazabuta-1,3-diene]nickel[4-(propyl)-5-(methyl)-catecholate]; [1,4-bis{3,4-di(propyl)phenyl}-2-(pentyl)-3-(hexacosynyl)1,4-diazabuta-1,3-diene]nickel[3-(butyl)-5-(pentyl)catecholate]; [1,4-bis{3-hexacosenylphenyl}-2,3-(dibutyl)1,4-diazabuta-1,3-diene]palladium[3-(ethyl)-4-(butyl)catecholate]; [1,4-bis{3,4-di(methyl)phenyl}-2,3-(dihydrido)1,4-diazabuta-1,3-diene]nickel[3-(butyl)-6-(propyl)-catecholate]; [1,4-bis{4-eicosynylphenyl}-2-(butyl)-3-(hydrido)1,4-diazabuta-1,3-diene]nickel[3-(methyl)catecholate]; [1,4-bis{3,5-di(pentyl)phenyl}-2-(hexyl)-3-(pentyl)1,4-diazabuta-1,3-diene]nickel[3-(butyl)-4,6-di(methyl)catecholate]; [1,4-bis{3,4-di(ethyl)-phenyl}-2-(pentyl)-3-(butyl)1,4-diazabuta-1,3-diene]nickel[3-(propyl)-4-(methyl)-catecholate]; [1,4-bis{phenyl}-2-(hexyl)-3-(butyl)1,4-diazabuta-1,3-diene]nickel[4-(ethyl)-5-(pentyl)catecholate]; [1,4-bis{phenyl}-2-(butyl)-3-(hexyl)1,4-diazabuta-1,3-diene]palladium[4-(pentyl)-5-(ethyl)catecholate]; [1,4-bis{phenyl}-2-(hexyl)-3-(butyl)-1,4-diazabuta-1,3-diene]nickel[4-(ethyl)catecholate]; [1,4-bis{3,5-di(pentyl)phenyl}-2-(hydrido)-3-(octyl)1,4-diazabuta-1,3-diene]nickel[3-(ethyl)catecholate]; [1,4-bis{3,5-di(butyl)phenyl}-2-(pentyl)-3-(butyl)1,4-diazabuta-1,3-diene]nickel[4-(pentyl)-catecholate]; [1,4-bis{4-eicosenylphenyl}-2,3-(dihydrido)1,4-diazabuta-1,3-diene]nickel[3-(propyl)-5-(pentyl)catecholate]; [1,4-bis{4-nonylphenyl}-2,3-(dibutyl)1,4-diazabuta-1,3-diene]nickel[3,4-di(pentyl)-6-(pentyl)catecholate]; [1,4-bis{4-heptenylphenyl}-2-(hydrido)-3-(octyl)1,4-diazabuta-1,3-diene]nickel[4-(propyl)-5-(pentyl)catecholate]; [1,4-bis{3-heptylphenyl}-2-(hydrido)-3-(octyl)1,4-diazabuta-1,3-diene]nickel[3-(propyl)-5-(pentyl)catecholate]; [1,4-bis{phenyl}-2-(pentyl)-3-(butyl)1,4-diazabuta-1,3-diene]nickel[4-(methyl)catecholate]; [1,4-bis{4-hexenylphenyl}-2-(methyl)-3-(hydrido)-1,4-diazabuta-1,3-diene]nickel[4-(methyl)-5-(pentyl)catecholate]; [1,4-bis{3,5-di(butyl)-phenyl}-2-(heptacosynyl)-3-(pentyl)1,4-diazabuta-1,3-diene]nickel[3-(ethyl)-6-(propyl)-catecholate]; [1,4-bis{3,4-di(pentyl)phenyl}-2-(hexyl)-3-(butyl)1,4-diazabuta-1,3-diene]nickel[3-(pentyl)-6-(ethyl)catecholate]; [1,4-bis{phenyl}-2-(nonynyl)-3-(pentynyl)1,4-diazabuta-1,3-diene]nickel[4-(pentyl)catecholate]; [1,4-bis{3,5-di(pentyl)phenyl}-2-(butyl)-3-(methyl)1,4-diazabuta-1,3-diene]palladium[3-(propyl)-4-(methyl)-5-(ethyl)-catecholate]; [1,4-bis{3,4-di(propyl)phenyl}-2-(hydrido)-3-(pentyl)1,4-diazabuta-1,3-diene]nickel[3-(butyl)catecholate]; [1,4-bis{phenyl}-2-(hexyl)-3-(pentyl)1,4-diazabuta-1,3-diene]palladium[4-(ethyl)catecholate]; [1,4-bis{3,4-di(methyl)phenyl}-2-(decenyl)-3-(methyl)1,4-diazabuta-1,3-diene]nickel[3-(butyl)catecholate]; [1,4-bis{3-undecenyl-phenyl}-2-(pentyl)-3-(hydrido)1,4-diazabuta-1,3-diene]nickel[3-(propyl)catecholate]; [1,4-bis{phenyl}-2-(butyl)-3-(octyl)1,4-diazabuta-1,3-diene]nickel[4-(methyl)-5-(ethyl)-catecholate]; [1,4-bis{3-eicosenylphenyl}-2-(butyl)-3-(hydrido)1,4-diazabuta-1,3-diene]palladium[3-(butyl)-4,6-di(methyl)catecholate]; [1,4-bis{3,5-di(butyl)phenyl}-2-(hydrido)-3-(hexacosynyl)1,4-diazabuta-1,3-diene]nickel[3-(ethyl)catecholate]; [1,4-bis{phenyl}-2-(octyl)-3-(hydrido)1,4-diazabuta-1,3-diene]nickel[3,5-di(methyl)-catecholate]; [1,4-bis{phenyl}-2-(pentyl)-3-(methyl)1,4-diazabuta-1,3-diene]nickel[3,4-di(ethyl)-5-(methyl)catecholate]; [1,4-bis{4-octacosynylphenyl}-2-(hexyl)-3-(methyl)1,4-diazabuta-1,3-diene]nickel[3-(methyl)-4-(methyl)catecholate]; [1,4-bis{3,4-di(ethyl)-phenyl}-2,3-(dihydrido)1,4-diazabuta-1,3-diene]nickel[3-(ethyl)catecholate]; [1,4-bis{3,4-di(pentyl)phenyl}-2-(tridecynyl)-3-(hydrido)1,4-diazabuta-1,3-diene]nickel[3-(pentyl)-6-(butyl)catecholate]; [1,4-bis{4-nonacosenylphenyl}-2-(octyl)-3-(butyl)1,4-diazabuta-1,3-diene]nickel[3-(trimethylsilylethyl)-4-(pentyl)catecholate]; [1,4-bis{3,4-di(butonyl)phenyl}-2,3-(dibutyl)1,4-diazabuta-1,3-diene]palladium[4-(methyl)-catecholate]; [1,4-bis{3,4-di(methyl)phenyl}-2-(decyl)-3-(octyl)1,4-diazabuta-1,3-diene]nickel[3-(pentyl)catecholate]; [1,4-bis{phenyl}-2-(eicosynyl)-3-(hydrido)1,4-diazabuta-1,3-diene]palladium[4-(methyl)catecholate]; [1,4-bis{4-nonadecenylphenyl}-2-(nonadecyl)-3-(butyl)1,4-diazabuta-1,3-diene]nickel[3,4-di(propyl)-6-(pentyl)-catecholate]; [1,4-bis{3,4-di(proponyl)phenyl}-2-(octyl)-3-(butyl)1,4-diazabuta-1,3-diene]palladium[3-(methyl)-5-((triethylsilylmethyl))catecholate]; [1,4-bis{3,5-di(propyl)phenyl}-2-(butyl)-3-(methyl)1,4-diazabuta-1,3-diene]nickel[3-(methyl)-6-(ethyl)catecholate]; [1,4-bis{3,5-di(propyl)phenyl}-2-(pentyl)-3-(butyl)1,4-diazabuta-1,3-diene]nickel[4-(butyl)catecholate]; [1,4-bis{4-octylaminophenyl}-2,3-(dihydrido)1,4-diazabuta-1,3-diene]nickel[3-(butanalyl)-6-(ethyl)catecholate]; [1,4-bis{phenyl}-2-(butyl)-3-(hexyl)1,4-diazabuta-1,3-diene]nickel[4-(butyl)catecholate]; [1,4-bis{3,5-di(ethyl)phenyl}-2-(methyl)-3-(hydrido)1,4-diazabuta-1,3-diene]nickel[3,6-di(pentyl)-catecholate]; [1,4-bis{4-nonenylphenyl}-2-(hydrido)-3-(butyl)1,4-diazabuta-1,3-diene]palladium[3-(butyl)-4-(pentyl)catecholate]; [1,4-bis{4-hexacosenylphenyl}-2-(pentyl)-3-(ethyl)1,4-diazabuta-1,3-diene]palladium[4-(pentyl)catecholate]; [1,4-bis{3-nonyl-phenyl}-2,3-(dibutyl)1,4-diazabuta-1,3-diene]palladium[3,6-di(ethyl)catecholate]; [1,4-bis{3,5-di(butonyl)phenyl}-2-(hydrido)-3-(butyl)1,4-diazabuta-1,3-diene]nickel[3-(methyl)-4-(butyl)-6-(ethyl)catecholate]; [1,4-bis{4-octacosynylphenyl}-2,3-(dihydrido)-1,4-diazabuta-1,3-diene]nickel[3-(butyl)-4-(methyl)catecholate]; [1,4-bis{3,4-di(propyl)phenyl}-2-(hexyl)-3-(butyl)1,4-diazabuta-1,3-diene]nickel[3-(pentyl)-4-(ethyl)catecholate]; [1,4-bis{4-heptadecenylphenyl}-2-(hydrido)-3-(butyl)1,4-diazabuta-1,3-diene]nickel[3-(propyl)catecholate]; [1,4-bis{3-pentadecylphenyl}-2-(hexacosyl)-3-(butyl)1,4-diazabuta-1,3-diene]nickel[4-(propyl)catecholate]; [1,4-bis{3,4-di(ethyl)-phenyl}-2-(nonadecyl)-3-(heptadecynyl)1,4-diazabuta-1,3-diene]palladium[3,4-di(propyl)-6-(hexyl)catecholate]; [1,4-bis{4-nonynylphenyl}-2-(methyl)-3-(pentyl)1,4-diazabuta-1,3-diene]nickel[4-(pentyl)catecholate]; [1,4-bis{3,5-di(pentyl)phenyl}-2-(hydrido)-3-(octadecyl)1,4-diazabuta-1,3-diene]nickel[4-(ethyl)catecholate]; [1,4-bis{3-tridecylphenyl}-2-(tetracosenyl)-3-(hydrido)1,4-diazabuta-1,3-diene]nickel[4-(methyl)-catecholate]; [1,4-bis{4-undecylphenyl}-2-(eicosyl)-3-(hydrido)1,4-diazabuta-1,3-diene]nickel[3,4-di(butyl)catecholate]; [1,4-bis{3-octylphenyl}-2-(butyl)-3-(ethyl)1,4-diazabuta-1,3-diene]palladium[3-(pentyl)-6-(propyl)catecholate]; [1,4-bis{4-heptadecyl-phenyl-}2-(butyl)-3-(octyl)1,4-diazabuta-1,3-diene]nickel[3-(propyl)catecholate]; [1,4-bis{phenyl}-2,3-(dibutyl)1,4-diazabuta-1,3-diene]nickel[3-(bromo)-4-(octylamino)-5-(ethyl)catecholate]; [1,4-bis{4-tricosylphenyl}-2,3-(dihydrido)1,4-diazabuta-1,3-diene]nickel[3-(butyl)-6-(pentyl)catecholate]; [1,4-bis{3,5-di(methyl)phenyl}-2,3-(dihydrido)-1,4-diazabuta-1,3-diene]nickel[3-(methyl)-6-(propyl)catecholate]; [1,4-bis{4-undecyl-phenyl}-2-(ethyl)-3-(octyl)1,4-diazabuta-1,3-diene]nickel[3,5-di(propyl)-4-(butonyl)-catecholate]; [1,4-bis{phenyl}-2,3-(dibutyl)1,4-diazabuta-1,3-diene]nickel[3-(methyl)-catecholate]; [1,4-bis{phenyl}-2,3-(dihydrido)1,4-diazabuta-1,3-diene]palladium[3-(butyl)catecholate]; [1,4-bis{3,5-di(methyl)phenyl}-2-(nonacosynyl)-3-(butyl)1,4-diazabuta-1,3-diene]

nickel[4-(methyl)catecholate]; [1,4-bis{phenyl}-2-(hydrido)-3-(pentyl)1,4-diazabuta-1,3-diene]nickel[3-(propyl)-6-(butyl)catecholate]; [1,4-bis{3,4-di(butyl)phenyl}-2-(hexyl)-3-(butyl)1,4-diazabuta-1,3-diene]palladium [3-(pentyl)-4,6-di(propyl)catecholate]; [1,4-bis{3,4-di(methyl)phenyl}-2-(butyl)-3-(octyl)1,4-diazabuta-1,3-diene]nickel[3-(propyl)catecholate]; [1,4-bis{3,5-di(methyl)phenyl}-2-(hydrido)-3-(ethyl)1,4-diazabuta-1,3-diene]nickel[3-(pentyl)-6-(butyl)catecholate]; [1,4-bis{phenyl}-2-(butyl)-3-(ethyl)1,4-diazabuta-1,3-diene]nickel[3-(propyl)-5-(pentyl)catecholate]; [1,4-bis{phenyl}-2-(hydrido)-3-(butyl)1,4-diazabuta-1,3-diene]nickel[3-(pentyl)-6-(butyl)catecholate]; [1,4-bis{3,5-di(pentyl)phenyl}-2-(butyl)-3-(hexyl)1,4-diazabuta-1,3-diene]nickel[3-(butyl)catecholate]; [1,4-bis{phenyl}-2-(butyl)-3-(hydrido)1,4-diazabuta-1,3-diene]nickel[4-(pentyl)catecholate]; [1,4-bis{3,4-di(butyl)phenyl}-2-(butyl)-3-(nonadecenyl)1,4-diazabuta-1,3-diene]nickel[3-(butyl)catecholate]; [1,4-bis{3-nonenyl-phenyl}-2-(hydrido)-3-(butyl)1,4-diazabuta-1,3-diene]palladium[3-(propyl)-6-(ethyl)-catecholate]; [1,4-bis{phenyl}-2-(hydrido)-3-(octyl)1,4-diazabuta-1,3-diene]nickel[4-(propyl)catecholate]; [1,4-bis{phenyl}-2-(octyl)-3-(butyl)1,4-diazabuta-1,3-diene]nickel[3,4-di(butyl)catecholate]; [1,4-bis{3,5-di(ethyl)phenyl}-2-(octyl)-3-(hydrido)1,4-diazabuta-1,3-diene]nickel[3-(ethyl)catecholate]; [1,4-bis{3,5-di(pentyl)phenyl}-2-(butyl)-3-(pentyl)1,4-diazabuta-1,3-diene]nickel[3-(propyl)-5-(ethyl)catecholate]; [1,4-bis{3,4-di(methyl)phenyl}-2-(hexyl)-3-(butyl)1,4-diazabuta-1,3-diene]nickel[3-(propyl)-4-(ethyl)catecholate]; [1,4-bis{3,5-di(pentyl)phenyl}-2-(ethyl)-3-(hexyl)1,4-diazabuta-1,3-diene]nickel[3-(propyl)-5-(methyl)catecholate]; [1,4-bis{4-trimethylsilylmethylphenyl}-2-(butyl)-3-(hydrido)1,4-diazabuta-1,3-diene]nickel[4-(pentyl)catecholate]; [1,4-bis{3,5-di(methyl)phenyl-}2-(hydrido)-3-(pentadecyl)1,4-diazabuta-1,3-diene]nickel[3-(ethyl)-4-(dodecamino)catecholate]; [1,4-bis{phenyl}-2-(butyl)-3-(nonyl)1,4-diazabuta-1,3-diene]nickel[4-(propyl)catecholate]; [1,4-bis{phenyl}-2-(hydrido)-3-(heptacosyl)1,4-diazabuta-1,3-diene]nickel[3-(propyl)-catecholate]; [1,4-bis{phenyl}-2-(butyl)-3-(methyl)1,4-diazabuta-1,3-diene]nickel[3-(ethyl)-5-(butyl)catecholate]; [1,4-bis{3,4-di(pentyl)phenyl}-2-(heptacosynyl)-3-(pentyl)-1,4-diazabuta-1,3-diene]nickel[3,6-di(propyl)catecholate]; [1,4-bis{phenyl}-2,3-(dibutyl)1,4-diazabuta-1,3-diene]palladium[3-(ethyl)catecholate]; [1,4-bis{phenyl}-2-(pentyl)-3-(butyl)1,4-diazabuta-1,3-diene]nickel[4-(pentyl)-5-(propyl)catecholate]; [1,4-bis{4-tetracosenylphenyl}-2,3-(dibutyl)-1,4-diazabuta-1,3-diene]nickel[4-(propyl)-5-(ethyl)catecholate]; [1,4-bis{phenyl}-2-(octenyl)-3-(octyl)1,4-diazabuta-1,3-diene]nickel[4-(propyl)-5-(ethyl)catecholate]; [1,4-bis{3-dodecenylphenyl}-2-(hexyl)-3-(pentyl)1,4-diazabuta-1,3-diene]nickel[4-(pentyl)catecholate]; [1,4-bis{phenyl}-2-(hydrido)-3-(butyl)1,4-diazabuta-1,3-diene]palladium[3-(ethyl)-4-(propyl)catecholate]; [1,4-bis{3,5-di(butyl)phenyl}-2-(butyl)-3-(hydrido)1,4-diazabuta-1,3-diene]palladium[3-(methyl)-4-(ethyl)-6-(pentyl)catecholate]; [1,4-bis{3,5-di(methyl)phenyl}-2-(butyl)-3-(hydrido)1,4-diazabuta-1,3]nickel[3-(methyl)catecholate]; [1,4-bis{3-heptadecynylphenyl}-2-(octyl)-3-(butyl)1,4-diazabuta-1,3-diene]palladium[3-(ethyl)catecholate]; [1,4-bis{3,5-di(ethyl)phenyl}-2-(hexyl)-3-(hydrido)1,4-diazabuta-1,3-diene]nickel[3-(butyl)-5-(methyl)catecholate]; [1,4-bis{3,4-di(ethyl)phenyl}-2-(hexyl)-3-(hydrido)1,4-diazabuta-1,3-diene]nickel[3-(propanalyl)-6-(propyl)catecholate]; [1,4-bis{3,4-di(ethyl)phenyl}-2,3-(dibutyl)1,4-diazabuta-1,3-diene]nickel[3-(pentyl)-4-(propyl)catecholate]; [1,4-bis{phenyl}-2-(butyl)-3-(ethyl)1,4-diazabuta-1,3-diene]nickel[4-(methyl)catecholate]; [1,4-bis{4-nonacosenylphenyl}-2,3-(dibutyl)1,4-diazabuta-1,3-diene]nickel[3-(propanalyl)-6-(propyl)catecholate]; [1,4-bis{3-dodecylphenyl}-2-(pentyl)-3-(butyl)1,4-diazabuta-1,3-diene]nickel[3-(propyl)-6-(methyl)catecholate]; [1,4-bis{phenyl}-2,3-(dihydrido)1,4-diazabuta-1,3-diene]nickel[4-(pentyl)catecholate]; [1,4-bis{3,4-di(methyldiethylsilylmethyl))phenyl}-2-(nonyl)-3-(hydrido)1,4-diazabuta-1,3-diene]nickel[3-(butyl)-6-(methyl)catecholate]; [1,4-bis{3,5-di(propyl)phenyl}-2,3-(dihydrido)-1,4-diazabuta-1,3-diene]nickel[3-(ethyl)catecholate]; [1,4-bis{phenyl}-2-(butyl)-3-(hydrido)1,4-diazabuta-1,3-diene]palladium[3-(methyl)-4-(propyl)catecholate]; [1,4-bis{3,4-di(pentyl)phenyl}-2-(triacontenyl)-3-(hydrido)1,4-diazabuta-1,3-diene]nickel[3-(ethyl)catecholate]; [1,4-bis{3,5-di(propyl)phenyl}-2,3-(dibutyl)1,4-diazabuta-1,3-diene]nickel[4-(pentyl)-5-(butyl)catecholate]; [1,4-bis{3,5-di(butyl)phenyl}-2,3-(dibutyl)1,4-diazabuta-1,3-diene]nickel[3-(propyl)catecholate]; [1,4-bis{phenyl}-2-(hydrido)-3-(butyl)1,4-diazabuta-1,3-diene]palladium[3-(propyl)-5-(ethyl)catecholate]; [1,4-bis{3,5-di(pentyl)phenyl}-2-(hydrido)-3-(butyl)1,4-diazabuta-1,3-diene]nickel[3,6-di(pentyl)-4-(ethyl)catecholate]; [1,4-bis{3,5-di(hexonyl)phenyl}-2-(hydrido)-3-(butyl)1,4-diazabuta-1,3-diene]nickel[3-(propyl)-5-(pentyl)catecholate]; [1,4-bis{phenyl}-2,3-(dihexyl)1,4-diazabuta-1,3-diene]palladium[4,5-di(pentyl)catecholate]; [1,4-bis{phenyl}-2-(hydrido)-3-(heptynyl)1,4-diazabuta-1,3-diene]nickel[3-(propyl)-5-(butyl)catecholate]; [1,4-bis{phenyl}-2,3-(dibutyl)1,4-diazabuta-1,3-diene]palladium[3-(methyl)catecholate]; [1,4-bis{3,4-di(methyl)phenyl}-2-(butyl)-3-(octacosenyl)1,4-diazabuta-1,3-diene]palladium[3,4-di(pentyl)-6-(butyl)catecholate]; [1,4-bis{3,4-di(ethyl)phenyl}-2-(butyl)-3-(pentyl)1,4-diazabuta-1,3-diene]nickel[3-(ethyl)-5-(pentyl)catecholate]; [1,4-bis{3,4-di(pentyl)phenyl}-2-(butyl)-3-(hexyl)1,4-diazabuta-1,3-diene]nickel[3-(butyl)-catecholate]; [1,4-bis{3-hexacosynylphenyl}-2-(ethyl)-3-(butyl)1,4-diazabuta-1,3-diene]nickel[3-(methyl)-4-(butyl)-5-(pentyl)catecholate]; [1,4-bis{3,5-di(butyl)phenyl}-2-(hydrido)-3-(butyl)1,4-diazabuta-1,3-diene]palladium[3,4-di(ethyl)-5-(methyl)-catecholate]; [1,4-bis{3,4-di(pentyl)phenyl}-2-(hydrido)-3-(butyl)1,4-diazabuta-1,3-diene]palladium[3-(butyl)-6-(ethyl)catecholate]; [1,4-bis{3,5-di(butyl)phenyl}-2-(hydrido)-3-(hexyl)1,4-diazabuta-1,3-diene]nickel[3-(butyl)-5-(propyl)catecholate]; [1,4-bis{phenyl}-2-(hexyl)-3-(propyl)1,4-diazabuta-1,3-diene]nickel[4-(propyl)-5-(methyl)catecholate]; [1,4-bis{phenyl}-2,3-(dibutyl)1,4-diazabuta-1,3-diene]nickel[3-(pentyl)catecholate]; [1,4-bis{3,4-di(propyl)phenyl}-2-(hydrido)-3-(butyl)1,4-diazabuta-1,3-diene]nickel[3-(methyl)-4-(ethyl)-6-(butyl)catecholate]; [1,4-bis{3,5-di(methyl)-phenyl}-2-(butyl)-3-(hydrido)1,4-diazabuta-1,3-diene]palladium[3-(butyl)catecholate]; [1,4-bis{phenyl}-2-(hexyl)-3-(butyl)1,4-diazabuta-1,3-diene]palladium[4-(propyl)-5-(methyl)catecholate]; [1,4-bis{3-tetracosylphenyl}-2-(methyl)-3-(tetradecenyl)1,4-diazabuta-1,3-diene]palladium[3,5-di(methyl)catecholate]; [1,4-bis{phenyl}-2-(hydrido)-3-(butyl)1,4-diazabuta-1,3-diene]palladium[3-(propyl)catecholate]; [1,4-bis{3,4-di(ethyl)phenyl}-2-(hydrido)-3-(butyl)1,4-diazabuta-1,3-diene]nickel[3-(propyl)catecholate]; [1,4-bis{3,5-di(pentyl)phenyl}-2,3-(dihydrido)1,4-diazabuta-1,3-diene]nickel[3-(methyl)catecholate]; [1,4-bis{phenyl}-2-(butyl)-3-(hydrido)1,4-diazabuta-1,3-diene]palladium[4-(propyl)catecholate]; [1,4- bis{4-octylaminophenyl}-2-(butyl)-3-(hydrido)1,4-diazabuta-1,3-diene]palladium[3-(ethyl)-4-(butyl)catecholate]; [1,4-bis{3,5-di(ethyl)phenyl}-2-(pentyl)-3-(butyl)1,4-diazabuta-1,3-diene]palladium[3-(ethyl)-6-(butyl)catecholate]; [1,4-bis{phenyl}-2,3-(dibutyl)1,4-diazabuta-1,3-diene]palladium[3,4-di(methyl)-6-(propyl)catecholate]; [1,4-bis{4-heptadecenylphenyl}-2-(pentenyl)-3-(pentyl)1,4-diazabuta-1,3-diene]nickel[3-(pentyl)-5-(ethyl)catecholate]; [1,4-bis{3,5-di(pentyl)phenyl}-2,3-(dihydrido)1,4-diazabuta-1,3-diene]nickel[4-(butyl)-catecholate]; [1,4-bis{3,4-di(pentyl)phenyl}-2-(butyl)-3-(pentyl)1,4-diazabuta-1,3-diene]nickel[3-(ethyl)-4-(butyl)catecholate]; [1,4-bis{4-trimethylsilylethylphenyl}-2,3-(dibutyl)1,4-diazabuta-1,3-diene]palladium[4,5-di(methyl)catecholate]; [1,4-bis{3,4-di(ethyl)phenyl}-2-(ethyl)-3-(octyl)1,4-diazabuta-1,3-diene]nickel[4-(methyl)-catecholate]; [1,4-bis{phenyl}-2-(butyl)-3-(hexyl)1,4-diazabuta-1,3-diene]nickel[3-(pentyl)catecholate]; [1,4-bis{phenyl}-2-(hydrido)-3-(ethyl)1,4-diazabuta-1,3-diene]nickel[4-(propyl)catecholate]; [1,4-bis{3,5-di(ethyl)phenyl}-2-(octyl)-3-(tetracosenyl)-1,4-diazabuta-1,3-diene]nickel[4-(trimethylsilylmethyl)-5-(butyl)catecholate]; [1,4-bis{phenyl}-2-(ethyl)-3-(octyl)1,4-diazabuta-1,3-diene]nickel[3,6-di(butyl)-4-(propyl)-catecholate]; [1,4-bis{3-decylphenyl}-2,3-(dibutyl)1,4-diazabuta-1,3-diene]nickel[3-(butyl)catecholate]; [1,4-bis{3,4-di(butyl)phenyl}-2,3-(dibutyl)1,4-diazabuta-1,3-diene]palladium[3-(butyl)catecholate]; [1,4-bis{phenyl}-2-(tetracosenyl)-3-(pentyl)1,4-diazabuta-1,3-diene]nickel[3-(propyl)catecholate]; [1,4-bis{3,5-di(methyl)phenyl}-2-(butyl)-3-(hydrido)1,4-diazabuta-1,3-diene]nickel[3-(ethyl)-4-(trimethylsilylethyl)-6-(butyl)catecholate]; [1,4-bis{4-nonacosylphenyl}-2-(hydrido)-3-(octyl)1,4-diazabuta-1,3-diene]nickel[3-(methyl)catecholate]; [1,4-bis{phenyl}-2-(hydrido)-3-(hexyl)1,4-diazabuta-1,3-diene]nickel[3-(ethyl)catecholate]; [1,4-bis{phenyl}-2,3-(dihydrido)1,4-diazabuta-1,3-diene]palladium[3-(pentyl)-5-(methyl)catecholate]; [1,4-bis{phenyl}-2,3-(dibutyl)1,4-diazabuta-1,3-diene]nickel[3-(propyl)-5-(ethyl)catecholate]; [1,4-bis{phenyl}-2-(hexyl)-3-(butyl)1,4-diazabuta-1,3-diene]palladium[3-(butyl)catecholate]; [1,4-bis{4-tricosynylphenyl}-2-(butyl)-3-(pentyl)1,4-diazabuta-1,3-diene]nickel[3-(butyl)-5-(ethyl)catecholate]; [1,4-bis{3,4-di(pentyl)phenyl}-2,3-(dihydrido)1,4-diazabuta-1,3-diene]palladium[3,5-di(butyl)catecholate]; [1,4-bis{phenyl}-2-(hydrido)-3-(octyl)1,4-diazabuta-1,3-diene]nickel[3-(butyl)-4-(methyl)catecholate]; [1,4-bis{3,4-di(propyl)phenyl}-2,3-(dibutyl)1,4-diazabuta-1,3-diene]nickel[4-(methyl)catecholate]; [1,4-bis{3,4-di(butyl)phenyl}-2-(pentyl)-3-(hydrido)1,4-diazabuta-1,3-diene]palladium[3-(ethyl)-4-(butyl)-5-(pentyl)catecholate]; [1,4-bis{phenyl}-2,3-(dihydrido)1,4-diazabuta-1,3-diene]palladium[3-(ethyl)-6-(propyl)catecholate]; [1,4-bis{phenyl}-2,3-(dibutyl)1,4-diazabuta-1,3-diene]nickel[3-(methyl)-5-(butyl)catecholate]; [1,4-bis{3,5-di(butyl)phenyl}-2-(pentyl)-3-(octyl)1,4-diazabuta-1,3-diene]nickel[3-(methyl)-catecholate]; [1,4-bis{phenyl}-2-(ethyl)-3-(octyl)1,4-diazabuta-1,3-diene]nickel[4-(ethyl)catecholate]; [1,4-bis{4-octadecylphenyl}-2-(octyl)-3-(pentyl)1,4-diazabuta-1,3-diene]palladium[3-(methyl)-4-(propyl)catecholate]; [1,4-bis{4-tricosylphenyl}-2-(octyl)-3-(butyl)1,4-diazabuta-1,3-diene]nickel[3-(ethyl)-4-(butyl)-6-(pentyl)catecholate]; [1,4-bis{phenyl}-2-(hydrido)-3-(pentyl)1,4-diazabuta-1,3-diene]nickel[4-(ethyl)catecholate]; [1,4-bis{3,4-di(propyl)phenyl}-2-(butyl)-3-(hexyl)1,4-diazabuta-1,3-diene]nickel[3-(ethyl)catecholate]; [1,4-bis{3,4-di(pentyl)phenyl}-2-(hydrido)-3-(octyl)-1,4-diazabuta-1,3-diene]nickel[3-(methyl)-4-(butyl)-6-(ethyl)catecholate]; [1,4-bis{3,4-di(propyl)phenyl}-2-(butyl)-3-(octyl)1,4-diazabuta-1,3-diene]palladium[3-(butyl)-5-(pentyl)catecholate]; [1,4-bis{3,4-di(methyl)phenyl}-2-(dodecyl)-3-(butyl)1,4-diazabuta-1,3-diene]nickel[3-(butyl)-4-(pentyl)catecholate]; [1,4-bis{3,5-di(pentyl)phenyl}-2-(pentyl)-3-(butyl)1,4-diazabuta-1,3-diene]nickel[3,6-di(ethyl)catecholate]; [1,4-bis{phenyl}-2-(octyl)-3-(hydrido)1,4-diazabuta-1,3-diene]nickel[3-(ethyl)-4-(propyl)-catecholate]; [1,4-bis{3,4-di(methyl)phenyl}-2-(hydrido)-3-(octyl)1,4-diazabuta-1,3-diene]palladium[3-(butyl)catecholate]; [1,4-bis{phenyl}-2-(pentacosynyl)-3-(pentyl)1,4-diazabuta-1,3-diene]nickel[3-(pentyl)catecholate]; [1,4-bis{3,5-di(pentyl)phenyl}-2,3-(dihydrido)1,4-diazabuta-1,3-diene]palladium[3-(butyl)catecholate]; [1,4-bis{3,5-di(butyl)phenyl}-2,3-(dibutyl)1,4-diazabuta-1,3-diene]nickel[3-(dodecanonyl)-5-(butyl)-catecholate]; [1,4-bis{3,4-di(butyl)phenyl}-2-(heneicosynyl)-3-(methyl)1,4-diazabuta-1,3-diene]nickel[3-(butyl)catecholate]; [1,4-bis{3,4-di(propyl)phenyl}-2-(butyl)-3-(tricosyl)1,4-diazabuta-1,3-diene]nickel[3-(butyl)-4-(hexonyl)catecholate]; [1,4-bis{4-decylphenyl}-2-(octyl)-3-(pentyl)1,4-diazabuta-1,3-diene]nickel[4-(pentyl)catecholate]; [1,4-bis{phenyl}-2-(butyl)-3-(hydrido)1,4-diazabuta-1,3-diene]nickel[3-(pentyl)-catecholate]; [1,4-bis{3-ethylphenyl}-2-(butyl)-3-(pentyl)1,4-diazabuta-1,3-diene]nickel[3-(methyl)-4-(ethyl)catecholate]; [1,4-bis{3,4-di(propyl)phenyl}-2,3-(dihydrido)1,4-diazabuta-1,3-diene]nickel[3-(propyl)catecholate]; [1,4-bis{phenyl}-2-(pentyl)-3-(hydrido)1,4-diazabuta-1,3-diene]palladium[3-(butyl)-6-(methyl)catecholate]; [1,4-bis{3,5-di(pentyl)phenyl}-2,3-(dipentyl)1,4-diazabuta-1,3-diene]nickel[4-(ethyl)-catecholate]; [1,4-bis{3,5-di(methyl)phenyl}-2-(butyl)-3-(hydrido)1,4-diazabuta-1,3-diene]nickel[3-(ethyl)-4-(pentyl)catecholate]; [1,4-bis{3,4-di(pentyl)phenyl}-2,3-(dibutyl)1,4-diazabuta-1,3-diene]nickel[3-(ethyl)-4-(butyl)-6-(pentyl)catecholate]; [1,4-bis{3,5-di(ethyl)phenyl}-2,3-(dibutyl)1,4-diazabuta-1,3-diene]nickel[3-(butyl)-catecholate]; [1,4-bis{phenyl}-2-(octyl)-3-(butyl)1,4-diazabuta-1,3-diene]nickel[3-(butyl)-4-(pentyl)-6-(ethyl)catecholate]; [1,4-bis{phenyl}-2-(octyl)-3-(hydrido)1,4-diazabuta-1,3-diene]palladium[3-(pentyl)catecholate]; [1,4-bis{3,5-di(pentyl)phenyl}-2-(butyl)-3-(hexyl)1,4-diazabuta-1,3-diene]nickel[3-(methyl)-4-(ethyl)-5-(pentyl)-catecholate]; [1,4-bis{phenyl}-2-(octyl)-3-(butyl)1,4-diazabuta-1,3-diene]nickel[3-(butyl)-5-(propyl)catecholate]; [1,4-bis{3,5-di(butyl)phenyl}-2-(butyl)-3-(hydrido)1,4-diazabuta-1,3-diene]nickel[3-(ethyl)-6-(butyl)catecholate]; [1,4-bis{phenyl}-2-(butyl)-3-(octyl)1,4-diazabuta-1,3-diene]nickel[3,6-di(pentyl)catecholate]; [1,4-bis{phenyl}-2-(hydrido)-3-(butyl)1,4-diazabuta-1,3-diene]palladium[3-(butyl)catecholate]; [1,4-bis{3,4-di(butyl)phenyl}-2-(hexacosynyl)-3-(triacontynyl)1,4-diazabuta-1,3-diene]nickel[3,4-di(ethyl)catecholate]; [1,4-bis{phenyl}-2,3-(dihydrido)1,4-diazabuta-1,3-diene]nickel[3,4-di(butyl)-6-(pentyl)catecholate]; [1,4-bis{phenyl}-2,3-(dihexyl)1,4-diazabuta-1,3-diene]nickel[3-(methyl)-4-(ethyl)catecholate]; [1,4-bis{3,4-di(ethyl)phenyl}-2-(butyl)-3-(methyl)1,4-diazabuta-1,3-diene]nickel[4-(butyl)catecholate]; [1,4-bis{3,5-di(pentyl)phenyl}-2-(octyl)-3-(hexyl)1,4-diazabuta-1,3-diene]nickel[4-(methyl)-catecholate]; [1,4-bis{3-methylphenyl}-2-(pentyl)-3-(hydrido)1,4-diazabuta-1,3-diene]nickel[3-(ethanalyl)-5-(pentyl)catecholate]; [1,4-bis{3,4-di(ethyl)phenyl}-2-(eicosyl)-3-(hexacosyl)-1,4-diazabuta-1,3-diene]nickel[3-(pentyl)-6-(butyl)catecholate]; [1,4-bis{phenyl}-2-(nonacosynyl)-3-(butyl)1,4-diazabuta-1,3-diene]nickel[3-

(ethyl)-catecholate]; [1,4-bis{3-nonadecenylphenyl}-2-(octyl)-3-(butyl)1,4-diazabuta-1,3-diene]palladium[3-(dodecaphosphino)catecholate]; [1,4-bis{3,4-di(dodecamino)phenyl}-2,3-(dibutyl)1,4-diazabuta-1,3-diene]nickel[4-(ethyl)-5-(pentyl)catecholate]; [1,4-bis{4-tricosynylphenyl}-2-(butyl)-3-(nonacosynyl)1,4-diazabuta-1,3-diene]nickel[3-(pentyl)-5-catecholate]; [1,4-bis{4-pentacosenylphenyl}-2-(butyl)-3-(undecynyl)1,4-diazabuta-1,3-diene]nickel[3-(propyl)-4-(methyl)catecholate]; [1,4-bis{3-trimethylsilylmethylphenyl}-2-(pentyl)-3-(hexadecenyl)1,4-diazabuta-1,3-diene]nickel[3-(butyl)-4-(propyl)catecholate]; [1,4-bis{phenyl}-2-(pentyl)-3-(hydrido)1,4-diazabuta-1,3-diene]nickel[3-(butanalyl)-4-(ethyl)-6-(methyl)catecholate]; [1,4-bis{3,4-di(pentyl)-phenyl}-2-(pentyl)-3-(hexyl)1,4-diazabuta-1,3-diene]nickel[3-(methyl)catecholate]; [1,4-bis{4-octylphenyl}-2-(hydrido)-3-(butyl)1,4-diazabuta-1,3-diene]nickel[3-(methyl)-4-(ethyl)-5-(pentyl)catecholate]; [1,4-bis{phenyl}-2,3-(dibutyl)1,4-diazabuta-1,3-diene]nickel[4-(methyl)catecholate]; [1,4-bis{3,4-di(butyl)phenyl}-2,3-(dibutyl)1,4-diazabuta-1,3-diene]nickel[3,4-di(ethyl)-6-(pentyl)catecholate]; [1,4-bis{3,4-di(butyl)-phenyl}-2-(propynyl)-3-(dodecenyl)1,4-diazabuta-1,3-diene]nickel[4-(ethyl)-5-(butyl)-catecholate]; [1,4-bis{3,4-di(methyl)phenyl}-2-(butyl)-3-(hydrido)1,4-diazabuta-1,3-diene]palladium[4-(pentyl)catecholate]; [1,4-bis{3,5-di(ethyl)phenyl}-2-(octyl)-3-(butyl)1,4-diazabuta-1,3-diene]nickel[3,5-di(pentyl)-4-(butyl)catecholate]; [1,4-bis{3,4-di(butyl)phenyl}-2-(pentyl)-3-(methyl)1,4-diazabuta-1,3-diene]nickel[3-(butyl)-catecholate]; [1,4-bis{3,5-di(methyl)phenyl}-2,3-(dibutyl)1,4-diazabuta-1,3-diene]palladium[3-(pentyl)-4-(ethyl)catecholate]; [1,4-bis{phenyl}-2-(octyl)-3-(butyl)1,4-diazabuta-1,3-diene]nickel[3-(propyl)-4-(ethyl)catecholate]; [1,4-bis{3-tricosylphenyl}-2-(hydrido)-3-(ethyl)1,4-diazabuta-1,3-diene]nickel[4-(pentyl)-5-(methyl)catecholate]; [1,4-bis{phenyl}-2,3-(dibutyl)1,4-diazabuta-1,3-diene]nickel[4-(pentyl)-5-(propyl)-catecholate]; [1,4-bis{3,5-di(methyl)phenyl}-2-(octyl)-3-(hydrido)1,4-diazabuta-1,3-diene]nickel[3-(propyl)catecholate]; [1,4-bis{phenyl}-2-(hydrido)-3-(pentacosynyl)1,4-diazabuta-1,3-diene]nickel[3,4-di(pentyl)catecholate]; [1,4-bis{phenyl}-2-(nonadecynyl)-3-(tetradecenyl)1,4-diazabuta-1,3-diene]nickel[4-(ethyl)catecholate];[1,4-bis{3,5-di(ethyl)phenyl}-2-(butyl)-3-(octyl)1,4-diazabuta-1,3-diene]nickel[3-(methyl)-5-(butyl)catecholate]; [1,4-bis{3-pentacosylphenyl}-2-(tricosyl)-3-(butyl)1,4-diazabuta-1,3-diene]nickel[4-(propyl)catecholate]; [1,4-bis{3,4-di(pentyl)phenyl}-2,3-(dihydrido)1,4-diazabuta-1,3-diene]palladium[4-(ethyl)-5-(propyl)catecholate]; [1,4-bis{phenyl}-2-(nonacosenyl)-3-(eicosyl)1,4-diazabuta-1,3-diene]nickel[3,6-di(ethyl)-catecholate]; [1,4-bis{phenyl}-2-(butyl)-3-(hydrido)1,4-diazabuta-1,3-diene]palladium[3-(ethyl)catecholate]; [1,4-bis{phenyl}-2,3-(dibutyl)1,4-diazabuta-1,3-diene]nickel[3-(methyl)-5-(pentyl)catecholate]; [1,4-bis{phenyl}-2-(butyl)-3-(octyl)1,4-diazabuta-1,3-diene]nickel[3,6-di(ethyl)catecholate]; [1,4-bis{phenyl}-2,3-(dibutyl)1,4-diazabuta-1,3-diene]nickel[3-(trimethylsilylethyl)-4-(ethyl)catecholate]; [1,4-bis{3,4-di(propyl)-phenyl}-2-(butyl)-3-(hydrido)1,4-diazabuta-1,3-diene]nickel[3-(ethyl)catecholate]; [1,4-bis{phenyl}-2-hydrido-3-(tridecyl)1,4-diazabuta-1,3]nickel[3,4-di(butyl)-catecholate]; [1,4-bis{phenyl}-2-(hydrido)-3-(ethyl)1,4-diazabuta-1,3-diene]nickel[3-(methyl)-6-(propyl)catecholate]; [1,4-bis{3-dodecylphenyl}-2-(pentyl)-3-(tricosenyl)1,4-diazabuta-1,3-diene]nickel[3-(pentyl)-4-(butyl)catecholate]; [1,4-bis{3,4-di(methyl)-phenyl}-2-(butyl)-3-(hydrido)1,4-diazabuta-1,3-diene]nickel[3,4-di(butyl)-5-(ethyl)-catecholate]; [1-(3,5-di(methyl)phenyl)-2,3-(dibutyl)-4-(3,4-di(methyl)phenyl)1,4-diazabuta-1,3-diene]nickel[3-(ethyl)-4-(butyl)catecholate];

[1-(3,5-di(methyl)phenyl)-2-(pentyl)-3-(heptacosynyl)-4-(3,4-di(butyl)phenyl)-1,4-diazabuta-1,3-diene]nickel[3-(propyl)-5-(pentyl)catecholate]; [1-(3,4-di(methyl)-phenyl)-2-(pentyl)-3-(octyl)-4-(3,4-di(ethyl)phenyl)1,4-diazabuta-1,3-diene]palladium[3-(ethanalyl)-4-(pentyl)catecholate]; [1-(phenyl)-2-(butyl)-3-(hydrido)-4-(3-dodecenyl-phenyl)1,4-diazabuta-1,3-diene]nickel[3-(methyl)-4-(pentyl)catecholate]; [1-(3,4-di(propyl)phenyl)-2-(octyl)-3-(hydrido)-4-(phenyl)1,4-diazabuta-1,3-diene]nickel[3,5-di(butyl)-4-(propyl)catecholate]; [1-(3-tetradecynylphenyl)-2-(butyl)-3-(hydrido)-4-(3,4-di(ethyl)phenyl)1,4-diazabuta-1,3-diene]nickel[3-(methyl)-6-(pentyl)catecholate]; [1-(phenyl)-2-(hydrido)-3-(butyl)-4-(3,5-di(methyl)phenyl)1,4-diazabuta-1,3-diene]nickel[4-(butyl)catecholate]; [1-(3,5-di(pentyl)phenyl)-2,3-(dihydrido)-4-(phenyl)1,4-diazabuta-1,3-diene]palladium[3-(ethyl)-5-(methyl)catecholate]; [1-(3,5-di(methyl)phenyl)-2-(hydrido)-3-(eicosenyl)-4-(4-octenylphenyl)1,4-diazabuta-1,3-diene]nickel[3-(propyl)-5-(ethyl)catecholate]; [-(4-eicosylphenyl)-2,3-(dibutyl)-4-(phenyl)1,4-diazabuta-1,3-diene]nickel[3-(methyl)-5-(propyl)catecholate]; [1-(3-dodecynylphenyl)-2-(pentyl)-3-(undecenyl)-4-(3,5-di(pentyl)phenyl)1,4-diazabuta-1,3-diene]palladium[4-(propyl)-catecholate]; [1-(3-heptacosenylphenyl)-2,3-(dibutyl)-4-(4-heptacosylphenyl)1,4-diazabuta-1,3-diene]nickel[4-(ethyl)catecholate]; [1-(3,4-di(propyl)phenyl)-2-(hexyl)-3-(butyl)-4-(4-butonylphenyl)1,4-diazabuta-1,3-diene]nickel[3-(propyl)-6-(butyl)-catecholate]; [1-(phenyl)-2-(hydrido)-3-(butyl)-4-(3,4-di(pentyl)phenyl)1,4-diazabuta-1,3-diene]nickel[3,4-di(methyl)-5-(pentyl)catecholate]; [1-(3,5-di(ethyl)phenyl)-2,3-(dioctyl)-4-(4-ethylphenyl)1,4-diazabuta-1,3-diene]palladium[3-(pentyl)-4-(butyl)-6-(methyl)catecholate]; [1-(phenyl)-2-(octyl)-3-(butyl)-4-(3,5-di(methyl)phenyl)1,4-diazabuta-1,3-diene]nickel[3-(octylamino)catecholate]; [1-(3-propynylphenyl)-2-(pentynyl)-3-(octyl)-4-(3-butynylphenyl)1,4-diazabuta-1,3-diene]nickel[3-(methyl)-5-(butyl)catecholate]; [1-(3-pentadecylphenyl)-2-(butyl)-3-(hydrido)-4-(phenyl)1,4-diazabuta-1,3-diene]palladium[3-(methyl)-5-(ethyl)catecholate]; [1-(4-pentacosyl-phenyl)-2-(hexyl)-3-(butyl)-4-(3,5-di(butyl)phenyl)1,4-diazabuta-1,3-diene]nickel[3-(methyl)catecholate]; [1-(3-heptacosynylphenyl)-2-(pentyl)-3-(hydrido)-4-(3,4-di(butyl)-phenyl)1,4-diazabuta-1,3-diene]nickel[3-(butyl)-6-(ethyl)catecholate]; [1-(3,4-di(methyl)phenyl)-2-(hydrido)-3-(hexyl)-4-(3,4-di(propyl)phenyl)1,4-diazabuta-1,3-diene]nickel[3-(butyl)catecholate]; [1-(4-octenylphenyl)-2,3-(dibutyl)-4-(3,4-di(butyl)-phenyl)1,4-diazabuta-1,3-diene]nickel[4-(methyl)catecholate]; [1-(phenyl)-2-(butyl)-3-(hydrido)-4-(3,5-di(ethyl)phenyl)1,4-diazabuta-1,3-diene]nickel[4-(butyl)catecholate]; [1-(3,4-di(methyl)phenyl)-2-(hexadecynyl)-3-(butyl)-4-(phenyl)1,4-diazabuta-1,3-diene]palladium[4-(methyl)-5-(butyl)catecholate]; [1-(3,4-di(ethyl)phenyl)-2,3-(dibutyl)-4-(3-tricosenylphenyl)1,4-diazabuta-1,3-diene]nickel[3-(propyl)catecholate]; [1-(4-heptacosylphenyl)-2-(butyl)-3-(methyl)-4-(3,5-di(methyl)phenyl)1,4-diazabuta-1,3-diene]nickel[4-(ethyl)-5-(propyl)catecholate]; [1-(3,5-di(pentyl)phenyl)-2-(pentyl)-3-(ethyl)-4-(4-eicosylphenyl)1,4-diazabuta-1,3-diene]palladium[3,6-di(ethyl)catecholate]; [1-(3,5-di(methyl)phenyl)-2-(butyl)-3-(octyl)-4-(3-pentylphenyl)1,4-diazabuta-1,3-diene]nickel[4-(pentyl)catecholate]; [1-(3,5-di(methyl)phenyl)-2-(ethyl)-3-(butyl)-4-(phenyl)1,4-diazabuta-1,3-diene]nickel[3-(pentyl)catecholate]; [1-(3,5-di(propyl)phenyl)-2-(butyl)-3-(pentyl)-4-(phenyl)1,4-diazabuta-1,3-diene]

palladium[3-(propyl)-5-(ethyl)catecholate]; [1-(phenyl)-2-(butyl)-3-(docosenyl)-4-(3,5-di(propyl)phenyl)1,4-diazabuta-1,3-diene]nickel[3-(butyl)-4-(pentyl)-6-(propyl)catecholate]; [1-(3,4-di(propyl)phenyl)-2-(butyl)-3-(pentyl)-4-(phenyl)1,4-diazabuta-1,3-diene]palladium[3,4-di(methyl)-6-(methyl)-catecholate]; [1-(3,5-di(butyl)phenyl)-2-(pentyl)-3-(butyl)-4-(phenyl)1,4-diazabuta-1,3-diene]nickel[3-(pentyl)catecholate]; [1-(3-hexynylphenyl)-2,3-(dibutyl)-4-(3,5-di(methyl)phenyl)1,4-diazabuta-1,3-diene]nickel[3-(butyl)catecholate]; [1-(phenyl)-2-(pentyl)-3-(butyl)-4-(4-decenylphenyl)1,4-diazabuta-1,3-diene]nickel[3-(methyl)-catecholate]; [1-(4-propynylphenyl)-2-(pentyl)-3-(butyl)-4-(3-pentylphenyl)1,4-diazabuta-1,3-diene]palladium[4-(ethyl)catecholate]; [1-(3,4-di(methyl)phenyl)-2,3-(diethyl)-4-(phenyl)1,4-diazabuta-1,3-diene]palladium[3,6-di(methyl)catecholate]; [1-(3,4-di(methyl)phenyl)-2-(butyl)-3-(hexyl)-4-(3,4-di(propyl)phenyl)1,4-diazabuta-1,3-diene]nickel[3-(propyl)-4-(ethyl)-6-(butyl)catecholate]; [1-(3-methyldiethylsilylmethyl)-phenyl)-2-(heptacosynyl)-3-(hydrido)-4-(4-octadecynylphenyl)1,4-diazabuta-1,3-diene]nickel[3-(butyl)catecholate]; [1-(3,4-di(ethyl)phenyl)-2-(ethyl)-3-(undecynyl)-4-(3,4-di(pentyl)phenyl)1,4-diazabuta-1,3-diene]nickel[3-(butyl)-6-(pentyl)catecholate]; [1-(3,5-di(methyl)phenyl)-2-(tetracosynyl)-3-(pentadecenyl)-4-(3-heptadecylphenyl)1,4-diazabuta-1,3-diene]nickel[3-(ethyl)catecholate]; [1-(3-heneicosenylphenyl)-2-(butyl)-3-(hexyl)-4-(phenyl)1,4-diazabuta-1,3-diene]nickel[4-(ethyl)catecholate]; [1-(phenyl)-2,3-(dibutyl)-4-(3,5-di(propyl)phenyl)1,4-diazabuta-1,3-diene]nickel[3-trimethylsilylmethyl)-4-(propyl)catecholate]; [1-(phenyl)-2-(hydrido)-3-(triacontyl)-4-(4-docosenylphenyl)1,4-diazabuta-1,3-diene]nickel[3-(butyl)catecholate]; [1-(3,5-di(pentyl)phenyl)-2-(nonenyl)-3-(butyl)-4-(3,4-di(butyl)phenyl)1,4-diazabuta-1,3-diene]nickel[3-(propyl)catecholate]; [1-(4-nonynylphenyl)-2,3-(dibutyl)-4-(3-undecylphenyl)-1,4-diazabuta-1,3-diene]nickel[4-(ethyl)-5-(butyl)catecholate]; [1-(3,5-di(pentyl)-phenyl)-2-(octadecyl)-3-(octyl)-4-(4-pentacosylphenyl)1,4-diazabuta-1,3-diene]nickel[3-(methyl)-6-(ethyl)catecholate]; [1-(4-butonylphenyl)-2-(hydrido)-3-(butyl)-4-(phenyl)-1,4-diazabuta-1,3-diene]nickel[3-(propyl)catecholate]; [1-(3-hexenylphenyl)-2-(eicosyl)-3-(tetracosenyl)-4-(3-heptadecylphenyl)1,4-diazabuta-1,3-diene]nickel[3,6-di(propyl)-catecholate]; [1-(phenyl)-2-(butyl)-3-(hydrido)-4-(4-butenylphenyl)1,4-diazabuta-1,3-diene]nickel[3-(propyl)-6-(butyl)catecholate]; [1-(phenyl)-2-(butyl)-3-(hexyl)-4-(3,4-di(propyl)phenyl)1,4-diazabuta-1,3-diene]nickel[3-(ethyl)-4,5-di(pentyl)catecholate]; [1-(3,5-di(butyl)phenyl)-2-(butyl)-3-(pentyl)-4-(4-pentenylphenyl)1,4-diazabuta-1,3-diene]nickel[3-(butyl)catecholate]; [1-(phenyl)-2-(hydrido)-3-(methyl)-4-(3,4-di(propyl)-phenyl)-1,4-diazabuta-1,3-diene]nickel[3-(propyl)-4-(methyl)-6-(ethyl)catecholate]; [1-(3,5-di(propyl)phenyl)-2-(pentyl)-3-(hexyl)-4-(3,4-di(diethylamino)phenyl)1,4-diazabuta-1,3-diene]nickel[3-(butyl)-4-(pentyl)-6-(ethyl)catecholate]; [1-(3,4-di(ethyl)phenyl)-2,3-(dibutyl)-4-(3,4-di(butyl)phenyl)1,4-diazabuta-1,3-diene]palladium[3-(pentyl)-5-(propyl)catecholate]; [1-(3-nonadecenylphenyl)-2-(hexyl)-3-(butyl)-4-(3,5-di(ethyl)-phenyl)1,4-diazabuta-1,3-diene]nickel[3-(methyl)-4-(butyl)-6-(ethyl)catecholate]; [1-(phenyl)-2-(butyl)-3-(hydrido)-4-(4-heptadecylphenyl)1,4-diazabuta-1,3-diene]nickel[3-(methyl)-4-(propyl)catecholate]; [1-(3,5-di(butyl)phenyl)-2-(octacosynyl)-3-(hydrido)-4-(4-methyldiethylsilylmethyl)phenyl)1,4-diazabuta-1,3-diene]nickel[4-(ethyl)-catecholate]; [1-(3,5-di(pentyl)phenyl)-2-(pentyl)-3-(hexyl)-4-(3-eicosynylphenyl)1,4-diazabuta-1,3-diene]palladium[4-(propyl)catecholate]; [1-(3-tetracosynylphenyl)-2,3-(dihydrido)-4-(3-heptacosynylphenyl)1,4-diazabuta-1,3-diene]palladium[3-(methyl)-5-(butyl)catecholate]; [1-(3,5-di(methyl)phenyl)-2-(hexyl)-3-(butyl)-4-(phenyl)1,4-diazabuta-1,3-diene]palladium[3-(methyl)catecholate]; [1-(3,5-di(ethyl)phenyl)-2,3-(dibutyl)-4-(3,4-di(dodecanonyl)phenyl)1,4-diazabuta-1,3-diene]nickel[3-(diethylamino)catecholate]; [1-(3,4-di(methyl)phenyl)-2-(hydrido)-3-(butyl)-4-(phenyl)-1,4-diazabuta-1,3-diene]palladium[3-(ethyl)-6-(propyl)catecholate]; [1-(phenyl)-2,3-(dibutyl)-4-(3,5-di(pentyl)phenyl)-1,4-diazabuta-1,3-diene]palladium[3,4-di(ethyl)-catecholate]; [1-(4-heptadecylphenyl)-2-(butyl)-3-(pentyl)-4-(3,5-di(methyl)phenyl)1,4-diazabuta-1,3-diene]nickel[4-(proponyl)catecholate]; [1-(3,5-di(propyl)phenyl)-2-(butyl)-3-(butenyl)-4-(3-tricosenylphenyl)1,4-diazabuta-1,3-diene]nickel[3-(butyl)-6-(methyl)catecholate]; [1-(phenyl)-2-(undecenyl)-3-(butyl)-4-(3,4-di(propyl)phenyl)1,4-diazabuta-1,3-diene]nickel[3-(methyl)-4-(butyl)-5-(ethyl)catecholate]; [1-(phenyl)-2-(pentyl)-3-(hexyl)-4-(3,5-di(methyl)phenyl)1,4-diazabuta-1,3-diene]palladium[3-(propyl)-4-(butyl)catecholate]; [1-(3,4-di(ethyl)phenyl)-2-(hexyl)-3-(heptenyl)-4-(3,5-di(pentyl)phenyl)1,4-diazabuta-1,3-diene]nickel[3-((triethylsilylmethyl))-5-(methyl)-catecholate]; [1-(4-hexenylphenyl)-2-(methyl)-3-(hydrido)-4-(phenyl)1,4-diazabuta-1,3-diene]palladium[4-(pentyl)-5-(butyl)catecholate]; [1-(3,4-di(pentyl)phenyl)-2-(ethyl)-3-(nonadecynyl)-4-(3-pentadecenylphenyl)1,4-diazabuta-1,3-diene]nickel[3,4-di(propyl)-catecholate]; [1-(3-tetracosynylphenyl)-2-(pentyl)-3-(tetracosynyl)-4-(3,4-di(propyl)-phenyl)1,4-diazabuta-1,3-diene]nickel[4-(ethyl)catecholate]; [1-(3,4-di(methyl)phenyl)-2,3-(dihydrido)-4-(3,5-di(pentyl)phenyl)1,4-diazabuta-1,3-diene]nickel[4-(butyl)-catecholate]; [1-(3,4-di(ethyl)phenyl)-2,3-(dioctyl)-4-(3,4-di(propyl)phenyl)1,4-diazabuta-1,3-diene]nickel[4-(pentyl)-5-(methyl)catecholate]; [1-(phenyl)-2-(pentyl)-3-(butyl)-4-(3,5-di(propyl)phenyl)1,4-diazabuta-1,3-diene]palladium[3-(pentyl)-4,6-di(ethyl)catecholate]; [1-(phenyl)-2,3-(dibutyl)-4-(3,4-di(pentyl)phenyl)1,4-diazabuta-1,3-diene]palladium[3-(methyl)-4-(ethyl)-6-(pentyl)catecholate]; [1-(4-triacontenyl-phenyl)-2-(butyl)-3-(octyl)-4-(4-tetracosenylphenyl)1,4-diazabuta-1,3-diene]palladium[3-(propyl)-4-(methyl)catecholate]; [1-(3,5-di(ethyl)phenyl)-2-(methyl)-3-(hexyl)-4-(phenyl)1,4-diazabuta-1,3-diene]palladium[4-(pentyl)-5-(butyl)catecholate]; [1-(3,5-di(pentyl)phenyl)-2-(butyl)-3-(hydrido)-4-(phenyl)1,4-diazabuta-1,3-diene]palladium[4-(pentyl)-5-(propyl)catecholate]; [1-(4-undecenylphenyl)-2,3-(dibutyl)-4-(phenyl)1,4-diazabuta-1,3-diene]nickel[3-(pentyl)catecholate]; [1-(3-heptadecylphenyl)-2-(butyl)-3-(pentyl)-4-(3,5-di(methyl)phenyl)1,4-diazabuta-1,3-diene]palladium[3,6-di(ethyl)-catecholate]; [1-(3,5-di(pentyl)phenyl)-2-(ethyl)-3-(hydrido)-4-(phenyl)1,4-diazabuta-1,3-diene]palladium[3-(butyl)-4-(pentyl)-5-(methyl)catecholate]; [1-(phenyl)-2-(hydrido)-3-(butyl)-4-(3,4-di(ethyl)phenyl)1,4-diazabuta-1,3-diene]palladium[4-(propyl)-catecholate]; [1-(3,5-di(pentyl)phenyl)-2-(ethyl)-3-(hydrido)-4-(phenyl)1,4-diazabuta-1,3-diene]palladium[3-(pentyl)-5-(ethyl)catecholate]; [1-(3-hexadecylphenyl)-2-(hexyl)-3-(hydrido)-4-(3,4-di(pentyl)phenyl)1,4-diazabuta-1,3-diene]nickel[3-(ethyl)-5-(butyl)-catecholate]; [1-(3,4-di(propyl)phenyl)-2,3-(dibutyl)-4-(3,5-di(ethyl)phenyl)1,4-diazabuta-1,3-diene]nickel[4-(butyl)catecholate]; [1-(3,5-di(methyl)phenyl)-2-(hexyl)-3-(octyl)-4-(3,4-di(pentyl)phenyl)1,4-diazabuta-1,3-diene]nickel[3-(methyl)-6-(pentyl)catecholate]; [1-(3,4-di(ethyl)phenyl)-2-(nonadecynyl)-3-(hexyl)-4-(3,4-di(propyl)-phenyl)1,4-diazabuta-1,3-diene]

nickel[3-(ethyl)-4-(pentyl)catecholate]; [1-(3,4-di(propyl)phenyl)-2,3-(diethyl)-4-(phenyl)1,4-diazabuta-1,3-diene]nickel[3-(pentyl)-4-(methyl)-5-(propyl)catecholate]; [1-(3,4-di(methyl)phenyl)-2-(nonadecenyl)-3-(methyl)-4-(phenyl)1,4-diazabuta-1,3-diene]nickel[3,5-di(butyl)-4-(methyl)catecholate]; [1-(3,5-di(ethyl)phenyl)-2-(hydrido)-3-(butyl)-4-(3,4-di(methylethylamino)phenyl)1,4-diazabuta-1,3-diene]nickel[3-(butyl)-4-(methyl)catecholate]; [1-(3,4-di(methyl)phenyl)-2-(hexyl)-3-(pentyl)-4-(3,5-di(ethyl)phenyl)1,4-diazabuta-1,3-diene]nickel[3-(methyl)-4-(propyl)-5-(butyl)catecholate]; [1-(4-butanalylphenyl)-2-(hexacosynyl)-3-(butyl)-4-(3,5-di(ethyl)-phenyl)1,4-diazabuta-1,3-diene]nickel[3-(butyl)-4,6-di(pentyl)catecholate]; [1-(3,5-di(pentyl)phenyl)-2-(octyl)-3-(nonynyl)-4-(3,5-di(methyl)phenyl)1,4-diazabuta-1,3-diene]nickel[4-(propyl)catecholate]; [1-(4-tridecylphenyl)-2-(docosenyl)-3-(methyl)-4-(3-trimethylsilylethylphenyl)1,4-diazabuta-1,3-diene]nickel[3-(pentyl)-6-(propyl)-catecholate]; [1-(3,4-di(methyl)phenyl)-2-(butyl)-3-(hexyl)-4-(3,5-di(methyl)phenyl)1,4-diazabuta-1,3-diene]nickel[3-(methyl)-6-(pentyl)catecholate]; [1-(4-tridecylphenyl)-2-(hexyl)-3-(octyl)-4-(3,4-di(methylethylamino)phenyl)1,4-diazabuta-1,3-diene]nickel[3-(pentyl)-4-(propyl)catecholate]; [1-(3-pentadecenylphenyl)-2-(butyl)-3-(ethyl)-4-(phenyl)1,4-diazabuta-1,3-diene]nickel[3-(butyl)catecholate]; [1-(phenyl)-2,3-(dibutyl)-4-(3-propynylphenyl)1,4-diazabuta-1,3-diene]nickel[3-(methyl)-4-(pentyl)catecholate]; [1-(4-hexonylphenyl)-2,3-(dihydrido)-4-(3-nonadecylphenyl)1,4-diazabuta-1,3-diene]nickel[3,6-di(propyl)catecholate]; [1-(3,4-di(propyl)phenyl)-2-(butyl)-3-(octyl)-4-(3,5-di(butyl)phenyl)1,4-diazabuta-1,3-diene]nickel[3-(dodecamino)-5-(butyl)catecholate]; [1-(4-pentonylphenyl)-2-(octyl)-3-(undecynyl)-4-(3,5-di(methyl)phenyl)1,4-diazabuta-1,3-diene]nickel[3-(propyl)-6-(methyl)catecholate]; [1-(phenyl)-2-(hexyl)-3-(butyl)-4-(3,5-di(butyl)phenyl)1,4-diazabuta-1,3-diene]nickel[4-(propanalyl)catecholate]; [1-(3,4-di(butyl)phenyl)-2-(hydrido)-3-(octyl)-4-(4-dodecenylphenyl)1,4-diazabuta-1,3-diene]palladium[3-(propyl)-5-(ethyl)catecholate]; [1-(3,4-di(ethyl)phenyl)-2-(methyl)-3-(hydrido)-4-(phenyl)1,4-diazabuta-1,3-diene]nickel[3-(ethyl)-5-(pentyl)catecholate]; [1-(phenyl)-2-(hexyl)-3-(butyl)-4-(3-octacosenylphenyl)1,4-diazabuta-1,3-diene]nickel[4-(bromo)-5-(pentyl)catecholate]; [1-(3,4-di(propyl)phenyl)-2,3-(dibutyl)-4-(4-tetradecenyl-phenyl)1,4-diazabuta-1,3-diene]nickel[4-(ethyl)catecholate]; [1-(3,5-di(ethyl)phenyl)-2-(octyl)-3-(butyl)-4-(4-hexonylphenyl)1,4-diazabuta-1,3-diene]nickel[3-(pentyl)-6-(propyl)catecholate]; [1-(phenyl)-2-(butyl)-3-(pentyl)-4-(3,4-di(propyl)phenyl)1,4-diazabuta-1,3-diene]nickel[3-(pentyl)catecholate]; [1-(3,4-di(methyl)phenyl)-2-(hydrido)-3-(butyl)-4-(4-tricosenylphenyl)1,4-diazabuta-1,3-diene]nickel[4-(methyl)-catecholate]; [1-(3,5-di(methyl)phenyl)-2-(octyl)-3-(methyl)-4-(phenyl)1,4-diazabuta-1,3-diene]palladium[4-(ethyl)catecholate]; [1-(phenyl)-2-(hydrido)-3-(hexyl)-4-(3,4-di(methyl)phenyl)1,4-diazabuta-1,3-diene]nickel[3-(butyl)-5-(methyl)catecholate]; [1-(3-dodecenylphenyl)-2,3-(dibutyl)-4-(3,5-di(ethyl)phenyl)1,4-diazabuta-1,3-diene]nickel[3-(butyl)-6-(methyl)catecholate]; [1-(3,5-di(pentyl)phenyl)-2-(butyl)-3-(hydrido)-4-(3,5-di(methyl)phenyl)1,4-diazabuta-1,3-diene]palladium[3-(pentyl)-4-(propyl)catecholate]; [1-(4-tridecylphenyl)-2-(octyl)-3-(ethyl)-4-(3-nonacosynylphenyl)1,4-diazabuta-1,3-diene]nickel[4-(propyl)catecholate]; [1-(3,5-di(pentyl)phenyl)-2-(pentyl)-3-(hydrido)-4-(3-hexacosenylphenyl)1,4-diazabuta-1,3-diene]nickel[3-(pentyl)catecholate]; [1-(3,4-di(ethyl)phenyl)-2-(pentyl)-3-(hydrido)-4-(3,5-di(ethyl)phenyl)1,4-diazabuta-1,3-diene]nickel[3-(ethyl)-4-(butyl)catecholate]; [1-(3,4-di(ethyl)phenyl)-2-(butyl)-3-(nonacosyl)-4-(3,5-di(ethyl)phenyl)1,4-diazabuta-1,3-diene]nickel[3-(butyl)-4,5-di(propyl)-catecholate]; [1-(3,4-di(ethyl)phenyl)-2-(butyl)-3-(hydrido)-4-(3,4-di(propyl)phenyl)1,4-diazabuta-1,3-diene]nickel[4-(pentyl)catecholate]; [1-(phenyl)-2-(butyl)-3-(tetracosynyl)-4-(3,4-di(methyl)phenyl)1,4-diazabuta-1,3-diene]palladium[3-(ethyl)-catecholate]; [1-(3,4-di(ethyl)phenyl)-2-(octyl)-3-(butyl)-4-(phenyl)1,4-diazabuta-1,3-diene]nickel[3-(propyl)-4-(methyl)catecholate]; [1-(3,4-di(propyl)phenyl)-2-(butyl)-3-(octyl)-4-(4-octadecenylphenyl)1,4-diazabuta-1,3-diene]palladium [3-(ethyl)catecholate]; [1-(3-undecylphenyl)-2-(octyl)-3-(hydrido)-4-(4-dodecanonylphenyl)1,4-diazabuta-1,3-diene]nickel[3-(propyl)catecholate]; [1-(4-decylphenyl)-2-(nonacosynyl)-3-(pentynyl)-4-(3,4-di(methyl)phenyl)1,4-diazabuta-1,3-diene]nickel[3-(butyl)catecholate]; [1-(phenyl)-2,3-(dibutyl)-4-(3,4-di(methyl)phenyl)1,4-diazabuta-1,3-diene]nickel[3-(methyl)-5-(propyl)catecholate]; [1-(4-dodecenylphenyl)-2-(butyl)-3-(hydrido)-4-(3,5-di(pentyl)phenyl)1,4-diazabuta-1,3-diene]nickel[3-(pentyl)-5-(methyl)catecholate]; [1-(phenyl)-2-(hydrido)-3-(methyl)-4-(4-decylphenyl)1,4-diazabuta-1,3-diene]nickel[4-(pentyl)-5-(ethyl)catecholate]; [1-(3,5-di(ethyl)phenyl)-2,3-(dibutyl)-4-(3,4-di(pentyl)-phenyl)1,4-diazabuta-1,3-diene]nickel[3,5-di(propyl)catecholate]; [1-(3,4-di(pentyl)-phenyl)-2-(hydrido)-3-(butyl)-4-(3,4-di(propyl)phenyl)1,4-diazabuta-1,3-diene]nickel[3,6-di(methyl)catecholate]; [1-(3,5-di(ethyl)phenyl)-2-(butyl)-3-(hydrido)-4-(phenyl)1,4-diazabuta-1,3-diene]nickel[3-(butyl)-4,6-di(methyl)catecholate]; [1-(3,4-di(butyl)-phenyl)-2-(methyl)-3-(pentyl)-4-(3-pentenylphenyl)1,4-diazabuta-1,3-diene]nickel[4-(propyl)-5-(methyl)catecholate]; [1-(phenyl)-2-(hydrido)-3-(hexadecenyl)-4-(3,5-di(pentyl)phenyl)1,4-diazabuta-1,3-diene]nickel[3-(pentyl)-5-(propanalyl)catecholate]; [1-(4-pentadecenylphenyl)-2,3-(dibutyl)-4-(3,4-di(butyl)phenyl)1,4-diazabuta-1,3-diene]nickel[3,6-di(ethyl)catecholate]; [1-(3,5-di(methyl)phenyl)-2-(hexyl)-3-(hydrido)-4-(phenyl)1,4-diazabuta-1,3-diene]nickel[4-(ethyl)catecholate]; [1-(phenyl)-2-(pentyl)-3-(butyl)-4-(3,5-di(pentyl)phenyl)1,4-diazabuta-1,3-diene]palladium[3-(methyl)-catecholate]; [1-(3,5-di(methyl)phenyl)-2-(pentyl)-3-(hexacosyl)-4-(phenyl)1,4-diazabuta-1,3-diene]nickel[3-(pentyl)-5-(ethyl)catecholate]; [1-(4-tridocosanalylphenyl)-2-(butyl)-3-(hexadecenyl)-4-(phenyl)1,4-diazabuta-1,3-diene]nickel[3,6-di(ethyl)-catecholate]; [1-(phenyl)-2-(pentyl)-3-(butyl)-4-(3,4-di(propyl)phenyl)1,4-diazabuta-1,3-diene]nickel[3-(ethyl)catecholate]; [1-(3,4-di(methyl)phenyl)-2-(eicosynyl)-3-(pentadecenyl)-4-(3-trimethylsilylmethylphenyl)1,4-diazabuta-1,3-diene]nickel[3-(ethyl)catecholate]; [1-(3,5-di(pentyl)phenyl)-2,3-(dibutyl)-4-(4-heptylphenyl)1,4-diazabuta-1,3-diene]nickel[4-(ethyl)-5-(methyl)catecholate]; [1-(phenyl)-2-(butyl)-3-(octyl)-4-(3,4-di(butyl)phenyl)1,4-diazabuta-1,3-diene]nickel[3-(pentyl)-4-(propyl)-catecholate]; [1-(3,4-di(proponyl)phenyl)-2-(pentyl)-3-(butyl)-4-(3-heptynylphenyl),4-diazabuta-1,3-diene]nickel[3-(methyl)-6-(ethyl)catecholate]; [1-(3,4-di(methyl)phenyl)-2-(butyl)-3-(pentyl)-4-(phenyl)1,4-diazabuta-1,3-diene]nickel[3-(ethyl)catecholate]; [1-(phenyl)-2-(dodecyl)-3-(pentyl)-4-(3,5-di(methyl)phenyl)1,4-diazabuta-1,3-diene]nickel[3-(pentyl)-5-(butyl)catecholate]; [1-(3,5-di(methyl)phenyl)-2-(butyl)-3-(methyl)-4-(3,4-di(ethyl)phenyl)1,4-diazabuta-1,3-diene]nickel[3-(propyl)-6-(pentyl)catecholate]; [1-(3,4-di(propyl)phenyl)-2,3-(dihydrido)-4-(phenyl)1,4-diazabuta-1,3-diene]nickel[3-(pentyl)-4-(ethyl)catecholate]; [1-(3- heneicosynylphenyl)-2-(pentyl)-3-(triacontyl)-4-(phenyl)1,4-diazabuta-1,3-diene]palladium[3-(methyl)catecholate]; [1-(phenyl)-2,3-(dihydrido)-4-(3,4-di(methyl)phenyl)1,4-diazabuta-1,3-diene]palladium[4-(methyl)-5-(ethyl)catecholate]; [1-(3-propanalylphenyl)-2-(butyl)-3-(pentyl)-4-(3,4-di(ethyl)phenyl)-1,4-diazabuta-1,3-diene]nickel[3,6-di(butyl)-4-(propyl)catecholate]; [1-(3-tricosenyl-phenyl)-2-(pentyl)-3-(hydrido)-4-(phenyl)1,4-diazabuta-1,3-diene]palladium[3,6-di(methyl)-4-(butyl)catecholate]; [1-(phenyl)-2-(butyl)-3-(hydrido)-4-(3,4-di(propyl)-phenyl)1,4-diazabuta-1,3-diene]nickel[3-(butyl)catecholate]; [1-(phenyl)-2,3-(dibutyl)-4-(3,5-di(methyl)phenyl)1,4-diazabuta-1,3-diene]nickel[4-(methyl)catecholate]; [1-(3,5-di(ethyl)phenyl)-2-(hydrido)-3-(butyl)-4-(phenyl)1,4-diazabuta-1,3-diene]nickel[3-(propyl)catecholate]; [1-(3,4-di(butonyl)phenyl)-2-(butyl)-3-(eicosynyl)-4-(3,5-di(pentyl)phenyl)1,4-diazabuta-1,3-diene]nickel[3-(ethyl)-5-(butyl)catecholate]; [1-(3,5-di(butyl)phenyl)-2,3-(dibutyl)-4-(phenyl)1,4-diazabuta-1,3-diene]nickel[4-(methyl)-catecholate]; [1-(3,4-di(methyl)phenyl)-2-(hexyl)-3-(hydrido)-4-(3,4-di(propyl)phenyl)-1,4-diazabuta-1,3-diene]palladium[3-(methyl)-4-(butyl)-6-(ethyl)catecholate]; [1-(4-propanalylphenyl)-2-(hydrido)-3-(butyl)-4-(3,4-di(propyl)phenyl)1,4-diazabuta-1,3-diene]nickel[3-(methyl)-5-((triethylsilylmethyl))catecholate]; [1-(3,4-di(propyl)phenyl)-2-(pentyl)-3-(octyl)-4-(phenyl)1,4-diazabuta-1,3-diene]nickel[3-(butyl)-6-(pentyl)-catecholate]; [1-(3-undecenylphenyl)-2-(butyl)-3-(hexyl)-4-(phenyl)1,4-diazabuta-1,3-diene]nickel[3-(pentyl)catecholate]; [1-(3,5-di(methyl)phenyl)-2-(butyl)-3-(hexyl)-4-(4-(triethylsilylmethyl)phenyl)1,4-diazabuta-1,3-diene]palladium[3-(butyl)-4-(ethyl)-5-(methyl)catecholate]; [1-(phenyl)-2,3-(dibutyl)-4-(3,4-di(pentyl)phenyl)1,4-diazabuta-1,3-diene]palladium[3-(propyl)-4-(butyl)-6-(ethyl)catecholate]; [1-(phenyl)-2,3-(dibutyl)-4-(3,5-di(pentyl)phenyl)1,4-diazabuta-1,3-diene]nickel[3-(propyl)-4,6-di(butyl)catecholate]; [1-(3-tridecylphenyl)-2-(butyl)-3-(hydrido)-4-(3,5-di(pentyl)-phenyl)1,4-diazabuta-1,3-diene]nickel[3-(methyl)-5-(ethyl)catecholate]; [-(4-hexenyl-phenyl)-2-(butyl)-3-(hexyl)-4-(3,4-di(methyldiethylsilylmethyl))phenyl)1,4-diazabuta-1,3-diene]nickel[4-(ethyl)catecholate]; [1-(3,5-di(methyl)phenyl)-2-(methyl)-3-(octyl)-4-(phenyl)1,4-diazabuta-1,3-diene]palladium[3-(propyl)-6-(butyl)catecholate]; [1-(phenyl)-2-(hexyl)-3-(hydrido)-4-(3,5-di(pentyl)phenyl)1,4-diazabuta-1,3-diene]nickel[3-(butyl)-4-(propyl)-6-(ethyl)catecholate]; [1-(3,5-di(pentyl)phenyl)-2-(ethyl)-3-(butyl)-4-(3-butynylphenyl)1,4-diazabuta-1,3-diene]nickel[3-(pentyl)catecholate]; [1-(4-octadecynylphenyl)-2-(butyl)-3-(octyl)-4-(3,5-di(pentyl)phenyl)1,4-diazabuta-1,3-diene]palladium[4-(methyl)catecholate]; [1-(3,5-di(pentyl)phenyl)-2,3-(dibutyl)-4-(3,4-di(methyl)phenyl)1,4-diazabuta-1,3-diene]nickel[3-(butyl)catecholate]; [1-(3-octacosenylphenyl)-2-(butyl)-3-(hydrido)-4-(4-hexadecynylphenyl)1,4-diazabuta-1,3-diene]nickel[4-(pentyl)catecholate]; [1-(3,5-di(pentyl)phenyl)-2-(pentyl)-3-(tetracosenyl)-4-(3,5-di(propyl)phenyl)1,4-diazabuta-1,3-diene]nickel[3,4-di(propyl)-5-(ethyl)catecholate]; [1-(3-nonacosynylphenyl)-2,3-(dihydrido)-4-(phenyl)1,4-diazabuta-1,3-diene]nickel[4-(methyl)-5-(butyl)catecholate]; [1-(4-hexadecynylphenyl)-2-(nonynyl)-3-(octyl)-4-(phenyl)1,4-diazabuta-1,3-diene]nickel[3-(propyl)-4-(ethyl)-5-(butyl)catecholate]; [1-(3,5-di(pentyl)phenyl)-2,3-(dioctyl)-4-(3,5-di(ethyl)phenyl)1,4-diazabuta-1,3-diene]nickel[4-(ethyl)catecholate]; [1-(3,4-di(pentyl)phenyl)-2,3-(dihydrido)-4-(3-(triethylsilylmethyl)phenyl)1,4-diazabuta-1,3-diene]nickel[3,6-di(ethyl)catecholate]; [1-(3-trimethylsilylmethylphenyl)-2-(butyl)-3-(methyl)-4-(4-dodecaphosphinophenyl)1,4-diazabuta-1,3-diene]nickel[3,5-di(ethyl)catecholate]; [1-(4-heptadecylphenyl)-2-(hydrido)-3-(heptynyl)-4-(phenyl)1,4-diazabuta-1,3-diene]nickel[3-(methyl)-4-(butyl)-5-(ethyl)catecholate]; [1-(4-nonacosynylphenyl)-2-(octyl)-3-(butyl)-4-(phenyl)1,4-diazabuta-1,3-diene]nickel[3-(methyl)catecholate]; [1-(phenyl)-2-(hydrido)-3-(butyl)-4-(3,4-di(propyl)phenyl)1,4-diazabuta-1,3-diene]nickel[3-(butyl)-5(methyl)catecholate]; [1-(3,4-di(propyl)phenyl)-2-(pentyl)-3-(methyl)-4-(phenyl)1,4-diazabuta-1,3-diene]nickel[4-(pentyl)-5-(butyl)catecholate]; [1-(phenyl)-2-(pentyl)-3-(hydrido)-4-(3,4-di(methyl)phenyl)1,4-diazabuta-1,3-diene]nickel[3-(butyl)catecholate]; [1-(4-pentylphenyl)-2-(hydrido)-3-(hexyl)-4-(3,4-di(pentyl)phenyl)1,4-diazabuta-1,3-diene]nickel[3-(propyl)catecholate]; [1-(3,4-di(pentyl)phenyl)-2-(pentadecenyl)-3-(butyl)-4-(3-pentadecynylphenyl)1,4-diazabuta-1,3-diene]palladium[4-(ethyl)-5-(pentyl)catecholate]; [1-(3-dodecynylphenyl)-2,3-(dihydrido)-4-(3,5-di(methyl)phenyl)-1,4-diazabuta-1,3-diene]nickel[3-(methyl)-4-(propyl)catecholate]; [1-(3,5-di(propyl)-phenyl)-2,3-(dibutyl)-4-(phenyl)1,4-diazabuta-1,3-diene]nickel[3,4-di(butyl)-catecholate]; [1-(phenyl)-2-(butyl)-3-(octyl)-4-(4-hexadecynylphenyl)1,4-diazabuta-1,3-diene]nickel[3-(pentyl)catecholate]; [1-(3,5-di(ethyl)phenyl)-2-(decyl)-3-(butyl)-4-(3,4-di(butyl)phenyl)1,4-diazabuta-1,3-diene]nickel[3-(ethyl)catecholate]; [1-(phenyl)-2-(hydrido)-3-(pentadecenyl)-4-(4-nonenylphenyl)1,4-diazabuta-1,3-diene]nickel[3-(pentyl)-4-(butyl)-5-(ethyl)catecholate]; [1-(3,4-di(pentyl)phenyl)-2-(hexyl)-3-(butyl)-4-(3,5-di(dodecamino)phenyl)1,4-diazabuta-1,3-diene]nickel[3-(butyl)catecholate]; [1-(3,4-di(butyl)phenyl)-2-(butyl)-3-(pentyl)-4-(4-diethylaminophenyl)1,4-diazabuta-1,3-diene]palladium [4-(butyl)-5-(ethyl)catecholate]; [1-(phenyl)-2,3-(dibutyl)-4-(3,4-di(propyl)phenyl)1,4-diazabuta-1,3-diene]nickel[3,5-di(ethyl)catecholate]; [1-(4-octylaminophenyl)-2-(tridecenyl)-3-(hexyl)-4-(3,4-di(methyl)phenyl)1,4-diazabuta-1,3-diene]palladium[3-(methyl)-6-(butyl)catecholate]; [1-(3,5-di(methyl)phenyl)-2,3-(dibutyl)-4-(phenyl)1,4-diazabuta-1,3-diene]palladium[3-(methyl)catecholate]; [1-(phenyl)-2,3-(dihydrido)-4-(3,4-di(propyl)phenyl)1,4-diazabuta-1,3-diene]nickel[3,4-di(propyl)-6-(propyl)catecholate]; [1-(3,4-di(pentyl)phenyl)-2,3-(dihydrido)-4-(phenyl)-1,4-diazabuta-1,3-diene]palladium [3-(butyl)catecholate]; [1-(3,5-di(methyl)phenyl)-2-(hexyl)-3-(butyl)-4-(phenyl)1,4-diazabuta-1,3-diene]palladium[3-(propyl)-6-(methyl)-catecholate]; [1-(3,5-di(butyl)phenyl)-2-(pentyl)-3-(butyl)-4-(phenyl)1,4-diazabuta-1,3-diene]nickel[4,5-di(pentyl)catecholate]; [1-(phenyl)-2-(butyl)-3-(hydrido)-4-(3,4-di(methyl)phenyl)1,4-diazabuta-1,3-diene]nickel[3-(propyl)-5-(pentyl)catecholate]; [1-(phenyl)-2,3-(dibutyl)-4-(3,4-di(pentyl)phenyl)1,4-diazabuta-1,3-diene]nickel[4-(methyl)catecholate]; [1-(3,4-di(methyl)phenyl)-2-(butyl)-3-(methyl)-4-(3,5-di(methyl)-phenyl)1,4-diazabuta-1,3-diene]nickel[3-(methyl)-5-(propyl)catecholate]; [1-(3,5-di(ethyl)phenyl)-2-(octyl)-3-(hexyl)-4-(3,4-di(propyl)phenyl)1,4-diazabuta-1,3-diene]palladium[3-(pentyl)catecholate]; [1-(3,5-di(pentyl)phenyl)-2,3-(dibutyl)-4-(3,5-di(butyl)phenyl)1,4-diazabuta-1,3-diene]nickel[4-(pentyl)catecholate]; [1-(3,5-di(pentyl)phenyl)-2-(tricosenyl)-3-(octyl)-4-(4-pentacosylphenyl)1,4-diazabuta-1,3-diene]palladium[3-(ethyl)catecholate]; [1-(3,4-di(propyl)phenyl)-2-(heneicosynyl)-3-(nonadecenyl)-4-(4-propylphenyl)-1,4-diazabuta-1,3-diene]nickel[3-(methyl)-4-(propyl)catecholate]; [1-(3,4-di(methyl)phenyl)-2,3-(dibutyl)-4-(phenyl)1,4-diazabuta-1,3-diene]nickel[3-(butyl)-4-(ethyl)catecholate]; [1-(4-heptylphenyl)-2-(hydrido)-3-(butyl)-4-

(3,4-di(butyl)phenyl)1,4-diazabuta-1,3-diene]nickel[3-(ethyl)-4-(butyl)catecholate]; [1-(3,4-di(methyl)phenyl-2,3-(diethyl)-4-(3-hexacosynylphenyl)1,4-diazabuta-1,3-diene]nickel[3-(ethyl)-6-(propyl)catecholate]; [1-(phenyl)-2-(dodecenyl)-3-(hexyl)-4-(3,5-di(ethyl)-phenyl)1,4-diazabuta-1,3-diene]palladium[3-(pentyl)-6-(ethyl)catecholate]; [1-(3,4-di(pentyl)phenyl)-2-(tricosyl)-3-(dodecynyl)-4-(3,4-di(methylethylamino)phenyl)1,4-diazabuta-1,3-diene]nickel[3-(butyl)-4-(ethyl)-5-(methyl)catecholate]; [1-(4-pentadecenylphenyl)-2-(butyl)-3-(methyl)-4-(3,5-di(butyl)phenyl)1,4-diazabuta-1,3-diene]palladium[3-(butyl)-5-(ethyl)catecholate]; [1-(3,4-di(butyl)phenyl)-2-(octyl)-3-(butyl)-4-(3,4-di(propyl)phenyl)1,4-diazabuta-1,3-diene]nickel[4-(ethyl)catecholate]; [1-(phenyl)-2,3-(dibutyl)-4-(3,5-di(ethyl)-phenyl)1,4-diazabuta-1,3-diene]palladium [3,4-di(propyl)-6-(propyl)catecholate]; [1-(3,5-di(pentyl)phenyl)-2-(butyl)-3-(methyl)-4-(3,5-di(methyl)phenyl)1,4-diazabuta-1,3-diene]nickel[3,4-di(pentyl)-6-(propyl)catecholate]; [1-(3,5-di(pentyl)phenyl)-2-(hydrido)-3-(hexyl)-4-(3,4-di(butyl)phenyl)1,4-diazabuta-1,3-diene]nickel[3-(pentyl)catecholate]; [1-(phenyl)-2-(octadecenyl)-3-(hydrido)-4-(3,4-di(propyl)phenyl)1,4-diazabuta-1,3-diene]nickel[4-(propyl)catecholate]; [1-(4-hexacosynylphenyl)-2-(methyl)-3-(hydrido)-4-(phenyl)1,4-diazabuta-1,3-diene]palladium [4-(ethyl)catecholate]; [1-(3,4-di(propyl)phenyl)-2-(octacosyl)-3-(hydrido)-4-(phenyl)1,4-diazabuta-1,3-diene]palladium[4-(pentyl)catecholate]; [1-(3,4-di(propyl)phenyl)-2,3-(dihydrido)-4-(phenyl)1,4-diazabuta-1,3-diene]nickel[4-(ethyl)catecholate]; [1-(3,4-di(ethyl)phenyl)-2-(butyl)-3-(hexyl)-4-(3-pentacosynylphenyl)1,4-diazabuta-1,3-diene]nickel[4-(ethyl)-5-(pentyl)catecholate]; [1-(3,4-di(butyl)phenyl)-2-(eicosyl)-3-(butyl)-4-(phenyl)1,4-diazabuta-1,3-diene]palladium[3-(ethyl)-5-(butyl)catecholate]; [1-(3,5-di(pentyl)phenyl)-2-(hexyl)-3-(hydrido)-4-(3,5-di(butyl)phenyl)1,4-diazabuta-1,3-diene]nickel[3-(butyl)catecholate]; [1-(3,4-di(ethyl)phenyl)-2-(octyl)-3-(butyl)-4-(3,5-di(methyl)phenyl)1,4-diazabuta-1,3-diene]palladium[3-(butyl)catecholate]; [1-(3,5-di(butyl)phenyl)-2-(hydrido)-3-(butyl)-4-(4-docosenylphenyl)1,4-diazabuta-1,3-diene]nickel[4-(ethyl)-5-(methyl)catecholate]; [1-(3,4-di(pentyl)phenyl)-2-(hexadecynyl)-3-(hexyl)-4-(3,4-di(propyl)phenyl)1,4-diazabuta-1,3-diene]palladium[4-(ethyl)-catecholate]; [1-(3-propynylphenyl)-2-(pentyl)-3-(butyl)-4-(4-propenylphenyl)1,4-diazabuta-1,3-diene]nickel[3-(trimethylsilylethyl)-5-(trimethylsilylmethyl)catecholate]; [1-(3,5-di(butyl)phenyl)-2-(methyl)-3-(butyl)-4-(3,4-di(ethyl)phenyl)1,4-diazabuta-1,3-diene]palladium[3-(pentyl)catecholate].

[1,4-bis(3,4-di(butyl)phenyl)-2-(butyl)-3-(hydrido)-1,4-diazabuta-1,3-diene][5-(butyl)-8-(octylamino)-naphthalene-2,3-bis(olate)]palladium; [1,4-bis(3,4-di(butyl)phenyl)-2-(ethyl)-3-(hexyl)-1,4-diazabuta-1,3-diene][4-(bromo)-5-(methyl)-naphthalene-1,2-bis(olate)]nickel; [1,4-bis(3,4-di(ethyl)phenyl)-2-(hydrido)-3-(hexyl)-1,4-diazabuta-1,3-diene][4-(butyl)-5-(methyl)-naphthalene-1,2-bis(olate)]nickel; [1,4-bis(3,4-di(butyl)phenyl)-2-(butyl)-3-(hexyl)-1,4-diazabuta-1,3-diene][6-(butonyl)-7-(butyl)-naphthalene-2,3-bis(olate)]nickel; [1,4-bis(3,4-di(ethyl)phenyl)-2-(butyl)-3-(hexyl)-1,4-diazabuta-1,3-diene][5-(dodecanonyl)-7-(propyl)-naphthalene-2,3-bis(olate)]nickel; [1,4-bis(3,4-di(butyl)phenyl)-2-(hexyl)-3-(hydrido)-1,4-diazabuta-1,3-diene][5-butyl-naphthalene-1,2-bis(olate)]palladium; [1,4-bis(3,4-di(ethyl)phenyl)-2-(hydrido)-3-(butyl)-1,4-diazabuta-1,3-diene][5-(dodecamino)-7-(methyl)-naphthalene-2,3-bis(olate)]nickel; [1,4-bis(3,4-di(ethyl)phenyl)-2-(methyl)-3-(hydrido)-1,4-diazabuta-1,3-diene][5-(dodecanonyl)-7-(pentyl)-naphthalene-2,3-bis(olate)]nickel; [1,4-bis(3,4-di(dodecanonyl)phenyl)-2-(tridecyl)-3-(butyl)-1,4-diazabuta-1,3-diene][5-(ethanalyl)-7-(methyl)-naphthalene-2,3-bis(olate)]nickel; [1,4-bis(3,4-di(ethyl)phenyl)-2-(methyl)-3-(heneicosynyl)-1,4-diazabuta-1,3-diene][5-(bromo)-6-(propyl)-naphthalene-2,3-bis(olate)]nickel; [1,4-bis(3,4-di(ethyl)phenyl)-2-(propynyl)-3-(octenyl)-1,4-diazabuta-1,3-diene][4-(ethyl)-5-(ethanalyl)-naphthalene-1,2-bis(olate)]palladium; [1,4-bis(3,4-di(butyl)phenyl)-2,3-(dihydrido))-1,4-diazabuta-1,3-diene][4-(ethyl)-5-(diethylamino)-naphthalene-1,2-bis(olate)]nickel; [1,4-bis(3,4-di(butyl)phenyl)-2-(hydrido)-3-(tetradecyl)-1,4-diazabuta-1,3-diene][5-(diethylamino)-6-(butyl)-naphthalene-1,8-bis(olate)]nickel; [1,4-bis(3,4-di(ethyl)phenyl)-2-(methyl)-3-(pentyl)-1,4-diazabuta-1,3-diene][3-(proponyl)-6-(butyl)-naphthalene-1,8-bis(olate)]nickel; [1,4-bis(3,4-di(ethyl)phenyl)-2-(butyl)-3-(octyl)-1,4-diazabuta-1,3-diene][7-dodecamino-naphthalene-1,2-bis(olate)]nickel; [1,4-bis(3,4-di(butyl)phenyl)-2-(hydrido)-3-(pentyl)-1,4-diazabuta-1,3-diene][5-(propanalyl)-7-(ethanalyl)-naphthalene-2,3-bis(olate)]palladium; [1,4-bis(3,4-di(butyl)phenyl)-2,3-(dihydrido))-1,4-diazabuta-1,3-diene][3-(hexonyl)-6-(methyl)-naphthalene-1,8-bis(olate)]nickel; [1,4-bis(3,4-di(butyl)phenyl)-2-(methyl)-3-(hydrido)-1,4-diazabuta-1,3-diene][7-methyl-naphthalene-1,2-bis(olate)]palladium; [1,4-bis(3,4-di(butyl)phenyl)-2-(butyl)-3-(triacontenyl)-1,4-diazabuta-1,3-diene][4-ethyl-naphthalene-1,2-bis(olate)]palladium; [1,4-bis(3,4-di(butyl)phenyl)-2,3-(dibutyl))-1,4-diazabuta-1,3-diene][4-(methylethylamino)-5-(methyl)-naphthalene-1,2-bis(olate)]nickel; [1,4-bis(3,4-di(ethyl)phenyl)-2-(pentyl)-3-(hexadecyl)-1,4-diazabuta-1,3-diene][6-(tridocosanalyl)-7-(butyl)-naphthalene-2,3-bis(olate)]palladium; [1,4-bis(3,4-di(ethyl)phenyl)-2-(hydrido)-3-(butyl)-1,4-diazabuta-1,3-diene][5-(methyl)-7-(hexonyl)-naphthalene-2,3-bis(olate)]nickel; [1,4-bis(3,4-di(ethyl)phenyl)-2-(octyl)-3-(pentyl)-1,4-diazabuta-1,3-diene][3-(pentyl)-6-(methyl)-naphthalene-1,8-bis(olate)]nickel; [1,4-bis(3,4-di(butyl)phenyl)-2-(butyl)-3-(hexyl)-1,4-diazabuta-1,3-diene][5,6-bis(methyl)napthalene-2,3-bis(olate)]nickel; [1,4-bis(3,4-di(ethyl)phenyl)-2-(octyl)-3-(pentyl)-1,4-diazabuta-1,3-diene][3-(ethyl)-6-(hexyl)-naphthalene-1,8-bis(olate)]nickel; [1,4-bis(3,4-di(ethyl)phenyl)-2-(butyl)-3-(octynyl)-1,4-diazabuta-1,3-diene][5-(propyl)-6-(dodecamino)-naphthalene-1,2-bis(olate)]nickel; [1,4-bis(3,4-di(ethyl)phenyl)-2-(hydrido)-3-(pentyl)-1,4-diazabuta-1,3-diene][5-(butonyl)-7-(methyl)-naphthalene-2,3-bis(olate)]nickel; [1,4-bis(3-(triethylsilylmethyl)phenyl)-2-(nonenyl)-3-(nonadecenyl)-1,4-diazabuta-1,3-diene][4-ethyl-naphthalene-1,2-bis(olate)]nickel; [1,4-bis(3,4-di(butyl)phenyl)-2,3-(dibutyl))-1,4-diazabuta-1,3-diene][5-(bromo)-7-(butyl)-naphthalene-1,2-bis(olate)]nickel; [1,4-bis(3,4-di(diethylamino)phenyl)-2,3-(dibutyl))-1,4-diazabuta-1,3-diene][4-(pentyl)-5-(dodecanonyl)-naphthalene-1,2-bis(olate)]nickel; [1,4-bis(3,4-di(ethyl)phenyl)-2,3-(dibutyl))-1,4-diazabuta-1,3-diene][5-(ethanalyl)-8-(propyl)-naphthalene-2,3-bis(olate)]nickel; [1,4-bis(3,4-di(dodecanonyl)phenyl)-2-(methyl)-3-(hexyl)-1,4-diazabuta-1,3-diene][7-ethyl-naphthalene-1,2-bis(olate)]nickel;[1,4-bis(3,4-di(butyl)phenyl)-2-(pentyl)-3-(butyl)-1,4-diazabuta-1,3-diene][4-(ethyl)-5-(ethanalyl)-naphthalene-1,2-bis(olate)]nickel; [1,4-bis(3,4-di(butyl)phenyl)-2-(octyl)-3-(ethyl)-1,4-diazabuta-1,3-diene][5-(methylethylamino)-6-(ethyl)-naphthalene-2,3-bis(olate)]palladium; [1,4-bis(3,4-di(butyl)phenyl)-2-(pentyl)-3-(butyl)-1,4-diazabuta-1,3-diene][3-(butyl)-6-((trimethylsilylethyl))-naphthalene-1,8-bis(olate)]nickel;

[1,4-bis(3,4-di(ethyl)phenyl)-2-(butyl)-3-(pentyl)-1,4-diazabuta-1,3-diene][5-((trimethylsilylmethyl))-8-(propyl)-naphthalene-2,3-bis(olate)]nickel; [1,4-bis(3,4-di(butyl)phenyl)-2-(hexadecenyl)-3-(methyl)-1,4-diazabuta-1,3-diene][5-(propyl)-8-(dodecaphosphino)-naphthalene-2,3-bis(olate)]nickel; [1,4-bis(3,4-di(ethyl)phenyl)-2-(pentadecenyl)-3-(octyl)-1,4-diazabuta-1,3-diene][5-(methyl)-8-(proponyl)-naphthalene-2,3-bis(olate)]nickel; [1,4-bis(3,4-di(ethyl)phenyl)-2-(butyl)-3-(hydrido)-1,4-diazabuta-1,3-diene][4-(methyl)-5-(ethyl)-naphthalene-1,2-bis(olate)]palladium; [1,4-bis(3,4-di(ethyl)phenyl)-2-(hydrido)-3-(butyl)-1,4-diazabuta-1,3-diene][5,7-bis(ethyl)-naphthalene-1,2-bis(olate)]palladium; [1,4-bis(3,4-di(ethyl)phenyl)-2-(butyl)-3-(pentyl)-1,4-diazabuta-1,3-diene][6-(butyl)-7-((triethylsilylmethyl))-naphthalene-2,3-bis(olate)]nickel; [1,4-bis(3,4-di(butyl)phenyl)-2-(hydrido)-3-(hexadecyl)-1,4-diazabuta-1,3-diene][3-(ethyl)-6-(pentonyl)-naphthalene-1,8-bis(olate)]palladium; [1,4-bis(3,4-di(ethyl)phenyl)-2,3-(di butyl))-1,4-diazabuta-1,3-diene][6-((trimethylsilylmethyl))-7-(ethyl)-naphthalene-2,3-bis(olate)]nickel; [1,4-bis(3,4-di(ethyl)phenyl)-2-(undecyl)-3-(octyl)-1,4-diazabuta-1,3-diene][3,6-bis(propyl)-naphthalene-1,8-bis(olate)]nickel; [1,4-bis(3,4-di(ethyl)phenyl)-2-(butyl)-3-(hexyl)-1,4-diazabuta-1,3-diene][5-((triethylsilylmethyl))-6-(pentyl)-naphthalene-1,2-bis(olate)]nickel; [1,4-bis(3,4-di(ethyl)phenyl)-2-(butyl)-3-(dodecenyl)-1,4-diazabuta-1,3-diene][7-ethyl-naphthalene-1,2-bis(olate)]nickel; [1,4-bis(3,4-di(butyl)phenyl)-2-(decyl)-3-(ethyl)-1,4-diazabuta-1,3-diene][5-(propyl)-8-((trimethylsilylmethyl))-naphthalene-2,3-bis(olate)]nickel; [1,4-bis(3,4-di(ethyl)phenyl)-2-(heptacosynyl)-3-(hydrido)-1,4-diazabuta-1,3-diene][3-(pentyl)-6-(methyl)-naphthalene-1,8-bis(olate)]nickel; [1,4-bis(3,4-di(ethyl)phenyl)-2,3-(dibutyl))-1,4-diazabuta-1,3-diene][3-(bromo)-6-(butyl)-naphthalene-1,8-bis(olate)]nickel; [1,4-bis(3,4-di(butyl)phenyl)-2-(hydrido)-3-(eicosynyl)-1,4-diazabuta-1,3-diene][5-(butyl)-7-(butanalyl)-naphthalene-1,2-bis(olate)]nickel; [1,4-bis(3,4-di(butyl)phenyl)-2,3-(dihydrido))-1,4-diazabuta-1,3-diene][4-(bromo)-5-(methyl)-naphthalene-1,2-bis(olate)]palladium; [1,4-bis(3,4-di(ethyl)phenyl)-2-(hydrido)-3-(butyl)-1,4-diazabuta-1,3-diene][5-((triethylsilylmethyl))-6-(pentyl)-naphthalene-1,2-bis(olate)]palladium; [1,4-bis(3,4-di(ethyl)phenyl)-2-(pentyl)-3-(octyl)-1,4-diazabuta-1,3-diene][6-butyl-naphthalene-1,2-bis(olate)]nickel; [1,4-bis(3,4-di(butyl)phenyl)-2-(hydrido)-3-(butyl)-1,4-diazabuta-1,3-diene][5-(propyl)-8-(dodecaphosphino)-naphthalene-2,3-bis(olate)]nickel; [1,4-bis(3,4-di(butyl)phenyl)-2-(hexyl)-3-(ethyl)-1,4-diazabuta-1,3-diene][6-butyl-naphthalene-1,2-bis(olate)]palladium; [1,4-bis(3,4-di(ethyl)phenyl)-2-(butyl)-3-(octacosynyl)-1,4-diazabuta-1,3-diene][5-(butonyl)-6-(pentyl)-naphthalene-1,8-bis(olate)]nickel; [1,4-bis(3-(trimethylsilylmethyl)phenyl)-2-(butyl)-3-(octyl)-1,4-diazabuta-1,3-diene][7-tridocosanalyl-naphthalene-1,2-bis(olate)]nickel; [1,4-bis(3,4-di(ethyl)phenyl)-2,3-(dibutyl))-1,4-diazabuta-1,3-diene][5-(pentyl)-7-(methyl)-naphthalene-2,3-bis(olate)]nickel; [1,4-bis(3,4-di(butyl)phenyl)-2-(butyl)-3-(hexyl)-1,4-diazabuta-1,3-diene][5-(propyl)-8-(ethanalyl)-naphthalene-2,3-bis(olate)]nickel; [1,4-bis(3,4-di(dodecamino)phenyl)-2-(hydrido)-3-(hexyl)-1,4-diazabuta-1,3-diene][5-(propyl)-6-((triethylsilylmethyl))-naphthalene-2,3-bis(olate)]nickel; [1,4-bis(3,4-di(butyl)phenyl)-2-(pentynyl)-3-(pentyl)-1,4-diazabuta-1,3-diene][5-(methylethylamino)-8-(methyl)-naphthalene-2,3-bis(olate)]nickel; [1,4-bis(3,4-di(ethyl)phenyl)-2-(hydrido)-3-(hexacosenyl)-1,4-diazabuta-1,3-diene][4-(pentyl)-5-(ethyl)-naphthalene-1,2-bis(olate)]nickel; [1,4-bis(3,4-di(butyl)phenyl)-2-(octyl)-3-(butyl)-1,4-diazabuta-1,3-diene][3-(methyl)-6-(dodecaphosphino)-naphthalene-1,8-bis(olate)]nickel; [1,4-bis(3,4-di(butyl)phenyl)-2-(butyl)-3-(hydrido)-1,4-diazabuta-1,3-diene][5-(pentyl)-6-(methylethylamino)-naphthalene-2,3-bis(olate)]nickel; [1,4-bis(3,4-di(butyl)phenyl)-2,3-(dihexyl))-1,4-diazabuta-1,3-diene][5-(bromo)-7-(butyl)-naphthalene-2,3-bis(olate)]nickel; [1,4-bis(3,4-di(ethyl)phenyl)-2-(hydrido)-3-(octyl)-1,4-diazabuta-1,3-diene][5-(butanalyl)-7-(pentyl)-naphthalene-1,2-bis(olate)]palladium; [1,4-bis(3,4-di(butyl)phenyl)-2-(octyl)-3-(butyl)-1,4-diazabuta-1,3-diene][3,6-bis(methyl)-naphthalene-1,8-bis(olate)]palladium; [1,4-bis(3,4-di(butyl)phenyl)-2-(butyl)-3-(octyl)-1,4-diazabuta-1,3-diene][6-butyl-naphthalene-1,2-bis(olate)]nickel; [1,4-bis(3,4-di(butyl)phenyl)-2-(ethyl)-3-(hexyl)-1,4-diazabuta-1,3-diene][5-(pentyl)-6-(hexyl)-naphthalene-2,3-bis(olate)]nickel; [1,4-bis(3,4-di(ethyl)phenyl)-2-(hydrido)-3-(ethyl)-1,4-diazabuta-1,3-diene][5-(dodecanonyl)-6-(butyl)-naphthalene-1,2-bis(olate)]nickel; [1,4-bis(3,4-di(ethyl)phenyl)-2-(hydrido)-3-(butyl)-1,4-diazabuta-1,3-diene][5-(bromo)-6-(ethyl)-naphthalene-1,2-bis(olate)]nickel; [1,4-bis(3,4-di(butyl)phenyl)-2-(octyl)-3-(hexyl)-1,4-diazabuta-1,3-diene][5-(bromo)-6-(propyl)-naphthalene-1,8-bis(olate)]nickel; [1,4-bis(3,4-di(butyl)phenyl)-2-(pentyl)-3-(ethyl)-1,4-diazabuta-1,3-diene][4-(propyl)-5-(ethanalyl)-naphthalene-1,2-bis(olate)]nickel; [1,4-bis(3,4-di(ethyl)phenyl)-2-(butyl)-3-(octyl)-1,4-diazabuta-1,3-diene][5-(butyl)-7-(tridocosanalyl)-naphthalene-1,8-bis(olate)]palladium; [1,4-bis(3,4-di(ethyl)phenyl)-2-(hydrido)-3-(butyl)-1,4-diazabuta-1,3-diene][5-(butyl)-6-(octylamino)-naphthalene-2,3-bis(olate)]palladium; [1,4-bis(3,4-di(ethyl)phenyl)-2-(hydrido)-3-(butyl)-1,4-diazabuta-1,3-diene][5-(propyl)-7-(butyl)-naphthalene-2,3-bis(olate)]nickel; [1,4-bis(3,4-di(butyl)phenyl)-2-(octyl)-3-(octacosenyl)-1,4-diazabuta-1,3-diene][3-(methyl)-6-(hexonyl)-naphthalene-1,8-bis(olate)]palladium; [1,4-bis(3,4-di(ethyl)phenyl)-2-(hydrido)-3-(butyl)-1,4-diazabuta-1,3-diene][5-(methyl)-6-((trimethylsilylethyl))-naphthalene-2,3-bis(olate)]nickel; [1,4-bis(3,4-di(ethyl)phenyl)-2-(hydrido)-3-(butyl)1,4-diazabuta-1,3-diene][5-(butonyl)-8-(butyl)-naphthalene-2,3-bis(olate)]palladium; [1,4-bis(3,4-di(ethyl)phenyl)-2,3-(dibutyl))-1,4-diazabuta-1,3-diene][4-ethyl-naphthalene-1,2-bis(olate)]nickel; [1,4-bis(3,4-di(ethyl)phenyl)-2-(butyl)-3-(hydrido)-1,4-diazabuta-1,3-diene][5-(propanalyl)-7-(ethanalyl)-naphthalene-2,3-bis(olate)]nickel; [1,4-bis(3,4-di(butyl)phenyl)-2,3-(dibutyl))-1,4-diazabuta-1,3-diene][5-(octylamino)-8-(propyl)-naphthalene-2,3-bis(olate)]palladium; [1,4-bis(3,4-di(butyl)phenyl)-2-(pentyl)-3-(hydrido)-1,4-diazabuta-1,3-diene][6-(butanalyl)-7-(butyl)-naphthalene-2,3-bis(olate)]nickel; [1,4-bis(3,4-di(ethyl)phenyl)-2,3-(dibutyl))-1,4-diazabuta-1,3-diene][5-(methylethylamino)-6-(ethyl)-naphthalene-2,3-bis(olate)]nickel; [1,4-bis(3,4-di(ethyl)phenyl)-2,3-(dibutyl))-1,4-diazabuta-1,3-diene][5,7-bis(propyl)-naphthalene-2,3-bis(olate)]palladium; [1,4-bis(3,4-di(ethyl)phenyl)-2,3-(dibutyl))-1,4-diazabuta-1,3-diene][5-(propyl)-6-(pentyl)-naphthalene-1,8-bis(olate)]nickel; [1,4-bis(3,4-di(ethyl)phenyl)-2-(hexyl)-3-(hydrido)-1,4-diazabuta-1,3-diene][5-(pentyl)-7-(methylethylamino)-naphthalene-1,2-bis(olate)]nickel; [1,4-bis(3,4-di(butyl)phenyl)-2-(hydrido)-3-(hexyl)-1,4-diazabuta-1,3-diene][4-butanalyl-naphthalene-1,2-bis(olate)]nickel; [1,4-bis(3,4-di(ethyl)phenyl)-2-(butyl)-3-(hydrido)-1,4-diazabuta-1,3-diene][5,7-bis(ethyl)-naphthalene-2,3-bis(olate)]nickel; [1,4-bis(3,4-di(dodecanonyl)phenyl)-2-(octyl)-3-(hydrido)-1,4-diazabuta-1,3-diene][5-(methyl)-8-(proponyl)-naphthalene-2,3-bis(olate)]nickel; [1,4-bis(3,4-di(ethyl)phenyl)-2,3-(dibutyl))-1,4-diazabuta-1,3-diene][5,8-bis(propyl)-naphthalene-2,3- bis(olate)]nickel; [1,4-bis(3,4-di(ethyl)phenyl)-2-(butyl)-3-(hydrido)-1,4-diazabuta-1,3-diene][3-(pentyl)-6-(methyl)-naphthalene-1,8-bis(olate)]nickel; [1,4-bis(3,4-di(butyl)phenyl)-2-(hexyl)-3-(hydrido)-1,4-diazabuta-1,3-diene][5-((trimethylsilylmethyl))-6-(methyl)-naphthalene-1,2-bis(olate)]nickel; [1,4-bis(3,4-di(ethyl)phenyl)-2-(hydrido)-3-(octyl)-1,4-diazabuta-1,3-diene][6-((trimethylsilylmethyl))-7-(ethyl)-naphthalene-2,3-bis(olate)]nickel; [1,4-bis(3,4-di(ethyl)phenyl)-2-(butyl)-3-(hydrido)-1,4-diazabuta-1,3-diene][5-(pentyl)-7-(methylethylamino)-naphthalene-1,2-bis(olate)]nickel; [1,4-bis(3,4-di(dodecanonyl)phenyl)-2-(butyl)-3-(pentyl)-1,4-diazabuta-1,3-diene][5-(pentyl)-7-(methyl)-naphthalene-2,3-bis(olate)]nickel; [1,4-bis(3,4-di(butyl)phenyl)-2-(octynyl)-3-(hydrido)-1,4-diazabuta-1,3-diene][5-(pentonyl)-8-(butyl)-naphthalene-2,3-bis(olate)]nickel; [1,4-bis(3,4-di(ethyl)phenyl)-2-(hexyl)-3-(ethyl)-1,4-diazabuta-1,3-diene][5-(butyl)-6-(octylamino)-naphthalene-2,3-bis(olate)]nickel; [1,4-bis(3,4-di(butyl)phenyl)-2-(octyl)-3-(butyl)-1,4-diazabuta-1,3-diene][5-(butyl)-7-((trimethylsilylethyl))-naphthalene-1,8-bis(olate)]nickel; [1,4-bis(3,4-di(ethyl)phenyl)-2-(methyl)-3-(docosynyl)-1,4-diazabuta-1,3-diene][5-(butyl)-6-(dodecaphosphino)-naphthalene-1,8-bis(olate)]palladium; [1,4-bis(3,4-di(butyl)phenyl)-2-(octyl)-3-(hydrido)-1,4-diazabuta-1,3-diene][5-(methyl)-6-(propanalyl)-naphthalene-2,3-bis(olate)]palladium; [1,4-bis(3,4-di(butyl)phenyl)-2-(hydrido)-3-(butyl)-1,4-diazabuta-1,3-diene][3-(butyl)-6-((trimethylsilylethyl))-naphthalene-1,8-bis(olate)]nickel; [1,4-bis(3,4-di(butyl)phenyl)-2,3-(dibutyl))-1,4-diazabuta-1,3-diene][6-(methylethylamino)-7-(propyl)-naphthalene-2,3-bis(olate)]nickel; [1,4-bis(3,4-di(dodecanonyl)phenyl)-2,3-(dibutyl))-1,4-diazabuta-1,3-diene][5-(butyl)-8-((triethylsilylmethyl))-naphthalene-2,3-bis(olate)]nickel; [1,4-bis(3-(triethylsilylmethyl)phenyl)-2-(butyl)-3-(hexyl)-1,4-diazabuta-1,3-diene][5-(hexonyl)-7-(dodecaphosphino)-naphthalene-1,8-bis(olate)]palladium; [1,4-bis(3,4-di(butyl)phenyl)-2-(nonenyl)-3-(octyl)-1,4-diazabuta-1,3-diene][3-(methyl)-6-(propyl)-naphthalene-1,8-bis(olate)]nickel; [1,4-bis(3,4-di(butyl)phenyl)-2-(eicosyl)-3-(hydrido)-1,4-diazabuta-1,3-diene][5-((trimethylsilylmethyl))-7-(ethyl)-naphthalene-1,8-bis(olate)]nickel; [1,4-bis(3,4-di(diethylamino)phenyl)-2-(methyl)-3-(butyl)-1,4-diazabuta-1,3-diene][5-(pentyl)-6-(tridocosanalyl)-naphthalene-1,8-bis(olate)]palladium; [1,4-bis(3,4-di(ethyl)phenyl)-2-(hydrido)-3-(octyl)-1,4-diazabuta-1,3-diene][5-(pentyl)-7-(methyldiethylsilylmethyl))-naphthalene-1,8-bis(olate)]palladium; [1,4-bis(3,4-di(butonyl)phenyl)-2-(hydrido)-3-(hexyl)-1,4-diazabuta-1,3-diene][5-(ethyl)-6-(butyl)-naphthalene-1,2-bis(olate)]palladium; [1,4-bis(3,4-di(ethyl)phenyl)-2,3-(dibutyl))-1,4-diazabuta-1,3-diene][5-(propanalyl)-7-(ethyl)-naphthalene-2,3-bis(olate)]nickel; [1,4-bis(3,4-di(butyl)phenyl)-2-(hydrido)-3-(butyl)-1,4-diazabuta-1,3-diene][5-(pentyl)-6-(octylamino)-naphthalene-1,2-bis(olate)]nickel; [1,4-bis(3,4-di(ethyl)phenyl)-2-(hexyl)-3-(butyl)-1,4-diazabuta-1,3-diene][3-(tridocosanalyl)-6-(methyl)-naphthalene-1,8-bis(olate)]nickel; [1,4-bis(3,4-di(ethyl)phenyl)-2-(decyl)-3-(hydrido)-1,4-diazabuta-1,3-diene][4-(propanalyl)-5-(ethyl)-naphthalene-1,2-bis(olate)]nickel; [1,4-bis(3,4-di(ethyl)phenyl)-2-(hydrido)-3-(butyl)-1,4-diazabuta-1,3-diene][5-(pentyl)-7-(methyl)-naphthalene-1,8-bis(olate)]nickel; [1,4-bis(3,4-di(dodecamino)phenyl)-2,3-(dibutyl))-1,4-diazabuta-1,3-diene][5-(methyl)-6-(hexyl)-naphthalene-1,2-bis(olate)]palladium; [1,4-bis(3,4-di(ethyl)phenyl)-2-(hexyl)-3-(octyl)-1,4-diazabuta-1,3-diene][5-(pentonyl)-8-(butyl)-naphthalene-2,3-bis(olate)]palladium; [1,4-bis(3,4-di(butyl)phenyl)-2-(ethyl)-3-(hydrido)-1,4-diazabuta-1,3-diene][5-(propyl)-8-((trimethylsilylmethyl))-naphthalene-2,3-bis(olate)]nickel; [1,4-bis(3,4-di(butyl)phenyl)-2-(butyl)-3-(octyl)-1,4-diazabuta-1,3-diene][5-(pentyl)-7-(diethylamino)-naphthalene-2,3-bis(olate)]nickel; [1,4-bis(3,4-di(butyl)phenyl)-2-(octyl)-3-(methyl)-1,4-diazabuta-1,3-diene][5-(butonyl)-7-(methyl)-naphthalene-2,3-bis(olate)]nickel; [1,4-bis(3,4-di(butyl)phenyl)-2-(butyl)-3-(hexyl)-1,4-diazabuta-1,3-diene][5-(diethylamino)-7-(butyl)-naphthalene-1,2-bis(olate)]nickel; [1,4-bis(3,4-di(ethyl)phenyl)-2-(heptacosynyl)-3-(hydrido)-1,4-diazabuta-1,3-diene][5,7-bis(propyl)-naphthalene-2,3-bis(olate)]palladium; [1,4-bis(3,4-di(ethyl)phenyl)-2-(butyl)-3-(octyl)-1,4-diazabuta-1,3-diene][3-(methyl)-6-((trimethylsilylmethyl))-naphthalene-1,8-bis(olate)]nickel; [1,4-bis(3,4-di(ethyl)phenyl)-2-(butyl)-3-(decynyl)-1,4-diazabuta-1,3-diene][5-(methyl)-6-(hexonyl)-naphthalene-2,3-bis(olate)]nickel; [1,4-bis(3,4-di(ethyl)phenyl)-2-(butyl)-3-(hydrido)-1,4-diazabuta-1,3-diene][6-(bromo)-7-(butyl)-naphthalene-2,3-bis(olate)]nickel; [1,4-bis(3,4-di(butyl)phenyl)-2-(hydrido)-3-(octyl)-1,4-diazabuta-1,3-diene][5-(dodecaphosphino)-7-(ethyl)-naphthalene-1,2-bis(olate)]palladium; [1,4-bis(3,4-di(ethyl)phenyl)-2-(propenyl)-3-(butyl)-1,4-diazabuta-1,3-diene][5-(tridocosanalyl)-6-(butyl)-naphthalene-1,8-bis(olate)]palladium; [1,4-bis(3,4-di(butyl)phenyl)-2-(hydrido)-3-(butyl)-1,4-diazabuta-1,3-diene][7-ethanalyl-naphthalene-1,2-bis(olate)]nickel; [1,4-bis(3,4-di(butyl)phenyl)-2,3-(dibutyl))-1,4-diazabuta-1,3-diene][5-(butyl)-7-(butanalyl)-naphthalene-1,2-bis(olate)]nickel; [1,4-bis(3,4-di(butyl)phenyl)-2,3-(dibutyl))-1,4-diazabuta-1,3-diene][5-(butyl)-7-(ethanalyl)-naphthalene-2,3-bis(olate)]nickel; [1,4-bis(3,4-di(butyl)phenyl)-2-(hexyl)-3-(hydrido)-1,4-diazabuta-1,3-diene][5-(hexyl)-6-(ethyl)-naphthalene-1,8-bis(olate)]nickel; [1,4-bis(3,4-di(ethyl)phenyl)-2-(butyl)-3-(pentyl)-1,4-diazabuta-1,3-diene][3,6-bis(methyl)-naphthalene-1,8-bis(olate)]palladium; [1,4-bis(3,4-di(butyl)phenyl)-2,3-(dioctyl))-1,4-diazabuta-1,3-diene][5-(butonyl)-7-(bromo)-naphthalene-1,2-bis(olate)]nickel; [1,4-bis(3,4-di(butyl)phenyl)-2,3-(dibutyl))-1,4-diazabuta-1,3-diene][5-(methyl)-8-(octylamino)-naphthalene-2,3-bis(olate)]palladium; [1,4-bis(3,4-di(ethyl)phenyl)-2-(hexyl)-3-(butyl)-1,4-diazabuta-1,3-diene][5-(pentyl)-8-(propanalyl)-naphthalene-2,3-bis(olate)]nickel; [1,4-bis(3,4-di(ethyl)phenyl)-2-(hydrido)-3-(hexyl)-1,4-diazabuta-1,3-diene][5-(pentyl)-7-(butyl)-naphthalene-1,2-bis(olate)]nickel; [1,4-bis(3,4-di(butyl)phenyl)-2-(butyl)-3-(hydrido)-1,4-diazabuta-1,3-diene][6-(butyl)-7-(dodecanonyl)-naphthalene-2,3-bis(olate)]nickel; [1,4-bis(3,4-di(ethyl)phenyl)-2-(hydrido)-3-(pentyl)-1,4-diazabuta-1,3-diene][3,6-bis(methyl)-naphthalene-1,8-bis(olate)]nickel; [1,4-bis(3,4-di(ethyl)phenyl)-2,3-(dibutyl))-1,4-diazabuta-1,3-diene][5-((trimethylsilylethyl))-6-(methyl)-naphthalene-1,2-bis(olate)]nickel; [1,4-bis(3,4-di(ethyl)phenyl)-2-(pentadecynyl)-3-(butyl)-1,4-diazabuta-1,3-diene][7-propyl-naphthalene-1,2-bis(olate)]palladium; [1,4-bis(3,4-di(butonyl)phenyl)-2,3-(dipentyl))-1,4-diazabuta-1,3-diene][5-((trimethylsilylmethyl))-6-(methyl)-naphthalene-1,2-bis(olate)]nickel; [1,4-bis(3,4-di(butyl)phenyl)-2,3-(dihydrido))-1,4-diazabuta-1,3-diene][5-(hexonyl)-7-(pentyl)-naphthalene-2,3-bis(olate)]nickel; [1,4-bis(3,4-di(butyl)phenyl)-2-(pentyl)-3-(hexyl)-1,4-diazabuta-1,3-diene][4-(propyl)-5-(dodecamino)-naphthalene-1,2-bis(olate)]nickel; [1,4-bis(3,4-di(butyl)phenyl)-2,3-(dibutyl))-1,4-diazabuta-1,3-diene][5-(pentyl)-7-(methyl)-naphthalene-1,8-bis(olate)]nickel; [1,4-bis(3,4-di(butyl)phenyl)-2-(nonenyl)-3-(hydrido)-1,4-diazabuta-1,3-diene][4-(methylethylamino)-5-(butyl)-naphthalene-1,2-bis(olate)]nickel; [1,4-bis(3,4-di(ethyl)phenyl)-2,3-(dibutyl))-1,4-diazabuta-1,3-diene][3-(butonyl)-6-(ethyl)-naphthalene-1,8-bis(olate)]nickel; [1,4-bis(3,4-di(butyl)phenyl)-2-(ethyl)-3-(butyl)-1,4-diazabuta-1,3-diene][5-(ethyl)-6-((triethylsilylmethyl))-naphthalene-1,2-bis(olate)]palladium; [1,4-bis(3,4-di(ethyl)phenyl)-2-(pentyl)-3-(triacontyl)-1,4-diazabuta-1,3-diene][5-(butyl)-7-(diethylamino)-naphthalene-1,8-bis(olate)]palladium; [1,4- bis(3,4-di(butyl)phenyl)-2-(hexyl)-3-(butyl)-1,4-diazabuta-1,3-diene][5-(pentyl)-8-(tridocosanalyl)-naphthalene-2,3-bis(olate)]nickel; [1,4-bis(3,4-di(butyl)phenyl)-2-(pentyl)-3-(octyl)-1,4-diazabuta-1,3-diene][5,6-bis(methyl)-naphthalene-2,3-bis(olate)]nickel.

EXAMPLES

The following examples are presented to illustrate the discussion above. Although the examples may be directed toward certain embodiments of the present invention, they do not limit the invention in any specific way. In these examples, certain abbreviations are used to facilitate the description. These include standard chemical abbreviations for the elements and certain commonly accepted abbreviations, such as: Me=methyl, Et=ethyl, Bu=butyl, Ph=phenyl, MAO=methylalumoxane, DAB=diazabutadiene, DAB(Me)$_2$=2,3-dimethyldiazabutadiene, COD=cyclooctadiene and cy=cyclohexyl.

All preparations were performed under an inert nitrogen atmosphere, using standard Schlenk or glovebox techniques, unless mentioned otherwise. Dry solvents (toluene, diethyl ether, pentane, and methylene chloride) were purchased as anhydrous solvents and further purified by passing them down an alumina (Fluka) column. 99.9% Ethylene was purchased from the BOC group (Surrey, United Kingdom). Formic acid (96%), methanol, 4-butylaniline, 2,3-butanedione, sodium sulfate, and 3,5-di-t-butyl-o-benzoquinone were purchased from Aldrich Chemical Company. Nickel tetracarbonyl can be purchased from Strem Chemicals, Inc. Deuterated solvents were dried with CaH and vacuum distilled prior to use. The compounds are illustrated below:

2,3-dimethyl-1,4-diphenyl-1,4-diaza-1,3-butadiene can be prepared from literature methods.

Compound 1

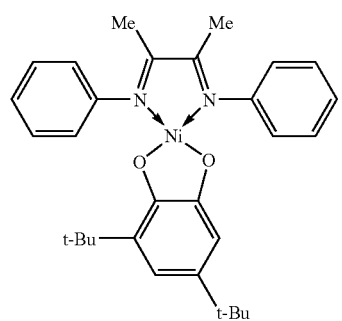

Preparation of [2,3-dimethyl-1,4-diphenyl-1,4-diaza-1,3-butadiene]nickel(II) 3,5-di-tert-butyl-catecholate)

(Compound 1). Nickel tetracarbonyl (0.86 g, 5 mmol) was condensed into an evacuated and frozen ampoule (having reserved volume of approximately 1 liter) containing 2,3-dimethyl-1,4-diphenyl-1,4-diaza-1,3-butadiene (1.11 g, 5 mmol) and 3,5-di-tert-butyl-o-benzoquinone (1.10 g, 5 mmol) in 100 ml of degassed toluene. The ampoule was slowly warmed at ~30° C. for one hour and at 80° C. for the next two hours. Resulting solution was maintained at −10° C. overnight. Dark green crystals were filtered, washed with light petroleum, and dried under vacuum. Yield 1.826 g (65%). IR (Nujol, cm$^{-1}$): 1585, 1515 m, 1490 m, 1420, 1390, 1340 m, 1300 s, 1265 m, 1250, 1215, 1075, 985 s, 850 m, 830, 765 s, 730, 695 s, 655, 625, 525.

$^1$H NMR (200 MHz, CDCl$_3$, δ, ppm): 0.94 and 1.11 s (2×9H, C(CH$_3$)$_3$); 1.78 s (6H, N=CCH$_3$); 7.27–7.50 m (10H, 2×C$_6$H$_5$).

Oligomerization Reactions

Oligomerization reactions were run in a 300-mL HastelloyC Parr reactor equipped with a mechanical stirrer. Catalyst was added to the reactor as a solution in toluene (75 ml) under argon. Ethylene was added to the reactor at 100 psig and then vented to maintain an ethylene atmosphere. Methylalumoxane solution (Albemarle, 30 wt % in toluene) was then added to the reactor. Thus, the catalyst was activated in the monomer's presence. The ethylene pressure was brought to the desired value. The aim was to maintain the reactor temperature at room temperature; but in cases where the reaction exotherm was very large, higher reaction temperatures were reached. After the reaction had run for an hour, the reactor was cooled in an acetone/dry ice bath, vented, and quenched with methanol. A sample of the product solution was analyzed by GC/MS after adding nonane as an internal standard. In the case of supported transition metal compounds, silica loaded samples were prepared by adding a solution of the transition metal complex in methylene chloride to silica followed by drying of the silica under vacuum overnight. MAO (0.35 g of 30 wt % MAO; Al/M molar ratio=240 for the non supported run) was added to the reactor solution prior to adding the supported transition metal compound. The results of the oligomerization reactions are tabulated in Table 2:

TABLE 2

Oligomerization Examples

| Compound | (mmol) | C$_2$ (psig) | Rxn Exotherm (° C.) | Final Rxn Temp (° C.) | Activity (mol C$_2$/mol Ni · hr) | K[a] | % α olefin (total)[b] |
|---|---|---|---|---|---|---|---|
| 1 | 0.0075 | 820 | 36–100 | 60 | 261,900 | 0.54 | 74 |
| 1 | 0.0075 | 100 | 34–84 | 44 | 95,200 | 0.49 | 60 |
| 1[c] | 0.0019 | 100 | 24–61 | 44 | 227,400 | 0.71 | 59 |

[a]K is based on C$_{14}$/C$_{12}$ molar ratio for all isomers.
[b]These numbers are subject to the interpretation of the GC/MS spectra and are calculated from averaging the weight % of alpha olefin from the C$_8$, C$_{10}$, and C$_{12}$ peaks.
[c]1 wt % of compound 1 loaded on silica; 0.09 g of 30 wt % MAO added to the reactor providing an Al/M molar ratio of 260.

While certain representative embodiments and details have been shown to illustrate the invention, it will be apparent to skilled artisans that various process and product changes from those disclosed in this application may be made without departing from this invention's scope, which the appended claims define.

All cited patents, test procedures, priority documents, and other cited documents are fully incorporated by reference to the extent that this material is consistent with this specification and for all jurisdictions in which such incorporation is permitted.

Certain features of the present invention are described in terms of a set of numerical upper limits and a set of numerical lower limits. This specification discloses all ranges formed by any combination of these limits. All combinations of these limits are within the scope of the invention unless otherwise indicated.

What is claimed is:

1. A composition comprising:
   (I) a metal selected from nickel or palladium connected to a ligand comprising 1,4-diazabutadiene:
      (a) having a phenyl ring connected to the 1 position of the diazabutadiene, and
      (b) having a phenyl ring connected to the 4 position of the diazabutadiene, and
      (c) where the 2 and 6 positions of both phenyl rings are connected to hydrogen radicals, and
      (d) where the 2 and 3 positions of the diazabutadiene are, each independently, connected to hydrogen or a hydrocarbyl group; and
   (II) a catecholate ligand connected to the metal.

2. The composition of claim 1 where the 2 and 3 positions of the diazabutadiene are, each independently, connected to hydrogen radical or a $C_1$–$C_{30}$ hydrocarbyl radical.

3. The composition of claim 1 where the 2 and 3 positions of the diazabutadiene are, each independently, connected to a $C_1$–$C_{30}$ hydrocarbyl radical and where hydrocarbyls form a ring structure comprising one or more substituted or unsubstituted aromatic or non-aromatic rings.

4. The composition of claim 1 where the 2 and 3 positions of the diazabutadiene are, each independently, connected to a hydrocarbyl radical selected from the group consisting of methyl, ethyl, and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, cyclohexyl, cyclopentyl, cycloheptyl, cyclooctyl, cyclodecyl, cyclododecyl, napthyl, phenyl, tolyl, benzyl, and phenethyl radicals.

5. The composition of claim 1 where the 2 and 3 positions of the diazabutadiene are, each independently, connected to a hydrogen, methyl, or ethyl radical.

6. The composition of claim 3 where the ring structure is 1,8-naphthalene or 2,2'-biphenyl.

7. The composition of claim 1 where the catecholate ligand comprises a $C_1$–$C_{30}$ hydrocarbyl radical.

8. The composition of claim 7 where the hydrocarbyl radical is selected from the group consisting of methyl, ethyl, ethenyl, ethynyl and all isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl, phenyl, benzyl, fluoro, chloro, bromo, iodo, methoxy, ethoxy, propoxy, butoxy, and phenoxy.

9. The composition of claim 7 where the hydrocarbyl radical comprises a butyl radical.

10. A method of producing a catalyst system comprising combining in a solvent: the composition of claim 1, an activator compound and optionally a support.

11. The method of claim 10 where the activator compound is selected from the group consisting of alumoxanes, discrete ionic activators, and Lewis acidic activators.

12. A catalyst produced using the method of claim 10.

13. A catalyst comprising the reaction product of the composition of claim 1, an activator and optionally a support.

14. A process to oligomerize alpha-olefins comprising combining the catalyst system of claim 13 and an α-olefin.

15. The composition of claim 14 where the α-olefin is ethylene.

16. The catalyst system of claim 13 where the support is an inorganic oxide support.

17. A composition comprising the composition of claim 1 and an activator.

18. The composition of claim 17 where the activator is selected from the group consisting of alumoxanes, discrete ionic activators and Lewis acidic activators.

19. The composition of claim 17 where the activator is selected from the group consisting of methylalumoxane, modified methylalumoxane, ethylalumoxane, trimethyl aluminum, triethyl aluminum, triisopropyl aluminum, diethyl aluminum chloride, $[Me_2PhNH][B(C_6F_5)_4]$, $[Bu_3NH][BF_4]$, $[NH_4][PF_6]$, $[NH_4][SbF_6]$, $[NH_4][AsF_6]$, $[NH_4][B(C_6H_5)_4]$, $B(C_6F_5)_3$ or $B(C_6H_5)_3$.

20. A composition comprising the composition of claim 1, an activator and a support.

21. The composition of claim 20 where the activator is selected from the group consisting of alumoxanes, discrete ionic activators and Lewis acidic activators and the support comprises an inorganic oxide.

22. The composition of claim 20 where the activator is selected from the group consisting of methylalumoxane, modified methylalumoxane, ethylalumoxane, trimethyl aluminum, triethyl aluminum, triisopropyl aluminum, diethyl aluminum chloride, $[Me_2PhNH][B(C_6F_5)_4]$, $[Bu_3NH][BF_4]$, $[NH_4][PF_6]$, $[NH_4][SbF_6]$, $[NH_4][AsF_6]$, $[NH_4][B(C_6H_5)_4]$, $B(C_6F_5)_3$ or $B(C_6H_5)_3$, and the support comprises silica.

23. A process to oligomerize ethylene comprising contacting ethylene, and optionally one or more of propylene or 1-butene, with a catalyst system comprising the composition of claim 8, an activator, and optionally a support.

24. A process to oligomerize ethylene comprising contacting ethylene, and optionally one or more of propylene or 1-butene, with a catalyst system comprising the composition of claim 1, an activator, and optionally a support.

25. The process of claim 24 where the activator is selected from the group consisting of methylalumoxane, modified methylalumoxane, ethylalumoxane, trimethyl aluminum, triethyl aluminum, triisopropyl aluminum, diethyl aluminum chloride, [Me$_2$PhNH][B(C$_6$F$_5$)$_4$], [Bu$_3$NH][BF$_4$], [NH$_4$][PF$_6$], [NH$_4$][SbF$_6$], [NH$_4$][AsF$_6$], [NH$_4$][B(C$_6$H$_5$)$_4$], B(C$_6$F$_5$)$_3$ or B(C$_6$H$_5$)$_3$.

26. The process of claim 24 where the contacting occurs at a temperature of −100° C. to 300° C. and a pressure of 0 kPa-35 MPa in the presence of one or more liquids selected from the group consisting of alkanes, alkenes, cycloalkanes, halogenated hydrocarbons, aromatic hydrocarbons, hydrofluorocarbons.

27. A process to oligomerize one or more alpha-olefins comprising contacting the alpha-olefins with a catalyst system comprising the composition of claim 1, an activator, and optionally a support where the contacting occurs at a temperature of −100° C. to 300° C. and a pressure of 0 kPa-35 MPa in the presence of one or more liquids selected from the group consisting of alkanes, alkenes, cycloalkanes, halogenated hydrocarbons, aromatic hydrocarbons, hydrofluorocarbons.

* * * * *